US011802146B2

(12) United States Patent
Himansu et al.

(10) Patent No.: US 11,802,146 B2
(45) Date of Patent: Oct. 31, 2023

(54) POLYNUCLEOTIDES ENCODING ANTI-CHIKUNGUNYA VIRUS ANTIBODIES

(71) Applicants: ModernaTX, Inc., Cambridge, MA (US); Vanderbilt University, Nashville, TN (US)

(72) Inventors: Sunny Himansu, Winchester, MA (US); James E. Crowe, Jr., Nashville, TN (US); Giuseppe Ciaramella, Sudbury, MA (US)

(73) Assignees: ModernaTX, Inc., Cambridge, MA (US); Vanderbilt University, Nashville, TN (US)

( * ) Notice: Subject to any disclaimer, the term of this patent is extended or adjusted under 35 U.S.C. 154(b) by 545 days.

(21) Appl. No.: 16/959,828

(22) PCT Filed: Jan. 4, 2019

(86) PCT No.: PCT/US2019/012339
§ 371 (c)(1),
(2) Date: Jul. 2, 2020

(87) PCT Pub. No.: WO2019/136241
PCT Pub. Date: Jul. 11, 2019

(65) Prior Publication Data

US 2020/0369748 A1 Nov. 26, 2020

Related U.S. Application Data

(60) Provisional application No. 62/712,599, filed on Jul. 31, 2018, provisional application No. 62/613,938, filed on Jan. 5, 2018.

(51) Int. Cl.
*C07K 16/10* (2006.01)
*A61P 31/14* (2006.01)
*A61K 39/00* (2006.01)

(52) U.S. Cl.
CPC .......... *C07K 16/1081* (2013.01); *A61P 31/14* (2018.01); *A61K 2039/505* (2013.01)

(58) Field of Classification Search
None
See application file for complete search history.

(56) References Cited

U.S. PATENT DOCUMENTS

| | | | |
|---|---|---|---|
| 7,326,414 | B2 | 2/2008 | Lambert |
| 2021/0009662 | A1 | 1/2021 | Crowe, Jr. |

FOREIGN PATENT DOCUMENTS

| | | |
|---|---|---|
| EP | 3480211 | 5/2019 |
| WO | WO2008083949 | 7/2008 |
| WO | WO2012045082 | 4/2012 |
| WO | WO2015105926 | 7/2015 |
| WO | WO2016168417 | 10/2016 |
| WO | WO2017049245 | 3/2017 |
| WO | WO2017106383 | 6/2017 |
| WO | WO2017186928 | 11/2017 |
| WO | WO2018003983 | 1/2018 |
| WO | WO2019156758 | 8/2019 |

OTHER PUBLICATIONS

August et al., Nature Medicine, Dec. 2021, 27:2224-2233. (Year: 2021).*
Milligan et al., Vaccine, 2019, 37:7427-7436. (Year: 2019).*
International Preliminary Report on Patentability in International Application No. PCT/US2019/012339, dated Jul. 16, 2020, 8 pages.
International Search Report and Written Opinion in International Application No. PCT/US2019/012339, dated Apr. 24, 2019, 16 pages.
Smith et al., "Isolation and Characterization of Broad and Ultrapotent Human Monoclonal Antibodies with Therapeutic Activity against Chikungunya Virus", Cell Host and Microbe, Jul. 2015, 18(1):86-95.

* cited by examiner

*Primary Examiner* — Stacy B Chen
(74) *Attorney, Agent, or Firm* — Fish & Richardson P.C.

(57) ABSTRACT

This disclosure relates to compositions and methods for treating and preventing chikungunya virus infection by delivering polynucleotides encoding anti-chikungunya virus antibodies to a subject. Compositions and treatments provided herein include one or more polynucleotides having an open reading frame encoding an anti-chikungunya virus antibody heavy chain or fragment thereof and/or an anti-chikungunya virus antibody light chain or fragment thereof. Methods for preparing and using such treatments are also provided.

23 Claims, 13 Drawing Sheets

Specification includes a Sequence Listing.

SEQUENCE LISTING

```
<160> NUMBER OF SEQ ID NOS: 253

<210> SEQ ID NO 1
<211> LENGTH: 472
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 1

Met Glu Thr Asp Thr Leu Leu Leu Trp Val Leu Leu Leu Trp Val Pro
1               5                   10                  15

Gly Ser Thr Gly Gln Val Gln Leu Val Glu Ser Gly Gly Gly Val Val
            20                  25                  30

Gln Pro Gly Lys Ser Leu Arg Leu Ser Cys Ala Ala Ser Gly Phe Thr
```

-continued

```
        35                  40                  45

Phe Arg Asn Tyr Gly Met His Trp Val Arg Gln Ala Pro Gly Lys Gly
    50                  55                  60

Leu Asp Trp Val Ala Leu Ile Ser Tyr Asp Gly Thr His Lys Tyr Tyr
65                  70                  75                  80

Lys Asp Ser Leu Lys Gly Arg Phe Thr Ile Ser Arg Asp Asn Phe Gln
                85                  90                  95

Asn Thr Val Asp Leu Gln Ile Asn Ser Leu Arg Pro Asp Asp Thr Ala
            100                 105                 110

Val Tyr Tyr Cys Ala Lys Glu Leu Ala Thr Ser Gly Val Val Glu Pro
        115                 120                 125

Leu Asp Ser Trp Gly Gln Gly Thr Leu Val Thr Val Ser Ser Ala Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240

Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Asp Glu Leu Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Leu His Glu Ala Leu His Ser His Tyr Thr Gln Lys
    450                 455                 460
```

Ser Leu Ser Leu Ser Pro Gly Lys
465 470

<210> SEQ ID NO 2
<211> LENGTH: 1416
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 2
auggaaaccg acacacugcu gcugugggug cugcuucuuu gggugcccgg aucuacagga 60
caggugcagc ugguugaauc uggcggcgga guugugcagc cuggcaaguc ucugagacug 120
agcugugccg ccagcggcuu caccuucaga aacuacggca ugcacugggu ccgacaggcu 180
ccaggcaaag gccuugauug ggucgcccug aucagcuacg acggcaccca caaguacuac 240
aaggacagcc ugaagggcag auucaccauc agccgggaca acuuccagaa caccguggac 300
cugcagauca acagccugag gccugacgac accgccgugu acuacugcgc caaagagcug 360
gcuacaagcg gcguggugga accucuggau ucuuggggac agggcacccu ggucacagug 420
ucuagcgccu cuacaaaggg acccagcgug uucccucugg cuccuagcag caagagcaca 480
agcggaggaa cagccgcucu gggcugucug gucaaggacu acuuucccga gccugugacc 540
guguccugga auucuggcgc ucugacaucc ggcgugcaca ccuuuccagc ugugcugcaa 600
agcagcggcc uguacucucu gagcagcguc gugacagugc caagcagcuc ucugggcacc 660
cagaccuaca ucugcaacgu gaaccacaag ccuagcaaca ccaaggugga caagaaggug 720
gaacccaaga gcugcgacaa gacccacacc uguccacccu guccugcucc agaacugcuc 780
ggcggaccuu ccguguuccu guuuccucca aagccuaagg acacccugau gaucagcaga 840
acacccgaag ugaccugcgu gguggaggac gugucucacg aggacccuga agugaaguuc 900
aauugguacg uggacggcgu ggaagugcac aacgccaaga ccaagccuag agaggaacag 960
uacaacagca ccuacagagu gguguccgug cugaccgugc ugcaccagga uuggcugaac 1020
ggcaaagagu acaagugcaa gguguccaac aaggcccugc cugcuccuau cgagaagacc 1080
aucagcaagg ccaagggcca gccuagggaa ccucaggugu acacacugcc uccaagcagg 1140
gacgagcuga ccaagaauca ggugucccug accugccucg ugaagggcuu cuacccuucc 1200
gauaucgccg uggaguggga gagcaacggc cagccugaga acaacuacaa gaccacuccu 1260
ccugugcugg acagcgacgg cucauucuuc cuguacagca agcugacagu ggacaagucc 1320
agguggcagc agggcaacgu guucagcugc agcgugcugc acgaagcccu gcacagccac 1380
uacacccaga agucccuguc ucugagcccu ggcaaa 1416

<210> SEQ ID NO 3
<211> LENGTH: 235
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 3

Met Glu Thr Pro Ala Gln Leu Leu Phe Leu Leu Leu Leu Trp Leu Pro
1 5 10 15

-continued

```
Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Leu Val Ser Ser Tyr Phe Gly Trp Tyr Gln Gln Lys Arg Gly Gln Ser
    50                  55                  60

Pro Arg Leu Leu Ile Tyr Ala Ala Ser Thr Arg Ala Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Gly Asn Thr Pro Phe Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 4
<211> LENGTH: 705
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4

```
auggaaacac ccgcucagcu gcuguuccug cugcugcugu ggcugccuga uaccacaggc      60

gagaucgugc ugacacagag cccuggcaca cugucacugu cuccaggcga aagagccaca     120

cugagcugua gagccagcca gagccuggug uccagcuacu ucggcuggua ucagcagaag     180

agaggccagu cuccucggcu gcugaucuac gccgcuucua caagagccac cggcauuccc     240

gauagauuca gcggcucugg cagcggcacc gauuucaccc ugacaaucag cagacuggaa     300

cccgaggacu ucgccgugua cuacugucag caguacggca acacacccuu caccuuuggc     360

ggaggcacca agguggaaau caagagaaca guggcugcuc ccagcguguu caucuuccca     420

ccuuccgacg agcagcugaa gucuggcaca gccucugucg ugugccugcu gaacaacuuc     480

uacccucggg aagccaaggu gcaguggaag guggacaacg cccugcagag cggcaacagc     540

caagagagcg ugacagagca ggacagcaag gacuccaccu acagccugag cagcacacug     600

acccugagca aggccgacua cgagaagcac aagguguacg ccugcgaagu gacacaccag     660

ggccugucua gcccugugac caagagcuuc aacagaggcg agugc                      705
```

<210> SEQ ID NO 5
<211> LENGTH: 1592
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 5
gggaaauaag agagaaaaga agaguaagaa gaaauauaag accccggcgc cgccaccaug 60
gaaaccgaca cacugcugcu gugggugcug cuucuuuggg ugcccggauc uacaggacag 120
gugcagcugg uugaaucugg cggcggaguu gugcagccug gcaagucucu gagacugagc 180
ugugccgcca gcggcuucac cuucagaaac uacggcaugc acuggguccg acaggcucca 240
ggcaaaggcc uugauugggu cgcccugauc agcuacgacg gcacccacaa guacuacaag 300
gacagccuga agggcagauu caccaucagc cgggacaacu uccagaacac cguggaccug 360
cagaucaaca gccugaggcc ugacgacacc gccguguacu acugcgccaa agagcuggcu 420
acaagcggcg ugguggaacc ucuggauucu uggggacagg gcacccuggu cacagugucu 480
agcgccucua caaagggacc cagcguguuc ccucuggcuc cuagcagcaa gagcacaagc 540
ggaggaacag ccgcucuggg cugucugguc aaggacuacu uucccgagcc ugugaccgug 600
uccuggaauu cuggcgcucu gacauccggc gugcacaccu uuccagcugu gcugcaaagc 660
agcggccugu acucucugag cagcgucgug acagugccaa gcagcucucu gggcacccag 720
accuacaucu gcaacgugaa ccacaagccu agcaacacca agguggacaa gaagguggaa 780
cccaagagcu gcgacaagac ccacaccugu ccacccuguc cugcuccaga acugcucggc 840
ggaccuuccg uguuccuguu uccuccaaag ccuaaggaca cccugaugau cagcagaaca 900
cccgaaguga ccugcguggu gguggacgug ucucacgagg acccugaagu gaaguucaau 960
ugguacgugg acggcgugga agugcacaac gccaagacca agccuagaga ggaacaguac 1020
aacagcaccu acagaguggu guccgugcug accgugcugc accaggauug gcugaacggc 1080
aaagaguaca agugcaaggu guccaacaag gcccugccug cuccuaucga gaagaccauc 1140
agcaaggcca agggccagcc uagggaaccu cagguguaca cacugccucc aagcagggac 1200
gagcugacca agaaucaggu gucccugacc ugccucguga agggcuucua cccuuccgau 1260
aucgccgugg agugggagag caacggccag ccugagaaca acuacaagac cacuccuccu 1320
gugcuggaca gcgacggcuc auucuuccug uacagcaagc ugacagugga caaguccagg 1380
uggcagcagg gcaacguguu cagcugcagc gugcugcacg aagcccugca cagccacuac 1440
acccagaagu cccugucucu gagcccuggc aaaugauaau aggcuggagc cucgguggcc 1500
uagcuucuug ccccuugggc cuccccccag ccccuccucc ccuuccugca cccguacccc 1560
cgugguCuuu gaauaaaguc ugagugggcg gc 1592

<210> SEQ ID NO 6
<211> LENGTH: 881
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6
gggaaauaag agagaaaaga agaguaagaa gaaauauaag accccggcgc cgccaccaug 60

```
gaaacacccg cucagcugcu guuccugcug cugcuguggc ugccugauac cacaggcgag    120

aucgugcuga cacagagccc uggcacacug ucacugucuc caggcgaaag agccacacug    180

agcuguagag ccagccagag ccuggugucc agcuacuucg gcugguauca gcagaagaga    240

ggccagucuc cucggcugcu gaucuacgcc gcuucuacaa gagccaccgg cauuccccgau    300

agauucagcg gcucuggcag cggcaccgau uucacccuga caaucagcag acuggaaccc    360

gaggacuucg ccguguacua cugucagcag uacggcaaca cacccuucac cuuuggcgga    420

ggcaccaagg uggaaaucaa gagaacagug gcugcuccca gcguguucau cuucccaccu    480

uccgacgagc agcugaaguc uggcacagcc ucugucgugu gccugcugaa caacuucuac    540

ccucgggaag ccaaggugca guggaaggug gacaacgccc ugcagagcgg caacagccaa    600

gagagcguga cagagcagga cagcaaggac uccaccuaca gccugagcag cacacugacc    660

cugagcaagg ccgacuacga gaagcacaag guguacgccu gcgaagugac acaccagggc    720

cugucuagcc cugugaccaa gagcuucaac agaggcgagu gcugauaaua ggcuggagcc    780

ucgguggccu agcuucuugc cccuugggcc ucccccccagc cccuccuccc cuuccugcac    840

ccguaccccc guggucuuug aauaaagucu gagugggcgg c                        881
```

<210> SEQ ID NO 7

<400> SEQUENCE: 7

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13
<211> LENGTH: 57
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 13
gggaaauaag agagaaaaga agaguaagaa gaaauauaag accccggcgc cgccacc 57

<210> SEQ ID NO 14
<211> LENGTH: 119
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14
ugauaauagg cuggagccuc gguggccuag cuucuugccc cuugggccuc cccccagccc 60
cuccuccccu uccugcaccc guacccccgu ggucuuugaa uaaagucuga gugggcggc 119

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

<210> SEQ ID NO 31

<400> SEQUENCE: 31

000

<210> SEQ ID NO 32

<400> SEQUENCE: 32

000

<210> SEQ ID NO 33

<400> SEQUENCE: 33

000

<210> SEQ ID NO 34

<400> SEQUENCE: 34

000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49

<400> SEQUENCE: 49

000

<210> SEQ ID NO 50

<400> SEQUENCE: 50

000

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 10
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 100
ccccggcgcc 10

<210> SEQ ID NO 101

<211> LENGTH: 7
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 101 ccccggc 7

<210> SEQ ID NO 102
<211> LENGTH: 6
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 102 gccgcc 6

<210> SEQ ID NO 103
<211> LENGTH: 41
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 103
gggaaauaag agagaaaaga agaguaagaa gaaauauaag a 41

<210> SEQ ID NO 104

<400> SEQUENCE: 104

000

<210> SEQ ID NO 105
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 105
uguaguguuu ccuacuuuau gga 23

<210> SEQ ID NO 106
<211> LENGTH: 54
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 106
gggaaauaag agagaaaaga agaguaagaa gaaauauaag accccggcgc cacc 54

<210> SEQ ID NO 107
<211> LENGTH: 6
<212> TYPE: RNA

<213> ORGANISM: Unknown
<220> FEATURE:
<221> NAME/KEY: source
<223> OTHER INFORMATION: /note="Description of Unknown:
Kozak sequence"

<400> SEQUENCE: 107 gccrcc 6

<210> SEQ ID NO 108
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 108
gggaaauaag agagaaaaga agaguaagaa gaaauauaag agccacc 47

<210> SEQ ID NO 109
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 109
gggagaucag agagaaaaga agaguaagaa gaaauauaag agccacc 47

<210> SEQ ID NO 110

<400> SEQUENCE: 110

000

<210> SEQ ID NO 111
<211> LENGTH: 42
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 111
gggagacaag cuuggcauuc cgguacuguu gguaaagcca cc 42

<210> SEQ ID NO 112

<400> SEQUENCE: 112

000

<210> SEQ ID NO 113

<400> SEQUENCE: 113

000

<210> SEQ ID NO 114

<400> SEQUENCE: 114

000

<210> SEQ ID NO 115
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 115
gggaauuaac agagaaaaga agaguaagaa gaaauauaag agccacc 47

<210> SEQ ID NO 116
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 116
gggaaauuag acagaaaaga agaguaagaa gaaauauaag agccacc 47

<210> SEQ ID NO 117
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 117
gggaaauaag agaguaaaga acaguaagaa gaaauauaag agccacc 47

<210> SEQ ID NO 118
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 118
gggaaaaaag agagaaaaga agacuaagaa gaaauauaag agccacc 47

<210> SEQ ID NO 119
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 119
gggaaauaag agagaaaaga agaguaagaa gauauauaag agccacc 47

<210> SEQ ID NO 120
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 120
gggaaauaag agacaaaaca agaguaagaa gaaauauaag agccacc 47

<210> SEQ ID NO 121
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 121
gggaaauuag agaguaaaga acaguaagua gaauuaaaag agccacc 47

<210> SEQ ID NO 122
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 122
gggaaauaag agagaauaga agaguaagaa gaaauauaag agccacc 47

<210> SEQ ID NO 123
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 123
gggaaauaag agagaaaaga agaguaagaa gaaaauuaag agccacc 47

<210> SEQ ID NO 124
<211> LENGTH: 47
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 124
gggaaauaag agagaaaaga agaguaagaa gaaauuuaag agccacc 47

<210> SEQ ID NO 125

<400> SEQUENCE: 125

000

<210> SEQ ID NO 126
<211> LENGTH: 92
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 126
ucaagcuuuu ggacccucgu acagaagcua auacgacuca cuauagggaa auaagagaga 60
aaagaagagu aagaagaaau auaagagcca cc 92

<210> SEQ ID NO 127
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 127
ugauaauagu ccauaaagua ggaaacacua cagcuggagc cucgguggcc augcuucuug 60
ccccuugggc cuccccccag ccccuccucc ccuuccugca cccguacccc cguggucuuu 120
gaauaaaguc ugagugggcg gc 142

<210> SEQ ID NO 128
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 128
ugauaauagg cuggagccuc gguggcucca uaaaguagga aacacuacac augcuucuug 60
ccccuugggc cuccccccag ccccuccucc ccuuccugca cccguacccc cguggucuuu 120
gaauaaaguc ugagugggcg gc 142

<210> SEQ ID NO 129
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 129
ugauaauagg cuggagccuc gguggccaug cuucuugccc cuuccauaaa guaggaaaca 60
cuacaugggc cuccccccag ccccuccucc ccuuccugca cccguacccc cguggucuuu 120
gaauaaaguc ugagugggcg gc 142

<210> SEQ ID NO 130
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 130
ugauaauagg cuggagccuc gguggccaug cuucuugccc cuugggccuc cccccagucc 60
auaaaguagg aaacacuaca ccccuccucc ccuuccugca cccguacccc cguggucuuu 120
gaauaaaguc ugagugggcg gc 142

<210> SEQ ID NO 131
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 131
ugauaauagg cuggagccuc gguggccaug cuucuugccc cuugggccuc cccccagccc 60
cuccuccccu ucuccauaaa guaggaaaca cuacacugca cccguacccc cguggucuuu 120
gaauaaaguc ugagugggcg gc 142

<210> SEQ ID NO 132
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 132
ugauaauagg cuggagccuc gguggccaug cuucuugccc cuugggccuc cccccagccc 60
cuccuccccu uccugcaccc guacccccuc cauaaaguag gaaacacuac aguggucuuu 120
gaauaaaguc ugagugggcg gc 142

<210> SEQ ID NO 133
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 133
ugauaauagg cuggagccuc gguggccaug cuucuugccc cuugggccuc cccccagccc 60
cuccuccccu uccugcaccc guacccccgu ggucuuugaa uaaaguucca uaaaguagga 120
aacacuacac ugagugggcg gc 142

<210> SEQ ID NO 134
<211> LENGTH: 87
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 134
gacagugcag ucacccauaa aguagaaagc acuacuaaca gcacuggagg guguaguguu 60
uccuacuuua uggaugagug uacugug 87

<210> SEQ ID NO 135
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 135
ugauaauagu ccauaaagua ggaaacacua cagcuggagc cucgguggcc augcuucuug 60
ccccuugggc cuccccccag ccccuccucc ccuuccugca cccguacccc ccgcauuauu 120
acucacggua cgaguggucu uugaauaaag ucugaguggg cggc 164

<210> SEQ ID NO 136
<211> LENGTH: 164
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 136
ugauaauagu ccauaaagua ggaaacacua cagcuggagc cucgguggcc uagcuucuug 60
ccccuugggc cuccccccag ccccuccucc ccuuccugca cccguacccc ccgcauuauu 120
acucacggua cgaguggucu uugaauaaag ucugaguggg cggc 164

<210> SEQ ID NO 137
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 137
ugauaauagg cuggagccuc gguggccuag cuucuugccc cuugggccuc cccccagccc 60
cuccuccccu uccugcaccc guaccccuc cauaaaguag gaaacacuac aguggucuuu 120
gaauaaaguc ugagugggcg gc 142

<210> SEQ ID NO 138
<211> LENGTH: 142
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 138
tgataatagg ctggagcctc ggtggcctag cttcttgccc cttgggcctc cccccagccc 60
ctcctcccct tcctgcaccc gtacccctc cataaagtag gaaacactac agtggtcttt 120
gaataaagtc tgagtgggcg gc 142

<210> SEQ ID NO 139
<211> LENGTH: 85
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 139
cgcuggcgac gggacauuau uacuuuuggu acgcgcugug acacuucaaa cucguaccgu 60
gaguaauaau gcgccgucca cggca 85

<210> SEQ ID NO 140
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 140
ucguaccgug aguaauaaug cg 22

<210> SEQ ID NO 141
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 141
cgcauuauua cucacgguac ga 22

<210> SEQ ID NO 142
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 142
cauuauuacu uuugguacgc g 21

<210> SEQ ID NO 143
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 143
cgcguaccaa aaguaauaau g 21

<210> SEQ ID NO 144
<211> LENGTH: 133
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 144
gcuggagccu cgguggccau gcuucuugcc ccuugggccu ccccccagcc ccuccucccc 60
uuccugcacc cguacccccu ccauaaagua ggaaacacua caguggucuu ugaauaaagu 120
cugagugggc ggc 133

<210> SEQ ID NO 145
<211> LENGTH: 22
<212> TYPE: RNA
<213> ORGANISM: Artificial Sequence
<220> FEATURE:

<221> NAME/KEY: source
<223> OTHER INFORMATION: /note="Description of Artificial Sequence:
Synthetic oligonucleotide"

<400> SEQUENCE: 145
ccucugaaau ucaguucuuc ag 22

<210> SEQ ID NO 146
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 146
ugagaacuga auuccauggg uu 22

<210> SEQ ID NO 147
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 147
cuccuacaua uuagcauuaa ca 22

<210> SEQ ID NO 148
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 148
uuaaugcuaa ucgugauagg ggu 23

<210> SEQ ID NO 149
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 149
ccaguauuaa cugugcugcu ga 22

<210> SEQ ID NO 150
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 150
uagcagcacg uaaauauugg cg 22

<210> SEQ ID NO 151
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 151
caacaccagu cgaugggcug u 21

<210> SEQ ID NO 152
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 152
uagcuuauca gacugauguu ga 22

<210> SEQ ID NO 153
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 153
ugucaguuug ucaaauaccc ca 22

<210> SEQ ID NO 154
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 154
cguguauuug acaagcugag uu 22

<210> SEQ ID NO 155
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 155
uggcucaguu cagcaggaac ag 22

<210> SEQ ID NO 156
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 156
ugccuacuga gcugauauca gu 22

<210> SEQ ID NO 157
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 157
uucacagugg cuaaguuccg c 21

<210> SEQ ID NO 158
<211> LENGTH: 22
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 158
agggcuuagc ugcuugugag ca 22

<210> SEQ ID NO 159
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 159
ugauaauagg cuggagccuc gguggccaug cuucuugccc cuugggccuc cccccagccc 60
cuccuccccu uccugcaccc guaccccccg cauuauuacu cacgguacga guggucuuug 120
aauaaagucu gagugggcgg c 141

<210> SEQ ID NO 160
<211> LENGTH: 119
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 160
ugauaauagg cuggagccuc gguggccaug cuucuugccc cuugggccuc cccccagccc 60
cuccuccccu uccugcaccc guacccccgu ggucuuugaa uaaagucuga gugggcggc 119

<210> SEQ ID NO 161

<400> SEQUENCE: 161

000

<210> SEQ ID NO 162

<400> SEQUENCE: 162

000

<210> SEQ ID NO 163
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 163
uuaaugcuaa uugugauagg ggu 23

<210> SEQ ID NO 164
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 164
accccuauca caauuagcau uaa 23

<210> SEQ ID NO 165
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 165
ugauaauagu ccauaaagua ggaaacacua cagcuggagc cucgguggcc augcuucuug 60
ccccuugggc cuccauaaag uaggaaacac uacaucccccc cagccccucc uccccuuccu 120
gcacccguac ccccuccaua aaguaggaaa cacuacagug gucuuugaau aaagucugag 180
ugggcggc 188

<210> SEQ ID NO 166
<211> LENGTH: 140
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 166
ugauaauagg cuggagccuc gguggccaug cuucuugccc cuugggccuc cccccagccc 60
cuccuccccu uccugcaccc guacccccag uagugcuuuc uacuuuaugg uggucuuuga 120
auaaagucug agugggcggc 140

<210> SEQ ID NO 167
<211> LENGTH: 182
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 167
ugauaauaga guagugcuuu cuacuuuaug gcuggagccu cgguggccau gcuucuugcc 60
ccuugggcca guagugcuuu cuacuuuaug uccccccagc cccuccuccc cuuccugcac 120
ccguaccccc aguagugcuu ucuacuuuau gguggucuuu gaauaaaguc ugagugggcg 180
gc 182

<210> SEQ ID NO 168
<211> LENGTH: 184
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 168
ugauaauaga guagugcuuu cuacuuuaug gcuggagccu cgguggccau gcuucuugcc 60
ccuugggccu ccauaaagua ggaaacacua caucccccca gccccuccuc cccuuccugc 120
acccguaccc ccaguagugc uuucuacuuu augguggucu uugaauaaag ucugaguggg 180
cggc 184

<210> SEQ ID NO 169
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 169
ugauaauagg cuggagccuc gguggccaug cuucuugccc cuugggccuc cccccagccc 60
cuccuccccu uccugcaccc guacccccac cccuaucaca auuagcauua agugggucuuu 120 gaauaaaguc ugagugggcg gc 142

<210> SEQ ID NO 170
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 170
ugauaauaga ccccuaucac aauuagcauu aagcuggagc cucgguggcc augcuucuug 60
ccccuugggc caccccuauc acaauuagca uuaaucccccc cagccccucc uccccuuccu 120
gcacccguac ccccacccccu aucacaauua gcauuaagug gucuuugaau aaagucugag 180
ugggcggc 188

<210> SEQ ID NO 171
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 171
ugauaauaga ccccuaucac aauuagcauu aagcuggagc cucgguggcc augcuucuug 60
ccccuugggc cuccauaaag uaggaaacac uacaucccccc cagccccucc uccccuuccu 120
gcacccguac ccccaccccu aucacaauua gcauuaagug gucuuugaau aaagucugag 180
ugggcggc 188

<210> SEQ ID NO 172
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 172
uccauaaagu aggaaacacu aca 23

<210> SEQ ID NO 173
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 173
cauaaaguag aaagcacuac u 21

<210> SEQ ID NO 174
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 174
ugauaauagg cuggagccuc gguggccaug cuucuugccc cuugggccuc cauaaaguag 60
gaaacacuac aucccccccag ccccuccucc ccuuccugca cccguacccc cguggucuuu 120
gaauaaaguc ugagugggcg gc 142

<210> SEQ ID NO 175
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 175
aguagugcuu ucuacuuuau g 21

<210> SEQ ID NO 176
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 176
gggaaauaag aguccauaaa guaggaaaca cuacaagaaa agaagaguaa gaagaaauau 60
aagagccacc 70

<210> SEQ ID NO 177
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 177
gggaaauaag agagaaaaga agaguaaucc auaaaguagg aaacacuaca gaagaaauau 60
aagagccacc 70

<210> SEQ ID NO 178
<211> LENGTH: 70
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 178
gggaaauaag agagaaaaga agaguaagaa gaaauauaau ccauaaagua ggaaacacua 60
cagagccacc 70

<210> SEQ ID NO 179

<400> SEQUENCE: 179

000

<210> SEQ ID NO 180
<211> LENGTH: 181
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 180
ugauaauaga guagugcuuu cuacuuuaug gcuggagccu cgguggccau gcuucuugcc 60
ccuugggcca guagugcuuu cuacuuuaug uccccccagc cccucucccc uuccugcacc 120
cguaccccca guagugcuuu cuacuuuaug guggucuuug aauaaagucu gagugggcgg 180
c 181

<210> SEQ ID NO 181

<400> SEQUENCE: 181

000

<210> SEQ ID NO 182

<400> SEQUENCE: 182

000

<210> SEQ ID NO 183

<400> SEQUENCE: 183

000

<210> SEQ ID NO 184

<400> SEQUENCE: 184

000

<210> SEQ ID NO 185

<400> SEQUENCE: 185

000

<210> SEQ ID NO 186

<400> SEQUENCE: 186

000

<210> SEQ ID NO 187
<211> LENGTH: 141
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 187
ugauaauagg cuggagccuc gguggccuag cuucuugccc cuugggccuc cccccagccc 60
cuccuccccu uccugcaccc guaccccccg cauuauuacu cacgguacga gugguctuug 120
aauaaagucu gagugggcgg c 141

<210> SEQ ID NO 188
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 188
ugauaauagu ccauaaagua ggaaacacua cagcuggagc cucgguggcc uagcuucuug 60
ccccuugggc cuccauaaag uaggaaacac uacaucccccc cagccccucc uccccuuccu 120
gcacccguac ccccuccaua aaguaggaaa cacuacagug gucuuugaau aaagucugag 180
ugggcggc 188

<210> SEQ ID NO 189
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 189
ugauaauagu ccauaaagua ggaaacacua cagcuggagc cucgguggcc uagcuucuug 60
ccccuugggc cuccccccag ccccuccucc ccuuccugca cccguacccc cgugguctuu 120
gaauaaaguc ugagugggcg gc 142

<210> SEQ ID NO 190
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 190
ugauaauagg cuggagccuc gguggcucca uaaaguagga aacacuacac uagcuucuug 60
ccccuugggc cuccccccag ccccuccucc ccuuccugca cccguacccc cguggucuuu 120
gaauaaaguc ugagugggcg gc 142

<210> SEQ ID NO 191
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 191
ugauaauagg cuggagccuc gguggccuag cuucuugccc cuugggccuc cauaaaguag 60
gaaacacuac aucccccag ccccuccucc ccuuccugca cccguacccc cguggucuuu 120
gaauaaaguc ugagugggcg gc 142

<210> SEQ ID NO 192
<211> LENGTH: 142
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 192
ugauaauagg cuggagccuc gguggccuag cuucuugccc cuugggccuc cccccagccc 60
cuccuccccu uccugcaccc guaccccac cccuaucaca auuagcauua aguggucuuu 120
gaauaaaguc ugagugggcg gc 142

<210> SEQ ID NO 193
<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 193
ugauaauaga ccccuaucac aauuagcauu aagcuggagc cucgguggcc uagcuucuug 60
ccccuugggc caccccuauc acaauuagca uuaaucccc cagccccucc uccccuuccu 120
gcacccguac ccccaccccu aucacaauua gcauuaagug gucuuugaau aaagucugag 180
ugggcggc 188

<210> SEQ ID NO 194

<211> LENGTH: 188
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 194
ugauaauaga ccccuaucac aauuagcauu aagcuggagc cucgguggcc uagcuucuug 60
ccccuugggc cuccauaaag uaggaaacac uacaucccccc cagccccucc uccccuuccu 120
gcacccguac ccccaccccu aucacaauua gcauuaagug gucuuugaau aaagucugag 180
ugggcggc 188

<210> SEQ ID NO 195
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 195 ugauaauag 9

<210> SEQ ID NO 196
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 196 ugauaguaa 9

<210> SEQ ID NO 197
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 197 uaaugauag 9

<210> SEQ ID NO 198
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 198 ugauaauaa 9

<210> SEQ ID NO 199
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 199 ugauaguag 9

<210> SEQ ID NO 200
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 200 uaaugauga 9

<210> SEQ ID NO 201
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 201 uaauaguag 9

<210> SEQ ID NO 202
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 202 ugaugauga 9

<210> SEQ ID NO 203
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 203 uaauaauaa 9

<210> SEQ ID NO 204
<211> LENGTH: 9
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 204 uaguaguag 9

<210> SEQ ID NO 205
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 205

Glu Ala Ala Ala Arg
1 5

<210> SEQ ID NO 206
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 206
gaagctgctg caagagaagc tgcagctagg gaggctgcag ctagggaggc tgctgcaaga 60

<210> SEQ ID NO 207
<211> LENGTH: 6
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 207 ggcagc 6

<210> SEQ ID NO 208
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 208

Gly Ser Gly Ser Gly Ser
1 5

<210> SEQ ID NO 209
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 209
ggtagcggca gcggtagc 18

<210> SEQ ID NO 210
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
ggtgaaaatt tgtattttca atctggtggt 30

<210> SEQ ID NO 211
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
tccgcttgtt actgtgagct ttcc 24

<210> SEQ ID NO 212
<211> LENGTH: 45
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212
ggtggaggag gttctggagg cggtggaagt ggtggcggag gtagc 45

<210> SEQ ID NO 213
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Gly Gly Ser Gly
1

<210> SEQ ID NO 214
<211> LENGTH: 12
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
ggtggttctg gt 12

<210> SEQ ID NO 215
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Gly Gly Ser Gly Gly Gly Ser Gly
1               5

<210> SEQ ID NO 216
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 216
ggtggttctg gtggtggttc tggt 24

<210> SEQ ID NO 217
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 217

Gly Gly Ser Gly Gly Gly Ser Gly Gly Gly Ser Gly
1 5 10

<210> SEQ ID NO 218
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 218
ggtggttctg gtggtggttc tggtggtggt tctggt 36

<210> SEQ ID NO 219
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 219
ggtggttctg ccggtggctc cggttctggc tccagcggtg gcagctctgg tgcgtccggc 60
acgggtactg cgggtggcac tggcagcggt tccggtactg gctctggc 108

<210> SEQ ID NO 220
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 220
ggtggttctg gcggcggttc tgaaggtggc ggctccgaag gcggcggcag cgagggcggt 60
ggtagcgaag gtggtggctc cgagggtggc ggttccggcg gcggtagc 108

<210> SEQ ID NO 221
<211> LENGTH: 20
<212> TYPE: PRT

<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 221

Gly Gly Gly Gly Ser Gly Gly Gly Gly Ser Gly Gly Gly Gly Ser Gly
1 5 10 15

Gly Gly Gly Ser
20

<210> SEQ ID NO 222
<211> LENGTH: 330
<212> TYPE: PRT
<213> ORGANISM: Homo sapiens

<400> SEQUENCE: 222

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Leu Leu Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 223
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 223

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 224
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 224

Gly Ser Gly Glu Gly Arg Gly Ser Leu Leu Thr Cys Gly Asp Val Glu
1 5 10 15

Glu Asn Pro Gly Pro
20

<210> SEQ ID NO 225
<211> LENGTH: 22
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 225

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 226
<211> LENGTH: 23
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 226

Gly Ser Gly Gln Cys Thr Asn Tyr Ala Leu Leu Lys Leu Ala Gly Asp
1 5 10 15

Val Glu Ser Asn Pro Gly Pro
20

<210> SEQ ID NO 227
<211> LENGTH: 66
<212> TYPE: RNA
<213> ORGANISM: Unknown
<220> FEATURE:
<221> NAME/KEY: source
<223> OTHER INFORMATION: /note="Description of Unknown:
2A sequence"

<400> SEQUENCE: 227
ggaagcggag cuacuaacuu cagccugcug aagcaggcug gagacgugga ggagaacccu 60
ggaccu 66

<210> SEQ ID NO 228
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: source
<223> OTHER INFORMATION: /note="Description of Combined DNA/RNA
Molecule: Synthetic oligonucleotide"

<400> SEQUENCE: 228
uccggacuca gauccgggga ucucaaaauu gucgcuccug ucaaacaaac ucuuaacuuu 60
gauuuacuca aacuggctgg ggauguagaa agcaauccag gtccacuc 108

<210> SEQ ID NO 229
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 229
attgggcacc cgtaaggg 18

<210> SEQ ID NO 230
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 230

Gly Gly Gly Gly Ser
1 5

<210> SEQ ID NO 231
<211> LENGTH: 9
<212> TYPE: RNA
<213> ORGANISM: Unknown
<220> FEATURE:
<221> NAME/KEY: source
<223> OTHER INFORMATION: /note="Description of Unknown:
Kozak sequence"

<400> SEQUENCE: 231 ccrccaugg 9

<210> SEQ ID NO 232
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 232
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa 100

<210> SEQ ID NO 233
<211> LENGTH: 33
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"
<220> FEATURE:
<221> NAME/KEY: SITE
<222> LOCATION: (1)..(10)
<223> OTHER INFORMATION: /note="This region may encompass 1-10 residues"
<220> FEATURE:
<221> NAME/KEY: SITE
<222> LOCATION: (12)..(21)
<223> OTHER INFORMATION: /note="This region may encompass 1-10 residues"
<220> FEATURE:
<221> NAME/KEY: SITE
<222> LOCATION: (23)..(32)
<223> OTHER INFORMATION: /note="This region may encompass 1-10 residues"

<400> SEQUENCE: 233

```
Gly Gly Gly Gly Gly Gly Gly Gly Gly Gly Ser Gly Gly Gly Gly Gly
1               5                   10                  15

Gly Gly Gly Gly Gly Ser Gly Gly Gly Gly Gly Gly Gly Gly Gly Gly
            20                  25                  30

Ser
```

<210> SEQ ID NO 234
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(150)
<223> OTHER INFORMATION: /note="This sequence may encompass 50-150 nucleotides"

<400> SEQUENCE: 234
aaaaaaaaaa aaaaaaaaaa aaaaaaaaaa aaaaaaaaaa aaaaaaaaaa aaaaaaaaaa 60
aaaaaaaaaa aaaaaaaaaa aaaaaaaaaa aaaaaaaaaa aaaaaaaaaa aaaaaaaaaa 120
aaaaaaaaaa aaaaaaaaaa aaaaaaaaaa 150

<210> SEQ ID NO 235
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<220> FEATURE:
<221> NAME/KEY: misc_feature
<222> LOCATION: (1)..(150)
<223> OTHER INFORMATION: /note="This sequence may encompass 75-150
      nucleotides"

<400> SEQUENCE: 235
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa                                     150

<210> SEQ ID NO 236
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(150)
<223> OTHER INFORMATION: /note="This sequence may encompass 85-150
      nucleotides"

<400> SEQUENCE: 236
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa                                     150

<210> SEQ ID NO 237
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(150)
<223> OTHER INFORMATION: /note="This sequence may encompass 90-150
      nucleotides"

<400> SEQUENCE: 237
aaaaaaaaaa aaaaaaaaaa aaaaaaaaaa aaaaaaaaaa aaaaaaaaaa aaaaaaaaaa     60
aaaaaaaaaa aaaaaaaaaa aaaaaaaaaa aaaaaaaaaa aaaaaaaaaa aaaaaaaaaa    120
aaaaaaaaaa aaaaaaaaaa aaaaaaaaaa                                     150

<210> SEQ ID NO 238
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(120)
<223> OTHER INFORMATION: /note="This sequence may encompass 90-120
      nucleotides"

<400> SEQUENCE: 238
aaaaaaaaaa aaaaaaaaaa aaaaaaaaaa aaaaaaaaaa aaaaaaaaaa aaaaaaaaaa     60

```
aaaaaaaaaa aaaaaaaaaa aaaaaaaaaa aaaaaaaaaa aaaaaaaaaa aaaaaaaaaa    120


<210> SEQ ID NO 239
<211> LENGTH: 130
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(130)
<223> OTHER INFORMATION: /note="This sequence may encompass 90-130
      nucleotides"

<400> SEQUENCE: 239

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa                                                           130


<210> SEQ ID NO 240
<211> LENGTH: 150
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(150)
<223> OTHER INFORMATION: /note="This sequence may encompass 90-150
      nucleotides"

<400> SEQUENCE: 240

aaaaaaaaaa aaaaaaaaaa aaaaaaaaaa aaaaaaaaaa aaaaaaaaaa aaaaaaaaaa     60

aaaaaaaaaa aaaaaaaaaa aaaaaaaaaa aaaaaaaaaa aaaaaaaaaa aaaaaaaaaa    120

aaaaaaaaaa aaaaaaaaaa aaaaaaaaaa                                     150


<210> SEQ ID NO 241
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Gly Gly Gly Ser
1


<210> SEQ ID NO 242
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: SITE
<222> LOCATION: (1)..(20)
<223> OTHER INFORMATION: /note="This sequence may encompass 2-5 'Gly Gly
      Gly Ser' repeating units"

<400> SEQUENCE: 242
```

```
Gly Gly Gly Ser Gly Gly Gly Ser Gly Gly Gly Ser Gly Gly Gly Ser
1               5                   10                  15

Gly Gly Gly Ser
            20


<210> SEQ ID NO 243
<211> LENGTH: 4
<212> TYPE: PRT
<213> ORGANISM: Unknown
<220> FEATURE:
<221> NAME/KEY: source
<223> OTHER INFORMATION: /note="Description of Unknown:
      2A sequence"

<400> SEQUENCE: 243

Asn Pro Gly Pro
1


<210> SEQ ID NO 244
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(30)
<223> OTHER INFORMATION: /note="This sequence may encompass 1-10 'ccg'
      repeating units"

<400> SEQUENCE: 244

ccgccgccgc cgccgccgcc gccgccgccg                                        30


<210> SEQ ID NO 245
<211> LENGTH: 24
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(24)
<223> OTHER INFORMATION: /note="This sequence may encompass 2-8 'ccg'
      repeating units"

<400> SEQUENCE: 245

ccgccgccgc cgccgccgcc gccg                                              24


<210> SEQ ID NO 246
<211> LENGTH: 18
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: misc_feature
<222> LOCATION: (1)..(18)
<223> OTHER INFORMATION: /note="This sequence may encompass 3-6 'ccg'
      repeating units"

<400> SEQUENCE: 246

ccgccgccgc cgccgccg                                                     18
```

<210> SEQ ID NO 247
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(15)
<223> OTHER INFORMATION: /note="This sequence may encompass 4-5 'ccg'
repeating units"

<400> SEQUENCE: 247
ccgccgccgc cgccg 15

<210> SEQ ID NO 248
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(15)
<223> OTHER INFORMATION: /note="This sequence may encompass 1-5 'ccg'
repeating units"

<400> SEQUENCE: 248
ccgccgccgc cgccg 15

<210> SEQ ID NO 249
<211> LENGTH: 12
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 249
ccgccgccgc cg 12

<210> SEQ ID NO 250
<211> LENGTH: 15
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 250
ccgccgccgc cgccg 15

<210> SEQ ID NO 251
<211> LENGTH: 30
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"
<220> FEATURE:
<221> NAME/KEY: misc_feature
<222> LOCATION: (1)..(30)
<223> OTHER INFORMATION: /note="This sequence may encompass 1-10 'gcc'

-continued

```
      repeating units"

<400> SEQUENCE: 251

gccgccgccg ccgccgccgc cgccgccgcc                                        30


<210> SEQ ID NO 252
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 252

tttttttttt tttttttttt tttttttttt tttttttttt tttttttttt tttttttttt      60

tttttttttt tttttttttt tttttttttt tttttttttt tttttttttt tttttttttt     120


<210> SEQ ID NO 253
<211> LENGTH: 120
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 253

aaaaaaaaaa aaaaaaaaaa aaaaaaaaaa aaaaaaaaaa aaaaaaaaaa aaaaaaaaaa      60

aaaaaaaaaa aaaaaaaaaa aaaaaaaaaa aaaaaaaaaa aaaaaaaaaa aaaaaaaaaa     120
```

POLYNUCLEOTIDES ENCODING ANTI-CHIKUNGUNYA VIRUS ANTIBODIES

CROSS-REFERENCE TO RELATED APPLICATIONS

This application claims priority to U.S. Provisional Appl. No. 62/613,938, filed Jan. 5, 2018, and U.S. Provisional Appl. No. 62/712,599, filed Jul. 31, 2018. The content of the prior applications are incorporated by reference herein in their entirety.

STATEMENT REGARDING FEDERALLY SPONSORED RESEARCH

This invention was made with government support under grant numbers R01 AI114816, HHSN272201400018C, W31P4Q-13-1-0003, and W911NF-13-1-0417 awarded by the National Institutes of Health and the Defense Advanced Research Projects Agency. The government has certain rights in the invention.

BACKGROUND

Chikungunya fever is an acute febrile illness that is caused by the chikungunya virus (CHIKV), an arthropod-borne alphavirus that is transmitted primarily by the bite of an infected *Aedes* species mosquito. CHIKV has caused millions of cases of disease in countries around the Indian Ocean, and has spread into novel ecological niches, including Europe and Australia. The incubation period for chikungunya fever is usually between three to seven days. Symptoms develop abruptly with high fever that can last for several days, and severe and often debilitating polyarthralgias. Arthritis with joint swelling can also occur. In some cases, infected individuals can develop a maculopapular rash, and develop non-specific symptoms, such as headache, fatigue, nausea, vomiting, conjunctivitis, and myalgias. Chikungunya fever rarely causes death, but patients can have prolonged symptoms for several months.

Chikungunya fever is limited generally to supportive care, which includes rest, fluids, antipyretics, and analgesics. Existing drugs, such as chloroquine, acyclovir, ribavirin, interferon-α, and corticosteroids, have been tested in vitro and in limited clinical studies, but these treatments are not used widely. There is an unmet need for an improved treatment for, and prevention of, chikungunya fever in view of the limited options that are available currently.

SUMMARY

The present disclosure provides compositions and methods of preventing and/or treating disease and/or symptoms caused by chikungunya virus (CHIKV), e.g., chikungunya fever, in a subject. In some embodiments, the disclosure relates to compositions and methods used to provide passive immunization against CHIKV infection. In some aspects, the disclosure relates to compositions and methods of alleviating or reducing symptoms related to CHIKV infection in a subject. For example, mRNA compositions described herein can be administered to a subject confirmed as having been infected by CHIKV, so as to prevent the onset of symptoms or alleviate the severity of symptoms related to CHIKV infection. In some cases, the mRNA compositions described herein can be administered to a subject suspected of having been exposed to CHIKV or being infected by CHIKV, or at risk of being exposed to CHIKV, so as to prevent the onset of disease symptoms or to reduce the severity of symptoms.

The mRNA therapeutics of the invention are particularly well-suited for the treatment of chikungunya fever, caused by infection by CHIKV, in a subject. The technology provides for the intracellular delivery of one or more mRNAs encoding an anti-CHIKV antibody, followed by de novo synthesis of functional anti-CHIKV antibody within target cells. The instant invention features the incorporation of modified nucleotides within therapeutic mRNAs to (1) minimize unwanted immune activation (e.g., the innate immune response associated with the in vivo introduction of foreign nucleic acids) and (2) optimize the translation efficiency of mRNA to protein. Exemplary aspects of the invention feature a combination of nucleotide modification to reduce the innate immune response and sequence optimization, in particular, within the open reading frame (ORF) of therapeutic mRNAs encoding anti-CHIKV antibody to enhance protein expression.

In further embodiments, the mRNA therapeutic technology described herein also features delivery of mRNAs encoding the heavy and light chains of an anti-CHIKV antibody via a lipid nanoparticle (LNP) delivery system. The instant disclosure features ionizable lipid-based LNPs, which have improved properties when combined with mRNA encoding the heavy and light chains of anti-CHIKV antibody and administered in vivo, for example, cellular uptake, intracellular transport and/or endosomal release or endosomal escape. LNP formulations described herein also demonstrate reduced immunogenicity associated with the in vivo administration of LNPs.

In certain aspects, the disclosure relates to compositions and delivery formulations comprising a polynucleotide, e.g., a ribonucleic acid (RNA), e.g., a mRNA, encoding a heavy chain of an anti-CHIKV antibody and/or a polynucleotide, e.g., a ribonucleic acid (RNA), e.g., a mRNA, encoding a light chain of an anti-CHIKV antibody, and methods for treating diseases or disorders associated with CHIKV infection, e.g., chikungunya fever, in a human subject in need thereof by administering the same.

The present disclosure provides a pharmaceutical composition comprising lipid nanoparticle encapsulated mRNAs that comprise an open reading frames (ORFs) encoding a heavy chain polypeptide of an anti-CHIKV antibody and a light chain polypeptide of an anti-CHIKV antibody, wherein the composition is suitable for administration to a human subject in need of treatment for CHIKV infection, e.g., a human subject with chikungunya fever.

The present disclosure further provides a pharmaceutical composition comprising: (a) a mRNA that comprises (i) an open reading frame (ORF) encoding a heavy chain polypeptide of an anti-CHIKV antibody, wherein the ORF comprises at least one chemically modified nucleobase, sugar, backbone, or any combination thereof, and (ii) an untranslated region (UTR) comprising a microRNA (miRNA) binding site; (b) a mRNA that comprises (i) an ORF encoding a light chain polypeptide of an anti-CHIKV antibody, wherein the ORF comprises at least one chemically modified nucleobase, sugar, backbone, or any combination thereof, and (ii) an untranslated region (UTR) comprising a microRNA (miRNA) binding site; and (c) a delivery agent, wherein the pharmaceutical composition is suitable for administration to a human subject in need of treatment for a disease or disorder associated with CHIKV infection, e.g., chikungunya fever.

In one aspect, the disclosure features a polynucleotide comprising an mRNA comprising: (i) a 5' UTR; (ii) an open reading frame (ORF) encoding a polypeptide comprising the heavy chain variable region of the heavy chain antibody sequence of SEQ ID NO:1, wherein the ORF comprises a nucleic acid sequence that is at least 80% identical to nucleotides 61-426 of SEQ ID NO:2; (iii) a stop codon; and (iv) a 3' UTR.

In some embodiments of this aspect, the nucleic acid sequence is at least 80% identical to nucleotides 61-1416 of SEQ ID NO:2. In some embodiments, the nucleic acid sequence is at least 80% identical to SEQ ID NO:2. In some embodiments, the nucleic acid sequence is at least 90%, at least 95%, at least 96%, at least 97%, at least 98%, at least 99%, or 100% identical to nucleotides 61-426 of SEQ ID NO:2. In some embodiments, the nucleic acid sequence is at least 90%, at least 95%, at least 96%, at least 97%, at least 98%, at least 99%, or 100% identical to nucleotides 61-1416 of SEQ ID NO:2. In some embodiments, the nucleic acid sequence is at least 90%, at least 95%, at least 96%, at least 97%, at least 98%, at least 99%, or 100% identical to SEQ ID NO:2.

In another aspect, the disclosure features a polynucleotide comprising an mRNA comprising: (i) a 5' UTR; (ii) an open reading frame (ORF) encoding a polypeptide comprising the light chain variable region of the light chain antibody sequence of SEQ ID NO:3, wherein the ORF comprises a nucleic acid sequence that is at least 80% identical to nucleotides 61-384 of SEQ ID NO:4; (iii) a stop codon; and (iv) a 3' UTR.

In some embodiments of this aspect, the nucleic acid sequence is at least 80% identical to nucleotides 61-705 of SEQ ID NO:4. In some embodiments, the nucleic acid sequence is at least 80% identical to SEQ ID NO:4. In some embodiments, the nucleic acid sequence is at least 90%, at least 95%, at least 96%, at least 97%, at least 98%, at least 99%, or 100% identical to nucleotides 61-384 of SEQ ID NO:4. In some embodiments, the nucleic acid sequence is at least 90%, at least 95%, at least 96%, at least 97%, at least 98%, at least 99%, or 100% identical to nucleotides 61-705 of SEQ ID NO:4. In some embodiments, the nucleic acid sequence is at least 90%, at least 95%, at least 96%, at least 97%, at least 98%, at least 99%, or 100% identical to SEQ ID NO:4.

In some embodiments of the above aspects, the mRNA comprises a microRNA (miR) binding site. In some embodiments, the microRNA is expressed in an immune cell of hematopoietic lineage or a cell that expresses TLR7 and/or TLR8 and secretes pro-inflammatory cytokines and/or chemokines. In some embodiments, the microRNA binding site is for a microRNA selected from miR-126, miR-142, miR-144, miR-146, miR-150, miR-155, miR-16, miR-21, miR-223, miR-24, miR-27, miR-26a, or any combination thereof. In some embodiments, the microRNA binding site is for a microRNA selected from miR126-3p, miR-142-3p, miR-142-5p, miR-155, or any combination thereof. In some embodiments, the microRNA binding site is a miR-142-3p binding site. In some embodiments, the microRNA binding site is located in the 3' UTR of the mRNA.

In some embodiments of the above aspects, the 5' UTR comprises a nucleic acid sequence at least 90%, at least 95%, at least 96%, at least 97%, at least 98%, at least 99%, or 100% identical to SEQ ID NO:13. In some embodiments of the above aspects, the 3' UTR comprises a nucleic acid sequence at least 90%, at least 95%, at least 96%, at least 97%, at least 98%, at least 99%, or 100% identical to SEQ ID NO:14.

In some embodiments of the above aspects, the mRNA comprises a 5' terminal cap. In some embodiments, the 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments of the above aspects, the mRNA comprises a poly-A region. In some embodiments, the poly-A region is at least about 10, at least about 20, at least about 30, at least about 40, at least about 50, at least about 60, at least about 70, at least about 80, at least about 90 nucleotides in length, or at least about 100 nucleotides in length. In some embodiments, the poly-A region is about 10 to about 200, about 20 to about 180, about 50 to about 160, about 70 to about 140, or about 80 to about 120 nucleotides in length.

In some embodiments of the above aspects, the mRNA comprises at least one chemically modified nucleobase, sugar, backbone, or any combination thereof. In some embodiments, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof. In some embodiments, at least about 25%, at least about 30%, at least about 40%, at least about 50%, at least about 60%, at least about 70%, at least about 80%, at least about 90%, at least about 95%, at least about 99%, or 100% of the uracils are N1-methylpseudouracils.

In some embodiments, the mRNA comprises the nucleic acid sequence set forth in SEQ ID NO:5. In some embodiments, the mRNA comprises the nucleic acid sequence set forth in SEQ ID NO:6.

In some embodiments, the mRNA comprises the nucleic acid sequence set forth in SEQ ID NO:5, a 5' terminal cap comprising Cap1, and a poly-A region 100 nucleotides in length. In some embodiments, the mRNA comprises the nucleic acid sequence set forth in SEQ ID NO:6, a 5' terminal cap comprising Cap1, and a poly-A region 100 nucleotides in length. In some embodiments, all of the uracils of the polynucleotide are N1-methylpseudouracils.

In another aspect, the disclosure provides a pharmaceutical composition comprising a polynucleotide described herein and a delivery agent.

In another aspect, the disclosure features a pharmaceutical composition comprising: a first polynucleotide comprising a first mRNA comprising (i) a first 5' UTR, (ii) a first open reading frame (ORF) encoding a first polypeptide comprising the heavy chain variable region of the heavy chain antibody sequence of SEQ ID NO:1, wherein the first ORF comprises a first nucleic acid sequence that is at least 80% identical to nucleotides 61-426 of SEQ ID NO:2, (iii) a first stop codon, and (iv) a first 3' UTR; a second polynucleotide comprising a second mRNA comprising (i) a second 5' UTR, (ii) a second ORF encoding a second polypeptide comprising the light chain variable region of the light chain antibody sequence of SEQ ID NO:3, wherein the second ORF comprises a second nucleic acid sequence that is at least 80% identical to nucleotides 61-384 of SEQ ID NO:4, (iii) a second stop codon, and (iv) a second 3' UTR; and a delivery agent, wherein the first polypeptide when paired with the second polypeptide forms an anti-Chikungunya virus antibody or an anti-Chikungunya virus antibody fragment.

In some embodiments of the above aspect, the first nucleic acid sequence is at least 80% identical to nucleotides 61-1416 of SEQ ID NO:2, and the second nucleic acid sequence is at least 80% identical to nucleotides 61-705 of SEQ ID NO:4. In some embodiments, the first nucleic acid sequence is at least 80% identical to SEQ ID NO:2, and the second nucleic acid sequence is at least 80% identical to SEQ ID NO:4. In some embodiments, the first nucleic acid sequence is at least 90%, at least 95%, at least 96%, at least 97%, at least 98%, at least 99%, or 100% identical to nucleotides 61-426 of SEQ ID NO:2, and the second nucleic acid sequence is at least 90%, at least 95%, at least 96%, at least 97%, at least 98%, at least 99%, or 100% identical to nucleotides 61-384 of SEQ ID NO:4. In some embodiments, the first nucleic acid sequence is at least 90%, at least 95%, at least 96%, at least 97%, at least 98%, at least 99%, or 100% identical to nucleotides 61-1416 of SEQ ID NO:2, and the second nucleic acid sequence is at least 90%, at least 95%, at least 96%, at least 97%, at least 98%, at least 99%, or 100% identical to nucleotides 61-705 of SEQ ID NO:4. In some embodiments, the first nucleic acid sequence is at least 90%, at least 95%, at least 96%, at least 97%, at least 98%, at least 99%, or 100% identical to SEQ ID NO:2, and the second nucleic acid sequence is at least 90%, at least 95%, at least 96%, at least 97%, at least 98%, at least 99%, or 100% identical to SEQ ID NO:4.

In some embodiments of the above aspect, the first 5' UTR and the second 5' UTR each comprise a nucleic acid sequence at least 90%, at least 95%, at least 96%, at least 97%, at least 98%, at least 99%, or 100% identical to SEQ ID NO:13. In some embodiments, the first 3' UTR and the second 3' UTR each comprise a nucleic acid sequence at least 90%, at least 95%, at least 96%, at least 97%, at least 98%, at least 99%, or 100% identical to SEQ ID NO:14.

In some embodiments of the above aspect, the first mRNA and the second mRNA each comprise a 5' terminal cap. In some embodiments, each 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments of the above aspect, the first mRNA and the second mRNA each comprise a poly-A region. In some embodiments, each poly-A region is at least about 10, at least about 20, at least about 30, at least about 40, at least about 50, at least about 60, at least about 70, at least about 80, at least about 90 nucleotides in length, or at least about 100 nucleotides in length. In some embodiments, each poly-A region is about 10 to about 200, about 20 to about 180, about 50 to about 160, about 70 to about 140, or about 80 to about 120 nucleotides in length.

In some embodiments of the above aspect, the first mRNA and the second mRNA each comprise at least one chemically modified nucleobase, sugar, backbone, or any combination thereof. In some embodiments, the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof. In some embodiments, at least about 25%, at least about 30%, at least about 40%, at least about 50%, at least about 60%, at least about 70%, at least about 80%, at least about 90%, at least about 95%, at least about 99%, or 100% of the uracils are N1-methylpseudouracils.

In some embodiments of the above aspect, the first mRNA comprises the nucleic acid sequence set forth in SEQ ID NO:5, and the second mRNA comprises the nucleic acid sequence set forth in SEQ ID NO:6. In some embodiments, the first mRNA comprises the nucleic acid sequence set forth in SEQ ID NO:5, a 5' terminal cap comprising Cap1, and a poly-A region 100 nucleotides in length, and the second mRNA comprises the nucleic acid sequence set forth in SEQ ID NO:6, a 5' terminal cap comprising Cap1, and a poly-A region 100 nucleotides in length. In some embodiments, all of the uracils of the first polynucleotide and the second polynucleotide are N1-methylpseudouracils.

In some embodiments of the above aspect, the delivery agent comprises a lipid nanoparticle comprising:

(i) Compound II, (ii) Cholesterol, and (iii) PEG-DMG or Compound I;

(i) Compound VI, (ii) Cholesterol, and (iii) PEG-DMG or Compound I;

(i) Compound II, (ii) DSPC or DOPE, (iii) Cholesterol, and (iv) PEG-DMG or Compound I;

(i) Compound VI, (ii) DSPC or DOPE, (iii) Cholesterol, and (iv) PEG-DMG or Compound I;

(i) Compound II, (ii) Cholesterol, and (iii) Compound I;

(i) Compound II, (ii) DSPC or DOPE, (iii) Cholesterol, and (iv) Compound I; or (i) Compound II, (ii) DSPC, (iii) Cholesterol, and (iv) Compound I.

In another aspect, the disclosure features a pharmaceutical composition comprising a first mRNA comprising a first open reading frame (ORF) encoding a first polypeptide comprising a heavy chain variable region of an anti-chikungunya virus antibody and a second mRNA comprising a second ORF encoding a second polypeptide comprising a light chain variable region of the anti-chikungunya virus antibody, wherein the first polypeptide and the second polypeptide pair to form the anti-chikungunya virus antibody, and wherein the pharmaceutical composition when administered to a human subject in need thereof as a single dose administration is sufficient to:

(i) protect the human subject from chikungunya virus infection, after exposure to a chikungunya virus, for at least 24 hours, 48 hours, 72 hours, 96 hours, 168 hours, 336 hours, or 720 hours after the single dose administration;

(ii) protect the human subject from onset of chikungunya fever, after exposure to a chikungunya virus, for at least 24 hours, 48 hours, 72 hours, 96 hours, 168 hours, 336 hours, or 720 hours after the single dose administration; and/or (iii) provide systemic production of the anti-chikungunya virus antibody in the human subject at a level of at least 5 μg/ml, 10 μg/ml, 15 μg/ml, 20 μg/ml, 25 μg/ml, or 30 μg/ml for at least 24 hours, 48 hours, 72 hours, 96 hours, 168 hours, 336 hours, or 720 hours after the single dose administration.

In some embodiments of the above aspect, the single dose administration is an intravenous administration. In some embodiments of the above aspect, the single dose administration is a subcutaneous administration.

In some embodiments of the above aspect, the pharmaceutical composition further comprises a delivery agent. In some embodiments, the delivery agent comprises a lipid nanoparticle comprising:

(i) Compound II, (ii) Cholesterol, and (iii) PEG-DMG or Compound I;

(i) Compound VI, (ii) Cholesterol, and (iii) PEG-DMG or Compound I;

(i) Compound II, (ii) DSPC or DOPE, (iii) Cholesterol, and (iv) PEG-DMG or Compound I;

(i) Compound VI, (ii) DSPC or DOPE, (iii) Cholesterol, and (iv) PEG-DMG or Compound I;

(i) Compound II, (ii) Cholesterol, and (iii) Compound I;

(i) Compound II, (ii) DSPC or DOPE, (iii) Cholesterol, and (iv) Compound I; or (i) Compound II, (ii) DSPC, (iii) Cholesterol, and (iv) Compound I.

In some embodiments of the above aspect, the first polypeptide comprises the heavy chain variable region of the heavy chain antibody sequence of SEQ ID NO:1, and the second polypeptide comprises the light chain variable region of the light chain antibody sequence of SEQ ID NO:3. In some embodiments of the above aspect, the first polypeptide comprises the heavy chain constant region of the heavy chain antibody sequence of SEQ ID NO:1, and the second polypeptide comprises the light chain constant region of the light chain antibody sequence of SEQ ID NO:3.

In some embodiments of the above aspect, the first mRNA and the second mRNA each comprise a microRNA (miR) binding site. In some embodiments, the microRNA is expressed in an immune cell of hematopoietic lineage or a cell that expresses TLR7 and/or TLR8 and secretes pro-inflammatory cytokines and/or chemokines. In some embodiments, the microRNA binding site is for a microRNA selected from the group consisting of miR-126, miR-142, miR-144, miR-146, miR-150, miR-155, miR-16, miR-21, miR-223, miR-24, miR-27, miR-26a, or any combination thereof. In some embodiments, the microRNA binding site is for a microRNA selected from the group consisting of miR126-3p, miR-142-3p, miR-142-5p, miR-155, or any combination thereof. In some embodiments, the microRNA binding site is a miR-142-3p binding site. In some embodiments, the microRNA binding site is located in the 3' UTR of the mRNA.

In some embodiments of the above aspect, the first mRNA and the second mRNA each comprise a 5' terminal cap. In some embodiments, each 5' terminal cap comprises a Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

In some embodiments of the above aspect, the first mRNA and the second mRNA each comprise a poly-A region. In some embodiments, each poly-A region is at least about 10, at least about 20, at least about 30, at least about 40, at least about 50, at least about 60, at least about 70, at least about 80, at least about 90 nucleotides in length, or at least about 100 nucleotides in length. In some embodiments, each poly-A region is about 10 to about 200, about 20 to about 180, about 50 to about 160, about 70 to about 140, or about 80 to about 120 nucleotides in length.

In some embodiments of the above aspect, the first mRNA and the second mRNA each comprise at least one chemically modified nucleobase, sugar, backbone, or any combination thereof. In some embodiments, the at least one chemically modified nucleobase is selected from the group consisting of pseudouracil (ψ), N-methylpseudouracil (m1ψ), 1-ethylpseudouracil, 2-thiouracil (s2U), 4'-thiouracil, 5-methylcytosine, 5-methyluracil, 5-methoxyuracil, and any combination thereof. In some embodiments, at least about 25%, at least about 30%, at least about 40%, at least about 50%, at least about 60%, at least about 70%, at least about 80%, at least about 90%, at least about 95%, at least about 99%, or 100% of the uracils are N1-methylpseudouracils.

In some embodiments of the above aspect, the human subject has a chikungunya virus infection.

In another aspect, the disclosure features a method of treating a chikungunya virus infection in a human subject that has been infected with a chikungunya virus, comprising administering to the human subject an effective amount of a pharmaceutical composition disclosed herein or a polynucleotide disclosed herein.

In another aspect, the disclosure features a method of reducing the likelihood of contracting a chikungunya virus infection in a human subject in need thereof, comprising administering to the human subject an effective amount of a pharmaceutical composition disclosed herein or a polynucleotide disclosed herein.

In another aspect, the disclosure features a method of preventing a chikungunya virus infection in a human subject in need thereof, comprising administering to the human subject an effective amount of a pharmaceutical composition disclosed herein or a polynucleotide disclosed herein.

In another aspect, the disclosure features a method of expressing an anti-chikungunya virus antibody in a human subject in need thereof, comprising administering to the human subject an effective amount of a pharmaceutical composition disclosed herein or a polynucleotide disclosed herein.

In another aspect, the disclosure features a method of reducing chikungunya virus levels in a human subject in need thereof, comprising administering to the human subject an effective amount of a pharmaceutical composition disclosed herein or a polynucleotide disclosed herein.

In some embodiments of the above aspects, (i) the human subject is protected from chikungunya virus infection, after exposure to the chikungunya virus, for at least 24 hours, 48 hours, 72 hours, 96 hours, 168 hours, 336 hours, or 720 hours after a single dose administration; (ii) the human subject is protected from onset of chikungunya fever, after exposure to the chikungunya virus, for at least 24 hours, 48 hours, 72 hours, 96 hours, 168 hours, 336 hours, or 720 hours after a single dose administration; and/or (iii) systemic production of the anti-chikungunya virus antibody in the human subject is at a level of at least 5 μg/ml, 10 μg/ml, 15 μg/ml, 20 μg/ml, 25 μg/ml, or 30 μg/ml for at least 24 hours, 48 hours, 72 hours, 96 hours, 168 hours, 336 hours, or 720 hours after a single dose administration.

In some embodiments of the above aspects, the pharmaceutical composition or polynucleotide is administered to the human subject multiple times at a frequency of about once a week, about once every two weeks, or about once a month. In some embodiments of the above aspects, the pharmaceutical composition or polynucleotide is administered intravenously. In some embodiments of the above aspects, the pharmaceutical composition or polynucleotide is administered subcutaneously.

In another aspect, the disclosure features a pharmaceutical composition comprising: (i) a first polynucleotide comprising a first nucleic acid sequence encoding a first polypeptide comprising a heavy chain variable region comprising the ChikV24 heavy chain CDR1, CDR2, and CDR3 sequences (amino acids 46-53 of SEQ ID NO:1, amino acids 71-78 of SEQ ID NO:1, and amino acids 117-131 of SEQ ID NO:1, respectively); and (ii) a second polynucleotide comprising a second nucleic acid sequence encoding a second polypeptide comprising a light chain variable region comprising the ChikV24 light chain CDR1, CDR2, and CDR3 sequences (amino acids 47-53 of SEQ ID NO:3, amino acids 71-73 of SEQ ID NO:3, and amino acids 110-118 of SEQ ID NO:3, respectively), wherein the first polypeptide when paired with the second polypeptide forms an anti-chikungunya virus antibody or an anti-chikungunya virus antibody fragment. The antibody or antibody fragment may comprise the ChikV24 light and heavy chain variable sequences (amino acids 21-128 of SEQ ID NO:3 and amino acids 21-142 of SEQ ID NO:1, respectively). The antibody may be an IgG. The pharmaceutical composition may comprise a delivery vehicle. The first polynucleotide and the second polynucleotide may each be DNA sequences, or may each be mRNA sequences. The first polynucleotide and the second polynucleotide may each comprise non-natural, modified nucleotides. The first polynucleotide (e.g., an mRNA) and the second polynucleotide (e.g., an mRNA) may each comprise a heterologous 5' UTR sequence. The first polynucleotide (e.g., an mRNA) and the second polynucleotide (e.g., an mRNA) may each comprise a heterologous 3' UTR sequence. The first polynucleotide (e.g., an mRNA) and the second polynucleotide (e.g., an mRNA) may each comprise a heterologous 5' UTR sequence and a heterologous 3' UTR sequence. A "heterologous" UTR sequence is a UTR sequence other than a naturally occurring UTR sequence present in a naturally occurring mRNA that encodes an antibody heavy or light chain comprising a ChikV24 variable region. Also provided is a method of treating a human subject infected with chikungunya virus, or reducing the likelihood of infection of a subject at risk of contracting chikungunya virus, comprising administering to the human subject an effective amount of the pharmaceutical composition of this paragraph.

Each of the limitations of the disclosure can encompass various embodiments of the disclosure. It is, therefore, anticipated that each of the limitations of the disclosure involving any one element or combinations of elements can be included in each aspect of the disclosure. This disclosure is not limited in its application to the details of construction and the arrangement of components set forth in the following description or illustrated in the drawings. The disclosure is capable of other embodiments and of being practiced or of being carried out in various ways.

DETAILED DESCRIPTION

Figure 1A:
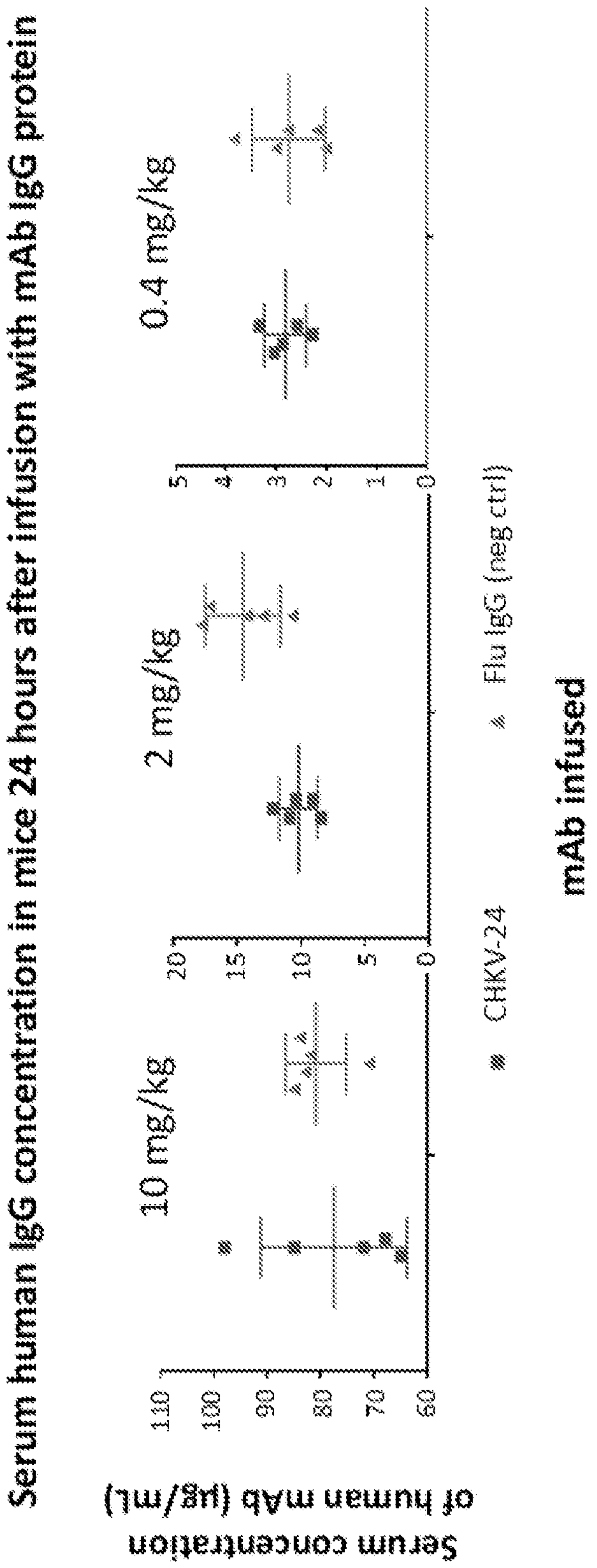
FIG. 1A is a graph showing the serum concentration levels of human ChikV24 antibody in AG129 mice 24 hours after intravenous administration of 10 mg/kg, 2 mg/kg, or 0.4 mg/kg of the recombinant ChikV24 antibody.

Described herein are compositions for the prevention or treatment of diseases or symptoms associated with chikungunya virus (CHIKV) infection, e.g., chikungunya fever. RNA therapeutics are well-suited for the prevention or treatment of chikungunya fever, as the technology provides for the intracellular delivery of mRNAs encoding the heavy and light chain polypeptides of an anti-CHIKV antibody, followed by de novo synthesis of functional anti-CHIKV antibody within target cells. After delivery of mRNA to the target cells, the anti-CHIKV antibody proteins are expressed by the cells' own translational machinery, and hence, fully functional antibody can bind to and neutralize the chikungunya virus, thereby preventing further viral infection.

As described herein, the disclosure provides a ribonucleic acid (RNA) polynucleotide having an open reading frame encoding a heavy chain polypeptide of an antibody, or a portion thereof (e.g., a heavy chain polypeptide variable region), having specificity for a chikungunya virus protein and a pharmaceutically acceptable carrier or excipient. In some embodiments, the disclosure provides an RNA polynucleotide having an open reading frame encoding a light chain polypeptide of an antibody, or a portion thereof (e.g., a light chain polypeptide variable region), having specificity for a chikungunya virus protein and a pharmaceutically acceptable carrier or excipient.

Described herein are compositions (including pharmaceutical compositions) and methods for the design, preparation, manufacture and/or formulation of antibodies with specificity for CHIKV, wherein at least one component of the antibody is encoded by a polynucleotide. As such the present invention is directed, in part, to polynucleotides, specifically IVT polynucleotides, chimeric polynucleotides and/or circular polynucleotides encoding one or more anti-CHIKV antibodies and/or components thereof.

The methods of the present invention are and can be used to engineer novel polynucleotides for the in vivo production of antibodies in such a manner as to provide improvements over standard antibody technology. In some cases, the polynucleotides provided herein encode antibodies, or portions thereof, that have been designed to produce a therapeutic outcome and optionally improve one or more of the stability and/or clearance in tissues, receptor uptake and/or kinetics, cellular access, engagement with translational machinery, mRNA half-life, translation efficiency, protein production capacity, secretion efficiency (when applicable), accessibility to circulation, protein half-life and/or modulation of a cell's status, antibody target affinity and/or specificity, reduction of antibody cross reactivity, increase of antibody purity, increase or alteration of antibody effector function and/or antibody activity.

1. Antibodies Specific for Chikungunya Virus

The polynucleotides, constructs, and/or compositions of the present disclosure are useful for producing antibodies that bind to a chikungunya virus (CHIKV), e.g., to a CHIKV antigenic polypeptide.

In some embodiments the compositions and methods are useful for the prevention, treatment, or management of CHIKV infection, e.g., chikungunya fever. Some embodiments of the present disclosure provide RNA polynucleotides, e.g., mRNA, encoding an anti-CHIKV antibody, fragment, or variant thereof, which may be used to treat or prevent chikungunya fever. In some embodiments, one or more RNA polynucleotides have open reading frames (ORFs) encoding at least one anti-CHIKV antibody that binds specifically to a CHIKV antigenic polypeptide. In some embodiments, the RNA polynucleotides encode two or more anti-CHIKV antibodies. In some embodiments, two or more RNA polynucleotides, e.g., two or more mRNAs, encode portions or fragments of an anti-CHIKV antibody. For example, one mRNA polynucleotide can have an ORF encoding a heavy chain of the anti-CHIKV antibody, and one mRNA polynucleotide can have an ORF encoding a light chain of the anti-CHIKV antibody, such that the two mRNAs in combination express the heavy and light chain polypeptides that together form the antibody, e.g., in a cell. In some embodiments, the mRNA polynucleotides described herein encode an antibody that neutralizes CHIKV.

An antibody is an immunoglobulin molecule capable of specific binding to a target through at least one antigen recognition site, located in the variable region of the immunoglobulin molecule. Most antibodies comprise two heavy chains and two light chains. There are several different types of antibody heavy chains, and several different kinds of antibodies, which are grouped into different isotypes based on which heavy chain they possess. Five different antibody isotypes (IgA, IgD, IgE, IgG and IgM) are known in mammals and trigger a different immune response for each different type of foreign object, epitope or microbe they encounter. The antibodies described herein can be derived from murine, rat, human, or any other origin. The majority of antibodies are generated using recombinant or cloning strategies and product heterogeneity is common to monoclonal antibody and other recombinant biological production. Such heterogeneity is typically introduced either upstream during expression or downstream during manufacturing. Recombinant antibody engineering involves the use of viruses or yeast to create antibodies, rather than mice which are used in cloning strategies. All of these however, suffer from drawbacks associated with the systems used for generation including degree of purity, speed of development, cross reactivity, low affinity and variable specificity.

As used herein, the term "antibody" encompasses not only intact (i.e., full-length) antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies), single domain antibodies such as heavy-chain antibodies, and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody's amino acid sequence of the constant domain of its heavy chains (if applicable), immunoglobulins can be assigned to different classes. There are five major classes of naturally-occurring immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An antibody described herein may comprise a heavy chain variable region ($V_H$), a light chain variable region ($V_L$), or a combination thereof. Optionally, the antibody may further comprise an antibody constant region or a portion thereof (e.g., $C_H1$, $C_H2$, $C_H3$, or a combination thereof). The heavy chain constant region can be of any suitable class as described herein and of any suitable origin, e.g., human, mouse, rat, or rabbit. In one specific example, the heavy chain constant region is derived from a human IgG (a gamma heavy chain). The light chain constant region can be a kappa chain or a lambda chain from a suitable origin. Antibody heavy and light chain constant regions are well known in the art, e.g., those provided in the IMGT database (www.imgt.org) or at www.vbase2.org/vbstat.php., both of which are incorporated by reference herein.

In some embodiments, the antibodies described herein specifically bind to the corresponding target antigen or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen (e.g., a viral antigen) or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen.

In some embodiments, the mRNA polynucleotides described herein encode an antibody that binds to CHIKV. The mRNAs of the present disclosure can encode one or more polypeptides that form an antibody, or an antigen-binding portion thereof, that specifically binds to and neutralizes CHIKV. In one exemplary embodiment, mRNA polynucleotides described herein encode a heavy chain polypeptide of an antibody, a light chain polypeptide of an antibody, or heavy and light chain polypeptides of an antibody. In exemplary aspects, polynucleotides of the disclosure, e.g., polynucleotides encoding an anti-CHIKV antibody or portion thereof, may include at least one chemical modification.

Chikungunya virus is a positive-sense single-stranded RNA alphavirus that is approximately 60-70 nm in diameter. The virion consists of an envelope and a nucleocapsid. The chikungunya virus genome is approximately 11.7 to 11.8 kb and encodes four nonstructural proteins (the nsP1, nsP2, nsP3 and nsP4 proteins), and five structural proteins (the capsid (C) protein, three envelope proteins (E1), (E2), and (E3), and the 6K protein). The structural proteins are translated from a subgenomic 26S mRNA as a single polyprotein. This polyprotein is processed into the five structural proteins. The four nonstructural proteins are also processed from a single polyprotein. Several chikungunya virus strains have been isolated and sequenced, and can be found at, e.g., NCBI GenBank Accession Nos: NC_004162.2, MF580946, AF369024, EU037962, KX702402, JF274082.1, KY038947.2, KY038946.1, and DQ443544.1.

In some embodiments, the anti-CHIKV antibodies described herein can bind to an antigenic polypeptide of CHIKV. In some embodiments, the anti-CHIKV antibodies described herein can bind to an antigenic polypeptide of any CHIKV strain. In some embodiments, the anti-CHIKV antibody binds specifically to an antigenic polypeptide which is a CHIKV structural protein or an antigenic fragment thereof. For example, a CHIKV structural protein may be an envelope protein (E), a 6K protein, or a capsid (C) protein. In some embodiments, the CHIKV structural protein is an envelope protein selected from E1, E2, and E3. In some embodiments, the CHIKV structural protein is E1 or E2. In some embodiments, the CHIKV structural protein is a capsid protein. In some embodiments, the antigenic polypeptide is a fragment or epitope of a CHIKV structural protein.

In some embodiments, an antibody described herein binds to an epitope on surface of the CHIKV capsid and/or envelope. In some embodiments, an antibody described herein binds to an epitope on the E2 protein of CHIKV. In some embodiments, the antibody binds to E2-A162, or an epitope formed by residues E2-G95, E2-A162, E2-A164, E2-E165, E2-E166 and/or E2-I167, or any combination thereof. In some embodiments, the antibody binds to an epitope formed by residues E2-Y69, E2-F84, E2-V113, E2-G114, E2-T116, and/or E2-D117, or any combination thereof. In some embodiments, the epitope comprises E2-G95.

In some embodiments, an antibody described herein binds to at least one of: Subunit I-E2-E24 and Subunit I-E2-I121 and at least one of: Subunit II-E2-G55, Subunit II-E2-W64, Subunit II-E2-K66, Subunit II-E2-R80. In some embodiments, the antibody binds to Subunit I-E2-E24 and Subunit I-E2-I121 and at least one of: Subunit II-E2-G55, Subunit II-E2-W64, Subunit II-E2-K66, Subunit II-E2-R80. In some embodiments, the antibody binds to at least two of Subunit II-E2-G55, Subunit II-E2-W64, Subunit II-E2-K66, Subunit II-E2-R80. In some embodiments, the antibody binds to at least three of Subunit II-E2-G55, Subunit II-E2-W64, Subunit II-E2-K66, Subunit II-E2-R80. In some embodiments, the antibody binds to at least three of Subunit II-E2-G55, Subunit II-E2-W64, Subunit II-E2-K66, and Subunit II-E2-R80. In some embodiments, the antibody binds to Subunit II-E2-G55, Subunit II-E2-W64, Subunit II-E2-K66, and Subunit II-E2-R80.

In some embodiments, the antibody binds to the membrane distal region of a CHIKV E1/E2 trimer. In some embodiments, the antibody binds to the exterior face of the E1/E2 heterocomplex. The exterior face refers to the portion of the E1/E2 heterocomplex that is exposed when the E1/E2 hetero-protein is in its native form on the virion surface, such as in its trimeric form.

In some embodiments, the antibodies, or antigen binding fragments thereof, have a heavy chain polypeptide having an amino acid sequence sharing at least 80%, 81%, 82%, 83%, 84%, 85%, 86%, 87%, 88%, 89%, 90%, 91%, 92%, 93%, 94%, 95%, 96%, 97% 98%, or 99% identity with SEQ ID NO: 1. In some embodiments, the antibodies, or antigen binding fragments thereof, have a heavy chain polypeptide having an amino acid sequence that is identical to SEQ ID NO: 1. In some embodiments, the antibodies or antigen binding fragments thereof, have a heavy chain polypeptide having an amino acid sequence differing by up to 20 amino acids from SEQ ID NO: 1, e.g., differing by 1, 2, 3, 4, 5, 6, 7, 8, 9, 10, 11, 12, 13, 14, 15, 16, 17, 18, 19, or 20 amino acids from SEQ ID NO: 1.

In some embodiments, the antibodies, or antigen binding fragments thereof, have a heavy chain variable region having an amino acid sequence sharing at least 80%, 81%, 82%, 83%, 84%, 85%, 86%, 87%, 88%, 89%, 90%, 91%, 92%, 93%, 94%, 95%, 96%, 97% 98%, or 99% identity with amino acids 21-142 of SEQ ID NO: 1. In some embodiments, the antibodies, or antigen binding fragments thereof, have a heavy chain variable region having an amino acid sequence that is identical to amino acids 21-142 of SEQ ID NO: 1.

In some embodiments, the antibodies, or antigen binding fragments thereof, have a heavy chain constant region having an amino acid sequence sharing at least 80%, 81%, 82%, 83%, 84%, 85%, 86%, 87%, 88%, 89%, 90%, 91%, 92%, 93%, 94%, 95%, 96%, 97% 98%, or 99% identity with amino acids 143-472 of SEQ ID NO: 1. In some embodiments, the antibodies, or antigen binding fragments thereof, have a heavy chain constant region having an amino acid sequence that is identical to amino acids 143-472 of SEQ ID NO: 1.

In some embodiments, the antibodies, or antigen binding fragments thereof, have a signal sequence having an amino acid sequence sharing at least 80%, 81%, 82%, 83%, 84%, 85%, 86%, 87%, 88%, 89%, 90%, 91%, 92%, 93%, 94%, 95%, 96%, 97% 98%, or 99% identity with amino acids 1-20 of SEQ ID NO: 1. In some embodiments, the antibodies, or antigen binding fragments thereof, have a signal sequence having an amino acid sequence that is identical to amino acids 1-20 of SEQ ID NO: 1.

In some embodiments, the antibodies, or antigen binding fragments thereof, have a light chain polypeptide having an amino acid sequence sharing at least 80%, 81%, 82%, 83%, 84%, 85%, 86%, 87%, 88%, 89%, 90%, 91%, 92%, 93%, 94%, 95%, 96%, 97% 98%, or 99% identity with SEQ ID NO: 3. In some embodiments, the antibodies, or antigen binding fragments thereof, have a light chain polypeptide having an amino acid sequence that is identical to SEQ ID NO: 3. In some embodiments, the antibodies or antigen binding fragments thereof, have a light chain polypeptide having an amino acid sequence differing by up to 20 amino acids from SEQ ID NO: 3, e.g., differing by 1, 2, 3, 4, 5, 6, 7, 8, 9, 10, 11, 12, 13, 14, 15, 16, 17, 18, 19, or 20 amino acids from SEQ ID NO: 3.

In some embodiments, the antibodies, or antigen binding fragments thereof, have a light chain variable region having an amino acid sequence sharing at least 80%, 81%, 82%, 83%, 84%, 85%, 86%, 87%, 88%, 89%, 90%, 91%, 92%, 93%, 94%, 95%, 96%, 97% 98%, or 99% identity with amino acids 21-128 of SEQ ID NO: 3. In some embodiments, the antibodies, or antigen binding fragments thereof, have a light chain variable region having an amino acid sequence that is identical to amino acids 21-128 of SEQ ID NO: 3.

In some embodiments, the antibodies, or antigen binding fragments thereof, have a light chain constant region having an amino acid sequence sharing at least 80%, 81%, 82%, 83%, 84%, 85%, 86%, 87%, 88%, 89%, 90%, 91%, 92%, 93%, 94%, 95%, 96%, 97% 98%, or 99% identity with amino acids 129-235 of SEQ ID NO: 3. In some embodiments, the antibodies, or antigen binding fragments thereof, have a light chain constant region having an amino acid sequence that is identical to amino acids 129-235 of SEQ ID NO: 3.

In some embodiments, the antibodies, or antigen binding fragments thereof, have a signal sequence having an amino acid sequence sharing at least 80%, 81%, 82%, 83%, 84%, 85%, 86%, 87%, 88%, 89%, 90%, 91%, 92%, 93%, 94%, 95%, 96%, 97% 98%, or 99% identity with amino acids 1-20 of SEQ ID NO: 3. In some embodiments, the antibodies, or antigen binding fragments thereof, have a signal sequence having an amino acid sequence that is identical to amino acids 1-20 of SEQ ID NO: 3.

The mRNA polynucleotides described herein may be designed to encode known antibodies, or antigen-binding fragments, such as Fab fragments, that bind to CHIKV, e.g., as described in Porta et al., 2016, J. Virol. 90(3): 1169-1177. In other embodiments, the mRNA polynucleotides encode variants of known antibodies, or antigen-binding fragments, such as Fab fragments, that bind to CHIKV.

In some examples, the antibody, or antigen binding portion thereof, binds the same chikungunya virus epitope as an antibody, or antigen-binding portion thereof, known in the art and/or exemplified herein and/or competes against such an antibody from binding to the antigen. Such an antibody may comprise the same heavy chain CDRs as those known in the art and/or exemplified herein. An antibody having the same CDR (e.g., CDR3) as a reference antibody, or antigen-binding portion thereof, means that the two antibodies have the same amino acid sequence in that CDR region as determined by the same methodology (e.g., the Kabat definition, the Chothia definition, the AbM definition, or the contact definition).

Alternatively, an antibody, or antigen-binding portion thereof, described herein may comprise up to 5 (e.g., 4, 3, 2, or 1) amino acid residue variations in one or more of the CDR regions of one of the antibodies, or antigen-binding portions thereof, known in the art and/or exemplified herein and binds the same epitope of antigen with substantially similar affinity (e.g., having a KD value in the same order). In one example, the amino acid residue variations are conservative amino acid residue substitutions. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

In some embodiments, the mRNA polynucleotides described herein encode one or more antibodies, or combinations of antibodies, selected from the group consisting of IgA, IgG, IgM, IgE, and IgD, that can bind specifically to CHIKV.

In some embodiments, a variable domain of the antibodies described herein comprises three complementarity determining regions (CDRs), each of which is flanked by a framework region (FW). For example, a VH domain may comprise a set of three heavy chain CDRs, HCDR1, HCDR2, and HCDR3. A VL domain may comprise a set of three light chain CDRs, LCDR1, LCDR2, and LCDR3. A set of HCDRs can be provided in a VH domain that is used in combination with a VL domain. A VH domain may be provided with a set of HCDRs, and if such a VH domain is paired with a VL domain, then the VL domain may be provided with a set of LCDRs disclosed herein.

In some embodiments, an antibody as described herein has a suitable binding affinity for the target antigen or antigenic epitopes thereof, e.g., an antigenic polypeptide or epitope of CHIKV. As used herein, "binding affinity" refers to the apparent association constant or KA. The KA is the reciprocal of the dissociation constant (KD). The antibody described herein may have a binding affinity (KD) of at least 10−5, 10−6, 10−7, 10−8, 10−9, 10−10 M, or lower for the target antigen or antigenic epitope. An increased binding affinity corresponds to a decreased KD. Higher affinity binding of an antibody for a first antigen relative to a second antigen can be indicated by a higher KA (or a smaller numerical value KD) for binding the first antigen than the KA (or numerical value KD) for binding the second antigen. In such cases, the antibody has specificity for the first antigen (e.g., a first protein in a first conformation or mimic thereof) relative to the second antigen (e.g., the same first protein in a second conformation or mimic thereof; or a second protein).

For example, in some embodiments, the chikungunya virus antibodies described herein have a higher binding affinity (a higher KA or smaller KD) to a first chikungunya virus strain or as compared to the binding affinity to a second chikungunya virus strain. Differences in binding affinity (e.g., for specificity or other comparisons) can be at least 1.5, 2, 3, 4, 5, 10, 15, 20, 37.5, 50, 70, 80, 91, 100, 500, 1000, 10,000 or 105 fold. In some embodiments, any of the anti-chikungunya virus antibodies may be further affinity matured to increase the binding affinity of the antibody to the target antigen or antigenic epitope thereof.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

[Bound]=[Free]/(Kd+[Free])

It is not always necessary to make an exact determination of KA or KD though, since sometimes it is sufficient to obtain a quantitative measurement of affinity, e.g., determined using a method such as ELISA or FACS analysis, is proportional to KA or KD, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

In some embodiments, the antibody described herein is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity and/or affinity. In some instances, one or more Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence (e.g., a germline sequence or a consensus sequence). The humanized antibody optimally may also comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, and/or six) which are altered with respect to the original antibody (termed one or more CDRs "derived from" one or more CDRs from the original antibody). Humanized antibodies may also involve optimized antibodies derived from affinity maturation.

In another example, the antibody as described herein is a chimeric antibody, which can include a heavy constant region and optionally a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In yet another example, the antibody described herein can be a single-domain antibody, which interacts with the target antigen via only one single variable domain such as a single heavy chain domain (as opposed to traditional antibodies, which interact with the target antigen via heavy chain and light chain variable domains). A single domain construct comprises one or two polynucleotides encoding a single monomeric variable antibody domain. In some cases, single domain antibodies comprise one variable domain (VH) of a heavy-chain antibody, and can be devoid of a light chain. In additional to a variable region (for example, a VH), a single-domain antibody may further comprise a constant region, for example, $C_H1$, $C_H2$, $C_H3$, $C_H4$, or a combination thereof.

In some examples, the antibody is a single chain antibody, which may comprise only one variable region (e.g., $V_H$) or comprise both a $V_H$ and a $V_L$. Such an antibody can be encoded by a single RNA molecule. In other examples, the antibody described herein is a multi-chain antibody comprising an independent heavy chain and an independent light chain. Such a multi-chain antibody may be encoded by a single ribonucleic acid (RNA) molecule, which can be a bicistronic molecule encoding two separate polypeptide chains. Such an RNA molecule may contain a signal sequence between the two coding sequences such that two separate polypeptides would be produced in the translation process. Alternatively, the RNA molecule may include a sequence coding for a cleavage site (e.g., a protease cleavage site) between the heavy and light chains such that it produces a single precursor polypeptide, which can be processed via cleavage at the cleavage site to produce the two separate heavy and light chains. Alternatively, the heavy and light antibody chains may be encoded by two separate RNA molecules, e.g., two separate mRNA molecules.

In some embodiments, the antibodies and antigen binding fragments thereof encoded by an RNA polynucleotide of the present application comprises a fragment crystallizable (Fc) region. The Fc region is the tail region of an antibodies and antigen binding fragments thereof which contains constant domains (e.g., CH2 and CH3); the other region of the antibodies and antigen binding fragments thereof being the Fab region which contains a variable domain (e.g., VH) and a constant domain (e.g., CH1), the former of which defines binding specificity.

As described herein, antibodies can comprise a VH domain. In some embodiments, the VH domain further comprises one or more constant domains (e.g., CH2 and/or CH3) of an Fc region and/or one or more constant domains (e.g., CH1) of a Fab region. In some embodiments, each of the one or more constant domains (e.g., CH1, CH2, and/or CH3) can comprise or consist of portions of a constant domain. For example, in some embodiments, the constant domain comprises 99% or less, 98% or less, 97% or less, 96% or less, 95% or less, 90% or less, 80% or less, 70% or less, 60% or less, 50% or less, 40% or less, 30% or less, 20% or less, or 10% or less of the corresponding full sequence.

In some embodiments the polynucleotides encode a single chain Fv (scFv) that binds to CHIKV. As used herein, the term “single-chain” refers to a molecule comprising amino acid monomers linearly linked by peptide bonds, e.g., a single chain Fv construct can be a polynucleotide encoding at least two coding regions and a linker region. The scFv construct may encode a fusion protein of the variable regions of the heavy (VH) and light chains (VL) of immunoglobulins, connected with a short linker peptide of ten to about 25 amino acids. The linker can be rich in glycine for flexibility, as well as serine or threonine for solubility, and can either connect the N-terminus of the VH with the C-terminus of the VL, or vice versa. Other linkers include those known in the art and disclosed herein. In some embodiments, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain. In some embodiments the scFv constructs may be oriented in a variety of ways. For instance, the order to VH and VL in the construct may vary and alter the expression and/or activity of the scFv. In some embodiments the scFv constructs are oriented, from N to C terminus, VL-linker-VH-linker-CH2-CH3.

In some embodiments, one or more flexible linkers can be used to link two or more portions or fragments of an antibody. For example, flexible linkers can attach scFv fragments to one another, and/or to Fc domains. In some embodiments, the variable heavy and variable light chains are covalently attached using flexible linkers. In some embodiments, flexible linkers such as those containing glycine and serine are used. The scFV-FC synthesis from a typical antibody format can involve the addition of linkers. In some embodiments, the linker is (GxS)3, wherein x can be 1, 2, 3, 4, 5, 6, 7, 8, 9, or 10. In some cases, longer linkers are more effective in producing highly neutralizing scFv, and increasing the VL-VH linker length could reduce strain and oligomerization. In some cases, it is desirable to have a linker that is 15 amino acids or greater in length, e.g., a linker that is 15 to 30 amino acids, 16-25 amino acids, 20 or to 30 amino acids in length. The (G4S)4 linker (also referred to as Linker20) is a longer linker that can less strain in some cases. In some embodiments the linker is (G4S)4

Examples of linkers which may be used in the polynucleotides of the present invention include those in Table 1.

TABLE 1

Linkers

| Name | Sequence in polynucleotide | SEQ ID NO |
|---|---|---|
| PLrigid<br>PLrigid is a 20 a.a. peptide that is based on an alpha-helix motif (EAAAR (SEQ ID NO: 205)) (Merutka et al., 1991; Sommese et al., 2010) | GAAGCTGCTGCAAGAGAAGCT GCAGCTAGGGAGGCTGCAGCT AGGGAGGCTGCTGCAAGA | 206 |
| 2aa GS linker<br>Highly flexibly glycine linker | GGCAGC | 207 |
| 6aa [GS]x linker (SEQ ID NO: 208)<br>Highly flexible 6 amino acid linker. Translates to gsgsgs (SEQ ID NO: 208). Codon-optimize for *E. coli*, yeast, mammalian | GGTAGCGGCAGCGGTAGC | 209 |
| 10 aa flexible protein domain linker | GGTGAAAATTTGTATTTTCAAT CTGGTGGT | 210 |
| 8 aa protein domain linker | TCCGCTTGTTACTGTGAGCTTT CC | 211 |
| 15 aa flexible glycine-serine protein domain linker; Freiburg standard | GGTGGAGGAGGTTCTGGAGGC GGTGGAAGTGGTGGCGGAGGT AGC | 212 |

TABLE 1-continued

Linkers

| Name | Sequence in polynucleotide | SEQ ID NO |
|---|---|---|
| Short Linker (Gly-Gly-Ser-Gly (SEQ ID NO: 213)) | GGTGGTTCTGGT | 214 |
| Middle Linker (Gly-Gly-Ser-Gly)x2 (SEQ ID NO: 215) | GGTGGTTCTGGTGGTGGTTCTG GT | 216 |
| Long Linker (Gly-Gly-Ser-Gly)x3 (SEQ ID NO: 217) | GGTGGTTCTGGTGGTGGTTCTG GTGGTGGTTCTGGT | 218 |
| GSAT Linker | GGTGGTTCTGCCGGTGGCTCC GGTTCTGGCTCCAGCGGTGGC AGCTCTGGTGCGTCCGGCACG GGTACTGCGGGTGGCACTGGC AGCGGTTCCGGTACTGGCTCT GGC | 219 |
| SEG-Linker | GGTGGTTCTGGCGGCGGTTCT GAAGGTGGCGGCTCCGAAGGC GGCGGCAGCGAGGGCGGTGGT AGCGAAGGTGGTGGCTCCGAG GGTGGCGGTTCCGGCGGCGGT AGC | 220 |
| | GGGGSGGGGSGGGGSGGGGS | 221 |

Table references: Merutka G, Shalongo W, Stellwagen E. (1991) A model peptide with enhanced helicity. Biochem. 30: 4245-4248 and Sommese R F, Sivaramakrishnan S, Baldwin R L, Spudich J A. (2010) Helicity of short E-R/K peptides. Protein Sci. 19: 2001-2005.

During construction of scFv initially, constant domains are removed. Two linkers are added to connect the FV region which binds the antigen, and the FC region. In some embodiments the FC region is a wild type of FC region. In other embodiments it is a variant of wild type. In some embodiments a wild type constant region is a wild type IgG1 constant region (e.g., ASTKGPSVFPLAPSSKST-SGGTAALGCLVKDYFPEPVTVSWNSGALT-SGVHTFPAVL QSSGLYS-LSSVVTVPSSSLGTQTYICNVNHKPSNTKVDKKVEP KSCDKTHTCPPCPAP ELLGGPSVFLFPPKPKDTLMIS-RTPEVTCVVVDVSHEDPEVKFNWYVDGVEVHNAK TKPREEQYN-STYRVVSVLTVLHQDWLNGKEYKCKVSNKALPA-PIEKTISKAKGQPR EPQVYTLPPSRDELTKNQVSLT-CLVKGFYPSDIAVEWESNGQPENNYKTTPPVLDSD GSFFLYSKLTVDKSRWQQGNVFSCSVMHEALHN-HYTQKSLSLSPGK (SEQ ID NO:222)).

In some instances, the antibody may be a germlined variant of any of the exemplary antibodies disclosed herein. A germlined variant contains one or more mutations in the framework regions as relative to its parent antibody towards the corresponding germline sequence. To make a germline variant, the heavy or light chain variable region sequence of the parent antibody or a portion thereof (e.g., a framework sequence) can be used as a query against an antibody germline sequence database (e.g., www.bioinfo.org.uk/abs/, www.vbase2.org, or www.imgt.org) to identify the corresponding germline sequence used by the parent antibody and amino acid residue variations in one or more of the framework regions between the germline sequence and the parent antibody. One or more amino acid substitutions can then be introduced into the parent antibody based on the germline sequence to produce a germlined variant.

The mRNA polynucleotides described herein can encode antibodies, or antigen-binding fragments thereof, with modified or variant variable domains and/or constant domains compared to sequences disclosed herein. In some cases, modifications or variations can include amino acid substitutions, amino acid deletions, or amino acid additions, compared to the sequences disclosed herein. The deleted amino acids typically may be from the carboxyl or amino terminal ends of the heavy chain variable region (VH) and/or the light chain variable region (VL).

When needed, the antibody as described herein may comprise a modified constant region. For example, it may comprise a modified constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. Alternatively, the constant region may be modified such that it has an elevated effort activity, for example, enhanced ADCC activity. In some embodiments, the constant region can be modified as described in Eur. J. Immunol. (1999) 29:2613-2624; PCT Application No. PCT/GB99/01441; and/or UK Patent Application No. 9809951.8.

In some embodiments, the heavy chain constant region used in the antibodies described herein may comprise mutations (e.g., amino acid residue substitutions) to enhance a desired characteristic of the antibody, for example, increasing the binding activity to the neonatal Fc receptor (FcRn) and thus the serum half-life of the antibodies. It was known that binding to FcRn is critical for maintaining antibody homeostasis and regulating the serum half-life of antibodies. One or more (e.g., 1, 2, 3, 4, 5, or more) mutations (e.g., amino acid residue substitutions) may be introduced into the constant region at suitable positions (e.g., in $C_H2$ region) to enhance FcRn binding and enhance the half-life of the antibody. See, e.g., Dall'Acqua et al., J.B.C., 2006, 281:

23514-23524; Robbie et al., Antimicrob. Agents Chemother, 2013, 57(12):6147; and Dall'Acqua et al., J. Immunol. 2002 169:5171-5180.

In some embodiments, a polynucleotide is an intrabody construct which has been modified for expression inside a target cell and where the expression product binds an intracellular protein. Such constructs may have sub picomolar binding affinities and may be formulated for targeting to particular sites or tissues. For example, intrabody constructs may be formulated in any of the lipid nanoparticle formulations disclosed herein.

In some embodiment, the polynucleotide is a bicistronic construct encoding a two-protein chain antibody on a single polynucleotide strand. A pseudo-bicistronic construct is a polynucleotide encoding a single chain antibody discontinuously on a single polynucleotide strand. For bicistronic constructs, the encoded two strands or two portions/regions and/or domains (as is the case with pseudo-bicistronic) are separated by at least one nucleotide not encoding the strands or domains. More often the separation comprises a cleavage signal or site or a non-coding region of nucleotides. Such cleavage sites include, for example, furin cleavage sites encoded as an "RKR" site in the resultant polypeptide.

In some embodiments the antibodies are administered to a subject as a bolus IV injection or bolus. This form of delivery can produce high levels of expressed antibody.

2. Polynucleotides and Open Reading Frames

In some aspects, the polynucleotides disclosed herein are or function as a messenger RNA (mRNA). As used herein, the term "messenger RNA" (mRNA) refers to any polynucleotide which encodes at least one peptide or polypeptide of interest and which is capable of being translated to produce the encoded peptide polypeptide of interest in vitro, in vivo, in situ or ex vivo. The basic components of an mRNA molecule typically include at least one coding region, a 5' untranslated region (UTR), a 3' UTR, a 5' cap, and a poly-A tail.

The instant invention features mRNAs for use in treating or preventing CHIKV infection in a subject. The mRNAs featured for use in the invention are administered to subjects and encode a human anti-CHIKV antibody in vivo. Accordingly, the invention relates to polynucleotides, e.g., mRNA, comprising an open reading frame of linked nucleosides encoding a human anti-CHIKV antibody polypeptide, functional fragments thereof, and fusion proteins. In some embodiments, the open reading frame is sequence-optimized. In particular embodiments, the invention provides sequence-optimized polynucleotides comprising nucleotides encoding a polypeptide sequence of a human anti-CHIKV antibody, or a portion or fragment thereof, e.g., nucleotides encoding a heavy chain or a light chain of an anti-CHIKV antibody.

In certain aspects, the invention provides polynucleotides (e.g., a RNA such as an mRNA) that comprise a nucleotide sequence (e.g., an ORF) encoding one or more anti-CHIKV antibody polypeptides. In some embodiments, the encoded anti-CHIKV antibody polypeptide of the invention can be selected from:

(i) a full length anti-CHIKV heavy chain polypeptide or a full length anti-CHIKV light chain polypeptide;

(ii) a functional fragment of an anti-CHIKV heavy chain or light chain polypeptide described herein (e.g., a truncated sequence shorter than the heavy or light chain; but still retaining CHIKV binding activity);

(iii) a variant (e.g., full length or truncated protein in which one or more amino acids have been replaced) with respect to a reference protein, e.g., a heavy chain (e.g., SEQ ID NO: 1) or light chain (e.g., SEQ ID NO: 3) of an anti-CHIKV antibody; or (iv) a fusion protein comprising (i) a full length heavy chain (e.g., SEQ ID NO: 1), a functional fragment or a variant thereof, or (ii) a full length light chain (e.g., SEQ ID NO: 3), a functional fragment or a variant thereof; and (ii) a heterologous protein.

In certain embodiments, the encoded polypeptide is a mammalian anti-CHIKV antibody polypeptide, such as a human anti-CHIKV antibody polypeptide, a functional fragment or a variant thereof.

In some embodiments, one or more mRNA polynucleotide as described herein expresses an anti-CHIKV antibody in a mammalian cell, e.g., a human cell. In some embodiments, a first mRNA polynucleotide encodes a first polypeptide that is a heavy chain of an anti-CHIKV antibody, of a portion thereof (e.g., a heavy chain variable region), and a second mRNA polynucleotide encodes a second polypeptide that is a light chain of an anti-CHIKV antibody, or a portion thereof (e.g., a light chain variable region), such that the first and second polynucleotides express the heavy and light chains of an anti-CHIKV antibody in a mammalian cell, e.g., a human cell, and the heavy and light chains pair to form the anti-CHIKV antibody.

In some embodiments, the anti-CHIKV antibody expressed in the cell is secreted and can bind to CHIKV and/or neutralize CHIKV. Anti-CHIKV antibody protein expression levels and/or anti-CHIKV antibody activity, e.g., antigen binding activity and/or virus neutralization activity, can be measured according to methods known in the art. In some embodiments, the polynucleotide is introduced to the cells in vitro. In some embodiments, the polynucleotide is introduced to the cells in vivo by administration of the polynucleotide to a subject.

In some embodiments, the polynucleotides (e.g., a RNA, e.g., an mRNA) of the invention comprise a nucleotide sequence (e.g., an ORF) that encodes a heavy chain polypeptide, e.g., SEQ ID NO: 1. In some embodiments, the polynucleotides (e.g., a RNA, e.g., an mRNA) of the invention comprise a nucleotide sequence (e.g., an ORF) that encodes a light chain polypeptide, e.g., SEQ ID NO: 3.

In some embodiments, the polynucleotides (e.g., a RNA, e.g., an mRNA) of the invention comprise a nucleotide sequence (e.g., an ORF) that is identical to SEQ ID NO:2 or SEQ ID NO:4.

In some embodiments, the polynucleotides (e.g., an mRNA) described herein comprise a nucleotide sequence that is identical to SEQ ID NO:5 or SEQ ID NO: 6

In some embodiments, the polynucleotides (e.g., a RNA, e.g., an mRNA) of the invention comprise a nucleotide sequence (e.g., an ORF) that encodes a portion or a fragment of a heavy chain polypeptide or a light chain polypeptide of an anti-CHIKV antibody. In some embodiments, the polynucleotides (e.g., a RNA, e.g., an mRNA) of the invention comprise a nucleotide sequence (e.g., an ORF) that encodes a heavy chain variable region of a heavy chain antibody sequence polypeptide, e.g., amino acids 21-142 of SEQ ID NO:1. In some embodiments, the polynucleotides (e.g., a RNA, e.g., an mRNA) of the invention comprise a nucleotide sequence (e.g., an ORF) that encodes a light chain variable region of a light chain antibody sequence polypeptide, e.g., amino acids 21-128 of SEQ ID NO:3. In some embodiments, the polynucleotides (e.g., a RNA, e.g., an mRNA) of the invention comprise a nucleotide sequence (e.g., an ORF) that is identical to nucleotides 61-426 of SEQ ID NO:2, or nucleotides 61-384 of SEQ ID NO:4.

In some embodiments, the polynucleotide (e.g., a RNA, e.g., an mRNA) of the invention comprises a codon optimized nucleic acid sequence, wherein the open reading frame (ORF) of the codon optimized nucleic acid sequence is derived from polypeptide of an anti-CHIKV antibody, e.g., a heavy chain polypeptide or a light chain polypeptide. For example, the polynucleotides of invention can comprise a sequence optimized ORF encoding a heavy chain or a light chain of an anti-CHIKV antibody. In some embodiments, the polynucleotides of the invention can comprise a sequence optimized functional fragment of a heavy chain or light chain of an anti-CHIKV antibody, e.g., a variable region of a heavy chain or light chain.

In some embodiments, the polynucleotides (e.g., a RNA, e.g., an mRNA) of the invention comprise a nucleotide sequence (e.g., an ORF) encoding a mutant polypeptide of an anti-CHIKV antibody relative to a reference anti-CHIKV antibody polypeptide. In some embodiments, the polynucleotides of the invention comprise an ORF encoding an anti-CHIKV antibody polypeptide that comprises at least one point mutation in the polypeptide sequence relative to a reference polypeptide, and retains antigen binding activity and/or virus neutralization activity of the reference polypeptide. For example, the polynucleotides can comprise an ORF encoding a heavy chain of an anti-CHIKV antibody with at least one point mutation relative to the heavy chain encoded by SEQ ID NO: 1. For example, the polynucleotides can comprise an ORF encoding a light chain of an anti-CHIKV antibody with at least one point mutation relative to the light chain encoded by SEQ ID NO: 3. In some embodiments, an anti-CHIKV antibody having a mutant heavy chain and/or a mutant light chain has an CHIKV neutralization activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the CHIKV neutralization activity of a corresponding anti-CHIKV antibody made up of the heavy and light chains of SEQ ID NOs: 1 and 3 In some embodiments, an anti-CHIKV antibody having a mutant heavy chain and/or a mutant light chain has an CHIKV binding activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the CHIKV binding activity of a corresponding anti-CHIKV antibody made up of the heavy and light chains of SEQ ID NOs: 1 and 3. In some embodiments, the polynucleotide (e.g., a RNA, e.g., an mRNA) of the invention comprising an ORF encoding a mutant anti-CHIKV antibody polypeptide is sequence optimized.

In some embodiments, the polynucleotide (e.g., a RNA, e.g., an mRNA) of the invention comprises a nucleotide sequence (e.g., an ORF) that encodes an anti-CHIKV antibody polypeptide with mutations that do not alter CHIKV binding and/or neutralization activity relative to an anti-CHIKV antibody comprising the heavy and light chains of SEQ ID NOs: 1 and 3. Such mutant polypeptides can be referred to as function-neutral. In some embodiments, the polynucleotide comprises an ORF that encodes a mutant anti-CHIKV antibody polypeptide comprising one or more function-neutral point mutations.

In some embodiments, the anti-CHIKV antibody having a mutant heavy chain and/or light chain polypeptide has higher CHIKV binding and/or neutralization activity than the corresponding anti-CHIKV antibody having the heavy and light chains of SEQ ID NOs: 1 and 3. In some embodiments, an anti-CHIKV antibody having a mutant heavy chain and/or a mutant light chain has a CHIKV binding and/or neutralization activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the CHIKV binding and/or neutralization activity of a corresponding anti-CHIKV antibody made up of the heavy and light chains of SEQ ID NOs: 1 and 3.

In some embodiments, the polynucleotides (e.g., a RNA, e.g., an mRNA) of the invention comprise a nucleotide sequence (e.g., an ORF) encoding a functional fragment of an anti-CHIKV antibody polypeptide, e.g., a functional fragment of a heavy chain polypeptide or a light chain polypeptide, such that the functional fragment of the polypeptide can, as part of an antibody, or antigen-binding portion thereof, bind to CHIKV and/or neutralize CHIKV. In some embodiments, an anti-CHIKV antibody, or antigen-binding portion thereof, having a functional fragment of the heavy and/or light chain has a CHIKV binding and/or neutralization activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% of the CHIKV binding and/or neutralization activity of an anti-CHIKV antibody made up of the heavy and light chains of SEQ ID NOs: 1 and 3. In some embodiments, an anti-CHIKV antibody, or antigen-binding portion thereof, having a functional fragment of the heavy and/or light chain has a CHIKV binding and/or neutralization activity which is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% higher than the CHIKV binding and/or neutralization activity of an anti-CHIKV antibody made up of the heavy and light chains of SEQ ID NOs: 1 and 3. In some embodiments, the polynucleotides (e.g., a RNA, e.g., an mRNA) of the invention comprising an ORF encoding a functional fragment of an anti-CHIKV antibody polypeptide is sequence optimized.

In some embodiments, the polynucleotide (e.g., a RNA, e.g., an mRNA) of the invention comprises a nucleotide sequence (e.g., an ORF) encoding an anti-CHIKV antibody polypeptide fragment that is at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24% or 25% shorter than a corresponding full length anti-CHIKV antibody polypeptide, e.g., a full length heavy chain or a full length light chain of an anti-CHIKV antibody.

In some embodiments, the polynucleotide (e.g., a RNA, e.g., an mRNA) of the invention comprises a nucleotide sequence (e.g., an ORF) encoding an anti-CHIKV antibody heavy chain (e.g., a full length heavy chain, functional fragment of a heavy chain, or variant thereof), wherein the nucleotide sequence is at least 70%, at least 75%, at least 80%, at least 85%, at least 90%, at least 95%, at least 96%, at least 97%, at least 98%, at least 99%, or 100% identical to the sequence of SEQ ID NO:2. In some embodiments, the polynucleotide (e.g., a RNA, e.g., an mRNA) of the invention comprises a nucleotide sequence (e.g., an ORF) encoding an anti-CHIKV antibody light chain (e.g., a full length light chain, functional fragment of a light chain, or variant thereof), wherein the nucleotide sequence is at least 70%, at least 75%, at least 80%, at least 85%, at least 90%, at least 95%, at least 96%, at least 97%, at least 98%, at least 99%, or 100% identical to the sequence of SEQ ID NO:4.

In some embodiments, the polynucleotide (e.g., a RNA, e.g., an mRNA) of the invention comprises an ORF encoding an anti-CHIKV antibody polypeptide, wherein the polynucleotide comprises a nucleic acid sequence having 70% to 100%, 75% to 100%, 80% to 100%, 85% to 100%, 70% to 95%, 80% to 95%, 70% to 85%, 75% to 90%, 80% to 95%, 70% to 75%, 75% to 80%, 80% to 85%, 85% to 90%, 90% to 95%, or 95% to 100%, sequence identity to SEQ ID NO:2 or SEQ ID NO:4.

In some embodiments, the polynucleotide (e.g., a RNA, e.g., an mRNA) of the invention comprises a nucleotide sequence (e.g., an ORF) encoding an anti-CHIKV antibody polypeptide, wherein the nucleotide sequence differs from SEQ ID NO:2 or SEQ ID NO:4 by no more than 100 nucleotides, e.g., by 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 nucleotides.

In some embodiments, the polynucleotide (e.g., a RNA, e.g., an mRNA) of the invention comprises a nucleotide sequence (e.g., an ORF) encoding a polypeptide comprising the heavy chain variable region of the heavy chain antibody sequence of SEQ ID NO:1, wherein the ORF has a nucleotide sequence that is at least 80% identical to nucleotides 61-426 of SEQ ID NO:2, e.g., 80%, 81%, 82%, 83%, 84%, 85%, 86%, 87%, 88%, 89%, 90%, 91%, 92%, 93%, 94%, 95%, 96%, 97%, 98%, 99%, or 100% identical to nucleotides 61-426 of SEQ ID NO:2. In some embodiments, the polynucleotide (e.g., a RNA, e.g., an mRNA) of the invention comprises a nucleotide sequence (e.g., an ORF) encoding a polypeptide comprising the heavy chain variable region of the heavy chain antibody sequence of SEQ ID NO:1, wherein the ORF comprises a nucleic acid sequence that differs from the nucleic acid sequence of nucleotides 61-426 of SEQ ID NO:2 by no more than 75 nucleotides, e.g., by 1, 2, 3, 4, 5, 6, 7, 8, 9, 10, 15, 20, 25, 30, 35, 40, 45, 50, 55, 60, 65, 70, or 75 nucleotides.

In some embodiments, the polynucleotide (e.g., a RNA, e.g., an mRNA) of the invention comprises a nucleotide sequence (e.g., an ORF) encoding a polypeptide comprising the light chain variable region of the light chain antibody sequence of SEQ ID NO:3, wherein the ORF has a nucleotide sequence that is at least 80% identical to nucleotides 61-384 of SEQ ID NO:4, e.g., 80%, 81%, 82%, 83%, 84%, 85%, 86%, 87%, 88%, 89%, 90%, 91%, 92%, 93%, 94%, 95%, 96%, 97%, 98%, 99%, or 100% identical to nucleotides 61-384 of SEQ ID NO:4. In some embodiments, the polynucleotide (e.g., a RNA, e.g., an mRNA) of the invention comprises a nucleotide sequence (e.g., an ORF) encoding a polypeptide comprising the light chain variable region of the light chain antibody sequence of SEQ ID NO:3, wherein the ORF comprises a nucleic acid sequence that differs from the nucleic acid sequence of nucleotides 61-384 of SEQ ID NO:4 by no more than 75 nucleotides, e.g., by 1, 2, 3, 4, 5, 6, 7, 8, 9, 10, 15, 20, 25, 30, 35, 40, 45, 50, 55, 60, 65, 70, or 75 nucleotides.

In some embodiments, the polynucleotide (e.g., a RNA, e.g., an mRNA) of the invention comprises a nucleic acid sequence that is at least 80% identical to SEQ ID NO:2, e.g., 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:2. In some embodiments, the polynucleotide (e.g., a RNA, e.g., an mRNA) of the invention comprises a nucleic acid sequence that is at least 80% identical to nucleotides 61-1416 of SEQ ID NO:2, e.g., 80%, 81%, 82%, 83%, 84%, 85%, 86%, 87%, 88%, 89%, 90%, 91%, 92%, 93%, 94%, 95%, 96%, 97%, 98%, 99%, or 100% identical to nucleotides 61-1416 of SEQ ID NO:2.

In some embodiments, the polynucleotide (e.g., a RNA, e.g., an mRNA) of the invention comprises a nucleic acid sequence that is at least 80% identical to SEQ ID NO:4, e.g., 80%, 81%, 82%, 83%, 84%, 85%, 86%, 87%, 88%, 89%, 90%, 91%, 92%, 93%, 94%, 95%, 96%, 97%, 98%, 99%, or 100% identical to SEQ ID NO:4. In some embodiments, polynucleotide (e.g., a RNA, e.g., an mRNA) of the invention comprises a nucleic acid sequence that is at least 80% identical to nucleotides 61-705 of SEQ ID NO:4, e.g., 80%, 81%, 82%, 83%, 84%, 85%, 86%, 87%, 88%, 89%, 90%, 91%, 92%, 93%, 94%, 95%, 96%, 97%, 98%, 99%, or 100% identical to nucleotides 61-705 of SEQ ID NO:4.

In some embodiments, the polynucleotide (e.g., a RNA, e.g., an mRNA) of the invention comprises from about 30 to about 100,000 nucleotides (e.g., from 30 to 100, from 30 to 200, from 50 to 300, from 100 to 400, from 200 to 500, from 200 to 600, from 300 to 700, from 400 to 800, from 500 to 900, from 900 to 1,000, from 900 to 1,100, from 900 to 1,200, from 900 to 1,300, from 900 to 1,400, from 900 to 1,500, from 1,000 to 1,100, from 1,000 to 1,100, from 1,000 to 1,200, from 1,000 to 1,300, from 1,000 to 1,400, from 1,000 to 1,500, from 1,187 to 1,200, from 1,187 to 1,400, from 1,187 to 1,600, from 1,187 to 1,800, from 1,187 to 2,000, from 1,187 to 3,000, from 1,187 to 5,000, from 1,187 to 7,000, from 1,187 to 10,000, from 1,187 to 25,000, from 1,187 to 50,000, from 1,187 to 70,000, or from 1,187 to 100,000).

In some embodiments, a polynucleotide (e.g., a RNA, e.g., an mRNA) described herein comprises a nucleotide sequence (e.g., an ORF) encoding a polypeptide, wherein the length of the nucleotide sequence (e.g., an ORF) is at least 30 nucleotides in length (e.g., at least or greater than about 30, 35, 40, 45, 50, 55, 60, 70, 80, 90, 100, 120, 140, 160, 180, 200, 250, 300, 350, 400, 450, 500, 600, 700, 800, 900, 1,000, 1,100, 1,200, 1,300, 1,400, 1,500, 1,600, 1,700, 1,800, 1,900, 2,000, 2,500, and 3,000, 4,000, 5,000, 6,000, 7,000, 8,000, 9,000, 10,000, 20,000, 30,000, 40,000, 50,000, 60,000, 70,000, 80,000, 90,000 or up to and including 100,000 nucleotides).

In some embodiments, the polynucleotide of the invention (e.g., a RNA, e.g., an mRNA) comprising a nucleotide sequence (e.g., an ORF) encoding an anti-CHIKV antibody polypeptide (e.g., a heavy chain polypeptide or light chain polypeptide of an anti-CHIKV antibody, fragments thereof, or variants thereof) further comprises at least one nucleic acid sequence that is noncoding, e.g., a microRNA binding site. In some embodiments, the polynucleotide (e.g., a RNA, e.g., an mRNA) of the invention further comprises a 5'-UTR (e.g., selected from the sequences of SEQ ID NOs:13 and 108-126) and a 3'UTR (e.g., selected from the sequences of SEQ ID NOs:14 and 127-138). In some embodiments, the polynucleotide (e.g., a RNA, e.g., an mRNA) of the invention comprises a sequence selected from SEQ ID NO:2 or SEQ ID NO:4. In a further embodiment, the polynucleotide (e.g., a RNA, e.g., an mRNA) comprises a 5' terminal cap (e.g., Cap0, Cap1, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof) and a poly-A-tail region (e.g., about 100 nucleotides in length). In some embodiments, an mRNA described herein comprises a 5' UTR comprising a nucleic acid sequence of SEQ ID NO:13. In some embodiments, an mRNA described herein comprises a 3' UTR comprising a nucleic acid sequence of SEQ ID NO:14. In some embodiments, the mRNA comprises a polyA tail. In some instances, the poly A tail is 50-150, 75-150, 85-150, 90-150, 90-120, 90-130, or 90-150 nucleotides in length. In some instances, the poly A tail is 100 nucleotides in length.

In some embodiments, the polynucleotide of the invention (e.g., a RNA, e.g., an mRNA) comprising a nucleotide sequence (e.g., an ORF) encoding an anti-CHIKV antibody polypeptide is single stranded or double stranded.

In some embodiments, the polynucleotide of the invention comprising a nucleotide sequence (e.g., an ORF) encoding an anti-CHIKV antibody polypeptide is DNA or RNA. In some embodiments, the polynucleotide of the invention is RNA. In some embodiments, the polynucleotide of the invention is, or functions as, an mRNA. In some embodiments, the mRNA comprises a nucleotide sequence (e.g., an ORF) that encodes at least one anti-CHIKV antibody polypeptide, and is capable of being translated to produce the encoded anti-CHIKV antibody polypeptide in vitro, in vivo, in situ or ex vivo.

In some embodiments, the polynucleotide of the invention (e.g., a RNA, e.g., an mRNA) comprises a sequence-optimized nucleotide sequence (e.g., an ORF) encoding an anti-CHIKV antibody polypeptide (e.g., SEQ ID NOs:2 or 4), wherein the polynucleotide comprises at least one chemically modified nucleobase, e.g., N1-methylpseudouracil or 5-methoxyuracil. In certain embodiments, all uracils in the polynucleotide are N1-methylpseudouracils. In other embodiments, all uracils in the polynucleotide are 5-methoxyuracils. In some embodiments, the polynucleotide further comprises a miRNA binding site, e.g., a miRNA binding site that binds to miR-142 and/or a miRNA binding site that binds to miR-126.

In some embodiments, the polynucleotide (e.g., a RNA, e.g., a mRNA) disclosed herein is formulated with a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 50:10:38.5:1.5. In some embodiments, the delivery agent comprises Compound VI, DSPC, Cholesterol, and Compound I or PEG-DMG, e.g., with a mole ratio in the range of about 30 to about 60 mol % Compound II or VI (or related suitable amino lipid) (e.g., 30-40, 40-45, 45-50, 50-55 or 55-60 mol % Compound II or VI (or related suitable amino lipid)), about 5 to about 20 mol % phospholipid (or related suitable phospholipid or “helper lipid”) (e.g., 5-10, 10-15, or 15-20 mol % phospholipid (or related suitable phospholipid or “helper lipid”)), about 20 to about 50 mol % cholesterol (or related sterol or “non-cationic” lipid) (e.g., about 20-30, 30-35, 35-40, 40-45, or 45-50 mol % cholesterol (or related sterol or “non-cationic” lipid)) and about 0.05 to about 10 mol % PEG lipid (or other suitable PEG lipid) (e.g., 0.05-1, 1-2, 2-3, 3-4, 4-5, 5-7, or 7-10 mol % PEG lipid (or other suitable PEG lipid)). An exemplary delivery agent can comprise mole ratios of, for example, 47.5:10.5:39.0:3.0 or 50:10:38.5:1.5. In certain instances, an exemplary delivery agent can comprise mole ratios of, for example, 47.5:10.5:39.0:3; 47.5:10:39.5:3; 47.5:11:39.5:2; 47.5:10.5:39.5:2.5; 47.5:11:39:2.5; 48.5:10:38.5:3; 48.5:10.5:39:2; 48.5:10.5:38.5:2.5; 48.5:10.5:39.5:1.5; 48.5:10.5:38.0:3; 47:10.5:39.5:3; 47:10:40.5:2.5; 47:11:40:2; 47:10.5:39.5:3; 48:10.5:38.5:3; 48:10:39.5:2.5; 48:11:39:2; or 48:10.5:38.5:3. In some embodiments, the delivery agent comprises Compound II or VI, DSPC, Cholesterol, and Compound I or PEG-DMG, e.g., with a mole ratio of about 47.5:10.5:39.0:3.0. In some embodiments, the delivery agent comprises Compound II or VI, DSPC, Cholesterol, and Compound I or PEG-DMG, e.g., with a mole ratio of about 50:10:38.5:1.5. In some embodiments, the delivery agent comprises Compound II, DSPC, Cholesterol, and Compound I, e.g., with a mole ratio of about 50:10:38:2. In certain instances, an exemplary delivery agent can comprise a mole ratio of about 50:10:38:2. In some embodiments, the delivery agent comprises Compound II, DSPC, Cholesterol, and Compound I, e.g., with a mole ratio in the range of about 30 to about 60 mol % Compound II (or related suitable amino lipid) (e.g., 30-40, 40-45, 45-50, 50-55 or 55-60 mol % Compound II (or related suitable amino lipid)), about 5 to about 20 mol % phospholipid (or related suitable phospholipid or “helper lipid”) (e.g., 5-10, 10-15, or 15-20 mol % phospholipid (or related suitable phospholipid or “helper lipid”)), about 20 to about 50 mol % cholesterol (or related sterol or “non-cationic” lipid) (e.g., about 20-30, 30-35, 35-40, 40-45, or 45-50 mol % cholesterol (or related sterol or “non-cationic” lipid)) and about 0.05 to about 10 mol % Compound I (or other suitable PEG lipid) (e.g., 0.05-1, 1-2, 2-3, 3-4, 4-5, 5-7, or 7-10 mol % PEG lipid (or other suitable PEG lipid)).

In some embodiments, the polynucleotide of the disclosure is an mRNA that comprises a 5'-terminal cap (e.g., Cap 1), a 5'UTR (e.g., SEQ ID NO:13), a ORF sequence selected from the group consisting of SEQ ID NOs.:2 and 4, a 3'UTR (e.g., SEQ ID NO:14), and a poly A tail (e.g., about 100 nucleotides in length), wherein all uracils in the polynucleotide are N1-methylpseudouracils. In some embodiments, the delivery agent comprises Compound II or Compound VI as the ionizable lipid and PEG-DMG or Compound I as the PEG lipid, or any combinations thereof (e.g., Compound I and Compound II). In some embodiments, the delivery agent comprises Compound II, DSPC, cholesterol, and Compound I.

Treatments for Chikungunya virus infection, as provided herein, comprise at least one (e.g., one or more) RNA (e.g., mRNA) polynucleotide having an open reading frame encoding at least one antibody, antibody domain, antibody portion, and/or antibody fragment thereof, wherein the antibody, antibody portion, or antibody fragment binds to Chikungunya virus, or wherein two or more antibody portions or fragments associate to form an antibody, or antigen-binding portion thereof, that binds to chikungunya virus. The terms “polynucleotide” and “nucleic acid,” in their broadest sense, include any compound and/or substance that comprises a polymer of nucleotides. Polynucleotides (also referred to as nucleic acids) may be or may include, for example, RNAs, deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization), ethylene nucleic acids (ENA), cyclohexenyl nucleic acids (CeNA) or chimeras or combinations thereof.

In some embodiments, an RNA polynucleotide encodes 1-10, 2-10, 2-9, 2-8, 2-7, 2-6, 2-5, 2-4, 2-3, 3-10, 3-9, 3-8, 3-7, 3-6, 3-5, 3-4, 4-10, 4-9, 4-8, 4-7, 4-6, 4-5, 5-10, 5-9, 5-8, 5-7, 5-6, 6-10, 6-9, 6-8, 6-7, 7-10, 7-9, 7-8, 8-10, 8-9 or 9-10 antibodies, antibody fragments, or antigen binding fragments.

3. Signal Sequences

The polynucleotides (e.g., a RNA, e.g., an mRNA) of the invention can also comprise nucleotide sequences that encode additional features that facilitate trafficking of the encoded polypeptides to therapeutically relevant sites. One such feature that aids in protein trafficking is the signal sequence, or targeting sequence. The peptides encoded by these signal sequences are known by a variety of names, including targeting peptides, transit peptides, and signal peptides. In some embodiments, the polynucleotide (e.g., a RNA, e.g., an mRNA) comprises a nucleotide sequence (e.g., an ORF) that encodes a signal peptide operably linked to a nucleotide sequence that encodes anti-CHIKV antibody polypeptide described herein.

In some embodiments, the "signal sequence" or "signal peptide" is a polynucleotide or polypeptide, respectively, which is from about 30-210 nucleotides, e.g., about 45-80 or 15-60 nucleotides (e.g., about 20, 30, 40, 50, 60, or 70 amino acids) in length that, optionally, is incorporated at the 5' (or N-terminus) of the coding region or the polypeptide, respectively. Addition of these sequences results in trafficking the encoded polypeptide to a desired site, such as the endoplasmic reticulum or the mitochondria through one or more targeting pathways. Some signal peptides are cleaved from the protein, for example by a signal peptidase after the proteins are transported to the desired site.

In some embodiments, the polynucleotide of the present disclosure comprises a nucleotide sequence encoding an anti-CHIKV antibody polypeptide (e.g., a heavy chain polypeptide or a light chain polypeptide), wherein the nucleotide sequence further comprises a 5' nucleic acid sequence encoding a native signal peptide. In another embodiment, the polynucleotide of the present disclosure comprises a nucleotide sequence encoding an anti-CHIKV antibody polypeptide (e.g., a heavy chain polypeptide or a light chain polypeptide), wherein the nucleotide sequence lacks the nucleic acid sequence encoding a native signal peptide.

In some embodiments, the polynucleotide of the present disclosure comprises a nucleotide sequence encoding an anti-CHIKV antibody polypeptide (e.g., a heavy chain polypeptide or a light chain polypeptide), wherein the nucleotide sequence further comprises a 5' nucleic acid sequence encoding a heterologous signal peptide.

4. Fusion Proteins

In some embodiments, the polynucleotide of the invention (e.g., a RNA, e.g., an mRNA) can comprise more than one nucleic acid sequence (e.g., an ORF) encoding a polypeptide of interest. In some embodiments, polynucleotides of the invention comprise a single ORF encoding an anti-CHIKV antibody polypeptide, a functional fragment, or a variant thereof. However, in some embodiments, the polynucleotide of the invention can comprise more than one ORF, for example, a first ORF encoding an anti-CHIKV antibody polypeptide (a first polypeptide of interest), a functional fragment, or a variant thereof, and a second ORF expressing a second polypeptide of interest. In some embodiments, two or more polypeptides of interest can be genetically fused, i.e., two or more polypeptides can be encoded by the same ORF. In some embodiments, the polynucleotide can comprise a nucleic acid sequence encoding a linker (e.g., a G4S (SEQ ID NO:230)) peptide linker or another linker known in the art) between two or more polypeptides of interest.

In some embodiments, a polynucleotide of the invention (e.g., a RNA, e.g., an mRNA) can comprise two, three, four, or more ORFs, each expressing a polypeptide of interest.

In some embodiments, the polynucleotide of the invention (e.g., a RNA, e.g., an mRNA) can comprise a first nucleic acid sequence (e.g., a first ORF) encoding an anti-CHIKV antibody polypeptide and a second nucleic acid sequence (e.g., a second ORF) encoding a second polypeptide of interest, e.g., a second anti-CHIKV antibody polypeptide.

Linkers and Cleavable Peptides

In certain embodiments, the mRNAs of the disclosure encode more than one anti-CHIKV antibody polypeptide (e.g., an antibody heavy chain and an antibody light chain) or a heterologous polypeptide, referred to herein as multimer constructs. In certain embodiments of the multimer constructs, the mRNA further encodes a linker located between each polypeptide. The linker can be, for example, a cleavable linker or protease-sensitive linker. In certain embodiments, the linker is selected from the group consisting of F2A linker, P2A linker, T2A linker, E2A linker, and combinations thereof. This family of self-cleaving peptide linkers, referred to as 2A peptides, has been described in the art (see for example, Kim, J. H. et al. (2011) PLoS ONE 6:e18556). In certain embodiments, the linker is an F2A linker. In certain embodiments, the linker is a GGGS linker. In certain embodiments, the linker is a (GGGS)n linker, wherein n=2, 3, 4, or 5. In certain embodiments, the multimer construct contains two or more polypeptides with intervening linkers, having the structure: polypeptide-linker-polypeptide-linker-polypeptide.

In one embodiment, the cleavable linker is an F2A linker (e.g., having the amino acid sequence GSGVKQTLNFDLLKLAGDVESNPGP (SEQ ID NO:223)). In other embodiments, the cleavable linker is a T2A linker (e.g., having the amino acid sequence GSGEGRGSLLTCGDVEENPGP (SEQ ID NO:224)), a P2A linker (e.g., having the amino acid sequence GSGATNFSLLKQAGDVEENPGP (SEQ ID NO:225)) or an E2A linker (e.g., having the amino acid sequence GSGQCTNYALLKLAGDVESNPGP (SEQ ID NO:226)). The skilled artisan will appreciate that other art-recognized linkers may be suitable for use in the constructs of the invention (e.g., encoded by the polynucleotides of the invention). The skilled artisan will likewise appreciate that other multicistronic constructs may be suitable for use in the invention. In exemplary embodiments, the construct design yields approximately equimolar amounts of intrabody and/or domain thereof encoded by the constructs of the invention.

In one embodiment, the self-cleaving peptide may be, but is not limited to, a 2A peptide. A variety of 2A peptides are known and available in the art and may be used, including e.g., the foot and mouth disease virus (FMDV) 2A peptide, the equine rhinitis A virus 2A peptide, the Thosea asigna virus 2A peptide, and the porcine teschovirus-1 2A peptide. 2A peptides are used by several viruses to generate two proteins from one transcript by ribosome-skipping, such that a normal peptide bond is impaired at the 2A peptide sequence, resulting in two discontinuous proteins being produced from one translation event. In one embodiment, the 2A peptide cleaves between the last glycine and last proline. One example of a polynucleotide sequence encoding the 2A peptide is: GGAAGCGGAGCUACUAACUUCAGCCUGCUGAAGCAGGCUGGAGACGUGGAGG AGAACCCUGGACCU (SEQ ID NO:227). In one illustrative embodiment, a 2A peptide is encoded by the following sequence: 5' UCCGGACUCAGAUCCGGGGAUCUCAAAAUUGUCGCUCCUGUCAAACAAACUCU UAACUUUGAUUUACUCAAACUGGCTGGGGAUGUAGAAAGCAAUCCAGGTCCAC UC-3' (SEQ ID NO:228). The polynucleotide sequence of the 2A peptide may be modified or codon optimized by the methods described herein and/or are known in the art.

In one embodiment, this sequence may be used to separate the coding regions of two or more polypeptides of interest. As a non-limiting example, the sequence encoding the F2A peptide may be between a first coding region A and a second coding region B (A-F2Apep-B). The presence of the F2A peptide results in the cleavage of the one long protein between the glycine and the proline at the end of the F2A peptide sequence (NPGP is cleaved to result in NPG and P) thus creating separate protein A (with 21 amino acids of the F2A peptide attached, ending with NPG) and separate protein B (with 1 amino acid, P, of the F2A peptide attached). Likewise, for other 2A peptides (P2A, T2A and E2A), the presence of the peptide in a long protein results in cleavage between the glycine and proline at the end of the 2A peptide sequence (NPGP is cleaved to result in NPG and P). Protein A and protein B may be the same or different peptides or polypeptides of interest (e.g., an anti-CHIKV antibody heavy chain and an anti-CHIKV antibody light chain, or fragments thereof). In particular embodiments, protein A and protein B are anti-CHIKV antibody heavy and light chains, in either order.

5. Sequence Optimization of Nucleotide Sequence Encoding an Antibody Polypeptide In some embodiments, the polynucleotide (e.g., a RNA, e.g., an mRNA) of the present disclosure is sequence optimized. In some embodiments, the polynucleotide (e.g., a RNA, e.g., an mRNA) of the present disclosure comprises a nucleotide sequence (e.g., an ORF) encoding an anti-CHIKV antibody polypeptide, optionally, a nucleotide sequence (e.g., an ORF) encoding another polypeptide of interest, a 5'-UTR, a 3'-UTR, the 5' UTR or 3' UTR optionally comprising at least one microRNA binding site, optionally a nucleotide sequence encoding a linker, a polyA tail, or any combination thereof), in which the ORF(s) that are sequence optimized.

A sequence-optimized nucleotide sequence, e.g., a codon-optimized mRNA sequence encoding an anti-CHIKV antibody polypeptide, is a sequence comprising at least one synonymous nucleobase substitution with respect to a reference sequence (e.g., a nucleotide sequence encoding a reference anti-CHIKV antibody polypeptide).

A sequence-optimized nucleotide sequence can be partially or completely different in sequence from the reference sequence. For example, a reference sequence encoding polyserine uniformly encoded by UCU codons can be sequence-optimized by having 100% of its nucleobases substituted (for each codon, U in position 1 replaced by A, C in position 2 replaced by G, and U in position 3 replaced by C) to yield a sequence encoding polyserine which would be uniformly encoded by AGC codons. The percentage of sequence identity obtained from a global pairwise alignment between the reference polyserine nucleic acid sequence and the sequence-optimized polyserine nucleic acid sequence would be 0%. However, the protein products from both sequences would be 100% identical.

Some sequence optimization (also sometimes referred to codon optimization) methods are known in the art (and discussed in more detail below) and can be useful to achieve one or more desired results. These results can include, e.g., matching codon frequencies in certain tissue targets and/or host organisms to ensure proper folding; biasing G/C content to increase mRNA stability or reduce secondary structures; minimizing tandem repeat codons or base runs that can impair gene construction or expression; customizing transcriptional and translational control regions; inserting or removing protein trafficking sequences; removing/adding post translation modification sites in an encoded protein (e.g., glycosylation sites); adding, removing or shuffling protein domains; inserting or deleting restriction sites; modifying ribosome binding sites and mRNA degradation sites; adjusting translational rates to allow the various domains of the protein to fold properly; and/or reducing or eliminating problem secondary structures within the polynucleotide. Sequence optimization tools, algorithms and services are known in the art, non-limiting examples include services from GeneArt (Life Technologies), DNA2.0 (Menlo Park CA) and/or proprietary methods.

Codon options for each amino acid are given in the following TABLE.

| Amino Acid | Single Letter Code | Codon Options |
|---|---|---|
| Isoleucine | I | AUU, AUC, AUA |
| Leucine | L | CUU, CUC, CUA, CUG, UUA, UUG |
| Valine | V | GUU, GUC, GUA, GUG |
| Phenylalanine | F | UUU, UUC |
| Methionine | M | AUG |
| Cysteine | C | UGU, UGC |
| Alanine | A | GCU, GCC, GCA, GCG |
| Glycine | G | GGU, GGC, GGA, GGG |
| Proline | P | CCU, CCC, CCA, CCG |
| Threonine | T | ACU, ACC, ACA, ACG |
| Serine | S | UCU, UCC, UCA, UCG, AGU, AGC |
| Tyrosine | Y | UAU, UAC |
| Tryptophan | W | UGG |
| Glutamine | Q | CAA, CAG |
| Asparagine | N | AAU, AAC |
| Histidine | H | CAU, CAC |
| Glutamic acid | E | GAA, GAG |
| Aspartic acid | D | GAU, GAC |
| Lysine | K | AAA, AAG |
| Arginine | R | CGU, CGC, CGA, CGG, AGA, AGG |
| Selenocysteine | Sec | UGA in mRNA in presence of Selenocysteine insertion element (SECIS) |
| Stop codons | Stop | UAA, UAG, UGA |

In some embodiments, a polynucleotide (e.g., a RNA, e.g., an mRNA) of the present disclosure comprises a sequence-optimized nucleotide sequence (e.g., an ORF) encoding an anti-CHIKV antibody polypeptide, a functional fragment, or a variant thereof, wherein the antibody polypeptide, functional fragment, or a variant thereof encoded by the sequence-optimized nucleotide sequence has improved properties (e.g., compared to an anti-CHIKV antibody polypeptide, functional fragment, or a variant thereof encoded by a reference nucleotide sequence that is not sequence optimized), e.g., improved properties related to expression efficacy after administration in vivo. Such properties include, but are not limited to, improving nucleic acid stability (e.g., mRNA stability), increasing translation efficacy in the target tissue, reducing the number of truncated proteins expressed, improving the folding or prevent misfolding of the expressed proteins, reducing toxicity of the expressed products, reducing cell death caused by the expressed products, increasing and/or decreasing protein aggregation.

In some embodiments, the sequence-optimized nucleotide sequence (e.g., an ORF) is codon optimized for expression in human subjects, having structural and/or chemical features that avoid one or more of the problems in the art, for example, features which are useful for optimizing formulation and delivery of nucleic acid-based therapeutics while retaining structural and functional integrity; overcoming a threshold of expression; improving expression rates; half-life and/or protein concentrations; optimizing protein localization; and avoiding deleterious bio-responses such as the immune response and/or degradation pathways.

In some embodiments, the polynucleotides of the invention comprise a nucleotide sequence (e.g., a nucleotide sequence (e.g., an ORF) encoding an anti-CHIKV antibody polypeptide, a nucleotide sequence (e.g., an ORF) encoding another polypeptide of interest, a 5'-UTR, a 3'-UTR, a microRNA binding site, a nucleic acid sequence encoding a linker, or any combination thereof) that is sequence-optimized according to a method comprising:

(i) substituting at least one codon in a reference nucleotide sequence (e.g., an ORF encoding an anti-CHIKV antibody polypeptide) with an alternative codon to increase or decrease uridine content to generate a uridine-modified sequence;

(ii) substituting at least one codon in a reference nucleotide sequence (e.g., an ORF encoding an anti-CHIKV antibody polypeptide) with an alternative codon having a higher codon frequency in the synonymous codon set;

(iii) substituting at least one codon in a reference nucleotide sequence (e.g., an ORF encoding an anti-CHIKV antibody polypeptide) with an alternative codon to increase G/C content; or (iv) a combination thereof.

In some embodiments, the sequence-optimized nucleotide sequence (e.g., an ORF encoding an anti-CHIKV antibody polypeptide) has at least one improved property with respect to the reference nucleotide sequence.

In some embodiments, the sequence optimization method is multiparametric and comprises one, two, three, four, or more methods disclosed herein and/or other optimization methods known in the art.

Features, which can be considered beneficial in some embodiments of the present disclosure, can be encoded by or within regions of the polynucleotide and such regions can be upstream (5') to, downstream (3') to, or within the region that encodes the anti-CHIKV antibody polypeptide. These regions can be incorporated into the polynucleotide before and/or after sequence-optimization of the protein encoding region or open reading frame (ORF). Examples of such features include, but are not limited to, untranslated regions (UTRs), microRNA sequences, Kozak sequences, oligo(dT) sequences, poly-A tail, and detectable tags and can include multiple cloning sites that can have XbaI recognition.

In some embodiments, the polynucleotide of the present disclosure comprises a 5' UTR. a 3' UTR and/or a miRNA binding site. In some embodiments, the polynucleotide comprises two or more 5' UTRs and/or 3' UTRs, which can be the same or different sequences. In some embodiments, the polynucleotide comprises two or more miRNA binding sites, which can be the same or different sequences. Any portion of the 5' UTR, 3' UTR, and/or miRNA binding site, including none, can be sequence-optimized and can independently contain one or more different structural or chemical modifications, before and/or after sequence optimization.

In some embodiments, after optimization, the polynucleotide is reconstituted and transformed into a vector such as, but not limited to, plasmids, viruses, cosmids, and artificial chromosomes. For example, the optimized polynucleotide can be reconstituted and transformed into chemically competent *E. coli*, yeast, neurospora, maize, drosophila, etc. where high copy plasmid-like or chromosome structures occur by methods described herein.

Exemplary amino acid sequences and nucleotide sequences encoding human anti-CHIKV antibody polypeptides are provided in the Construct Sequences Appendix.

6. Sequence-Optimized Nucleotide Sequences Encoding Antibody Polypeptides

In some embodiments, the polynucleotide described herein comprises a sequence-optimized nucleotide sequence encoding an anti-CHIKV antibody polypeptide disclosed herein. In some embodiments, the polynucleotide of the present disclosure comprises an open reading frame (ORF) encoding an anti-CHIKV antibody polypeptide, wherein the ORF has been sequence optimized.

Exemplary sequence-optimized nucleotide sequences encoding human anti-CHIKV antibody polypeptides are set forth as SEQ ID NOs: 2 and 4 (CHIKV24 heavy chain and CHIKV24 light chain, respectively). In some embodiments, the sequence optimized anti-CHIKV antibody sequences, fragments, and variants thereof are used to practice the methods disclosed herein.

In some embodiments, a polynucleotide of the present disclosure, for example a polynucleotide comprising an mRNA nucleotide sequence encoding an anti-CHIKV antibody polypeptide, comprises from 5' to 3' end:

(i) a 5' cap provided herein, for example, Cap1;

(ii) a 5' UTR, such as the sequences provided herein, for example, SEQ ID NO: 13;

(iii) an open reading frame encoding an anti-CHIKV antibody polypeptide, e.g., a sequence optimized nucleic acid sequence encoding an anti-CHIKV antibody polypeptide set forth as SEQ ID NO:2 or SEQ ID NO:4, or a fragment thereof (e.g., a heavy chain variable region or a light chain variable region);

(iv) at least one stop codon;

(v) a 3' UTR, such as the sequences provided herein, for example, SEQ ID NO: 14; and (vi) a poly-A tail provided above.

In certain embodiments, all uracils in the polynucleotide are N1 methylpseudouracils (G5). In certain embodiments, all uracils in the polynucleotide are 5-methoxyuracils (G6).

The sequence-optimized nucleotide sequences disclosed herein are distinct from the corresponding wild type nucleotide acid sequences and from other known sequence-optimized nucleotide sequences, e.g., these sequence-optimized nucleic acids have unique compositional characteristics.

In some embodiments, the percentage of uracil or thymine nucleobases in a sequence-optimized nucleotide sequence (e.g., encoding an anti-CHIKV antibody polypeptide, a functional fragment, or a variant thereof) is modified (e.g., reduced) with respect to the percentage of uracil or thymine nucleobases in the reference wild-type nucleotide sequence. Such a sequence is referred to as a uracil-modified or thymine-modified sequence. The percentage of uracil or thymine content in a nucleotide sequence can be determined by dividing the number of uracils or thymines in a sequence by the total number of nucleotides and multiplying by 100. In some embodiments, the sequence-optimized nucleotide sequence has a lower uracil or thymine content than the uracil or thymine content in the reference wild-type sequence. In some embodiments, the uracil or thymine content in a sequence-optimized nucleotide sequence of the present disclosure is greater than the uracil or thymine content in the reference wild-type sequence and still maintain beneficial effects, e.g., increased expression and/or reduced Toll-Like Receptor (TLR) response when compared to the reference wild-type sequence.

Methods for optimizing codon usage are known in the art. For example, an ORF of any one or more of the sequences provided herein may be codon optimized. Codon optimization, in some embodiments, may be used to match codon frequencies in target and host organisms to ensure proper folding; bias GC content to increase mRNA stability or reduce secondary structures; minimize tandem repeat codons or base runs that may impair gene construction or expression; customize transcriptional and translational control regions; insert or remove protein trafficking sequences; remove/add post translation modification sites in encoded protein (e.g., glycosylation sites); add, remove or shuffle protein domains; insert or delete restriction sites; modify ribosome binding sites and mRNA degradation sites; adjust translational rates to allow the various domains of the protein to fold properly; or reduce or eliminate problem secondary structures within the polynucleotide. Codon optimization tools, algorithms and services are known in the art—non-limiting examples include services from GeneArt (Life Technologies), DNA2.0 (Menlo Park CA) and/or proprietary methods. In some embodiments, the open reading frame (ORF) sequence is optimized using optimization algorithms.

7. Characterization of Sequence Optimized Nucleic Acids

In some embodiments of the present disclosure, the polynucleotide (e.g., a RNA, e.g., an mRNA) comprising a sequence optimized nucleic acid disclosed herein encoding an anti-CHIKV antibody polypeptide can be can be tested to determine whether at least one nucleic acid sequence property (e.g., stability when exposed to nucleases) or expression property has been improved with respect to the non-sequence optimized nucleic acid.

As used herein, "expression property" refers to a property of a nucleic acid sequence either in vivo (e.g., translation efficacy of a synthetic mRNA after administration to a subject in need thereof) or in vitro (e.g., translation efficacy of a synthetic mRNA tested in an in vitro model system). Expression properties include but are not limited to the amount of protein produced by an mRNA encoding an antibody after administration, and the amount of soluble or otherwise functional protein produced. In some embodiments, sequence optimized nucleic acids disclosed herein can be evaluated according to the viability of the cells expressing a protein encoded by a sequence optimized nucleic acid sequence (e.g., a RNA, e.g., an mRNA) encoding an anti-CHIKV antibody polypeptide disclosed herein.

In a particular embodiment, a plurality of sequence optimized nucleic acids disclosed herein (e.g., a RNA, e.g., an mRNA) containing codon substitutions with respect to the non-optimized reference nucleic acid sequence can be characterized functionally to measure a property of interest, for example an expression property in an in vitro model system, or in vivo in a target tissue or cell.

a. Optimization of Nucleic Acid Sequence Intrinsic Properties

In some embodiments of the present disclosure, the desired property of the polynucleotide is an intrinsic property of the nucleic acid sequence. For example, the nucleotide sequence (e.g., a RNA, e.g., an mRNA) can be sequence optimized for in vivo or in vitro stability. In some embodiments, the nucleotide sequence can be sequence optimized for expression in a particular target tissue or cell. In some embodiments, the nucleic acid sequence is sequence optimized to increase its plasma half by preventing its degradation by endo and exonucleases.

In other embodiments, the nucleic acid sequence is sequence optimized to increase its resistance to hydrolysis in solution, for example, to lengthen the time that the sequence optimized nucleic acid or a pharmaceutical composition comprising the sequence optimized nucleic acid can be stored under aqueous conditions with minimal degradation.

In other embodiments, the sequence optimized nucleic acid can be optimized to increase its resistance to hydrolysis in dry storage conditions, for example, to lengthen the time that the sequence optimized nucleic acid can be stored after lyophilization with minimal degradation.

b. Nucleic Acids Sequence Optimized for Protein Expression

In some embodiments of the present disclosure, the desired property of the polynucleotide is the level of expression of an antibody encoded by a sequence optimized sequence disclosed herein. Protein expression levels can be measured using one or more expression systems. In some embodiments, expression can be measured in cell culture systems, e.g., CHO cells or HEK293 cells. In some embodiments, expression can be measured using in vitro expression systems prepared from extracts of living cells, e.g., rabbit reticulocyte lysates, or in vitro expression systems prepared by assembly of purified individual components. In other embodiments, the protein expression is measured in an in vivo system, e.g., mouse, rabbit, monkey, etc.

In some embodiments, protein expression in solution form can be desirable. Accordingly, in some embodiments, a reference sequence can be sequence optimized to yield a sequence optimized nucleic acid sequence having optimized levels of expressed proteins in soluble form. Levels of protein expression and other properties such as solubility, levels of aggregation, and the presence of truncation products (i.e., fragments due to proteolysis, hydrolysis, or defective translation) can be measured according to methods known in the art, for example, using electrophoresis (e.g., native or SDS-PAGE) or chromatographic methods (e.g., HPLC, size exclusion chromatography, etc.).

c. Optimization of Target Tissue or Target Cell Viability

In some embodiments, the expression of heterologous therapeutic proteins encoded by a nucleic acid sequence can have deleterious effects in the target tissue or cell, reducing protein yield, or reducing the quality of the expressed product (e.g., due to the presence of protein fragments or precipitation of the expressed protein in inclusion bodies), or causing toxicity.

Accordingly, in some embodiments of the present disclosure, the sequence optimization of a nucleic acid sequence disclosed herein, e.g., a nucleic acid sequence encoding an anti-CHIKV antibody polypeptide, can be used to increase the viability of target cells expressing the protein encoded by the sequence optimized nucleic acid.

Heterologous protein expression can also be deleterious to cells transfected with a nucleic acid sequence for autologous or heterologous transplantation. Accordingly, in some embodiments of the present disclosure the sequence optimization of a nucleic acid sequence disclosed herein can be used to increase the viability of target cells expressing the protein encoded by the sequence optimized nucleic acid sequence. Changes in cell or tissue viability, toxicity, and other physiological reaction can be measured according to methods known in the art.

d Reduction of Immune and/or Inflammatory Response

In some cases, the administration of a sequence optimized nucleic acid encoding an anti-CHIKV antibody polypeptide or a functional fragment thereof can trigger an immune response, which could be caused by (i) the therapeutic agent (e.g., an mRNA encoding an anti-CHIKV antibody polypeptide), or (ii) the expression product of such therapeutic agent (e.g., the anti-CHIKV antibody polypeptide encoded by the mRNA), or (iv) a combination thereof. Accordingly, in some embodiments of the present disclosure the sequence optimization of nucleic acid sequence (e.g., an mRNA)

disclosed herein can be used to decrease an immune or inflammatory response (other than coagulation pathway activation) triggered by the administration of a nucleic acid encoding an anti-CHIKV antibody polypeptide or by the expression product of anti-CHIKV antibody polypeptide encoded by such nucleic acid.

In some aspects, an inflammatory response can be measured by detecting increased levels of one or more inflammatory cytokines using methods known in the art, e.g., ELISA. The term "inflammatory cytokine" refers to cytokines that are elevated in an inflammatory response. Examples of inflammatory cytokines include interleukin-6 (IL-6), CXCL1 (chemokine (C—X—C motif) ligand 1; also known as GROα, interferon-γ (IFNγ), tumor necrosis factor α (TNFα), interferon γ-induced protein 10 (IP-10), or granulocyte-colony stimulating factor (G-CSF). The term inflammatory cytokines also includes other cytokines associated with inflammatory responses known in the art, e.g., interleukin-1 (IL-1), interleukin-8 (IL-8), interleukin-12 (IL-12), interleukin-13 (Il-13), interferon α (IFN-α), etc.

8. Modified Nucleotide Sequences Encoding Antibody Polypeptides

In some embodiments, the polynucleotide (e.g., a RNA, e.g., an mRNA) of the present disclosure comprises a chemically modified nucleobase, for example, a chemically modified uracil, e.g., pseudouracil, N1-methylpseuodouracil, 5-methoxyuracil, or the like. In some embodiments, the mRNA is a uracil-modified sequence comprising an ORF encoding an antibody, wherein the mRNA comprises a chemically modified nucleobase, for example, a chemically modified uracil, e.g., pseudouracil, 1-methylpseuodouracil, or 5-methoxyuracil.

In certain aspects of the present disclosure, when the modified uracil base is connected to a ribose sugar, as it is in polynucleotides, the resulting modified nucleoside or nucleotide is referred to as modified uradine. In some embodiments, uracil in the polynucleotide is at least about 25%, at least about 30%, at least about 40%, at least about 50%, at least about 60%, at least about 70%, at least about 80%, at least 90%, at least 95%, at least 99%, or about 100% modified uracil. In one embodiment, uracil in the polynucleotide is at least 95% modified uracil. In another embodiment, uracil in the polynucleotide is 100% modified uracil.

In embodiments where uracil in the polynucleotide is at least 95% modified uracil overall uracil content can be adjusted such that an mRNA provides suitable protein expression levels while inducing little to no immune response. In some embodiments, the uracil content of the ORF is between about 100% and about 150%, between about 100% and about 110%, between about 105% and about 115%, between about 110% and about 120%, between about 115% and about 125%, between about 120% and about 130%, between about 125% and about 135%, between about 130% and about 140%, between about 135% and about 145%, between about 140% and about 150% of the theoretical minimum uracil content in the corresponding wild-type ORF (% UTM). In other embodiments, the uracil content of the ORF is between about 121% and about 136% or between 123% and 134% of the % UTM. In some embodiments, the uracil content of the ORF encoding an anti-CHIKV antibody polypeptide is about 115%, about 120%, about 125%, about 130%, about 135%, about 140%, about 145%, or about 150% of the % UTM. In this context, the term "uracil" can refer to modified uracil and/or naturally occurring uracil.

In some embodiments, the uracil content in the ORF of the mRNA encoding an anti-CHIKV antibody polypeptide, as described herein, is less than about 30%, about 25%, about 20%, about 15%, or about 10% of the total nucleobase content in the ORF. In some embodiments, the uracil content in the ORF is between about 10% and about 20% of the total nucleobase content in the ORF. In other embodiments, the uracil content in the ORF is between about 10% and about 25% of the total nucleobase content in the ORF. In one embodiment, the uracil content in the ORF of the mRNA encoding an anti-CHIKV antibody polypeptide is less than about 20% of the total nucleobase content in the open reading frame. In this context, the term "uracil" can refer to modified uracil and/or naturally occurring uracil.

In further embodiments, the ORF of the mRNA encoding an anti-CHIKV antibody polypeptide having modified uracil and adjusted uracil content has increased Cytosine (C), Guanine (G), or Guanine/Cytosine (G/C) content (absolute or relative). In some embodiments, the overall increase in C, G, or G/C content (absolute or relative) of the ORF is at least about 2%, at least about 3%, at least about 4%, at least about 5%, at least about 6%, at least about 7%, at least about 10%, at least about 15%, at least about 20%, at least about 40%, at least about 50%, at least about 60%, at least about 70%, at least about 80%, at least about 90%, at least about 95%, or at least about 100% relative to the G/C content (absolute or relative) of the wild-type ORF. In some embodiments, the G, the C, or the G/C content in the ORF is less than about 100%, less than about 90%, less than about 85%, or less than about 80% of the theoretical maximum G, C, or G/C content of the corresponding wild type nucleotide sequence encoding the anti-CHIKV antibody polypeptide (% GTMX; % CTMX, or % G/CTMX). In some embodiments, the increases in G and/or C content (absolute or relative) described herein can be conducted by replacing synonymous codons with low G, C, or G/C content with synonymous codons having higher G, C, or G/C content. In other embodiments, the increase in G and/or C content (absolute or relative) is conducted by replacing a codon ending with U with a synonymous codon ending with G or C.

In further embodiments, the ORF of the mRNA encoding an anti-CHIKV antibody polypeptide of the invention comprises modified uracil and has an adjusted uracil content containing less uracil pairs (UU) and/or uracil triplets (UUU) and/or uracil quadruplets (UUUU) than the corresponding wild-type nucleotide sequence encoding the anti-CHIKV antibody polypeptide. In some embodiments, the ORF of the mRNA encoding a CHIKV antibody polypeptide, as disclosed herein, contains no uracil pairs and/or uracil triplets and/or uracil quadruplets. In some embodiments, uracil pairs and/or uracil triplets and/or uracil quadruplets are reduced below a certain threshold, e.g., no more than 1, 2, 3, 4, 5, 6, 7, 8, 9, 10, 11, 12, 13, 14, 15, 16, 17, 18, 19, or 20 occurrences in the ORF of the mRNA encoding the anti-CHIKV antibody polypeptide. In a particular embodiment, the ORF of the mRNA encoding the anti-CHIKV antibody polypeptide of the invention contains less than 20, 19, 18, 17, 16, 15, 14, 13, 12, 11, 10, 9, 8, 7, 6, 5, 4, 3, 2, or 1 non-phenylalanine uracil pairs and/or triplets. In another embodiment, the ORF of the mRNA encoding the anti-CHIKV antibody polypeptide contains no non-phenylalanine uracil pairs and/or triplets.

In further embodiments, the ORF of the mRNA encoding an anti-CHIKV antibody polypeptide of the invention comprises modified uracil and has an adjusted uracil content containing less uracil-rich clusters than a corresponding wild-type nucleotide sequence encoding the anti-CHIKV antibody polypeptide. In some embodiments, the ORF of the mRNA encoding the anti-CHIKV antibody polypeptide of the invention contains uracil-rich clusters that are shorter in length than corresponding uracil-rich clusters in a corresponding wild-type nucleotide sequence encoding the anti-CHIKV antibody polypeptide.

In further embodiments, alternative lower frequency codons are employed. At least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or 100% of the codons in the anti-CHIKV antibody polypeptide-encoding ORF of the modified uracil-comprising mRNA are substituted with alternative codons, each alternative codon having a codon frequency lower than the codon frequency of the substituted codon in the synonymous codon set. The ORF also has adjusted uracil content, as described above. In some embodiments, at least one codon in the ORF of the mRNA encoding the anti-CHIKV antibody polypeptide is substituted with an alternative codon having a codon frequency lower than the codon frequency of the substituted codon in the synonymous codon set.

In some embodiments, the adjusted uracil content, anti-CHIKV antibody polypeptide-encoding ORF of the modified uracil-comprising mRNA exhibits expression levels of anti-CHIKV antibody polypeptide when administered to a mammalian cell that are higher than expression levels of anti-CHIKV antibody polypeptide from a corresponding wild-type mRNA. In some embodiments, the mammalian cell is a mouse cell, a rat cell, or a rabbit cell. In other embodiments, the mammalian cell is a monkey cell or a human cell. In some embodiments, the human cell is a HeLa cell, a BJ fibroblast cell, or a peripheral blood mononuclear cell (PBMC). In some embodiments, anti-CHIKV antibody polypeptide is expressed at a level higher than expression levels of anti-CHIKV antibody polypeptide from a corresponding wild-type mRNA when the mRNA is administered to a mammalian cell in vivo. In some embodiments, the mRNA is administered to mice, rabbits, rats, monkeys, or humans. In one embodiment, mice are null mice. In some embodiments, the mRNA is administered to mice in an amount of about 0.01 mg/kg, about 0.05 mg/kg, about 0.1 mg/kg, about 0.2 mg/kg, about 0.3 mg/kg, about 0.4 mg/kg, about 0.5 mg/kg, about 1 mg/kg, or about 5 mg/kg. In some embodiments, the mRNA is administered intravenously or intramuscularly. In other embodiments, the anti-CHIKV antibody polypeptide is expressed when the mRNA is administered to a mammalian cell in vitro. In some embodiments, the expression is increased by at least about 2-fold, at least about 5-fold, at least about 10-fold, at least about 50-fold, at least about 500-fold, at least about 1500-fold, or at least about 3000-fold. In other embodiments, the expression is increased by at least about 10%, about 20%, about 30%, about 40%, about 50%, 60%, about 70%, about 80%, about 90%, or about 100%.

In some embodiments, adjusted uracil content, anti-CHIKV antibody polypeptide-encoding ORF of the modified uracil-comprising mRNA exhibits increased stability. In some embodiments, the mRNA exhibits increased stability in a cell relative to the stability of a corresponding wild-type mRNA under the same conditions. In some embodiments, the mRNA exhibits increased stability including resistance to nucleases, thermal stability, and/or increased stabilization of secondary structure. In some embodiments, increased stability exhibited by the mRNA is measured by determining the half-life of the mRNA (e.g., in a plasma, serum, cell, or tissue sample) and/or determining the area under the curve (AUC) of the protein expression by the mRNA over time (e.g., in vitro or in vivo). An mRNA is identified as having increased stability if the half-life and/or the AUC is greater than the half-life and/or the AUC of a corresponding wild-type mRNA under the same conditions.

In some embodiments, the mRNA of the present invention induces a detectably lower immune response (e.g., innate or acquired) relative to the immune response induced by a corresponding wild-type mRNA under the same conditions. In other embodiments, the mRNA of the present disclosure induces a detectably lower immune response (e.g., innate or acquired) relative to the immune response induced by an mRNA that encodes for an anti-CHIKV antibody polypeptide but does not comprise modified uracil under the same conditions, or relative to the immune response induced by an mRNA that encodes for an anti-CHIKV antibody polypeptide and that comprises modified uracil but that does not have adjusted uracil content under the same conditions. The innate immune response can be manifested by increased expression of pro-inflammatory cytokines, activation of intracellular PRRs (RIG-I, MDA5, etc.), cell death, and/or termination or reduction in protein translation. In some embodiments, a reduction in the innate immune response can be measured by expression or activity level of Type 1 interferons (e.g., IFN-α, IFN-β, IFN-κ, IFN-δ, IFN-ε, IFN-τ, IFN-ω, and IFN-ζ) or the expression of interferon-regulated genes such as the toll-like receptors (e.g., TLR7 and TLR8), and/or by decreased cell death following one or more administrations of the mRNA of the invention into a cell.

In some embodiments, the expression of Type-1 interferons by a mammalian cell in response to the mRNA of the present disclosure is reduced by at least 10%, 20%, 30%, 40%, 50%, 60%, 70%, 80%, 90%, 95%, 99%, 99.9%, or greater than 99.9% relative to a corresponding wild-type mRNA, to an mRNA that encodes an anti-CHIKV antibody polypeptide but does not comprise modified uracil, or to an mRNA that encodes an anti-CHIKV antibody polypeptide and that comprises modified uracil but that does not have adjusted uracil content. In some embodiments, the interferon is IFN-β. In some embodiments, cell death frequency caused by administration of mRNA of the present disclosure to a mammalian cell is 10%, 25%, 50%, 75%, 85%, 90%, 95%, or over 95% less than the cell death frequency observed with a corresponding wild-type mRNA, an mRNA that encodes for an anti-CHIKV antibody polypeptide but does not comprise modified uracil, or an mRNA that encodes for an anti-CHIKV antibody polypeptide and that comprises modified uracil but that does not have adjusted uracil content. In some embodiments, the mammalian cell is a BJ fibroblast cell. In other embodiments, the mammalian cell is a splenocyte. In some embodiments, the mammalian cell is that of a mouse or a rat. In other embodiments, the mammalian cell is that of a human. In one embodiment, the mRNA of the present disclosure does not substantially induce an innate immune response of a mammalian cell into which the mRNA is introduced.

9. Methods of Modifying Polynucleotides

The disclosure includes modified polynucleotides comprising a polynucleotide described herein (e.g., a polynucleotide, e.g. mRNA, comprising a nucleotide sequence encoding an anti-CHIKV antibody polypeptide). The modified polynucleotides can be chemically modified and/or structurally modified. When the polynucleotides of the present invention are chemically and/or structurally modified the polynucleotides can be referred to as "modified polynucleotides."

The present disclosure provides for modified nucleosides and nucleotides of a polynucleotide (e.g., RNA polynucleotides, such as mRNA polynucleotides) encoding an anti-CHIKV antibody polypeptide. A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside including a phosphate group. Modified nucleotides can be synthesized by any useful method, such as, for example, chemically, enzymatically, or recombinantly, to include one or more modified or non-natural nucleosides. Polynucleotides can comprise a region or regions of linked nucleosides. Such regions can have variable backbone linkages. The linkages can be standard phosphodiester linkages, in which case the polynucleotides would comprise regions of nucleotides.

The modified polynucleotides disclosed herein can comprise various distinct modifications. In some embodiments, the modified polynucleotides contain one, two, or more (optionally different) nucleoside or nucleotide modifications. In some embodiments, a modified polynucleotide, introduced to a cell can exhibit one or more desirable properties, e.g., improved protein expression, reduced immunogenicity, or reduced degradation in the cell, as compared to an unmodified polynucleotide.

In some embodiments, a polynucleotide of the present invention (e.g., a polynucleotide comprising a nucleotide sequence encoding an anti-CHIKV antibody polypeptide) is structurally modified. As used herein, a "structural" modification is one in which two or more linked nucleosides are inserted, deleted, duplicated, inverted or randomized in a polynucleotide without significant chemical modification to the nucleotides themselves. Because chemical bonds will necessarily be broken and reformed to effect a structural modification, structural modifications are of a chemical nature and hence are chemical modifications. However, structural modifications will result in a different sequence of nucleotides. For example, the polynucleotide "ATCG" can be chemically modified to "AT-5meC-G". The same polynucleotide can be structurally modified from "ATCG" to "ATCCCG". Here, the dinucleotide "CC" has been inserted, resulting in a structural modification to the polynucleotide.

Therapeutic compositions of the present disclosure comprise, in some embodiments, at least one nucleic acid (e.g., RNA) having an open reading frame encoding at least one anti-CHIKV antibody polypeptide, wherein the nucleic acid comprises nucleotides and/or nucleosides that can be standard (unmodified) or modified as is known in the art. In some embodiments, nucleotides and nucleosides of the present disclosure comprise modified nucleotides or nucleosides. Such modified nucleotides and nucleosides can be naturally-occurring modified nucleotides and nucleosides or non-naturally occurring modified nucleotides and nucleosides. Such modifications can include those at the sugar, backbone, or nucleobase portion of the nucleotide and/or nucleoside as are recognized in the art.

In some embodiments, a naturally-occurring modified nucleotide or nucleotide of the disclosure is one as is generally known or recognized in the art. Non-limiting examples of such naturally occurring modified nucleotides and nucleotides can be found, inter alia, in the widely recognized MODOMICS database.

In some embodiments, a non-naturally occurring modified nucleotide or nucleoside of the disclosure is one as is generally known or recognized in the art. Non-limiting examples of such non-naturally occurring modified nucleotides and nucleosides can be found, inter alia, in published US application Nos. PCT/US2012/058519; PCT/US2013/075177; PCT/US2014/058897; PCT/US2014/058891; PCT/US2014/070413; PCT/US2015/36773; PCT/US2015/36759; PCT/US2015/36771; or PCT/IB2017/051367 all of which are incorporated by reference herein.

In some embodiments, at least one RNA (e.g., mRNA) of the present disclosure is not chemically modified and comprises the standard ribonucleotides consisting of adenosine, guanosine, cytosine and uridine. In some embodiments, nucleotides and nucleosides of the present disclosure comprise standard nucleoside residues such as those present in transcribed RNA (e.g. A, G, C, or U). In some embodiments, nucleotides and nucleosides of the present disclosure comprise standard deoxyribonucleosides such as those present in DNA (e.g. dA, dG, dC, or dT).

Hence, nucleic acids of the disclosure (e.g., DNA nucleic acids and RNA nucleic acids, such as mRNA nucleic acids) can comprise standard nucleotides and nucleosides, naturally-occurring nucleotides and nucleosides, non-naturally-occurring nucleotides and nucleosides, or any combination thereof.

Nucleic acids of the disclosure (e.g., DNA nucleic acids and RNA nucleic acids, such as mRNA nucleic acids), in some embodiments, comprise various (more than one) different types of standard and/or modified nucleotides and nucleosides. In some embodiments, a particular region of a nucleic acid contains one, two or more (optionally different) types of standard and/or modified nucleotides and nucleosides.

In some embodiments, a modified RNA nucleic acid (e.g., a modified mRNA nucleic acid), introduced to a cell or organism, exhibits reduced degradation in the cell or organism, respectively, relative to an unmodified nucleic acid comprising standard nucleotides and nucleosides.

In some embodiments, a modified RNA nucleic acid (e.g., a modified mRNA nucleic acid), introduced into a cell or organism, may exhibit reduced immunogenicity in the cell or organism, respectively (e.g., a reduced innate response) relative to an unmodified nucleic acid comprising standard nucleotides and nucleosides.

Nucleic acids (e.g., RNA nucleic acids, such as mRNA nucleic acids), in some embodiments, comprise non-natural modified nucleotides that are introduced during synthesis or post-synthesis of the nucleic acids to achieve desired functions or properties. The modifications may be present on internucleotide linkages, purine or pyrimidine bases, or sugars. The modification may be introduced with chemical synthesis or with a polymerase enzyme at the terminal of a chain or anywhere else in the chain. Any of the regions of a nucleic acid may be chemically modified.

The present disclosure provides for modified nucleosides and nucleotides of a nucleic acid (e.g., RNA nucleic acids, such as mRNA nucleic acids). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A "nucleotide" refers to a nucleoside, including a phosphate group. Modified nucleotides may by synthesized by any useful method, such as, for example, chemically, enzymatically, or recombinantly, to include one or more modified or non-natural nucleosides. Nucleic acids can comprise a region or regions of linked nucleosides. Such regions may have variable backbone linkages. The linkages can be standard phosphodiester linkages, in which case the nucleic acids would comprise regions of nucleotides.

Modified nucleotide base pairing encompasses not only the standard adenosine-thymine, adenosine-uracil, or guanosine-cytosine base pairs, but also base pairs formed between nucleotides and/or modified nucleotides comprising non-standard or modified bases, wherein the arrangement of hydrogen bond donors and hydrogen bond acceptors permits hydrogen bonding between a non-standard base and a standard base or between two complementary non-standard base structures, such as, for example, in those nucleic acids having at least one chemical modification. One example of such non-standard base pairing is the base pairing between the modified nucleotide inosine and adenine, cytosine or uracil. Any combination of base/sugar or linker may be incorporated into nucleic acids of the present disclosure.

In some embodiments, modified nucleobases in nucleic acids (e.g., RNA nucleic acids, such as mRNA nucleic acids) comprise N1-methylpseudouridine (m1ψ), 1-ethyl-pseudouridine (e1ψ), 5-methoxy-uridine (mo5U), 5-methyl-cytidine (m5C), and/or pseudouridine (ψ). In some embodiments, modified nucleobases in nucleic acids (e.g., RNA nucleic acids, such as mRNA nucleic acids) comprise 5-methoxymethyl uridine, 5-methylthio uridine, 1-methoxymethyl pseudouridine, 5-methyl cytidine, and/or 5-methoxy cytidine. In some embodiments, the polyribonucleotide includes a combination of at least two (e.g., 2, 3, 4 or more) of any of the aforementioned modified nucleobases, including but not limited to chemical modifications.

In some embodiments, a RNA nucleic acid of the disclosure comprises N1-methyl-pseudouridine (m1ψ) substitutions at one or more or all uridine positions of the nucleic acid.

In some embodiments, a RNA nucleic acid of the disclosure comprises N1-methyl-pseudouridine (m1ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises pseudouridine (ψ) substitutions at one or more or all uridine positions of the nucleic acid.

In some embodiments, a RNA nucleic acid of the disclosure comprises pseudouridine (ψ) substitutions at one or more or all uridine positions of the nucleic acid and 5-methyl cytidine substitutions at one or more or all cytidine positions of the nucleic acid.

In some embodiments, a RNA nucleic acid of the disclosure comprises uridine at one or more or all uridine positions of the nucleic acid.

In some embodiments, nucleic acids (e.g., RNA nucleic acids, such as mRNA nucleic acids) are uniformly modified (e.g., fully modified, modified throughout the entire sequence) for a particular modification. For example, a nucleic acid can be uniformly modified with N1-methyl-pseudouridine, meaning that all uridine residues in the mRNA sequence are replaced with N1-methyl-pseudouridine. Similarly, a nucleic acid can be uniformly modified for any type of nucleoside residue present in the sequence by replacement with a modified residue such as those set forth above.

The nucleic acids of the present disclosure may be partially or fully modified along the entire length of the molecule. For example, one or more or all or a given type of nucleotide (e.g., purine or pyrimidine, or any one or more or all of A, G, U, C) may be uniformly modified in a nucleic acid of the disclosure, or in a predetermined sequence region thereof (e.g., in the mRNA including or excluding the polyA tail). In some embodiments, all nucleotides X in a nucleic acid of the present disclosure (or in a sequence region thereof) are modified nucleotides, wherein X may be any one of nucleotides A, G, U, C, or any one of the combinations A+G, A+U, A+C, G+U, G+C, U+C, A+G+U, A+G+C, G+U+C or A+G+C.

The nucleic acid may contain from about 1% to about 100% modified nucleotides (either in relation to overall nucleotide content, or in relation to one or more types of nucleotide, i.e., any one or more of A, G, U or C) or any intervening percentage (e.g., from 1% to 20%, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%). It will be understood that any remaining percentage is accounted for by the presence of unmodified A, G, U, or C.

The nucleic acids may contain at a minimum 1% and at maximum 100% modified nucleotides, or any intervening percentage, such as at least 5% modified nucleotides, at least 10% modified nucleotides, at least 25% modified nucleotides, at least 50% modified nucleotides, at least 80% modified nucleotides, or at least 90% modified nucleotides. For example, the nucleic acids may contain a modified pyrimidine such as a modified uracil or cytosine. In some embodiments, at least 5%, at least 10%, at least 25%, at least 50%, at least 80%, at least 90% or 100% of the uracil in the nucleic acid is replaced with a modified uracil (e.g., a 5-substituted uracil). The modified uracil can be replaced by a compound having a single unique structure, or can be replaced by a plurality of compounds having different structures (e.g., 2, 3, 4 or more unique structures). In some embodiments, at least 5%, at least 10%, at least 25%, at least 50%, at least 80%, at least 90% or 100% of the cytosine in the nucleic acid is replaced with a modified cytosine (e.g., a 5-substituted cytosine). The modified cytosine can be replaced by a compound having a single unique structure, or can be replaced by a plurality of compounds having different structures (e.g., 2, 3, 4 or more unique structures).

10. Untranslated Regions (UTRs)

Translation of a polynucleotide comprising an open reading frame encoding a polypeptide can be controlled and regulated by a variety of mechanisms that are provided by various cis-acting nucleic acid structures. For example, naturally-occurring, cis-acting RNA elements that form hairpins or other higher-order (e.g., pseudoknot) intramolecular mRNA secondary structures can provide a translational regulatory activity to a polynucleotide, wherein the RNA element influences or modulates the initiation of polynucleotide translation, particularly when the RNA element is positioned in the 5' UTR close to the 5'-cap structure (Pelletier and Sonenberg (1985) Cell 40(3):515-526; Kozak (1986) Proc Natl Acad Sci 83:2850-2854).

Untranslated regions (UTRs) are nucleic acid sections of a polynucleotide before a start codon (5' UTR) and after a stop codon (3' UTR) that are not translated. In some embodiments, a polynucleotide (e.g., a ribonucleic acid (RNA), e.g., a messenger RNA (mRNA)) of the invention comprising an open reading frame (ORF) encoding an antibody further comprises UTR (e.g., a 5'UTR or functional fragment thereof, a 3'UTR or functional fragment thereof, or a combination thereof).

Cis-acting RNA elements can also affect translation elongation, being involved in numerous frameshifting events (Namy et al., (2004) Mol Cell 13(2):157-168). Internal ribosome entry sequences (IRES) represent another type of cis-acting RNA element that are typically located in 5' UTRs, but have also been reported to be found within the coding region of naturally-occurring mRNAs (Holcik et al. (2000) Trends Genet 16(10):469-473). In cellular mRNAs, IRES often coexist with the 5'-cap structure and provide mRNAs with the functional capacity to be translated under conditions in which cap-dependent translation is compromised (Gebauer et al., (2012) Cold Spring Harb Perspect Biol 4(7):a012245). Another type of naturally-occurring cis-acting RNA element comprises upstream open reading frames (uORFs). Naturally-occurring uORFs occur singularly or multiply within the 5' UTRs of numerous mRNAs and influence the translation of the downstream major ORF, usually negatively (with the notable exception of GCN4 mRNA in yeast and ATF4 mRNA in mammals, where uORFs serve to promote the translation of the downstream major ORF under conditions of increased eIF2 phosphorylation (Hinnebusch (2005) Annu Rev Microbiol 59:407-450)). Additional exemplary translational regulatory activities provided by components, structures, elements, motifs, and/or specific sequences comprising polynucleotides (e.g., mRNA) include, but are not limited to, mRNA stabilization or destabilization (Baker & Parker (2004) Curr Opin Cell Biol 16(3):293-299), translational activation (Villalba et al., (2011) Curr Opin Genet Dev 21(4):452-457), and translational repression (Blumer et al., (2002) Mech Dev 110(1-2):97-112). Studies have shown that naturally-occurring, cis-acting RNA elements can confer their respective functions when used to modify, by incorporation into, heterologous polynucleotides (Goldberg-Cohen et al., (2002) J Biol Chem 277(16):13635-13640).

Modified Polynucleotides Comprising Functional RNA Elements

The present disclosure provides synthetic polynucleotides comprising a modification (e.g., an RNA element), wherein the modification provides a desired translational regulatory activity. In some embodiments, the disclosure provides a polynucleotide comprising a 5' untranslated region (UTR), an initiation codon, a full open reading frame encoding a polypeptide, a 3' UTR, and at least one modification, wherein the at least one modification provides a desired translational regulatory activity, for example, a modification that promotes and/or enhances the translational fidelity of mRNA translation. In some embodiments, the desired translational regulatory activity is a cis-acting regulatory activity. In some embodiments, the desired translational regulatory activity is an increase in the residence time of the 43S pre-initiation complex (PIC) or ribosome at, or proximal to, the initiation codon. In some embodiments, the desired translational regulatory activity is an increase in the initiation of polypeptide synthesis at or from the initiation codon. In some embodiments, the desired translational regulatory activity is an increase in the amount of polypeptide translated from the full open reading frame. In some embodiments, the desired translational regulatory activity is an increase in the fidelity of initiation codon decoding by the PIC or ribosome. In some embodiments, the desired translational regulatory activity is inhibition or reduction of leaky scanning by the PIC or ribosome. In some embodiments, the desired translational regulatory activity is a decrease in the rate of decoding the initiation codon by the PIC or ribosome. In some embodiments, the desired translational regulatory activity is inhibition or reduction in the initiation of polypeptide synthesis at any codon within the mRNA other than the initiation codon. In some embodiments, the desired translational regulatory activity is inhibition or reduction of the amount of polypeptide translated from any open reading frame within the mRNA other than the full open reading frame. In some embodiments, the desired translational regulatory activity is inhibition or reduction in the production of aberrant translation products. In some embodiments, the desired translational regulatory activity is a combination of one or more of the foregoing translational regulatory activities.

Accordingly, the present disclosure provides a polynucleotide, e.g., an mRNA, comprising an RNA element that comprises a sequence and/or an RNA secondary structure(s) that provides a desired translational regulatory activity as described herein. In some aspects, the mRNA comprises an RNA element that comprises a sequence and/or an RNA secondary structure(s) that promotes and/or enhances the translational fidelity of mRNA translation. In some aspects, the mRNA comprises an RNA element that comprises a sequence and/or an RNA secondary structure(s) that provides a desired translational regulatory activity, such as inhibiting and/or reducing leaky scanning. In some aspects, the disclosure provides an mRNA that comprises an RNA element that comprises a sequence and/or an RNA secondary structure(s) that inhibits and/or reduces leaky scanning thereby promoting the translational fidelity of the mRNA.

In some embodiments, the RNA element comprises natural and/or modified nucleotides. In some embodiments, the RNA element comprises of a sequence of linked nucleotides, or derivatives or analogs thereof, that provides a desired translational regulatory activity as described herein. In some embodiments, the RNA element comprises a sequence of linked nucleotides, or derivatives or analogs thereof, that forms or folds into a stable RNA secondary structure, wherein the RNA secondary structure provides a desired translational regulatory activity as described herein. RNA elements can be identified and/or characterized based on the primary sequence of the element (e.g., GC-rich element), by RNA secondary structure formed by the element (e.g. stem-loop), by the location of the element within the RNA molecule (e.g., located within the 5' UTR of an mRNA), by the biological function and/or activity of the element (e.g., "translational enhancer element"), and any combination thereof.

In some aspects, the disclosure provides an mRNA having one or more structural modifications that inhibits leaky scanning and/or promotes the translational fidelity of mRNA translation, wherein at least one of the structural modifications is a GC-rich RNA element. In some aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is 70-80% cytosine, 60-70% cytosine, 50%-60% cytosine, 40-50% cytosine, 30-40% cytosine bases. In any of the foregoing or related aspects, the disclosure provides a GC-rich RNA element which comprises a sequence of 3-30, 5-25, 10-20, 15-20, about 20, about 15, about 12, about 10, about 7, about 6 or about 3 nucleotides, derivatives or analogs thereof, linked in any order, wherein the sequence composition is about 80% cytosine, about 70% cytosine, about 60% cytosine, about 50% cytosine, about 40% cytosine, or about 30% cytosine.

In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is 70-80% cytosine, 60-70% cytosine, 50%-60% cytosine, 40-50% cytosine, or 30-40% cytosine. In any of the foregoing or related aspects, the disclosure provides a GC-rich RNA element which comprises a sequence of 20, 19, 18, 17, 16, 15, 14, 13, 12, 11, 10, 9, 8, 7, 6, 5, 4, or 3 nucleotides, or derivatives or analogs thereof, linked in any order, wherein the sequence composition is about 80% cytosine, about 70% cytosine, about 60% cytosine, about 50% cytosine, about 40% cytosine, or about 30% cytosine.

In some embodiments, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of 3, 4, 5, 6, 7, 8, 9, 10, 11, 12, 13, 14, 15, 16, 17, 18, 19, or 20 nucleotides, or derivatives or analogs thereof, linked in any order, wherein the sequence composition is >50% cytosine. In some embodiments, the sequence composition is >55% cytosine, >60% cytosine, >65% cytosine, >70% cytosine, >75% cytosine, >80% cytosine, >85% cytosine, or >90% cytosine.

In other aspects, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA, and wherein the GC-rich RNA element comprises a sequence of about 3-30, 5-25, 10-20, 15-20 or about 20, about 15, about 12, about 10, about 6 or about 3 nucleotides, or derivatives or analogues thereof, wherein the sequence comprises a repeating GC-motif, wherein the repeating GC-motif is [CCG]n, wherein n=1 to 10, n=2 to 8, n=3 to 6, or n=4 to 5. In some embodiments, the sequence comprises a repeating GC-motif [CCG]n, wherein n=1, 2, 3, 4 or 5. In some embodiments, the sequence comprises a repeating GC-motif [CCG]n, wherein n=1, 2, or 3. In some embodiments, the sequence comprises a repeating GC-motif [CCG]n, wherein n=1. In some embodiments, the sequence comprises a repeating GC-motif [CCG]n, wherein n=2. In some embodiments, the sequence comprises a repeating GC-motif [CCG]n, wherein n=3. In some embodiments, the sequence comprises a repeating GC-motif [CCG]n, wherein n=4. In some embodiments, the sequence comprises a repeating GC-motif [CCG]n, wherein n=5.

In another aspect, the disclosure provides a modified mRNA comprising at least one modification, wherein at least one modification is a GC-rich RNA element comprising a sequence of linked nucleotides, or derivatives or analogs thereof, preceding a Kozak consensus sequence in a 5' UTR of the mRNA, wherein the GC-rich RNA element comprises any one of the sequences set forth in Table 2. In one embodiment, the GC-rich RNA element is located about 30, about 25, about 20, about 15, about 10, about 5, about 4, about 3, about 2, or about 1 nucleotide(s) upstream of a Kozak consensus sequence in the 5' UTR of the mRNA. In another embodiment, the GC-rich RNA element is located about 15-30, 15-20, 15-25, 10-15, or 5-10 nucleotides upstream of a Kozak consensus sequence. In another embodiment, the GC-rich RNA element is located immediately adjacent to a Kozak consensus sequence in the 5' UTR of the mRNA.

In other aspects, the disclosure provides a modified mRNA comprising at least one modification, wherein at least one modification is a GC-rich RNA element comprising the sequence V1 [CCCCGGCGCC (SEQ ID NO: 100)] as set forth in Table 2, or derivatives or analogs thereof, preceding a Kozak consensus sequence in the 5' UTR of the mRNA. In some embodiments, the GC-rich element comprises the sequence V1 as set forth in Table 2 located immediately adjacent to and upstream of the Kozak consensus sequence in the 5' UTR of the mRNA. In some embodiments, the GC-rich element comprises the sequence V1 as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence V1 as set forth in Table 2 located 1-3, 3-5, 5-7, 7-9, 9-12, or 12-15 bases upstream of the Kozak consensus sequence in the 5' UTR of the mRNA. In other aspects, the disclosure provides a modified mRNA comprising at least one modification, wherein at least one modification is a GC-rich RNA element comprising the sequence V2 [CCCCGGC (SEQ ID NO: 101)] as set forth in Table 2, or derivatives or analogs thereof, preceding a Kozak consensus sequence in the 5' UTR of the mRNA. In some embodiments, the GC-rich element comprises the sequence V2 as set forth in Table 2 located immediately adjacent to and upstream of the Kozak consensus sequence in the 5' UTR of the mRNA. In some embodiments, the GC-rich element comprises the sequence V2 as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence V2 as set forth in Table 2 located 1-3, 3-5, 5-7, 7-9, 9-12, or 12-15 bases upstream of the Kozak consensus sequence in the 5' UTR of the mRNA.

In other aspects, the disclosure provides a modified mRNA comprising at least one modification, wherein at least one modification is a GC-rich RNA element comprising the sequence EK [GCCGCC (SEQ ID NO: 102)] as set forth in Table 2, or derivatives or analogs thereof, preceding a Kozak consensus sequence in the 5' UTR of the mRNA. In some embodiments, the GC-rich element comprises the sequence EK as set forth in Table 2 located immediately adjacent to and upstream of the Kozak consensus sequence in the 5' UTR of the mRNA. In some embodiments, the GC-rich element comprises the sequence EK as set forth in Table 2 located 1, 2, 3, 4, 5, 6, 7, 8, 9 or 10 bases upstream of the Kozak consensus sequence in the 5' UTR of the mRNA. In other embodiments, the GC-rich element comprises the sequence EK as set forth in Table 2 located 1-3, 3-5, 5-7, 7-9, 9-12, or 12-15 bases upstream of the Kozak consensus sequence in the 5' UTR of the mRNA.

In yet other aspects, the disclosure provides a modified mRNA comprising at least one modification, wherein at least one modification is a GC-rich RNA element comprising the sequence V1 [CCCCGGCGCC (SEQ ID NO: 100)] as set forth in Table 2, or derivatives or analogs thereof, preceding a Kozak consensus sequence in the 5' UTR of the mRNA, wherein the 5' UTR comprises the following sequence shown in Table 2: GGGAAAUAAGAGAGAAAAGAAGAGUAAGAAGA AAUAUAAGA (SEQ ID NO: 103). The skilled artisan will of course recognize that all Us in the RNA sequences described herein will be Ts in a corresponding template DNA sequence, for example, in DNA templates or constructs from which mRNAs of the disclosure are transcribed, e.g., via IVT.

In some embodiments, the GC-rich element comprises the sequence V1 as set forth in Table 2 located immediately adjacent to and upstream of the Kozak consensus sequence in the 5' UTR sequence shown in Table 2. In some embodiments, the GC-rich element comprises the sequence V1 as set forth in Table 2 located 1, 2, 3, 4, 5, 6, 7, 8, 9 or 10 bases upstream of the Kozak consensus sequence in the 5' UTR of the mRNA, wherein the 5' UTR comprises the following sequence shown in Table 2: GGGAAAUAAGAGAGAAAAGAAGAGUAAGAAGA AAUAUAAGA (SEQ ID NO: 103).

In other embodiments, the GC-rich element comprises the sequence V1 as set forth in Table 2 located 1-3, 3-5, 5-7, 7-9, 9-12, or 12-15 bases upstream of the Kozak consensus sequence in the 5' UTR of the mRNA, wherein the 5' UTR comprises the following sequence shown in Table 2: GGGAAAUAAGAGAGAAAAGAAGAGUAAGAAGA AAUAUAAGA (SEQ ID NO: 103).

In some embodiments, the 5' UTR comprises the following sequence set forth in Table 2:

(SEQ ID NO: 13)
GGGAAAUAAGAGAGAAAAGAAGAGUAAGAAGAAAUAUAAGACCCCGGCGC
CGCCACC

TABLE 2

| 5' UTRs | 5' UTR Sequence |
|---|---|
| Standard | GGGAAAUAAGAGAGAAAAGAAGAGU AAGAAGAAAUAUAAGAGCCACC (SEQ ID NO: 108) |
| V1-UTR | GGGAAAUAAGAGAGAAAAGAAGAGU AAGAAGAAAUAUAAGACCCCGGCGC CGCCACC (SEQ ID NO: 13) |
| V2-UTR | GGGAAAUAAGAGAGAAAAGAAGAGUAA GAAGAAAUAUAAGACCCCGGCGCCACC (SEQ ID NO: 106) |

TABLE 2-continued

| GC-Rich RNA Elements | Sequence |
|---|---|
| K0 (Traditional Kozak consensus) | [GCCA/GCC] (SEQ ID NO: 107) |
| EK | [GCCGCC] (SEQ ID NO: 102) |
| V1 | [CCCCGGCGCC] (SEQ ID NO: 100) |
| V2 | [CCCCGGC] (SEQ ID NO: 101) |
| $(CCG)_n$, where n = 1-10 | $[CCG]_n$ |
| $(GCC)_n$, where n = 1-10 | $[GCC]_n$ |

In another aspect, the disclosure provides a modified mRNA comprising at least one modification, wherein at least one modification is a GC-rich RNA element comprising a stable RNA secondary structure comprising a sequence of nucleotides, or derivatives or analogs thereof, linked in an order which forms a hairpin or a stem-loop. In one embodiment, the stable RNA secondary structure is upstream of the Kozak consensus sequence. In another embodiment, the stable RNA secondary structure is located about 30, about 25, about 20, about 15, about 10, or about 5 nucleotides upstream of the Kozak consensus sequence. In another embodiment, the stable RNA secondary structure is located about 20, about 15, about 10 or about 5 nucleotides upstream of the Kozak consensus sequence. In another embodiment, the stable RNA secondary structure is located about 5, about 4, about 3, about 2, about 1 nucleotides upstream of the Kozak consensus sequence. In another embodiment, the stable RNA secondary structure is located about 15-30, about 15-20, about 15-25, about 10-15, or about 5-10 nucleotides upstream of the Kozak consensus sequence. In another embodiment, the stable RNA secondary structure is located 12-15 nucleotides upstream of the Kozak consensus sequence. In another embodiment, the stable RNA secondary structure has a deltaG of about −30 kcal/mol, about −20 to −30 kcal/mol, about −20 kcal/mol, about −10 to −20 kcal/mol, about −10 kcal/mol, about −5 to −10 kcal/mol.

In another embodiment, the modification is operably linked to an open reading frame encoding a polypeptide and wherein the modification and the open reading frame are heterologous.

In another embodiment, the sequence of the GC-rich RNA element is comprised exclusively of guanine (G) and cytosine (C) nucleobases.

RNA elements that provide a desired translational regulatory activity as described herein can be identified and characterized using known techniques, such as ribosome profiling. Ribosome profiling is a technique that allows the determination of the positions of PICs and/or ribosomes bound to mRNAs (see e.g., Ingolia et al., (2009) Science 324(5924):218-23, incorporated herein by reference). The technique is based on protecting a region or segment of mRNA, by the PIC and/or ribosome, from nuclease digestion. Protection results in the generation of a 30-bp fragment of RNA termed a 'footprint'. The sequence and frequency of RNA footprints can be analyzed by methods known in the art (e.g., RNA-seq). The footprint is roughly centered on the A-site of the ribosome. If the PIC or ribosome dwells at a particular position or location along an mRNA, footprints generated at these position would be relatively common. Studies have shown that more footprints are generated at positions where the PIC and/or ribosome exhibits decreased processivity and fewer footprints where the PIC and/or ribosome exhibits increased processivity (Gardin et al., (2014) eLife 3:e03735). In some embodiments, residence time or the time of occupancy of the PIC or ribosome at a discrete position or location along an polynucleotide comprising any one or more of the RNA elements described herein is determined by ribosome profiling.

A UTR can be homologous or heterologous to the coding region in a polynucleotide. In some embodiments, the UTR is homologous to the ORF encoding the antibody. In some embodiments, the UTR is heterologous to the ORF encoding the antibody. In some embodiments, the polynucleotide comprises two or more 5'UTRs or functional fragments thereof, each of which have the same or different nucleotide sequences. In some embodiments, the polynucleotide comprises two or more 3'UTRs or functional fragments thereof, each of which have the same or different nucleotide sequences.

In some embodiments, the 5'UTR or functional fragment thereof, 3' UTR or functional fragment thereof, or any combination thereof is sequence optimized.

In some embodiments, the 5'UTR or functional fragment thereof, 3' UTR or functional fragment thereof, or any combination thereof comprises at least one chemically modified nucleobase, e.g., N1 methylpseudouracil or 5-methoxyuracil.

UTRs can have features that provide a regulatory role, e.g., increased or decreased stability, localization and/or translation efficiency. A polynucleotide comprising a UTR can be administered to a cell, tissue, or organism, and one or more regulatory features can be measured using routine methods. In some embodiments, a functional fragment of a 5'UTR or 3'UTR comprises one or more regulatory features of a full length 5' or 3' UTR, respectively.

Natural 5'UTRs bear features that play roles in translation initiation. They harbor signatures like Kozak sequences that are commonly known to be involved in the process by which the ribosome initiates translation of many genes. Kozak sequences have the consensus CCR(A/G)CCAUGG (SEQ ID NO: 231, where R is a purine (adenine or guanine) three bases upstream of the start codon (AUG), which is followed by another 'G'. 5'UTRs also have been known to form secondary structures that are involved in elongation factor binding.

By engineering the features typically found in abundantly expressed genes of specific target organs, one can enhance the stability and protein production of a polynucleotide. For example, introduction of 5'UTR of liver-expressed mRNA, such as albumin, serum amyloid A, Apolipoprotein A/B/E, transferrin, alpha fetoprotein, erythropoietin, or antibody, can enhance expression of polynucleotides in hepatic cell lines or liver. Likewise, use of 5'UTR from other tissue-specific mRNA to improve expression in that tissue is possible for muscle (e.g., MyoD, Myosin, Myoglobin, Myogenin, Herculin), for endothelial cells (e.g., Tie-1, CD36), for myeloid cells (e.g., C/EBP, AML1, G-CSF, GM-CSF, CD11b, MSR, Fr-1, i-NOS), for leukocytes (e.g., CD45, CD18), for adipose tissue (e.g., CD36, GLUT4, ACRP30, adiponectin) and for lung epithelial cells (e.g., SP-A/B/C/D).

In some embodiments, UTRs are selected from a family of transcripts whose proteins share a common function, structure, feature or property. For example, an encoded polypeptide can belong to a family of proteins (i.e., that share at least one function, structure, feature, localization, origin, or expression pattern), which are expressed in a particular cell, tissue or at some time during development. The UTRs from any of the genes or mRNA can be swapped for any other UTR of the same or different family of proteins to create a new polynucleotide.

In some embodiments, the 5'UTR and the 3'UTR can be heterologous. In some embodiments, the 5'UTR can be derived from a different species than the 3'UTR. In some embodiments, the 3'UTR can be derived from a different species than the 5'UTR.

Co-owned International Patent Application No. PCT/US2014/021522 (Publ. No. WO/2014/164253, incorporated herein by reference in its entirety) provides a listing of exemplary UTRs that can be utilized in the polynucleotide of the present disclosure as flanking regions to an ORF.

Exemplary UTRs of the application include, but are not limited to, one or more 5'UTR and/or 3'UTR derived from the nucleic acid sequence of: a globin, such as an α- or β-globin (e.g., a *Xenopus*, mouse, rabbit, or human globin); a strong Kozak translational initiation signal; a CYBA (e.g., human cytochrome b-245 α polypeptide); an albumin (e.g., human albumin7); a HSD17B4 (hydroxysteroid (17-β) dehydrogenase); a virus (e.g., a tobacco etch virus (TEV), a Venezuelan equine encephalitis virus (VEEV), a Dengue virus, a cytomegalovirus (CMV) (e.g., CMV immediate early 1 (IE1)), a hepatitis virus (e.g., hepatitis B virus), a sindbis virus, or a PAV barley yellow dwarf virus); a heat shock protein (e.g., hsp70); a translation initiation factor (e.g., elF4G); a glucose transporter (e.g., hGLUT1 (human glucose transporter 1)); an actin (e.g., human α or β actin); a GAPDH; a tubulin; a histone; a citric acid cycle enzyme; a topoisomerase (e.g., a 5'UTR of a TOP gene lacking the 5' TOP motif (the oligopyrimidine tract)); a ribosomal protein Large 32 (L32); a ribosomal protein (e.g., human or mouse ribosomal protein, such as, for example, rps9); an ATP synthase (e.g., ATP5A1 or the β subunit of mitochondrial $H^+$-ATP synthase); a growth hormone e (e.g., bovine (bGH) or human (hGH)); an elongation factor (e.g., elongation factor 1 α1 (EEF1A1)); a manganese superoxide dismutase (MnSOD); a myocyte enhancer factor 2A (MEF2A); a β-F1-ATPase, a creatine kinase, a myoglobin, a granulocyte-colony stimulating factor (G-CSF); a collagen (e.g., collagen type I, alpha 2 (Col1A2), collagen type I, alpha 1 (Col1A1), collagen type VI, alpha 2 (Col6A2), collagen type VI, alpha 1 (Col6A1)); a ribophorin (e.g., ribophorin I (RPNI)); a low density lipoprotein receptor-related protein (e.g., LRP1); a cardiotrophin-like cytokine factor (e.g., Nnt1); calreticulin (Calr); a procollagen-lysine, 2-oxoglutarate 5-dioxygenase 1 (Plod1); and a nucleobindin (e.g., Nucb1).

In some embodiments, the 5'UTR is selected from the group consisting of a β-globin 5'UTR; a 5'UTR containing a strong Kozak translational initiation signal; a cytochrome b-245 α polypeptide (CYBA) 5'UTR; a hydroxysteroid (17-β) dehydrogenase (HSD17B4) 5'UTR; a Tobacco etch virus (TEV) 5'UTR; a Venezuelen equine encephalitis virus (TEEV) 5'UTR; a 5' proximal open reading frame of rubella virus (RV) RNA encoding nonstructural proteins; a Dengue virus (DEN) 5'UTR; a heat shock protein 70 (Hsp70) 5'UTR; a eIF4G 5'UTR; a GLUT1 5'UTR; functional fragments thereof and any combination thereof.

In some embodiments, the 3'UTR is selected from the group consisting of a β-globin 3'UTR; a CYBA 3'UTR; an albumin 3'UTR; a growth hormone (GH) 3'UTR; a VEEV 3'UTR; a hepatitis B virus (HBV) 3'UTR; α-globin 3'UTR; a DEN 3'UTR; a PAV barley yellow dwarf virus (BYDV-PAV) 3'UTR; an elongation factor 1 α1 (EEF1A1) 3'UTR; a manganese superoxide dismutase (MnSOD) 3'UTR; a β subunit of mitochondrial H(+)-ATP synthase (β-mRNA)

3'UTR; a GLUT1 3'UTR; a MEF2A 3'UTR; a β-F1-ATPase 3'UTR; functional fragments thereof and combinations thereof.

Wild-type UTRs derived from any gene or mRNA can be incorporated into the polynucleotides of the present disclosure. In some embodiments, a UTR can be altered relative to a wild type or native UTR to produce a variant UTR, e.g., by changing the orientation or location of the UTR relative to the ORF; or by inclusion of additional nucleotides, deletion of nucleotides, swapping or transposition of nucleotides. In some embodiments, variants of 5' or 3' UTRs can be utilized, for example, mutants of wild type UTRs, or variants wherein one or more nucleotides are added to or removed from a terminus of the UTR.

Additionally, one or more synthetic UTRs can be used in combination with one or more non-synthetic UTRs. See, e.g., Mandal and Rossi, Nat. Protoc. 2013 8(3):568-82, the contents of which are incorporated herein by reference in their entirety.

UTRs or portions thereof can be placed in the same orientation as in the transcript from which they were selected or can be altered in orientation or location. Hence, a 5' and/or 3' UTR can be inverted, shortened, lengthened, or combined with one or more other 5' UTRs or 3' UTRs.

In some embodiments, the polynucleotide comprises multiple UTRs, e.g., a double, a triple or a quadruple 5'UTR or 3'UTR. For example, a double UTR comprises two copies of the same UTR either in series or substantially in series. For example, a double beta-globin 3'UTR can be used (see US2010/0129877, the contents of which are incorporated herein by reference in its entirety).

In certain embodiments, the polynucleotides of the invention comprise a 5' UTR and/or a 3' UTR selected from any of the UTRs disclosed herein. In some embodiments, the 5' UTR comprises:

5' UTR-001 (Upstream UTR) (SEQ ID NO: 108)
(GGGAAAUAAGAGAGAAAAGAAGAGUAAGAAGAAAUAUAAGAGCCACC);

5' UTR-002 (Upstream UTR) (SEQ ID NO: 109)
(GGGAGAUCAGAGAGAAAAGAAGAGUAAGAAGAAAUAUAAGAGCCACC);

5' UTR-003 (Upstream UTR) (SEQ ID NO: 110)
(See WO2016/100812);

5' UTR-004 (Upstream UTR) (SEQ ID NO: 111)
(GGGAGACAAGCUUGGCAUUCCGGUACUGUUGGUAAAGCCACC);

5' UTR-005 (Upstream UTR) (SEQ ID NO: 109)
(GGGAGAUCAGAGAGAAAAGAAGAGUAAGAAGAAAUAUAAGAGCCACC);

5' UTR-006 (Upstream UTR) (SEQ ID NO: 113)
(See WO2016/100812);

5' UTR-007 (Upstream UTR) (SEQ ID NO: 111)
(GGGAGACAAGCUUGGCAUUCCGGUACUGUUGGUAAAGCCACC);

5' UTR-008 (Upstream UTR) (SEQ ID NO: 115)
(GGGAAUUAACAGAGAAAAGAAGAGUAAGAAGAAAUAUAAGAGCCACC);

5' UTR-009 (Upstream UTR) (SEQ ID NO: 116)
(GGGAAAUUAGACAGAAAAGAAGAGUAAGAAGAAAUAUAAGAGCCACC);

-continued

5' UTR-010, Upstream (SEQ ID NO: 117)
(GGGAAAUAAGAGAGUAAAGAACAGUAAGAAGAAAUAUAAGAGCCACC);

5' UTR-011 (Upstream UTR) (SEQ ID NO: 118)
(GGGAAAAAAGAGAGAAAAGAAGACUAAGAAGAAAUAUAAGAGCCACC);

5' UTR-012 (Upstream UTR) (SEQ ID NO: 119)
(GGGAAAUAAGAGAGAAAAGAAGAGUAAGAAGAUAUAUAAGAGCCACC);

5' UTR-013 (Upstream UTR) (SEQ ID NO: 120)
(GGGAAAUAAGAGACAAAACAAGAGUAAGAAGAAAUAUAAGAGCCACC);

5' UTR-014 (Upstream UTR) (SEQ ID NO: 121)
(GGGAAAUUAGAGAGUAAAGAACAGUAAGUAGAAUUAAAAGAGCCACC);

5' UTR-015 (Upstream UTR) (SEQ ID NO: 122)
(GGGAAAUAAGAGAGAAUAGAAGAGUAAGAAGAAAUAUAAGAGCCACC);

5' UTR-016 (Upstream UTR) (SEQ ID NO: 123)
(GGGAAAUAAGAGAGAAAAGAAGAGUAAGAAGAAAAUUAAGAGCCACC);

5' UTR-017 (Upstream UTR);
or (SEQ ID NO: 124)
(GGGAAAUAAGAGAGAAAAGAAGAGUAAGAAGAAAUUUAAGAGCCACC);

5' UTR-018 (Upstream UTR) 5' UTR (SEQ ID NO: 126)
(UCAAGCUUUUGGACCCUCGUACAGAAGCUAAUACGACUCACUAUAGGG
AAAUAAGAGAGAAAAGAAGAGUAAGAAGAAAUAUAAGAGCCACC).

In some embodiments, the 3' UTR comprises:

142-3p 3' UTR
(UTR including miR142-3p binding site) (SEQ ID NO: 127)
(UGAUAAUAGUCCAUAAAGUAGGAAACACUACAGCUGGAGCCUCGGUGGC
CAUGCUUCUUGCCCCUUGGGCCUCCCCCCAGCCCCUCCUCCCCUUCCUGC
ACCCGUACCCCCGUGGUCUUUGAAUAAAGUCUGAGUGGGCGGC);

142-3p 3' UTR
(UTR including miR142-3p binding site) (SEQ ID NO: 128)
(UGAUAAUAGGCUGGAGCCUCGGUGGCUCCAUAAAGUAGGAAACACUACA
CAUGCUUCUUGCCCCUUGGGCCUCCCCCCAGCCCCUCCUCCCCUUCCUGC
ACCCGUACCCCCGUGGUCUUUGAAUAAAGUCUGAGUGGGCGGC);
or 142-3p 3' UTR
(UTR including miR142-3p binding site) (SEQ ID NO: 129)
(UGAUAAUAGGCUGGAGCCUCGGUGGCCAUGCUUCUUGCCCCUUCCAUAA
AGUAGGAAACACUACAUGGGCCUCCCCCCAGCCCCUCCUCCCCUUCCUGC
ACCCGUACCCCCGUGGUCUUUGAAUAAAGUCUGAGUGGGCGGC);

142-3p 3' UTR
(UTR including miR142-3p binding site) (SEQ ID NO: 130)
(UGAUAAUAGGCUGGAGCCUCGGUGGCCAUGCUUCUUGCCCCUUGGGCCU
CCCCCCAGUCCAUAAAGUAGGAAACACUACACCCCUCCUCCCCUUCCUGC
ACCCGUACCCCCGUGGUCUUUGAAUAAAGUCUGAGUGGGCGGC);

-continued 142-3p 3' UTR
(UTR including miR142-3p binding site)
(SEQ ID NO: 131)
(UGAUAAUAGGCUGGAGCCUCGGUGGCCAUGCUUCUUGCCCCUUGGGCCU

CCCCCCAGCCCCUCCUCCCCUUCUCCAUAAAGUAGGAAACACUACACUGC

ACCCGUACCCCCGUGGUCUUUGAAUAAAGUCUGAGUGGGCGGC);

142-3p 3' UTR
(UTR including miR142-3p binding site)
(SEQ ID NO: 132)
(UGAUAAUAGGCUGGAGCCUCGGUGGCCAUGCUUCUUGCCCCUUGGGCCU

CCCCCCAGCCCCUCCUCCCCUUCCUGCACCCGUACCCCCUCCAUAAAGUA

GGAAACACUACAGUGGUCUUUGAAUAAAGUCUGAGUGGGCGGC).

142-3p 3' UTR
(UTR including miR142-3p binding site)
(SEQ ID NO: 133)
(UGAUAAUAGGCUGGAGCCUCGGUGGCCAUGCUUCUUGCCCCUUGGGCCU

CCCCCCAGCCCCUCCUCCCCUUCCUGCACCCGUACCCCCGUGGUCUUUGA

AUAAAGUUCCAUAAAGUAGGAAACACUACACUGAGUGGGCGGC);

3'UTR-018 (See SEQ ID NO: 134)

3' UTR (miR142 and miR126 binding sites variant 1)
(SEQ ID NO: 135)
(UGAUAAUAGUCCAUAAAGUAGGAAACACUACAGCUGGAGCCUCGGUGGC

CAUGCUUCUUGCCCCUUGGGCCUCCCCCCAGCCCCUCCUCCCCUUCCUGC

ACCCGUACCCCCCGCAUUAUUACUCACGGUACGAGUGGUCUUUGAAUAAA

GUCUGAGUGGGCGGC)

3' UTR (miR142 and miR126 binding sites variant 2)
(SEQ ID NO: 136)
(UGAUAAUAGUCCAUAAAGUAGGAAACACUACAGCUGGAGCCUCGGUGGC

CUAGCUUCUUGCCCCUUGGGCCUCCCCCCAGCCCCUCCUCCCCUUCCUGC

ACCCGUACCCCCCGCAUUAUUACUCACGGUACGAGUGGUCUUUGAAUAAA

GUCUGAGUGGGCGGC);
or

3' UTR (miR142-3p binding site variant 3)
(SEQ ID NO: 137)
UGAUAAUAGGCUGGAGCCUCGGUGGCCUAGCUUCUUGCCCCUUGGGCCUC

CCCCCAGCCCCUCCUCCCCUUCCUGCACCCGUACCCCCUCCAUAAAGUAG

GAAACACUACAGUGGUCUUUGAAUAAAGUCUGAGUGGGCGGC.

3' UTR (miR142-3p binding site variant 3.
DNA sequence)
(SEQ ID NO: 138)
TGATAATAGGCTGGAGCCTCGGTGGCCTAGCTTCTTGCCCCTTGGGCCTC

CCCCCAGCCCCTCCTCCCCTTCCTGCACCCGTACCCCCTCCATAAAGTAG

GAAACACTACAGTGGTCTTTGAATAAAGTCTGAGTGGGCGGC.

In certain embodiments, the 5'UTR and/or 3'UTR sequence of the present disclosure comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 5'UTR sequences comprising any of SEQ ID NOs: 13 and 108-126 and/or 3'UTR sequences comprises any of SEQ ID NOs: 14 and 127-138, and any combination thereof. In certain embodiments, the 5' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to SEQ ID NO: 13. In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to SEQ ID NO: 14.

The polynucleotides of the present disclosure can comprise combinations of features. For example, the ORF can be flanked by a 5'UTR that comprises a strong Kozak translational initiation signal and/or a 3'UTR comprising an oligo (dT) sequence for templated addition of a poly-A tail. A 5'UTR can comprise a first polynucleotide fragment and a second polynucleotide fragment from the same and/or different UTRs (see, e.g., US2010/0293625, herein incorporated by reference in its entirety).

Other non-UTR sequences can be used as regions or subregions within the polynucleotides of the present disclosure. For example, introns or portions of intron sequences can be incorporated into the polynucleotides of the present disclosure. Incorporation of intronic sequences can increase protein production as well as polynucleotide expression levels. In some embodiments, the polynucleotide of the present disclosure comprises an internal ribosome entry site (IRES) instead of or in addition to a UTR (see, e.g., Yakubov et al., Biochem. Biophys. Res. Commun. 2010 394(1):189-193, the contents of which are incorporated herein by reference in their entirety). In some embodiments, the polynucleotide comprises an IRES instead of a 5'UTR sequence. In some embodiments, the polynucleotide comprises an ORF and a viral capsid sequence. In some embodiments, the polynucleotide comprises a synthetic 5'UTR in combination with a non-synthetic 3'UTR.

In some embodiments, the UTR can also include at least one translation enhancer polynucleotide, translation enhancer element, or translational enhancer elements (collectively, "TEE," which refers to nucleic acid sequences that increase the amount of polypeptide or protein produced from a polynucleotide. As a non-limiting example, the TEE can be located between the transcription promoter and the start codon. In some embodiments, the 5'UTR comprises a TEE.

In one aspect, a TEE is a conserved element in a UTR that can promote translational activity of a nucleic acid such as, but not limited to, cap-dependent or cap-independent translation.

In some embodiments, a 5'UTR and/or 3'UTR comprising at least one TEE described herein can be incorporated in a monocistronic sequence such as, but not limited to, a vector system or a nucleic acid vector.

In some embodiments, a 5'UTR and/or 3'UTR of a polynucleotide of the present disclosure comprises a TEE or portion thereof described herein. In some embodiments, the TEEs in the 3'UTR can be the same and/or different from the TEE located in the 5'UTR.

In some embodiments, a 5'UTR and/or 3'UTR of a polynucleotide of the present disclosure can include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18 at least 19, at least 20, at least 21, at least 22, at least 23, at least 24, at least 25, at least 30, at least 35, at least 40, at least 45, at least 50, at least 55 or more than 60 TEE sequences. In one embodiment, the 5'UTR of a polynucleotide of the present disclosure can include 1-60, 1-55, 1-50, 1-45, 1-40, 1-35, 1-30, 1-25, 1-20, 1-15, 1-10, 9, 8, 7, 6, 5, 4, 3, 2, or 1 TEE sequences. The TEE sequences in the 5'UTR of the polynucleotide of the present disclosure can be the same or different TEE sequences. A combination of different TEE sequences in the 5'UTR of the polynucleotide of the present disclosure can include combinations in which more than one copy of any of the different TEE sequences are incorporated.

In some embodiments, the 5'UTR and/or 3'UTR comprises a spacer to separate two TEE sequences. As a non-limiting example, the spacer can be a 15 nucleotide spacer and/or other spacers known in the art. As another non-limiting example, the 5'UTR and/or 3'UTR comprises a TEE sequence-spacer module repeated at least once, at least twice, at least 3 times, at least 4 times, at least 5 times, at least 6 times, at least 7 times, at least 8 times, at least 9 times, at least 10 times, or more than 10 times in the 5'UTR and/or 3'UTR, respectively. In some embodiments, the 5'UTR and/or 3'UTR comprises a TEE sequence-spacer module repeated 1, 2, 3, 4, 5, 6, 7, 8, 9, or 10 times.

In some embodiments, the spacer separating two TEE sequences can include other sequences known in the art that can regulate the translation of the polynucleotide of the present disclosure, e.g., miR binding site sequences described herein (e.g., miR binding sites and miR seeds). As a non-limiting example, each spacer used to separate two TEE sequences can include a different miR binding site sequence or component of a miR sequence (e.g., miR seed sequence).

In some embodiments, a polynucleotide of the present disclosure comprises a miR and/or TEE sequence. In some embodiments, the incorporation of a miR sequence and/or a TEE sequence into a polynucleotide of the present disclosure can change the shape of the stem loop region, which can increase and/or decrease translation. See e.g., Kedde et al., Nature Cell Biology 2010 12(10):1014-20, herein incorporated by reference in its entirety).

11. MicroRNA (miRNA) Binding Sites

Polynucleotides of the present disclosure can include regulatory elements, for example, microRNA (miRNA) binding sites, transcription factor binding sites, structured mRNA sequences and/or motifs, artificial binding sites engineered to act as pseudo-receptors for endogenous nucleic acid binding molecules, and combinations thereof. In some embodiments, polynucleotides including such regulatory elements are referred to as including "sensor sequences".

In some embodiments, a polynucleotide (e.g., a ribonucleic acid (RNA), e.g., a messenger RNA (mRNA)) of the present disclosure comprises an open reading frame (ORF) encoding a polypeptide of interest and further comprises one or more miRNA binding site(s). Inclusion or incorporation of miRNA binding site(s) provides for regulation of polynucleotides of the present disclosure, and in turn, of the polypeptides encoded therefrom, based on tissue-specific and/or cell-type specific expression of naturally-occurring miRNAs.

A miRNA, e.g., a natural-occurring miRNA, is a 19-25 nucleotide long noncoding RNA that binds to a polynucleotide and down-regulates gene expression either by reducing stability or by inhibiting translation of the polynucleotide. A miRNA sequence comprises a "seed" region, i.e., a sequence in the region of positions 2-8 of the mature miRNA. A miRNA seed can comprise positions 2-8 or 2-7 of the mature miRNA.

microRNAs derive enzymatically from regions of RNA transcripts that fold back on themselves to form short hairpin structures often termed a pre-miRNA (precursor-miRNA). A pre-miRNA typically has a two-nucleotide overhang at its 3' end, and has 3' hydroxyl and 5' phosphate groups. This precursor-mRNA is processed in the nucleus and subsequently transported to the cytoplasm where it is further processed by DICER (a RNase III enzyme), to form a mature microRNA of approximately 22 nucleotides. The mature microRNA is then incorporated into a ribonuclear particle to form the RNA-induced silencing complex, RISC, which mediates gene silencing. Art-recognized nomenclature for mature miRNAs typically designates the arm of the pre-miRNA from which the mature miRNA derives; "5p" means the microRNA is from the 5 prime arm of the pre-miRNA hairpin and "3p" means the microRNA is from the 3 prime end of the pre-miRNA hairpin. A miR referred to by number herein can refer to either of the two mature microRNAs originating from opposite arms of the same pre-miRNA (e.g., either the 3p or 5p microRNA). All miRs referred to herein are intended to include both the 3p and 5p arms/sequences, unless particularly specified by the 3p or 5p designation.

As used herein, the term "microRNA (miRNA or miR) binding site" refers to a sequence within a polynucleotide, e.g., within a DNA or within an RNA transcript, including in the 5'UTR and/or 3'UTR, that has sufficient complementarity to all or a region of a miRNA to interact with, associate with or bind to the miRNA. In some embodiments, a polynucleotide of the present disclosure comprising an ORF encoding a polypeptide of interest and further comprises one or more miRNA binding site(s). In exemplary embodiments, a 5'UTR and/or 3'UTR of the polynucleotide (e.g., a ribonucleic acid (RNA), e.g., a messenger RNA (mRNA)) comprises the one or more miRNA binding site(s).

A miRNA binding site having sufficient complementarity to a miRNA refers to a degree of complementarity sufficient to facilitate miRNA-mediated regulation of a polynucleotide, e.g., miRNA-mediated translational repression or degradation of the polynucleotide. In exemplary aspects of the present disclosure, a miRNA binding site having sufficient complementarity to the miRNA refers to a degree of complementarity sufficient to facilitate miRNA-mediated degradation of the polynucleotide, e.g., miRNA-guided RNA-induced silencing complex (RISC)-mediated cleavage of mRNA. The miRNA binding site can have complementarity to, for example, a 19-25 nucleotide miRNA sequence, to a 19-23 nucleotide miRNA sequence, or to a 22 nucleotide miRNA sequence. A miRNA binding site can be complementary to only a portion of a miRNA, e.g., to a portion less than 1, 2, 3, or 4 nucleotides of the full length of a naturally-occurring miRNA sequence. Full or complete complementarity (e.g., full complementarity or complete complementarity over all or a significant portion of the length of a naturally-occurring miRNA) is preferred when the desired regulation is mRNA degradation.

In some embodiments, a miRNA binding site includes a sequence that has complementarity (e.g., partial or complete complementarity) with an miRNA seed sequence. In some embodiments, the miRNA binding site includes a sequence that has complete complementarity with a miRNA seed sequence. In some embodiments, a miRNA binding site includes a sequence that has complementarity (e.g., partial or complete complementarity) with an miRNA sequence. In some embodiments, the miRNA binding site includes a sequence that has complete complementarity with a miRNA sequence. In some embodiments, a miRNA binding site has complete complementarity with a miRNA sequence but for 1, 2, or 3 nucleotide substitutions, terminal additions, and/or truncations.

In some embodiments, the miRNA binding site is the same length as the corresponding miRNA. In other embodiments, the miRNA binding site is one, two, three, four, five, six, seven, eight, nine, ten, eleven or twelve nucleotide(s) shorter than the corresponding miRNA at the 5' terminus, the 3' terminus, or both. In still other embodiments, the microRNA binding site is two nucleotides shorter than the corresponding microRNA at the 5' terminus, the 3' terminus, or both. The miRNA binding sites that are shorter than the corresponding miRNAs are still capable of degrading the mRNA incorporating one or more of the miRNA binding sites or preventing the mRNA from translation.

In some embodiments, the miRNA binding site binds the corresponding mature miRNA that is part of an active RISC containing Dicer. In another embodiment, binding of the miRNA binding site to the corresponding miRNA in RISC degrades the mRNA containing the miRNA binding site or prevents the mRNA from being translated. In some embodiments, the miRNA binding site has sufficient complementarity to miRNA so that a RISC complex comprising the miRNA cleaves the polynucleotide comprising the miRNA binding site. In other embodiments, the miRNA binding site has imperfect complementarity so that a RISC complex comprising the miRNA induces instability in the polynucleotide comprising the miRNA binding site. In another embodiment, the miRNA binding site has imperfect complementarity so that a RISC complex comprising the miRNA represses transcription of the polynucleotide comprising the miRNA binding site.

In some embodiments, the miRNA binding site has one, two, three, four, five, six, seven, eight, nine, ten, eleven or twelve mismatch(es) from the corresponding miRNA.

In some embodiments, the miRNA binding site has at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one contiguous nucleotides complementary to at least about ten, at least about eleven, at least about twelve, at least about thirteen, at least about fourteen, at least about fifteen, at least about sixteen, at least about seventeen, at least about eighteen, at least about nineteen, at least about twenty, or at least about twenty-one, respectively, contiguous nucleotides of the corresponding miRNA.

By engineering one or more miRNA binding sites into a polynucleotide of the present disclosure, the polynucleotide can be targeted for degradation or reduced translation, provided the miRNA in question is available. This can reduce off-target effects upon delivery of the polynucleotide. For example, if a polynucleotide of the present disclosure is not intended to be delivered to a tissue or cell but ends up is said tissue or cell, then a miRNA abundant in the tissue or cell can inhibit the expression of the gene of interest if one or multiple binding sites of the miRNA are engineered into the 5'UTR and/or 3'UTR of the polynucleotide. Thus, in some embodiments, incorporation of one or more miRNA binding sites into an mRNA of the disclosure may reduce the hazard of off-target effects upon nucleic acid molecule delivery and/or enable tissue-specific regulation of expression of a polypeptide encoded by the mRNA. In yet other embodiments, incorporation of one or more miRNA binding sites into an mRNA of the disclosure can modulate immune responses upon nucleic acid delivery in vivo. In further embodiments, incorporation of one or more miRNA binding sites into an mRNA of the disclosure can modulate accelerated blood clearance (ABC) of lipid-comprising compounds and compositions described herein.

Conversely, miRNA binding sites can be removed from polynucleotide sequences in which they naturally occur in order to increase protein expression in specific tissues. For example, a binding site for a specific miRNA can be removed from a polynucleotide to improve protein expression in tissues or cells containing the miRNA.

Regulation of expression in multiple tissues can be accomplished through introduction or removal of one or more miRNA binding sites, e.g., one or more distinct miRNA binding sites. The decision whether to remove or insert a miRNA binding site can be made based on miRNA expression patterns and/or their profilings in tissues and/or cells in development and/or disease. Identification of miRNAs, miRNA binding sites, and their expression patterns and role in biology have been reported (e.g., Bonauer et al., Curr Drug Targets 2010 11:943-949; Anand and Cheresh Curr Opin Hematol 2011 18:171-176; Contreras and Rao Leukemia 2012 26:404-413 (2011 Dec. 20. doi: 10.1038/leu.2011.356); Bartel Cell 2009 136:215-233; Landgraf et al, Cell, 2007 129:1401-1414; Gentner and Naldini, Tissue Antigens. 2012 80:393-403 and all references therein; each of which is incorporated herein by reference in its entirety).

Examples of tissues where miRNA are known to regulate mRNA, and thereby protein expression, include, but are not limited to, liver (miR-122), muscle (miR-133, miR-206, miR-208), endothelial cells (miR-17-92, miR-126), myeloid cells (miR-142-3p, miR-142-5p, miR-16, miR-21, miR-223, miR-24, miR-27), adipose tissue (let-7, miR-30c), heart (miR-1d, miR-149), kidney (miR-192, miR-194, miR-204), and lung epithelial cells (let-7, miR-133, miR-126).

Specifically, miRNAs are known to be differentially expressed in immune cells (also called hematopoietic cells), such as antigen presenting cells (APCs) (e.g., dendritic cells and macrophages), macrophages, monocytes, B lymphocytes, T lymphocytes, granulocytes, natural killer cells, etc. Immune cell specific miRNAs are involved in immunogenicity, autoimmunity, the immune-response to infection, inflammation, as well as unwanted immune response after gene therapy and tissue/organ transplantation. Immune cells specific miRNAs also regulate many aspects of development, proliferation, differentiation and apoptosis of hematopoietic cells (immune cells). For example, miR-142 and miR-146 are exclusively expressed in immune cells, particularly abundant in myeloid dendritic cells. It has been demonstrated that the immune response to a polynucleotide can be shut-off by adding miR-142 binding sites to the 3'-UTR of the polynucleotide, enabling more stable gene transfer in tissues and cells. miR-142 efficiently degrades exogenous polynucleotides in antigen presenting cells and suppresses cytotoxic elimination of transduced cells (e.g., Annoni A et al., blood, 2009, 114, 5152-5161; Brown B D, et al., Nat med. 2006, 12(5), 585-591; Brown B D, et al., blood, 2007, 110(13): 4144-4152, each of which is incorporated herein by reference in its entirety).

An antigen-mediated immune response can refer to an immune response triggered by foreign antigens, which, when entering an organism, are processed by the antigen presenting cells and displayed on the surface of the antigen presenting cells. T cells can recognize the presented antigen and induce a cytotoxic elimination of cells that express the antigen.

Introducing a miR-142 binding site into the 5'UTR and/or 3'UTR of a polynucleotide of the present disclosure can selectively repress gene expression in antigen presenting cells through miR-142 mediated degradation, limiting antigen presentation in antigen presenting cells (e.g., dendritic cells) and thereby preventing antigen-mediated immune response after the delivery of the polynucleotide. The polynucleotide is then stably expressed in target tissues or cells without triggering cytotoxic elimination.

In one embodiment, binding sites for miRNAs that are known to be expressed in immune cells, in particular, antigen presenting cells, can be engineered into a polynucleotide of the present disclosure to suppress the expression of the polynucleotide in antigen presenting cells through miRNA mediated RNA degradation, subduing the antigen-mediated immune response. Expression of the polynucleotide is maintained in non-immune cells where the immune cell specific miRNAs are not expressed. For example, in some embodiments, to prevent an immunogenic reaction against a liver specific protein, any miR-122 binding site can be removed and a miR-142 (and/or mirR-146) binding site can be engineered into the 5'UTR and/or 3'UTR of a polynucleotide of the present disclosure.

To further drive the selective degradation and suppression in APCs and macrophage, a polynucleotide of the present disclosure can include a further negative regulatory element in the 5'UTR and/or 3'UTR, either alone or in combination with miR-142 and/or miR-146 binding sites. As a non-limiting example, the further negative regulatory element is a Constitutive Decay Element (CDE).

Immune cell specific miRNAs include, but are not limited to, hsa-let-7a-2-3p, hsa-let-7a-3p, hsa-7a-5p, hsa-let-7c, hsa-let-7e-3p, hsa-let-7e-5p, hsa-let-7g-3p, hsa-let-7g-5p, hsa-let-7i-3p, hsa-let-7i-5p, miR-10a-3p, miR-10a-5p, miR-1184, hsa-let-7f-1-3p, hsa-let-7f-2-5p, hsa-let-7f-5p, miR-125b-1-3p, miR-125b-2-3p, miR-125b-5p, miR-1279, miR-130a-3p, miR-130a-5p, miR-132-3p, miR-132-5p, miR-142-3p, miR-142-5p, miR-143-3p, miR-143-5p, miR-146a-3p, miR-146a-5p, miR-146b-3p, miR-146b-5p, miR-147a, miR-147b, miR-148a-5p, miR-148a-3p, miR-150-3p, miR-150-5p, miR-151b, miR-155-3p, miR-155-5p, miR-15a-3p, miR-15a-5p, miR-15b-5p, miR-15b-3p, miR-16-1-3p, miR-16-2-3p, miR-16-5p, miR-17-5p, miR-181a-3p, miR-181a-5p, miR-181a-2-3p, miR-182-3p, miR-182-5p, miR-197-3p, miR-197-5p, miR-21-5p, miR-21-3p, miR-214-3p, miR-214-5p, miR-223-3p, miR-223-5p, miR-221-3p, miR-221-5p, miR-23b-3p, miR-23b-5p, miR-24-1-5p, miR-24-2-5p, miR-24-3p, miR-26a-1-3p, miR-26a-2-3p, miR-26a-5p, miR-26b-3p, miR-26b-5p, miR-27a-3p, miR-27a-5p, miR-27b-3p, miR-27b-5p, miR-28-3p, miR-28-5p, miR-2909, miR-29a-3p, miR-29a-5p, miR-29b-1-5p, miR-29b-2-5p, miR-29c-3p, miR-29c-5p, miR-30e-3p, miR-30e-5p, miR-331-5p, miR-339-3p, miR-339-5p, miR-345-3p, miR-345-5p, miR-346, miR-34a-3p, miR-34a-5p, miR-363-3p, miR-363-5p, miR-372, miR-377-3p, miR-377-5p, miR-493-3p, miR-493-5p, miR-542, miR-548b-5p, miR548c-5p, miR-548i, miR-548j, miR-548n, miR-574-3p, miR-598, miR-718, miR-935, miR-99a-3p, miR-99a-5p, miR-99b-3p, and miR-99b-5p. Furthermore, novel miRNAs can be identified in immune cell through micro-array hybridization and microtome analysis (e.g., Jima D D et al, Blood, 2010, 116:e118-e127; Vaz C et al., BMC Genomics, 2010, 11,288, the content of each of which is incorporated herein by reference in its entirety.)

miRNAs that are known to be expressed in the liver include, but are not limited to, miR-107, miR-122-3p, miR-122-5p, miR-1228-3p, miR-1228-5p, miR-1249, miR-129-5p, miR-1303, miR-151a-3p, miR-151a-5p, miR-152, miR-194-3p, miR-194-5p, miR-199a-3p, miR-199a-5p, miR-199b-3p, miR-199b-5p, miR-296-5p, miR-557, miR-581, miR-939-3p, and miR-939-5p. MiRNA binding sites from any liver specific miRNA can be introduced to or removed from a polynucleotide of the present disclosure to regulate expression of the polynucleotide in the liver. Liver specific miRNA binding sites can be engineered alone or further in combination with immune cell (e.g., APC) miRNA binding sites in a polynucleotide of the present disclosure.

miRNAs that are known to be expressed in the lung include, but are not limited to, let-7a-2-3p, let-7a-3p, let-7a-5p, miR-126-3p, miR-126-5p, miR-127-3p, miR-127-5p, miR-130a-3p, miR-130a-5p, miR-130b-3p, miR-130b-5p, miR-133a, miR-133b, miR-134, miR-18a-3p, miR-18a-5p, miR-18b-3p, miR-18b-5p, miR-24-1-5p, miR-24-2-5p, miR-24-3p, miR-296-3p, miR-296-5p, miR-32-3p, miR-337-3p, miR-337-5p, miR-381-3p, and miR-381-5p. miRNA binding sites from any lung specific miRNA can be introduced to or removed from a polynucleotide of the present disclosure to regulate expression of the polynucleotide in the lung. Lung specific miRNA binding sites can be engineered alone or further in combination with immune cell (e.g., APC) miRNA binding sites in a polynucleotide of the present disclosure.

miRNAs that are known to be expressed in the heart include, but are not limited to, miR-1, miR-133a, miR-133b, miR-149-3p, miR-149-5p, miR-186-3p, miR-186-5p, miR-208a, miR-208b, miR-210, miR-296-3p, miR-320, miR-451a, miR-451b, miR-499a-3p, miR-499a-5p, miR-499b-3p, miR-499b-5p, miR-744-3p, miR-744-5p, miR-92b-3p, and miR-92b-5p. miRNA binding sites from any heart specific microRNA can be introduced to or removed from a polynucleotide of the present disclosure to regulate expression of the polynucleotide in the heart. Heart specific miRNA binding sites can be engineered alone or further in combination with immune cell (e.g., APC) miRNA binding sites in a polynucleotide of the present disclosure.

miRNAs that are known to be expressed in the nervous system include, but are not limited to, miR-124-5p, miR-125a-3p, miR-125a-5p, miR-125b-1-3p, miR-125b-2-3p, miR-125b-5p, miR-1271-3p, miR-1271-5p, miR-128, miR-132-5p, miR-135a-3p, miR-135a-5p, miR-135b-3p, miR-135b-5p, miR-137, miR-139-5p, miR-139-3p, miR-149-3p, miR-149-5p, miR-153, miR-181c-3p, miR-181c-5p, miR-183-3p, miR-183-5p, miR-190a, miR-190b, miR-212-3p, miR-212-5p, miR-219-1-3p, miR-219-2-3p, miR-23a-3p, miR-23a-5p, miR-30a-5p, miR-30b-3p, miR-30b-5p, miR-30c-1-3p, miR-30c-2-3p, miR-30c-5p, miR-30d-3p, miR-30d-5p, miR-329, miR-342-3p, miR-3665, miR-3666, miR-380-3p, miR-380-5p, miR-383, miR-410, miR-425-3p, miR-425-5p, miR-454-3p, miR-454-5p, miR-483, miR-510, miR-516a-3p, miR-548b-5p, miR-548c-5p, miR-571, miR-7-1-3p, miR-7-2-3p, miR-7-5p, miR-802, miR-922, miR-9-3p, and miR-9-5p. miRNAs enriched in the nervous system further include those specifically expressed in neurons, including, but not limited to, miR-132-3p, miR-132-3p, miR-148b-3p, miR-148b-5p, miR-151a-3p, miR-151a-5p, miR-212-3p, miR-212-5p, miR-320b, miR-320e, miR-323a-3p, miR-323a-5p, miR-324-5p, miR-325, miR-326, miR-328, miR-922 and those specifically expressed in glial cells, including, but not limited to, miR-1250, miR-219-1-3p, miR-219-2-3p, miR-219-5p, miR-23a-3p, miR-23a-5p, miR-3065-3p, miR-3065-5p, miR-30e-3p, miR-30e-5p, miR-32-5p, miR-338-5p, and miR-657. miRNA binding sites from any CNS specific miRNA can be introduced to or removed from a polynucleotide of the present disclosure to regulate expression of the polynucleotide in the nervous system. Nervous system specific miRNA binding sites can be engineered alone or further in combination with immune cell (e.g., APC) miRNA binding sites in a polynucleotide of the present disclosure.

miRNAs that are known to be expressed in the pancreas include, but are not limited to, miR-105-3p, miR-105-5p, miR-184, miR-195-3p, miR-195-5p, miR-196a-3p, miR-196a-5p, miR-214-3p, miR-214-5p, miR-216a-3p, miR-216a-5p, miR-30a-3p, miR-33a-3p, miR-33a-5p, miR-375, miR-7-1-3p, miR-7-2-3p, miR-493-3p, miR-493-5p, and miR-944. MiRNA binding sites from any pancreas specific miRNA can be introduced to or removed from a polynucleotide of the present disclosure to regulate expression of the polynucleotide in the pancreas. Pancreas specific miRNA binding sites can be engineered alone or further in combination with immune cell (e.g. APC) miRNA binding sites in a polynucleotide of the present disclosure.

miRNAs that are known to be expressed in the kidney include, but are not limited to, miR-122-3p, miR-145-5p, miR-17-5p, miR-192-3p, miR-192-5p, miR-194-3p, miR-194-5p, miR-20a-3p, miR-20a-5p, miR-204-3p, miR-204-5p, miR-210, miR-216a-3p, miR-216a-5p, miR-296-3p, miR-30a-3p, miR-30a-5p, miR-30b-3p, miR-30b-5p, miR-30c-1-3p, miR-30c-2-3p, miR30c-5p, miR-324-3p, miR-335-3p, miR-335-5p, miR-363-3p, miR-363-5p, and miR-562. miRNA binding sites from any kidney specific miRNA can be introduced to or removed from a polynucleotide of the present disclosure to regulate expression of the polynucleotide in the kidney. Kidney specific miRNA binding sites can be engineered alone or further in combination with immune cell (e.g., APC) miRNA binding sites in a polynucleotide of the present disclosure.

miRNAs that are known to be expressed in the muscle include, but are not limited to, let-7g-3p, let-7g-5p, miR-1, miR-1286, miR-133a, miR-133b, miR-140-3p, miR-143-3p, miR-143-5p, miR-145-3p, miR-145-5p, miR-188-3p, miR-188-5p, miR-206, miR-208a, miR-208b, miR-25-3p, and miR-25-5p. MiRNA binding sites from any muscle specific miRNA can be introduced to or removed from a polynucleotide of the present disclosure to regulate expression of the polynucleotide in the muscle. Muscle specific miRNA binding sites can be engineered alone or further in combination with immune cell (e.g., APC) miRNA binding sites in a polynucleotide of the present disclosure.

miRNAs are also differentially expressed in different types of cells, such as, but not limited to, endothelial cells, epithelial cells, and adipocytes.

miRNAs that are known to be expressed in endothelial cells include, but are not limited to, let-7b-3p, let-7b-5p, miR-100-3p, miR-100-5p, miR-101-3p, miR-101-5p, miR-126-3p, miR-126-5p, miR-1236-3p, miR-1236-5p, miR-130a-3p, miR-130a-5p, miR-17-5p, miR-17-3p, miR-18a-3p, miR-18a-5p, miR-19a-3p, miR-19a-5p, miR-19b-1-5p, miR-19b-2-5p, miR-19b-3p, miR-20a-3p, miR-20a-5p, miR-217, miR-210, miR-21-3p, miR-21-5p, miR-221-3p, miR-221-5p, miR-222-3p, miR-222-5p, miR-23a-3p, miR-23a-5p, miR-296-5p, miR-361-3p, miR-361-5p, miR-421, miR-424-3p, miR-424-5p, miR-513a-5p, miR-92a-1-5p, miR-92a-2-5p, miR-92a-3p, miR-92b-3p, and miR-92b-5p. Many novel miRNAs are discovered in endothelial cells from deep-sequencing analysis (e.g., Voellenkle C et al., RNA, 2012, 18, 472-484, herein incorporated by reference in its entirety). miRNA binding sites from any endothelial cell specific miRNA can be introduced to or removed from a polynucleotide of the present disclosure to regulate expression of the polynucleotide in the endothelial cells.

miRNAs that are known to be expressed in epithelial cells include, but are not limited to, let-7b-3p, let-7b-5p, miR-1246, miR-200a-3p, miR-200a-5p, miR-200b-3p, miR-200b-5p, miR-200c-3p, miR-200c-5p, miR-338-3p, miR-429, miR-451a, miR-451b, miR-494, miR-802 and miR-34a, miR-34b-5p, miR-34c-5p, miR-449a, miR-449b-3p, miR-449b-5p specific in respiratory ciliated epithelial cells, let-7 family, miR-133a, miR-133b, miR-126 specific in lung epithelial cells, miR-382-3p, miR-382-5p specific in renal epithelial cells, and miR-762 specific in corneal epithelial cells. miRNA binding sites from any epithelial cell specific miRNA can be introduced to or removed from a polynucleotide of the present disclosure to regulate expression of the polynucleotide in the epithelial cells.

In addition, a large group of miRNAs are enriched in embryonic stem cells, controlling stem cell self-renewal as well as the development and/or differentiation of various cell lineages, such as neural cells, cardiac, hematopoietic cells, skin cells, osteogenic cells and muscle cells (e.g., Kuppusamy K T et al., Curr. Mol Med, 2013, 13(5), 757-764; Vidigal J A and Ventura A, Semin Cancer Biol. 2012, 22(5-6), 428-436; Goff L A et al., PLoS One, 2009, 4:e7192; Morin R D et al., Genome Res, 2008, 18, 610-621; Yoo J K et al., Stem Cells Dev. 2012, 21(11), 2049-2057, each of which is herein incorporated by reference in its entirety). MiRNAs abundant in embryonic stem cells include, but are not limited to, let-7a-2-3p, let-a-3p, let-7a-5p, let7d-3p, let-7d-5p, miR-103a-2-3p, miR-103a-5p, miR-106b-3p, miR-106b-5p, miR-1246, miR-1275, miR-138-1-3p, miR-138-2-3p, miR-138-5p, miR-154-3p, miR-154-5p, miR-200c-3p, miR-200c-5p, miR-290, miR-301a-3p, miR-301a-5p, miR-302a-3p, miR-302a-5p, miR-302b-3p, miR-302b-5p, miR-302c-3p, miR-302c-5p, miR-302d-3p, miR-302d-5p, miR-302e, miR-367-3p, miR-367-5p, miR-369-3p, miR-369-5p, miR-370, miR-371, miR-373, miR-380-5p, miR-423-3p, miR-423-5p, miR-486-5p, miR-520c-3p, miR-548e, miR-548f, miR-548g-3p, miR-548g-5p, miR-548i, miR-548k, miR-548l, miR-548m, miR-548n, miR-548o-3p, miR-548o-5p, miR-548p, miR-664a-3p, miR-664a-5p, miR-664b-3p, miR-664b-5p, miR-766-3p, miR-766-5p, miR-885-3p, miR-885-5p, miR-93-3p, miR-93-5p, miR-941, miR-96-3p, miR-96-5p, miR-99b-3p and miR-99b-5p. Many predicted novel miRNAs are discovered by deep sequencing in human embryonic stem cells (e.g., Morin R D et al., Genome Res, 2008, 18, 610-621; Goff L A et al., PLoS One, 2009, 4:e7192; Bar M et al., Stem cells, 2008, 26, 2496-2505, the content of each of which is incorporated herein by reference in its entirety).

In some embodiments, miRNAs are selected based on expression and abundance in immune cells of the hematopoietic lineage, such as B cells, T cells, macrophages, dendritic cells, and cells that are known to express TLR7/TLR8 and/or able to secrete cytokines such as endothelial cells and platelets. In some embodiments, the miRNA set thus includes miRs that may be responsible in part for the immunogenicity of these cells, and such that a corresponding miR-site incorporation in polynucleotides of the present invention (e.g., mRNAs) could lead to destabilization of the mRNA and/or suppression of translation from these mRNAs in the specific cell type. Non-limiting representative examples include miR-142, miR-144, miR-150, miR-155 and miR-223, which are specific for many of the hematopoietic cells; miR-142, miR150, miR-16 and miR-223, which are expressed in B cells; miR-223, miR-451, miR-26a, miR-16, which are expressed in progenitor hematopoietic cells; and miR-126, which is expressed in plasmacytoid dendritic cells, platelets and endothelial cells. For further discussion of tissue expression of miRs see e.g., Teruel-Montoya, R. et al. (2014) PLoS One 9:e102259; Landgraf, P. et al. (2007) Cell 129:1401-1414; Bissels, U. et al. (2009) RNA 15:2375-2384. Any one miR-site incorporation in the 3' UTR and/or 5' UTR may mediate such effects in multiple cell types of interest (e.g., miR-142 is abundant in both B cells and dendritic cells).

In some embodiments, it may be beneficial to target the same cell type with multiple miRs and to incorporate binding sites to each of the 3p and 5p arm if both are abundant (e.g., both miR-142-3p and miR142-5p are abundant in hematopoietic stem cells). Thus, in certain embodiments, polynucleotides of the invention contain two or more (e.g., two, three, four or more) miR bindings sites from: (i) the group consisting of miR-142, miR-144, miR-150, miR-155 and miR-223 (which are expressed in many hematopoietic cells); or (ii) the group consisting of miR-142, miR150, miR-16 and miR-223 (which are expressed in B cells); or the group consisting of miR-223, miR-451, miR-26a, miR-16 (which are expressed in progenitor hematopoietic cells).

In some embodiments, it may also be beneficial to combine various miRs such that multiple cell types of interest are targeted at the same time (e.g., miR-142 and miR-126 to target many cells of the hematopoietic lineage and endothelial cells). Thus, for example, in certain embodiments, polynucleotides of the invention comprise two or more (e.g., two, three, four or more) miRNA bindings sites, wherein: (i) at least one of the miRs targets cells of the hematopoietic lineage (e.g., miR-142, miR-144, miR-150, miR-155 or miR-223) and at least one of the miRs targets plasmacytoid dendritic cells, platelets or endothelial cells (e.g., miR-126); or (ii) at least one of the miRs targets B cells (e.g., miR-142, miR150, miR-16 or miR-223) and at least one of the miRs targets plasmacytoid dendritic cells, platelets or endothelial cells (e.g., miR-126); or (iii) at least one of the miRs targets progenitor hematopoietic cells (e.g., miR-223, miR-451, miR-26a or miR-16) and at least one of the miRs targets plasmacytoid dendritic cells, platelets or endothelial cells (e.g., miR-126); or (iv) at least one of the miRs targets cells of the hematopoietic lineage (e.g., miR-142, miR-144, miR-150, miR-155 or miR-223), at least one of the miRs targets B cells (e.g., miR-142, miR150, miR-16 or miR-223) and at least one of the miRs targets plasmacytoid dendritic cells, platelets or endothelial cells (e.g., miR-126); or any other possible combination of the foregoing four classes of miR binding sites (i.e., those targeting the hematopoietic lineage, those targeting B cells, those targeting progenitor hematopoietic cells and/or those targeting plamacytoid dendritic cells/platelets/endothelial cells).

In one embodiment, to modulate immune responses, polynucleotides of the present invention can comprise one or more miRNA binding sequences that bind to one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) reduces or inhibits immune cell activation (e.g., B cell activation, as measured by frequency of activated B cells) and/or cytokine production (e.g., production of IL-6, IFN-γ and/or TNFα). Furthermore, it has now been discovered that incorporation into an mRNA of one or more miRs that are expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells) can reduce or inhibit an anti-drug antibody (ADA) response against a protein of interest encoded by the mRNA.

In another embodiment, to modulate accelerated blood clearance of a polynucleotide delivered in a lipid-comprising compound or composition, polynucleotides of the invention can comprise one or more miR binding sequences that bind to one or more miRNAs expressed in conventional immune cells or any cell that expresses TLR7 and/or TLR8 and secrete pro-inflammatory cytokines and/or chemokines (e.g., in immune cells of peripheral lymphoid organs and/or splenocytes and/or endothelial cells). It has now been discovered that incorporation into an mRNA of one or more miR binding sites reduces or inhibits accelerated blood clearance (ABC) of the lipid-comprising compound or composition for use in delivering the mRNA. Furthermore, it has now been discovered that incorporation of one or more miR binding sites into an mRNA reduces serum levels of anti-PEG anti-IgM (e.g., reduces or inhibits the acute production of IgMs that recognize polyethylene glycol (PEG) by B cells) and/or reduces or inhibits proliferation and/or activation of plasmacytoid dendritic cells following administration of a lipid-comprising compound or composition comprising the mRNA.

In some embodiments, miR sequences may correspond to any known microRNA expressed in immune cells, including but not limited to those taught in US Publication US2005/0261218 and US Publication US2005/0059005, the contents of which are incorporated herein by reference in their entirety. Non-limiting examples of miRs expressed in immune cells include those expressed in spleen cells, myeloid cells, dendritic cells, plasmacytoid dendritic cells, B cells, T cells and/or macrophages. For example, miR-142-3p, miR-142-5p, miR-16, miR-21, miR-223, miR-24 and miR-27 are expressed in myeloid cells, miR-155 is expressed in dendritic cells, B cells and T cells, miR-146 is upregulated in macrophages upon TLR stimulation and miR-126 is expressed in plasmacytoid dendritic cells. In certain embodiments, the miR(s) is expressed abundantly or preferentially in immune cells. For example, miR-142 (miR-142-3p and/or miR-142-5p), miR-126 (miR-126-3p and/or miR-126-5p), miR-146 (miR-146-3p and/or miR-146-5p) and miR-155 (miR-155-3p and/or miR155-5p) are expressed abundantly in immune cells. These microRNA sequences are known in the art and, thus, one of ordinary skill in the art can readily design binding sequences or target sequences to which these microRNAs will bind based upon Watson-Crick complementarity.

Accordingly, in various embodiments, polynucleotides of the present invention comprise at least one microRNA binding site for a miR selected from the group consisting of miR-142, miR-146, miR-155, miR-126, miR-16, miR-21, miR-223, miR-24 and miR-27. In another embodiment, the mRNA comprises at least two miR binding sites for microRNAs expressed in immune cells. In various embodiments, the polynucleotide of the invention comprises 1-4, one, two, three or four miR binding sites for microRNAs expressed in immune cells. In another embodiment, the polynucleotide of the invention comprises three miR binding sites. These miR binding sites can be for microRNAs selected from the group consisting of miR-142, miR-146, miR-155, miR-126, miR-16, miR-21, miR-223, miR-24, miR-27, and combinations thereof. In one embodiment, the polynucleotide of the invention comprises two or more (e.g., two, three, four) copies of the same miR binding site expressed in immune cells, e.g., two or more copies of a miR binding site selected from the group of miRs consisting of miR-142, miR-146, miR-155, miR-126, miR-16, miR-21, miR-223, miR-24, miR-27.

In one embodiment, the polynucleotide of the invention comprises three copies of the same miRNA binding site. In certain embodiments, use of three copies of the same miR binding site can exhibit beneficial properties as compared to use of a single miRNA binding site. Non-limiting examples of sequences for 3' UTRs containing three miRNA bindings sites are shown in SEQ ID NO: 165 (three miR-142-3p binding sites) and SEQ ID NO: 167 (three miR-142-5p binding sites).

In another embodiment, the polynucleotide of the invention comprises two or more (e.g., two, three, four) copies of at least two different miR binding sites expressed in immune cells. Non-limiting examples of sequences of 3' UTRs containing two or more different miR binding sites are shown in SEQ ID NO: 135 (one miR-142-3p binding site and one miR-126-3p binding site), SEQ ID NO: 168 (two miR-142-5p binding sites and one miR-142-3p binding sites), and SEQ ID NO: 171 (two miR-155-5p binding sites and one miR-142-3p binding sites).

In another embodiment, the polynucleotide of the invention comprises at least two miR binding sites for microRNAs expressed in immune cells, wherein one of the miR binding sites is for miR-142-3p. In various embodiments, the polynucleotide of the invention comprises binding sites for miR-142-3p and miR-155 (miR-155-3p or miR-155-5p), miR-142-3p and miR-146 (miR-146-3 or miR-146-5p), or miR-142-3p and miR-126 (miR-126-3p or miR-126-5p).

In another embodiment, the polynucleotide of the invention comprises at least two miR binding sites for microRNAs expressed in immune cells, wherein one of the miR binding sites is for miR-126-3p. In various embodiments, the polynucleotide of the invention comprises binding sites for miR-126-3p and miR-155 (miR-155-3p or miR-155-5p), miR-126-3p and miR-146 (miR-146-3p or miR-146-5p), or miR-126-3p and miR-142 (miR-142-3p or miR-142-5p).

In another embodiment, the polynucleotide of the invention comprises at least two miR binding sites for microRNAs expressed in immune cells, wherein one of the miR binding sites is for miR-142-5p. In various embodiments, the polynucleotide of the invention comprises binding sites for miR-142-5p and miR-155 (miR-155-3p or miR-155-5p), miR-142-5p and miR-146 (miR-146-3 or miR-146-5p), or miR-142-5p and miR-126 (miR-126-3p or miR-126-5p).

In yet another embodiment, the polynucleotide of the invention comprises at least two miR binding sites for microRNAs expressed in immune cells, wherein one of the miR binding sites is for miR-155-5p. In various embodiments, the polynucleotide of the invention comprises binding sites for miR-155-5p and miR-142 (miR-142-3p or miR-142-5p), miR-155-5p and miR-146 (miR-146-3 or miR-146-5p), or miR-155-5p and miR-126 (miR-126-3p or miR-126-5p).

In one embodiment, the binding sites of embryonic stem cell specific miRNAs can be included in or removed from the 3'UTR of a polynucleotide of the present disclosure to modulate the development and/or differentiation of embryonic stem cells, to inhibit the senescence of stem cells in a degenerative condition (e.g. degenerative diseases), or to stimulate the senescence and apoptosis of stem cells in a disease condition (e.g. cancer stem cells).

As a non-limiting example, miRNA binding sites for miRNAs that are over-expressed in certain cancer and/or tumor cells can be removed from the 3'UTR of a polynucleotide of the present disclosure, restoring the expression suppressed by the over-expressed miRNAs in cancer cells, thus ameliorating the corresponsive biological function, for instance, transcription stimulation and/or repression, cell cycle arrest, apoptosis and cell death. Normal cells and tissues, wherein miRNAs expression is not up-regulated, will remain unaffected.

miRNA can also regulate complex biological processes such as angiogenesis (e.g., miR-132) (Anand and Cheresh Curr Opin Hematol 2011 18:171-176). In the polynucleotides of the present disclosure, miRNA binding sites that are involved in such processes can be removed or introduced, in order to tailor the expression of the polynucleotides to biologically relevant cell types or relevant biological processes. In this context, the polynucleotides of the present disclosure are defined as auxotrophic polynucleotides.

In some embodiments, a polynucleotide of the present disclosure comprises a miRNA binding site, wherein the miRNA binding site comprises one or more nucleotide sequences selected from Table 3, including one or more copies of any one or more of the miRNA binding site sequences. In some embodiments, a polynucleotide of the present disclosure further comprises at least one, two, three, four, five, six, seven, eight, nine, ten, or more of the same or different miRNA binding sites selected from Table 3, including any combination thereof.

In some embodiments, the miRNA binding site binds to miR-142 or is complementary to miR-142. In some embodiments, the miR-142 comprises SEQ ID NO:134. In some embodiments, the miRNA binding site binds to miR-142-3p or miR-142-5p. In some embodiments, the miR-142-3p binding site comprises SEQ ID NO:172. In some embodiments, the miR-142-5p binding site comprises SEQ ID NO:175. In some embodiments, the miRNA binding site comprises a nucleotide sequence at least 80%, at least 85%, at least 90%, at least 95%, or 100% identical to SEQ ID NO:172 or SEQ ID NO:175.

In some embodiments, the miRNA binding site binds to miR-126 or is complementary to miR-126. In some embodiments, the miR-126 comprises SEQ ID NO: 139. In some embodiments, the miRNA binding site binds to miR-126-3p or miR-126-5p. In some embodiments, the miR-126-3p binding site comprises SEQ ID NO: 141. In some embodiments, the miR-126-5p binding site comprises SEQ ID NO: 143. In some embodiments, the miRNA binding site comprises a nucleotide sequence at least 80%, at least 85%, at least 90%, at least 95%, or 100% identical to SEQ ID NO: 141 or SEQ ID NO: 143.

In one embodiment, the 3' UTR comprises two miRNA binding sites, wherein a first miRNA binding site binds to miR-142 and a second miRNA binding site binds to miR-126. In a specific embodiment, the 3' UTR binding to miR-142 and miR-126 comprises, consists, or consists essentially of the sequence of SEQ ID NO: 127 or 128.

TABLE 3 miR-142 and miR-142 binding sites

| SEQ ID NO. | Description | Sequence |
|---|---|---|
| 134 | miR-142 | GACAGUGCAGUCACCCAUAAAGUAGA AAGCACUACUAACAGCACUGGAGGGU GUAGUGUUUCCUACUUUAUGGAUGAG UGUACUGUG |

TABLE 3-continued

| miR-142 and miR-142 binding sites | | |
|---|---|---|
| SEQ ID NO. | Description | Sequence |
| 105 | miR-142-3p | UGUAGUGUUUCCUACUUUAUGGA |
| 172 | miR-142-3p binding site | UCCAUAAAGUAGGAAACACUACA |
| 173 | miR-142-5p | CAUAAAGUAGAAAGCACUACU |
| 175 | miR-142-5p binding site | AGUAGUGCUUUCUACUUUAUG |
| 139 | miR-126 | CGCUGGCGACGGGACAUUAUUACUUUUGGUACGCGCUGUGACACUUCAAACUCGUACCGUGAGUAAUAAUGCGCCGUCCACGGCA |
| 140 | miR-126-3p | UCGUACCGUGAGUAAUAAUGCG |
| 141 | miR-126-3p binding site | CGCAUUAUUACUCACGGUACGA |
| 142 | miR-126-5p | CAUUAUUACUUUUGGUACGCG |
| 143 | miR-126-5p binding site | CGCGUACCAAAAGUAAUAAUG |

In some embodiments, a miRNA binding site is inserted in the polynucleotide of the present disclosure in any position of the polynucleotide (e.g., the 5'UTR and/or 3'UTR). In some embodiments, the 5'UTR comprises a miRNA binding site. In some embodiments, the 3'UTR comprises a miRNA binding site. In some embodiments, the 5'UTR and the 3'UTR comprise a miRNA binding site. The insertion site in the polynucleotide can be anywhere in the polynucleotide as long as the insertion of the miRNA binding site in the polynucleotide does not interfere with the translation of a functional polypeptide in the absence of the corresponding miRNA; and in the presence of the miRNA, the insertion of the miRNA binding site in the polynucleotide and the binding of the miRNA binding site to the corresponding miRNA are capable of degrading the polynucleotide or preventing the translation of the polynucleotide.

In some embodiments, a miRNA binding site is inserted in at least about 30 nucleotides downstream from the stop codon of an ORF in a polynucleotide of the present disclosure comprising the ORF. In some embodiments, a miRNA binding site is inserted in at least about 10 nucleotides, at least about 15 nucleotides, at least about 20 nucleotides, at least about 25 nucleotides, at least about 30 nucleotides, at least about 35 nucleotides, at least about 40 nucleotides, at least about 45 nucleotides, at least about 50 nucleotides, at least about 55 nucleotides, at least about 60 nucleotides, at least about 65 nucleotides, at least about 70 nucleotides, at least about 75 nucleotides, at least about 80 nucleotides, at least about 85 nucleotides, at least about 90 nucleotides, at least about 95 nucleotides, or at least about 100 nucleotides downstream from the stop codon of an ORF in a polynucleotide of the present disclosure. In some embodiments, a miRNA binding site is inserted in about 10 nucleotides to about 100 nucleotides, about 20 nucleotides to about 90 nucleotides, about 30 nucleotides to about 80 nucleotides, about 40 nucleotides to about 70 nucleotides, about 50 nucleotides to about 60 nucleotides, about 45 nucleotides to about 65 nucleotides downstream from the stop codon of an ORF in a polynucleotide of the present disclosure.

In some embodiments, a miRNA binding site is inserted within the 3' UTR immediately following the stop codon of the coding region within the polynucleotide of the invention, e.g., mRNA. In some embodiments, if there are multiple copies of a stop codon in the construct, a miRNA binding site is inserted immediately following the final stop codon. In some embodiments, a miRNA binding site is inserted further downstream of the stop codon, in which case there are 3' UTR bases between the stop codon and the miR binding site(s). In some embodiments, three non-limiting examples of possible insertion sites for a miR in a 3' UTR are shown in SEQ ID NOs: 127, 128, and 174, which show a 3' UTR sequence with a miR-142-3p site inserted in one of three different possible insertion sites, respectively, within the 3' UTR.

In some embodiments, one or more miRNA binding sites can be positioned within the 5' UTR at one or more possible insertion sites. For example, three non-limiting examples of possible insertion sites for a miR in a 5' UTR are shown in SEQ ID NOs: 176, 177, and 178, which show a 5' UTR sequence with a miR-142-3p site inserted into one of three different possible insertion sites, respectively, within the 5' UTR.

In one embodiment, a codon optimized open reading frame encoding a polypeptide of interest comprises a stop codon and the at least one microRNA binding site is located within the 3' UTR 1-100 nucleotides after the stop codon. In one embodiment, the codon optimized open reading frame encoding the polypeptide of interest comprises a stop codon and the at least one microRNA binding site for a miR expressed in immune cells is located within the 3' UTR 30-50 nucleotides after the stop codon. In another embodiment, the codon optimized open reading frame encoding the polypeptide of interest comprises a stop codon and the at least one microRNA binding site for a miR expressed in immune cells is located within the 3' UTR at least 50 nucleotides after the stop codon. In other embodiments, the codon optimized open reading frame encoding the polypeptide of interest comprises a stop codon and the at least one microRNA binding site for a miR expressed in immune cells is located within the 3' UTR immediately after the stop codon, or within the 3' UTR 15-20 nucleotides after the stop codon or within the 3' UTR 70-80 nucleotides after the stop codon. In other embodiments, the 3' UTR comprises more than one miRNA binding site (e.g., 2-4 miRNA binding sites), wherein there can be a spacer region (e.g., of 10-100, 20-70 or 30-50 nucleotides in length) between each miRNA binding site. In another embodiment, the 3' UTR comprises a spacer region between the end of the miRNA binding site(s) and the poly A tail nucleotides. For example, a spacer region of 10-100, 20-70 or 30-50 nucleotides in length can be situated between the end of the miRNA binding site(s) and the beginning of the poly A tail.

In one embodiment, a codon optimized open reading frame encoding a polypeptide of interest comprises a start codon and the at least one microRNA binding site is located within the 5' UTR 1-100 nucleotides before (upstream of) the start codon. In one embodiment, the codon optimized open reading frame encoding the polypeptide of interest comprises a start codon and the at least one microRNA binding site for a miR expressed in immune cells is located within the 5' UTR 10-50 nucleotides before (upstream of) the start codon. In another embodiment, the codon optimized open reading frame encoding the polypeptide of interest comprises a start codon and the at least one microRNA binding site for a miR expressed in immune cells is located within the 5' UTR at least 25 nucleotides before (upstream of) the start codon. In other embodiments, the codon optimized open reading frame encoding the polypeptide of interest comprises a start codon and the at least one microRNA binding site for a miR expressed in immune cells is located within the 5' UTR immediately before the start codon, or within the 5' UTR 15-20 nucleotides before the start codon or within the 5' UTR 70-80 nucleotides before the start codon. In other embodiments, the 5' UTR comprises more than one miRNA binding site (e.g., 2-4 miRNA binding sites), wherein there can be a spacer region (e.g., of 10-100, 20-70 or 30-50 nucleotides in length) between each miRNA binding site.

In one embodiment, the 3' UTR comprises more than one stop codon, wherein at least one miRNA binding site is positioned downstream of the stop codons. For example, a 3' UTR can comprise 1, 2 or 3 stop codons. Non-limiting examples of triple stop codons that can be used include: UGAUAAUAG (SEQ ID NO:195), UGAUAGUAA (SEQ ID NO:196), UAAUGAUAG (SEQ ID NO:197), UGAUAAUAA (SEQ ID NO:198), UGAUAGUAG (SEQ ID NO:199), UAAUGAUGA (SEQ ID NO:200), UAAUAGUAG (SEQ ID NO:201), UGAUGAUGA (SEQ ID NO:202), UAAUAAUAA (SEQ ID NO:203), and UAGUAGUAG (SEQ ID NO:204). Within a 3' UTR, for example, 1, 2, 3 or 4 miRNA binding sites, e.g., miR-142-3p binding sites, can be positioned immediately adjacent to the stop codon(s) or at any number of nucleotides downstream of the final stop codon. When the 3' UTR comprises multiple miRNA binding sites, these binding sites can be positioned directly next to each other in the construct (i.e., one after the other) or, alternatively, spacer nucleotides can be positioned between each binding site.

In one embodiment, the 3' UTR comprises three stop codons with a single miR-142-3p binding site located downstream of the 3rd stop codon. Non-limiting examples of sequences of 3' UTR having three stop codons and a single miR-142-3p binding site located at different positions downstream of the final stop codon are shown in SEQ ID NOs: 132, 127, 128, and 174.

TABLE 4

5' UTRs, 3'UTRs, miR sequences, and miR binding sites

| SEQ ID NO: | Sequence |
|---|---|
| 144 | GCUGGAGCCUCGGUGGCCAUGCUUCUUGCCCCUUGGGCCUCCCCCCAGCCCC UCCUCCCCUUCCUGCACCCGUACCCCCUCCAUAAAGUAGGAAACACUACAGU GGUCUUUGAAUAAAGUCUGAGUGGGCGGC (3' UTR with miR 142-3p binding site) |
| 172 | UCCAUAAAGUAGGAAACACUACA (miR 142-3p binding site) |
| 105 | UGUAGUGUUUCCUACUUUAUGGA (miR 142-3p sequence) |
| 173 | CAUAAAGUAGAAAGCACUACU (miR 142-5p sequence) |
| 145 | CCUCUGAAAUUCAGUUCUUCAG (miR 146-3p sequence) |
| 146 | UGAGAACUGAAUUCCAUGGGUU (miR 146-5p sequence) |
| 147 | CUCCUACAUAUUAGCAUUAACA (miR 155-3p sequence) |
| 148 | UUAAUGCUAAUCGUGAUAGGGGU (miR 155-5p sequence) |
| 140 | UCGUACCGUGAGUAAUAAUGCG (miR 126-3p sequence) |
| 142 | CAUUAUUACUUUUGGUACGCG (miR 126-5p sequence) |
| 149 | CCAGUAUUAACUGUGCUGCUGA (miR 16-3p sequence) |
| 150 | UAGCAGCACGUAAAUAUUGGCG (miR 16-5p sequence) |
| 151 | CAACACCAGUCGAUGGGCUGU (miR 21-3p sequence) |
| 152 | UAGCUUAUCAGACUGAUGUUGA (miR 21-5p sequence) |

TABLE 4-continued

| SEQ ID NO: | Sequence |
|---|---|
| | 5' UTRs, 3'UTRs, miR sequences, and miR binding sites |
| 153 | UGUCAGUUUGUCAAAUACCCCA (miR 223-3p sequence) |
| 154 | CGUGUAUUUGACAAGCUGAGUU (miR 223-5p sequence) |
| 155 | UGGCUCAGUUCAGCAGGAACAG (miR 24-3p sequence) |
| 156 | UGCCUACUGAGCUGAUAUCAGU (miR 24-5p sequence) |
| 157 | UUCACAGUGGCUAAGUUCCGC (miR 27-3p sequence) |
| 158 | AGGGCUUAGCUGCUUGUGAGCA (miR 27-5p sequence) |
| 141 | CGCAUUAUUACUCACGGUACGA (miR 126-3p binding site) |
| 159 | **UGAUAAUAG**GCUGGAGCCUCGGUGGCCAUGCUUCUUGCCCCUUGGGCCUCCCCCCAGCCCCUCCUCCCCUUCCUGCACCCGUACCCCCCGCAUUAUUACUCACGGUACGAGUGGUCUUUGAAUAAAGUCUGAGUGGGCGGC (3' UTR with miR 126-3p binding site) |
| 160 | **UGAUAAUAG**GCUGGAGCCUCGGUGGCCAUGCUUCUUGCCCCUUGGGCCUCCCCCCAGCCCCUCCUCCCCUUCCUGCACCCGUACCCCCGUGGUCUUUGAAUAAAGUCUGAGUGGGCGGC (3' UTR, no miR binding sites) |
| 132 | **UGAUAAUAG**GCUGGAGCCUCGGUGGCCAUGCUUCUUGCCCCUUGGGCCUCCCCCCAGCCCCUCCUCCCCUUCCUGCACCCGUACCCCCUCCAUAAAGUAGGAAACACUACAGUGGUCUUUGAAUAAAGUCUGAGUGGGCGGC (3' UTR with miR 142-3p binding site) |
| 135 | **UGAUAAUAG**UCCAUAAAGUAGGAAACACUACAGCUGGAGCCUCGGUGGCCAUGCUUCUUGCCCCUUGGGCCUCCCCCCAGCCCCUCCUCCCCUUCCUGCACCCGUACCCCCCGCAUUAUUACUCACGGUACGAGUGGUCUUUGAAUAAAGUCUGAGUGGGCGGC (3' UTR with miR 142-3p and miR 126-3p binding sites variant 1) |
| 163 | UUAAUGCUAAUUGUGAUAGGGGU (miR 155-5p sequence) |
| 164 | ACCCCUAUCACAAUUAGCAUUAA (miR 155-5p binding site) |
| 165 | **UGAUAAUAG**UCCAUAAAGUAGGAAACACUACAGCUGGAGCCUCGGUGGCCAUGCUUCUUGCCCCUUGGGCCUCCAUAAAGUAGGAAACACUACAUCCCCCCAGC |

TABLE 4-continued

| 5' UTRs, 3'UTRs, miR sequences, and miR binding sites | |
|---|---|
| SEQ ID NO: | Sequence |
| | CCCUCCUCCCCUUCCUGCACCCGUACCCCCUCCAUAAAGUAGGAAACACUACAGUGGUCUUUGAAUAAAGUCUGAGUGGGCGGC (3' UTR with 3 miR 142-3p binding sites) |
| 166 | **UGAUAAUAG**GCUGGAGCCUCGGUGGCCAUGCUUCUUGCCCCUUGGGCCUCCCCCCAGCCCCUCCUCCCCUUCCUGCACCCGUACCCCCAGUAGUGCUUUCUACUUUAUGGUGGUCUUUGAAUAAAGUCUGAGUGGGCGGC (3' UTR with miR 142-5p binding site) |
| 167 | **UGAUAAUAG**AGUAGUGCUUUCUACUUUAUGGCUGGAGCCUCGGUGGCCAUGCUUCUUGCCCCUUGGGCCAGUAGUGCUUUCUACUUUAUGUCCCCCCAGCCCCUCCUCCCCUUCCUGCACCCGUACCCCCAGUAGUGCUUUCUACUUUAUGGUGGUCUUUGAAUAAAGUCUGAGUGGGCGGC (3' UTR with 3 miR 142-5p binding sites) |
| 168 | **UGAUAAUAG**AGUAGUGCUUUCUACUUUAUGGCUGGAGCCUCGGUGGCCAUGCUUCUUGCCCCUUGGGCCUCCAUAAAGUAGGAAACACUACAUCCCCCCAGCCCCUCCUCCCCUUCCUGCACCCGUACCCCCAGUAGUGCUUUCUACUUUAUGGUGGUCUUUGAAUAAAGUCUGAGUGGGCGGC (3' UTR with 2 miR 142-5p binding sites and 1 miR 142-3p binding site) |
| 169 | **UGAUAAUAG**GCUGGAGCCUCGGUGGCCAUGCUUCUUGCCCCUUGGGCCUCCCCCCAGCCCCUCCUCCCCUUCCUGCACCCGUACCCCCACCCCUAUCACAAUUAGCAUUAAGUGGUCUUUGAAUAAAGUCUGAGUGGGCGGC (3' UTR with miR 155-5p binding site) |
| 170 | **UGAUAAUAG**ACCCCUAUCACAAUUAGCAUUAAGCUGGAGCCUCGGUGGCCAUGCUUCUUGCCCCUUGGGCCACCCCUAUCACAAUUAGCAUUAAUCCCCCCAGCCCCUCCUCCCCUUCCUGCACCCGUACCCCCACCCCUAUCACAAUUAGCAUUAAGUGGUCUUUGAAUAAAGUCUGAGUGGGCGGC (3' UTR with 3 miR 155-5p binding sites) |
| 171 | **UGAUAAUAG**ACCCCUAUCACAAUUAGCAUUAAGCUGGAGCCUCGGUGGCCAUGCUUCUUGCCCCUUGGGCCUCCAUAAAGUAGGAAACACUACAUCCCCCCAGC |

TABLE 4-continued

5' UTRs, 3'UTRs, miR sequences, and miR binding sites

| SEQ ID NO: | Sequence |
|---|---|
| | CCCUCCUCCCCUUCCUGCACCCGUACCCCCACCCCUAUCACAAUUAGCAUUA AGUGGUCUUUGAAUAAAGUCUGAGUGGGCGGC (3' UTR with 2 miR 155-5p binding sites and 1 miR 142-3p binding site) |
| 127 | **UGAUAAUAG**UCCAUAAAGUAGGAAACACUACAGCUGGAGCCUCGGUGGCCAU GCUUCUUGCCCCUUGGGCCUCCCCCCAGCCCCUCCUCCCCUUCCUGCACCCG UACCCCCGUGGUCUUUGAAUAAAGUCUGAGUGGGCGGC (3' UTR with miR 142-3p binding site, P1 insertion) |
| 128 | **UGAUAAUAG**GCUGGAGCCUCGGUGGCUCCAUAAAGUAGGAAACACUACACAU GCUUCUUGCCCCUUGGGCCUCCCCCCAGCCCCUCCUCCCCUUCCUGCACCCG UACCCCCGUGGUCUUUGAAUAAAGUCUGAGUGGGCGGC (3' UTR with miR 142-3p binding site, P2 insertion) |
| 174 | **UGAUAAUAG**GCUGGAGCCUCGGUGGCCAUGCUUCUUGCCCCUUGGGCCUCCA UAAAGUAGGAAACACUACAUCCCCCCAGCCCCUCCUCCCCUUCCUGCACCCG UACCCCCGUGGUCUUUGAAUAAAGUCUGAGUGGGCGGC (3' UTR with miR 142-3p binding site, P3 insertion) |
| 175 | AGUAGUGCUUUCUACUUUAUG (miR-142-5p binding site) |
| 134 | GACAGUGCAGUCACCCAUAAAGUAGAAAGCACUACUAACAGCACUGGAGGGU GUAGUGUUUCCUACUUUAUGGAUGAGUGUACUGUG (miR-142) |
| 108 | GGGAAAUAAGAGAGAAAAGAAGAGUAAGAAGAAAUAUAAGAGCCACC (5' UTR) |
| 176 | GGGAAAUAAGAGUCCAUAAAGUAGGAAACACUACAAGAAAAGAAGAGUAAGA AGAAAUAUAAGAGCCACC (5' UTR with miR 142-3p binding site at position p1) |
| 177 | GGGAAAUAAGAGAGAAAAGAAGAGUAAUCCAUAAAGUAGGAAACACUACAGA AGAAAUAUAAGAGCCACC (5' UTR with miR 142-3p binding site at position p2) |
| 178 | GGGAAAUAAGAGAGAAAAGAAGAGUAAGAAGAAAUAUAAUCCAUAAAGUAGG AAACACUACAGAGCCACC (5' UTR with miR 142-3p binding site at position p3) |
| 180 | **UGAUAAUAG**AGUAGUGCUUUCUACUUUAUGGCUGGAGCCUCGGUGGCCAUGC UUCUUGCCCCUUGGGCCAGUAGUGCUUUCUACUUUAUGUCCCCCCAGCCCCU CUCCCCUUCCUGCACCCGUACCCCCAGUAGUGCUUUCUACUUUAUGGUGGUC |

TABLE 4-continued

| SEQ ID NO: | 5' UTRs, 3'UTRs, miR sequences, and miR binding sites<br>Sequence |
|---|---|
| | UUUGAAUAAAGUCUGAGUGGGCGGC |
| | (3' UTR with 3 miR 142-5p binding sites) |
| 129 | **UGAUAAUAG**GCUGGAGCCUCGGUGGCCAUGCUUCUUGCCCCUUCCAUAAAGUAGGAAACACUACAUGGGCCUCCCCCCAGCCCCUCCUCCCCUUCCUGCACCCGUACCCCCGUGGUCUUUGAAUAAAGUCUGAGUGGGCGGC |
| | (3' UTR including miR 142-3p binding site) |
| 130 | **UGAUAAUAG**GCUGGAGCCUCGGUGGCCAUGCUUCUUGCCCCUUGGGCCUCCCCCCAGUCCAUAAAGUAGGAAACACUACACCCCUCCUCCCCUUCCUGCACCCGUACCCCCGUGGUCUUUGAAUAAAGUCUGAGUGGGCGGC |
| | (3' UTR including miR 142-3p binding site) |
| 131 | **UGAUAAUAG**GCUGGAGCCUCGGUGGCCAUGCUUCUUGCCCCUUGGGCCUCCCCCCAGCCCCUCCUCCCCUUCUCCAUAAAGUAGGAAACACUACACUGCACCCGUACCCCCGUGGUCUUUGAAUAAAGUCUGAGUGGGCGGC |
| | (3' UTR including miR 142-3p binding site) |
| 133 | **UGAUAAUAG**GCUGGAGCCUCGGUGGCCAUGCUUCUUGCCCCUUGGGCCUCCCCCCAGCCCCUCCUCCCCUUCCUGCACCCGUACCCCCGUGGUCUUUGAAUAAAGUUCCAUAAAGUAGGAAACACUACACUGAGUGGGCGGC |
| | (3' UTR including miR 142-3p binding site) |
| 136 | **UGAUAAUAG**UCCAUAAAGUAGGAAACACUACAGCUGGAGCCUCGGUGGCCUAGCUUCUUGCCCCUUGGGCCUCCCCCCAGCCCCUCCUCCCCUUCCUGCACCCGUACCCCCCGCAUUAUUACUCACGGUACGAGUGGUCUUUGAAUAAAGUCUGAGUGGGCGGC |
| | (3' UTR with miR 142-3p and miR 126-3p binding sites variant 2) |
| 14 | **UGAUAAUAG**GCUGGAGCCUCGGUGGCCUAGCUUCUUGCCCCUUGGGCCUCCCCCCAGCCCCUCCUCCCCUUCCUGCACCCGUACCCCCGUGGUCUUUGAAUAAAGUCUGAGUGGGCGGC |
| | (3' UTR, no miR binding sites variant 2) |
| 137 | **UGAUAAUAG**GCUGGAGCCUCGGUGGCCUAGCUUCUUGCCCCUUGGGCCUCCCCCCAGCCCCUCCUCCCCUUCCUGCACCCGUACCCCCUCCAUAAAGUAGGAAACACUACAGUGGUCUUUGAAUAAAGUCUGAGUGGGCGGC |
| | (3' UTR with miR 142-3p binding site variant 3) |
| 187 | **UGAUAAUAG**GCUGGAGCCUCGGUGGCCUAGCUUCUUGCCCCUUGGGCCUCCCCCCAGCCCCUCCUCCCCUUCCUGCACCCGUACCCCCGCAUUAUUACUCACGGUACGAGUGGUCUUUGAAUAAAGUCUGAGUGGGCGGC |

TABLE 4-continued

5' UTRs, 3'UTRs, miR sequences, and miR binding sites

| SEQ ID NO: | Sequence |
|---|---|
| | (3' UTR with miR 126-3p binding site variant 3) |
| 188 | **UGAUAAUAG**UCCAUAAAGUAGGAAACACUACAGCUGGAGCCUCGGUGGCCUAGCUUCUUGCCCCUUGGGCCUCCAUAAAGUAGGAAACACUACAUCCCCCCAGCCCCUCCUCCCCUUCCUGCACCCGUACCCCCUCCAUAAAGUAGGAAACACUACAGUGGUCUUUGAAUAAAGUCUGAGUGGGCGGC |
| | (3' UTR with 3 miR 142-3p binding sites variant 2) |
| 189 | **UGAUAAUAG**UCCAUAAAGUAGGAAACACUACAGCUGGAGCCUCGGUGGCCUAGCUUCUUGCCCCUUGGGCCUCCCCCCAGCCCCUCCUCCCCUUCCUGCACCCGUACCCCCGUGGUCUUUGAAUAAAGUCUGAGUGGGCGGC |
| | (3' UTR with miR 142-3p binding site, P1 insertion variant 2) |
| 190 | **UGAUAAUAG**GCUGGAGCCUCGGUGGCUCCAUAAAGUAGGAAACACUACACUAGCUUCUUGCCCCUUGGGCCUCCCCCCAGCCCCUCCUCCCCUUCCUGCACCCGUACCCCCGUGGUCUUUGAAUAAAGUCUGAGUGGGCGGC |
| | (3' UTR with miR 142-3p binding site, P2 insertion variant 2) |
| 191 | **UGAUAAUAG**GCUGGAGCCUCGGUGGCCUAGCUUCUUGCCCCUUGGGCCUCCAUAAAGUAGGAAACACUACAUCCCCCCAGCCCCUCCUCCCCUUCCUGCACCCGUACCCCCGUGGUCUUUGAAUAAAGUCUGAGUGGGCGGC |
| | (3' UTR with miR 142-3p binding site, P3 insertion variant 2) |
| 192 | **UGAUAAUAG**GCUGGAGCCUCGGUGGCCUAGCUUCUUGCCCCUUGGGCCUCCCCCCAGCCCCUCCUCCCCUUCCUGCACCCGUACCCCCACCCCUAUCACAAUUAGCAUUAAGUGGUCUUUGAAUAAAGUCUGAGUGGGCGGC |
| | (3' UTR with miR 155-5p binding site variant 2) |
| 193 | **UGAUAAUAG**ACCCCUAUCACAAUUAGCAUUAAGCUGGAGCCUCGGUGGCCUAGCUUCUUGCCCCUUGGGCCACCCCUAUCACAAUUAGCAUUAAUCCCCCCAGCCCCUCCUCCCCUUCCUGCACCCGUACCCCCACCCCUAUCACAAUUAGCAUUAAGUGGUCUUUGAAUAAAGUCUGAGUGGGCGGC |
| | (3' UTR with 3 miR 155-5p binding sites variant 2) |
| 194 | **UGAUAAUAG**ACCCCUAUCACAAUUAGCAUUAAGCUGGAGCCUCGGUGGCCUAGCUUCUUGCCCCUUGGGCCUCCAUAAAGUAGGAAACACUACAUCCCCCCAGCCCCUCCUCCCCUUCCUGCACCCGUACCCCCACCCCUAUCACAAUUAGCAUUAAGUGGUCUUUGAAUAAAGUCUGAGUGGGCGGC |

TABLE 4-continued

| 5' UTRs, 3'UTRs, miR sequences, and miR binding sites |
|---|
| SEQ ID NO: Sequence |
| (3' UTR with 2 miR 155-5p binding sites and 1 miR 142-3p binding site variant 2) |

Stop codon = bold
miR 142-3p binding site = underline
miR 126-3p binding site = bold underline
miR 155-5p binding site = shaded
miR 142-5p binding site = shaded and bold underline In one embodiment, the polynucleotide of the invention comprises a 5' UTR, a codon optimized open reading frame encoding a polypeptide of interest, a 3' UTR comprising the at least one miRNA binding site for a miR expressed in immune cells, and a 3' tailing region of linked nucleosides. In various embodiments, the 3' UTR comprises 1-4, at least two, one, two, three or four miRNA binding sites for miRs expressed in immune cells, preferably abundantly or preferentially expressed in immune cells.

In one embodiment, the at least one miRNA expressed in immune cells is a miR-142-3p microRNA binding site. In one embodiment, the miR-142-3p microRNA binding site comprises the sequence shown in SEQ ID NO:172. In one embodiment, the 3' UTR of the mRNA comprising the miR-142-3p microRNA binding site comprises the sequence shown in SEQ ID NO: 144.

In one embodiment, the at least one miRNA expressed in immune cells is a miR-126 microRNA binding site. In one embodiment, the miR-126 binding site is a miR-126-3p binding site. In one embodiment, the miR-126-3p microRNA binding site comprises the sequence shown in SEQ ID NO: 141. In one embodiment, the 3' UTR of the mRNA of the invention comprising the miR-126-3p microRNA binding site comprises the sequence shown in SEQ ID NO: 159.

Non-limiting exemplary sequences for miRs to which a microRNA binding site(s) of the disclosure can bind include the following: miR-142-3p (SEQ ID NO:172), miR-142-5p (SEQ ID NO: 175), miR-146-3p (SEQ ID NO: 145), miR-146-5p (SEQ ID NO: 146), miR-155-3p (SEQ ID NO: 147), miR-155-5p (SEQ ID NO: 148), miR-126-3p (SEQ ID NO: 140), miR-126-5p (SEQ ID NO: 142), miR-16-3p (SEQ ID NO: 149), miR-16-5p (SEQ ID NO: 150), miR-21-3p (SEQ ID NO: 151), miR-21-5p (SEQ ID NO: 152), miR-223-3p (SEQ ID NO: 153), miR-223-5p (SEQ ID NO: 154), miR-24-3p (SEQ ID NO: 155), miR-24-5p (SEQ ID NO: 156), miR-27-3p (SEQ ID NO: 157) and miR-27-5p (SEQ ID NO: 158). Other suitable miR sequences expressed in immune cells (e.g., abundantly or preferentially expressed in immune cells) are known and available in the art, for example at the University of Manchester's microRNA database, miRBase. Sites that bind any of the aforementioned miRs can be designed based on Watson-Crick complementarity to the miR, typically 100% complementarity to the miR, and inserted into an mRNA construct of the disclosure as described herein.

In another embodiment, a polynucleotide of the present invention (e.g., and mRNA, e.g., the 3' UTR thereof) can comprise at least one miRNA binding site to thereby reduce or inhibit accelerated blood clearance, for example by reducing or inhibiting production of IgMs, e.g., against PEG, by B cells and/or reducing or inhibiting proliferation and/or activation of pDCs, and can comprise at least one miRNA binding site for modulating tissue expression of an encoded protein of interest.

miRNA gene regulation can be influenced by the sequence surrounding the miRNA such as, but not limited to, the species of the surrounding sequence, the type of sequence (e.g., heterologous, homologous, exogenous, endogenous, or artificial), regulatory elements in the surrounding sequence and/or structural elements in the surrounding sequence. The miRNA can be influenced by the 5'UTR and/or 3'UTR. As a non-limiting example, a non-human 3'UTR can increase the regulatory effect of the miRNA sequence on the expression of a polypeptide of interest compared to a human 3'UTR of the same sequence type.

In one embodiment, other regulatory elements and/or structural elements of the 5'UTR can influence miRNA mediated gene regulation. One example of a regulatory element and/or structural element is a structured IRES (Internal Ribosome Entry Site) in the 5'UTR, which is necessary for the binding of translational elongation factors to initiate protein translation. EIF4A2 binding to this secondarily structured element in the 5'-UTR is necessary for miRNA mediated gene expression (Meijer H A et al., Science, 2013, 340, 82-85, herein incorporated by reference in its entirety). The polynucleotides of the present disclosure can further include this structured 5'UTR in order to enhance microRNA mediated gene regulation.

At least one miRNA binding site can be engineered into the 3'UTR of a polynucleotide of the present disclosure. In this context, at least two, at least three, at least four, at least five, at least six, at least seven, at least eight, at least nine, at least ten, or more miRNA binding sites can be engineered into a 3'UTR of a polynucleotide of the present disclosure. For example, 1 to 10, 1 to 9, 1 to 8, 1 to 7, 1 to 6, 1 to 5, 1 to 4, 1 to 3, 2, or 1 miRNA binding sites can be engineered into the 3'UTR of a polynucleotide of the present disclosure. In one embodiment, miRNA binding sites incorporated into a polynucleotide of the present disclosure can be the same or can be different miRNA sites. A combination of different miRNA binding sites incorporated into a polynucleotide of the present disclosure can include combinations in which more than one copy of any of the different miRNA sites are incorporated. In another embodiment, miRNA binding sites incorporated into a polynucleotide of the present disclosure can target the same or different tissues in the body. As a non-limiting example, through the introduction of tissue-, cell-type-, or disease-specific miRNA binding sites in the 3'-UTR of a polynucleotide of the present disclosure, the degree of expression in specific cell types (e.g., hepatocytes, myeloid cells, endothelial cells, cancer cells, etc.) can be reduced.

In one embodiment, a miRNA binding site can be engineered near the 5' terminus of the 3'UTR, about halfway between the 5' terminus and 3' terminus of the 3'UTR and/or near the 3' terminus of the 3'UTR in a polynucleotide of the present disclosure. As a non-limiting example, a miRNA binding site can be engineered near the 5' terminus of the 3'UTR and about halfway between the 5' terminus and 3' terminus of the 3'UTR. As another non-limiting example, a miRNA binding site can be engineered near the 3' terminus of the 3'UTR and about halfway between the 5' terminus and 3' terminus of the 3'UTR. As yet another non-limiting example, a miRNA binding site can be engineered near the 5' terminus of the 3'UTR and near the 3' terminus of the 3'UTR.

In another embodiment, a 3'UTR can comprise 1, 2, 3, 4, 5, 6, 7, 8, 9, or 10 miRNA binding sites. The miRNA binding sites can be complementary to a miRNA, miRNA seed sequence, and/or miRNA sequences flanking the seed sequence.

In one embodiment, a polynucleotide of the present disclosure can be engineered to include more than one miRNA site expressed in different tissues or different cell types of a subject. As a non-limiting example, a polynucleotide of the present disclosure can be engineered to include miR-192 and miR-122 to regulate expression of the polynucleotide in the liver and kidneys of a subject. In another embodiment, a polynucleotide of the present disclosure can be engineered to include more than one miRNA site for the same tissue.

In some embodiments, the expression of a polynucleotide of the present disclosure can be controlled by incorporating at least one miR binding site in the polynucleotide and formulating the polynucleotide for administration. As a non-limiting example, a polynucleotide of the present disclosure can be targeted to a tissue or cell by incorporating a miRNA binding site and formulating the polynucleotide in a lipid nanoparticle comprising an ionizable lipid, including any of the lipids described herein.

A polynucleotide of the present disclosure can be engineered for more targeted expression in specific tissues, cell types, or biological conditions based on the expression patterns of miRNAs in the different tissues, cell types, or biological conditions. Through introduction of tissue-specific miRNA binding sites, a polynucleotide of the present disclosure can be designed for optimal protein expression in a tissue or cell, or in the context of a biological condition.

In some embodiments, a polynucleotide of the present disclosure can be designed to incorporate miRNA binding sites that either have 100% identity to known miRNA seed sequences or have less than 100% identity to miRNA seed sequences. In some embodiments, a polynucleotide of the present disclosure can be designed to incorporate miRNA binding sites that have at least: 60%, 65%, 70%, 75%, 80%, 85%, 90%, 95%, 96%, 97%, 98%, or 99% identity to known miRNA seed sequences. The miRNA seed sequence can be partially mutated to decrease miRNA binding affinity and as such result in reduced downmodulation of the polynucleotide. In essence, the degree of match or mis-match between the miRNA binding site and the miRNA seed can act as a rheostat to more finely tune the ability of the miRNA to modulate protein expression. In addition, mutation in the non-seed region of a miRNA binding site can also impact the ability of a miRNA to modulate protein expression.

In one embodiment, a miRNA sequence can be incorporated into the loop of a stem loop.

In another embodiment, a miRNA seed sequence can be incorporated in the loop of a stem loop and a miRNA binding site can be incorporated into the 5' or 3' stem of the stem loop.

In one embodiment the miRNA sequence in the 5'UTR can be used to stabilize a polynucleotide of the present disclosure described herein.

In another embodiment, a miRNA sequence in the 5'UTR of a polynucleotide of the present disclosure can be used to decrease the accessibility of the site of translation initiation such as, but not limited to a start codon. See, e.g., Matsuda et al., PLoS One. 2010 11(5):e15057; incorporated herein by reference in its entirety, which used antisense locked nucleic acid (LNA) oligonucleotides and exon-junction complexes (EJCs) around a start codon (−4 to +37 where the A of the AUG codons is +1) in order to decrease the accessibility to the first start codon (AUG). Matsuda showed that altering the sequence around the start codon with an LNA or EJC affected the efficiency, length and structural stability of a polynucleotide. A polynucleotide of the present disclosure can comprise a miRNA sequence, instead of the LNA or EJC sequence described by Matsuda et al, near the site of translation initiation in order to decrease the accessibility to the site of translation initiation. The site of translation initiation can be prior to, after or within the miRNA sequence. As a non-limiting example, the site of translation initiation can be located within a miRNA sequence such as a seed sequence or binding site. As another non-limiting example, the site of translation initiation can be located within a miR-122 sequence such as the seed sequence or the mir-122 binding site.

In some embodiments, a polynucleotide of the present disclosure can include at least one miRNA in order to dampen the antigen presentation by antigen presenting cells. The miRNA can be the complete miRNA sequence, the miRNA seed sequence, the miRNA sequence without the seed, or a combination thereof. As a non-limiting example, a miRNA incorporated into a polynucleotide of the present disclosure can be specific to the hematopoietic system. As another non-limiting example, a miRNA incorporated into a polynucleotide of the present disclosure to dampen antigen presentation is miR-142-3p.

In some embodiments, a polynucleotide of the present disclosure can include at least one miRNA in order to dampen expression of the encoded polypeptide in a tissue or cell of interest. As a non-limiting example, a polynucleotide of the present disclosure can include at least one miR-122 binding site in order to dampen expression of an encoded polypeptide of interest in the liver. As another non-limiting example a polynucleotide of the present disclosure can include at least one miR-142-3p binding site, miR-142-3p seed sequence, miR-142-3p binding site without the seed, miR-142-5p binding site, miR-142-5p seed sequence, miR-142-5p binding site without the seed, miR-146 binding site, miR-146 seed sequence and/or miR-146 binding site without the seed sequence.

In some embodiments, a polynucleotide of the present disclosure can comprise at least one miRNA binding site in the 3'UTR in order to selectively degrade mRNA therapeutics in the immune cells to subdue unwanted immunogenic reactions caused by therapeutic delivery. As a non-limiting example, the miRNA binding site can make a polynucleotide of the present disclosure more unstable in antigen presenting cells. Non-limiting examples of these miRNAs include mir-142-5p, mir-142-3p, mir-146a-5p, and mir-146-3p.

In one embodiment, a polynucleotide of the present disclosure comprises at least one miRNA sequence in a region of the polynucleotide that can interact with a RNA binding protein.

In some embodiments, the polynucleotide of the present disclosure (e.g., a RNA, e.g., an mRNA) comprising (i) a sequence-optimized nucleotide sequence (e.g., an ORF) encoding an anti-CHIKV antibody polypeptide (e.g., a heavy chain or light chain, functional fragment, or variant thereof) and (ii) a miRNA binding site (e.g., a miRNA binding site that binds to miR-142) and/or a miRNA binding site that binds to miR-126.

In some embodiments, the polynucleotide of the present disclosure (e.g., a RNA, e.g., an mRNA) comprises a sequence-optimized nucleotide sequence (e.g., an ORF) encoding an anti-CHIKV antibody polypeptide (e.g., full length antibody polypeptide (e.g., a heavy chain or a light chain), scFv, functional fragment, or variant thereof), wherein the polynucleotide comprises N1-methylpseudouridines. In some embodiments, the polynucleotide further comprises a 5' UTR having SEQ ID NO. 13 and a 3'UTR having SEQ ID NO. 14. In some embodiments, the polynucleotide disclosed herein is formulated with a delivery agent, e.g., a lipid nanoparticle comprised of an PEG-lipid of Compound I and an ionizable lipid of Compound II or Compound VI.

12. 3' UTRs

In certain embodiments, a polynucleotide of the present disclosure (e.g., a polynucleotide comprising a nucleotide sequence encoding an anti-CHIKV antibody polypeptide of the present disclosure) further comprises a 3' UTR.

3'-UTR is the section of mRNA that immediately follows the translation termination codon and often contains regulatory regions that post-transcriptionally influence gene expression. Regulatory regions within the 3'-UTR can influence polyadenylation, translation efficiency, localization, and stability of the mRNA. In one embodiment, the 3'-UTR useful for the present disclosure comprises a binding site for regulatory proteins or microRNAs.

In certain embodiments, the 3' UTR useful for the polynucleotides of the invention comprises a 3' UTR selected from the group consisting of SEQ ID NOs:14 and 127-138 or any combination thereof. In some embodiments, the 3' UTR comprises a nucleic acid sequence of SEQ ID NO: 14.

In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to a sequence selected from the group consisting of 3' UTR sequences selected from the group consisting of SEQ ID NOs: 14 and 127-138 or any combination thereof. In certain embodiments, the 3' UTR sequence useful for the invention comprises a nucleotide sequence at least about 60%, at least about 70%, at least about 80%, at least about 90%, at least about 95%, at least about 96%, at least about 97%, at least about 98%, at least about 99%, or about 100% identical to SEQ ID NO: 14.

13. Regions having a 5' Cap

The present disclosure also includes a polynucleotide that comprises both a 5' Cap and a polynucleotide of the present disclosure (e.g., a polynucleotide comprising a nucleotide sequence encoding an anti-CHIKV antibody polypeptide).

The 5' cap structure of a natural mRNA is involved in nuclear export, increasing mRNA stability and binds the mRNA Cap Binding Protein (CBP), which is responsible for mRNA stability in the cell and translation competency through the association of CBP with poly(A) binding protein to form the mature cyclic mRNA species. The cap further assists the removal of 5' proximal introns during mRNA splicing.

Endogenous mRNA molecules can be 5'-end capped generating a 5'-ppp-5'-triphosphate linkage between a terminal guanosine cap residue and the 5'-terminal transcribed sense nucleotide of the mRNA molecule. This 5'-guanylate cap can then be methylated to generate an N7-methyl-guanylate residue. The ribose sugars of the terminal and/or anteterminal transcribed nucleotides of the 5' end of the mRNA can optionally also be 2'-O-methylated. 5'-decapping through hydrolysis and cleavage of the guanylate cap structure can target a nucleic acid molecule, such as an mRNA molecule, for degradation.

In some embodiments, the polynucleotides of the present disclosure (e.g., a polynucleotide comprising a nucleotide sequence encoding an anti-CHIKV antibody polypeptide) incorporate a cap moiety.

In some embodiments, polynucleotides of the present disclosure (e.g., a polynucleotide comprising a nucleotide sequence encoding an anti-CHIKV antibody polypeptide) comprise a non-hydrolyzable cap structure preventing decapping and thus increasing mRNA half-life. Because cap structure hydrolysis requires cleavage of 5'-ppp-5' phosphorodiester linkages, modified nucleotides can be used during the capping reaction. For example, a Vaccinia Capping Enzyme from New England Biolabs (Ipswich, MA) can be used with u-thio-guanosine nucleotides according to the manufacturer's instructions to create a phosphorothioate linkage in the 5'-ppp-5' cap. Additional modified guanosine nucleotides can be used such as α-methyl-phosphonate and seleno-phosphate nucleotides.

Additional modifications include, but are not limited to, 2'-O-methylation of the ribose sugars of 5'-terminal and/or 5'-anteterminal nucleotides of the polynucleotide (as mentioned above) on the 2'-hydroxyl group of the sugar ring. Multiple distinct 5'-cap structures can be used to generate the 5'-cap of a nucleic acid molecule, such as a polynucleotide that functions as an mRNA molecule. Cap analogs, which herein are also referred to as synthetic cap analogs, chemical caps, chemical cap analogs, or structural or functional cap analogs, differ from natural (i.e., endogenous, wild-type or physiological) 5'-caps in their chemical structure, while retaining cap function. Cap analogs can be chemically (i.e., non-enzymatically) or enzymatically synthesized and/or linked to the polynucleotides of the present disclosure.

For example, the Anti-Reverse Cap Analog (ARCA) cap contains two guanines linked by a 5'-5'-triphosphate group, wherein one guanine contains an N7 methyl group as well as a 3'-O-methyl group (i.e., N7,3'-O-dimethyl-guanosine-5'-triphosphate-5'-guanosine ($m^7$G-3'mppp-G; which can equivalently be designated 3' O-Me-m7G(5')ppp(5')G). The 3'-0 atom of the other, unmodified, guanine becomes linked to the 5'-terminal nucleotide of the capped polynucleotide. The N7- and 3'-O-methlyated guanine provides the terminal moiety of the capped polynucleotide.

Another exemplary cap is mCAP, which is similar to ARCA but has a 2'-O-methyl group on guanosine (i.e., N7,2'-O-dimethyl-guanosine-5'-triphosphate-5'-guanosine, $m^7$Gm-ppp-G).

In some embodiments, the cap is a dinucleotide cap analog. As a non-limiting example, the dinucleotide cap analog can be modified at different phosphate positions with a boranophosphate group or a phophoroselenoate group such as the dinucleotide cap analogs described in U.S. Pat. No. 8,519,110, the contents of which are herein incorporated by reference in its entirety.

In another embodiment, the cap is a cap analog is a N7-(4-chlorophenoxyethyl) substituted dinucleotide form of a cap analog known in the art and/or described herein. Non-limiting examples of a N7-(4-chlorophenoxyethyl) substituted dinucleotide form of a cap analog include a N7-(4-chlorophenoxyethyl)-G(5')ppp(5')G and a N7-(4-chlorophenoxyethyl)-$m^{3'-O}$G(5')ppp(5')G cap analog (See, e.g., the various cap analogs and the methods of synthesizing cap analogs described in Kore et al. Bioorganic & Medicinal Chemistry 2013 21:4570-4574; the contents of which are herein incorporated by reference in its entirety). In another embodiment, a cap analog of the present disclosure is a 4-chloro/bromophenoxyethyl analog.

While cap analogs allow for the concomitant capping of a polynucleotide or a region thereof, in an in vitro transcription reaction, up to 20% of transcripts can remain uncapped. This, as well as the structural differences of a cap analog from an endogenous 5'-cap structures of nucleic acids produced by the endogenous, cellular transcription machinery, can lead to reduced translational competency and reduced cellular stability.

Polynucleotides of the present disclosure (e.g., a polynucleotide comprising a nucleotide sequence encoding an anti-CHIKV antibody polypeptide) can also be capped post-manufacture (whether IVT or chemical synthesis), using enzymes, in order to generate more authentic 5'-cap structures. As used herein, the phrase "more authentic" refers to a feature that closely mirrors or mimics, either structurally or functionally, an endogenous or wild type feature. That is, a "more authentic" feature is better representative of an endogenous, wild-type, natural or physiological cellular function and/or structure as compared to synthetic features or analogs, etc., of the prior art, or which outperforms the corresponding endogenous, wild-type, natural or physiological feature in one or more respects. Non-limiting examples of more authentic 5'cap structures of the present disclosure are those that, among other things, have enhanced binding of cap binding proteins, increased half-life, reduced susceptibility to 5' endonucleases and/or reduced 5'decapping, as compared to synthetic 5'cap structures known in the art (or to a wild-type, natural or physiological 5'cap structure). For example, recombinant Vaccinia Virus Capping Enzyme and recombinant 2'-O-methyltransferase enzyme can create a canonical 5'-5'-triphosphate linkage between the 5'-terminal nucleotide of a polynucleotide and a guanine cap nucleotide wherein the cap guanine contains an N7 methylation and the 5'-terminal nucleotide of the mRNA contains a 2'-O-methyl. Such a structure is termed the Cap1 structure. This cap results in a higher translational-competency and cellular stability and a reduced activation of cellular pro-inflammatory cytokines, as compared, e.g., to other 5'cap analog structures known in the art. Cap structures include, but are not limited to, 7mG(5')ppp(5')N, pN2p (cap 0), 7mG(5')ppp(5')NlmpNp (cap 1), and 7mG(5')-ppp(5')NlmpN2mp (cap 2).

As a non-limiting example, capping chimeric polynucleotides post-manufacture can be more efficient as nearly 100% of the chimeric polynucleotides can be capped. This is in contrast to ~80% when a cap analog is linked to a chimeric polynucleotide in the course of an in vitro transcription reaction.

According to the present disclosure, 5' terminal caps can include endogenous caps or cap analogs. According to the present disclosure, a 5' terminal cap can comprise a guanine analog. Useful guanine analogs include, but are not limited to, inosine, N1-methyl-guanosine, 2'fluoro-guanosine, 7-deaza-guanosine, 8-oxo-guanosine, 2-amino-guanosine, LNA-guanosine, and 2-azido-guanosine.

14. Poly-A Tails

In some embodiments, the polynucleotides of the present disclosure (e.g., a polynucleotide comprising a nucleotide sequence encoding an anti-CHIKV antibody polypeptide) further comprise a poly-A tail. In further embodiments, terminal groups on the poly-A tail can be incorporated for stabilization. In other embodiments, a poly-A tail comprises des-3' hydroxyl tails.

During RNA processing, a long chain of adenine nucleotides (poly-A tail) can be added to a polynucleotide such as an mRNA molecule in order to increase stability. Immediately after transcription, the 3' end of the transcript can be cleaved to free a 3' hydroxyl. Then poly-A polymerase adds a chain of adenine nucleotides to the RNA. The process, called polyadenylation, adds a poly-A tail that can be between, for example, approximately 80 to approximately 250 residues long, including approximately 80, 90, 100, 110, 120, 130, 140, 150, 160, 170, 180, 190, 200, 210, 220, 230, 240 or 250 residues long.

Poly A tails can also be added after the construct is exported from the nucleus.

According to the present disclosure, terminal groups on the poly A tail can be incorporated for stabilization. Polynucleotides of the present disclosure can include des-3' hydroxyl tails. They can also include structural moieties or 2'-Omethyl modifications as taught by Junjie Li, et al. (Current Biology, Vol. 15, 1501-1507, Aug. 23, 2005, the contents of which are incorporated herein by reference in its entirety).

The polynucleotides of the present disclosure can be designed to encode transcripts with alternative polyA tail structures including histone mRNA. According to Norbury, "Terminal uridylation has also been detected on human replication-dependent histone mRNAs. The turnover of these mRNAs is thought to be important for the prevention of potentially toxic histone accumulation following the completion or inhibition of chromosomal DNA replication. These mRNAs are distinguished by their lack of a 3' poly(A) tail, the function of which is instead assumed by a stable stem-loop structure and its cognate stem-loop binding protein (SLBP); the latter carries out the same functions as those of PABP on polyadenylated mRNAs" (Norbury, "Cytoplasmic RNA: a case of the tail wagging the dog," Nature Reviews Molecular Cell Biology; AOP, published online 29 Aug. 2013; doi:10.1038/nrm3645) the contents of which are incorporated herein by reference in its entirety.

Unique poly-A tail lengths provide certain advantages to the polynucleotides of the present disclosure. Generally, the length of a poly-A tail, when present, is greater than 30 nucleotides in length. In another embodiment, the poly-A tail is greater than 35 nucleotides in length (e.g., at least or greater than about 35, 40, 45, 50, 55, 60, 70, 80, 90, 100, 120, 140, 160, 180, 200, 250, 300, 350, 400, 450, 500, 600, 700, 800, 900, 1,000, 1, 100, 1,200, 1,300, 1,400, 1,500, 1,600, 1,700, 1,800, 1,900, 2,000, 2,500, and 3,000 nucleotides).

In some embodiments, the polynucleotide or region thereof includes from about 30 to about 3,000 nucleotides (e.g., from 30 to 50, from 30 to 100, from 30 to 250, from 30 to 500, from 30 to 750, from 30 to 1,000, from 30 to 1,500, from 30 to 2,000, from 30 to 2,500, from 50 to 100, from 50 to 250, from 50 to 500, from 50 to 750, from 50 to 1,000, from 50 to 1,500, from 50 to 2,000, from 50 to 2,500, from 50 to 3,000, from 100 to 500, from 100 to 750, from 100 to 1,000, from 100 to 1,500, from 100 to 2,000, from 100 to 2,500, from 100 to 3,000, from 500 to 750, from 500 to 1,000, from 500 to 1,500, from 500 to 2,000, from 500 to 2,500, from 500 to 3,000, from 1,000 to 1,500, from 1,000 to 2,000, from 1,000 to 2,500, from 1,000 to 3,000, from 1,500 to 2,000, from 1,500 to 2,500, from 1,500 to 3,000, from 2,000 to 3,000, from 2,000 to 2,500, and from 2,500 to 3,000).

In some embodiments, the poly-A tail is designed relative to the length of the overall polynucleotide or the length of a particular region of the polynucleotide. This design can be based on the length of a coding region, the length of a particular feature or region or based on the length of the ultimate product expressed from the polynucleotides.

In this context, the poly-A tail can be 10, 20, 30, 40, 50, 60, 70, 80, 90, or 100% greater in length than the polynucleotide or feature thereof. The poly-A tail can also be designed as a fraction of the polynucleotides to which it belongs. In this context, the poly-A tail can be 10, 20, 30, 40, 50, 60, 70, 80, or 90% or more of the total length of the construct, a construct region or the total length of the construct minus the poly-A tail. Further, engineered binding sites and conjugation of polynucleotides for Poly-A binding protein can enhance expression.

Additionally, multiple distinct polynucleotides can be linked together via the PABP (Poly-A binding protein) through the 3'-end using modified nucleotides at the 3'-terminus of the poly-A tail. Transfection experiments can be conducted in relevant cell lines at and protein production can be assayed by ELISA at 12 hr, 24 hr, 48 hr, 72 hr and day 7 post-transfection.

In some embodiments, the polynucleotides of the present disclosure are designed to include a polyA-G Quartet region. The G-quartet is a cyclic hydrogen bonded array of four guanine nucleotides that can be formed by G-rich sequences in both DNA and RNA. In this embodiment, the G-quartet is incorporated at the end of the poly-A tail. The resultant polynucleotide is assayed for stability, protein production and other parameters including half-life at various time points. It has been discovered that the polyA-G quartet results in protein production from an mRNA equivalent to at least 75% of that seen using a poly-A tail of 120 nucleotides alone.

15. Start Codon Region

The present disclosure also includes a polynucleotide that comprises both a start codon region and the polynucleotide described herein (e.g., a polynucleotide comprising a nucleotide sequence encoding an anti-CHIKV antibody polypeptide). In some embodiments, the polynucleotides of the present disclosure can have regions that are analogous to or function like a start codon region.

In some embodiments, the translation of a polynucleotide can initiate on a codon that is not the start codon AUG. Translation of the polynucleotide can initiate on an alternative start codon such as, but not limited to, ACG, AGG, AAG, CTG/CUG, GTG/GUG, ATA/AUA, ATT/AUU, TTG/UUG (see Touriol et al. Biology of the Cell 95 (2003) 169-178 and Matsuda and Mauro PLoS ONE, 2010 5:11; the contents of each of which are herein incorporated by reference in its entirety).

As a non-limiting example, the translation of a polynucleotide begins on the alternative start codon ACG. As another non-limiting example, polynucleotide translation begins on the alternative start codon CTG or CUG. As yet another non-limiting example, the translation of a polynucleotide begins on the alternative start codon GTG or GUG.

Nucleotides flanking a codon that initiates translation such as, but not limited to, a start codon or an alternative start codon, are known to affect the translation efficiency, the length and/or the structure of the polynucleotide. (See, e.g., Matsuda and Mauro PLoS ONE, 2010 5:11; the contents of which are herein incorporated by reference in its entirety). Masking any of the nucleotides flanking a codon that initiates translation can be used to alter the position of translation initiation, translation efficiency, length and/or structure of a polynucleotide.

In some embodiments, a masking agent can be used near the start codon or alternative start codon in order to mask or hide the codon to reduce the probability of translation initiation at the masked start codon or alternative start codon. Non-limiting examples of masking agents include antisense locked nucleic acids (LNA) polynucleotides and exon-junction complexes (EJCs) (See, e.g., Matsuda and Mauro describing masking agents LNA polynucleotides and EJCs (PLoS ONE, 2010 5:11); the contents of which are herein incorporated by reference in its entirety).

In another embodiment, a masking agent can be used to mask a start codon of a polynucleotide in order to increase the likelihood that translation will initiate on an alternative start codon. In some embodiments, a masking agent can be used to mask a first start codon or alternative start codon in order to increase the chance that translation will initiate on a start codon or alternative start codon downstream to the masked start codon or alternative start codon.

In some embodiments, a start codon or alternative start codon can be located within a perfect complement for a miR binding site. The perfect complement of a miR binding site can help control the translation, length and/or structure of the polynucleotide similar to a masking agent. As a non-limiting example, the start codon or alternative start codon can be located in the middle of a perfect complement for a miRNA binding site. The start codon or alternative start codon can be located after the first nucleotide, second nucleotide, third nucleotide, fourth nucleotide, fifth nucleotide, sixth nucleotide, seventh nucleotide, eighth nucleotide, ninth nucleotide, tenth nucleotide, eleventh nucleotide, twelfth nucleotide, thirteenth nucleotide, fourteenth nucleotide, fifteenth nucleotide, sixteenth nucleotide, seventeenth nucleotide, eighteenth nucleotide, nineteenth nucleotide, twentieth nucleotide or twenty-first nucleotide.

In another embodiment, the start codon of a polynucleotide can be removed from the polynucleotide sequence in order to have the translation of the polynucleotide begin on a codon that is not the start codon. Translation of the polynucleotide can begin on the codon following the removed start codon or on a downstream start codon or an alternative start codon. In a non-limiting example, the start codon ATG or AUG is removed as the first 3 nucleotides of the polynucleotide sequence in order to have translation initiate on a downstream start codon or alternative start codon. The polynucleotide sequence where the start codon was removed can further comprise at least one masking agent for the downstream start codon and/or alternative start codons in order to control or attempt to control the initiation of translation, the length of the polynucleotide and/or the structure of the polynucleotide.

16. Stop Codon Region

The present disclosure also includes a polynucleotide that comprises both a stop codon region and the polynucleotide described herein (e.g., a polynucleotide comprising a nucleotide sequence encoding an antibody). In some embodiments, the polynucleotides of the present disclosure can include at least two stop codons before the 3' untranslated region (UTR). The stop codon can be selected from TGA, TAA and TAG in the case of DNA, or from UGA, UAA and UAG in the case of RNA. In some embodiments, the polynucleotides of the present disclosure include the stop codon TGA in the case or DNA, or the stop codon UGA in the case of RNA, and one additional stop codon. In a further embodiment the addition stop codon can be TAA or UAA. In another embodiment, the polynucleotides of the present disclosure include three consecutive stop codons, four stop codons, or more.

17. Polynucleotide Comprising an mRNA Encoding an Antibody Polypeptide

In certain embodiments, a polynucleotide of the present disclosure, for example a polynucleotide comprising an mRNA nucleotide sequence encoding an anti-CHIKV antibody polypeptide, comprises from 5' to 3' end:

(i) a 5' cap provided above;
(ii) a 5' UTR, such as a sequence provided above;
(iii) an open reading frame encoding an anti-CHIKV antibody polypeptide, e.g., a sequence optimized nucleic acid sequence encoding an anti-CHIKV antibody polypeptide disclosed herein;
(iv) at least one stop codon;
(v) a 3' UTR, such as a sequence provided above; and
(vi) a poly-A tail provided above.

In some embodiments, the polynucleotide further comprises a miRNA binding site, e.g., a miRNA binding site that binds to miRNA-142. In some embodiments, the 5'UTR comprises the miRNA binding site. In some embodiments, the 3' UTR comprises the miRNA binding site.

In some embodiments, a polynucleotide of the present disclosure comprises a nucleotide sequence encoding a polypeptide sequence at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the protein sequence of an anti-CHIKV antibody polypeptide described herein, such as a heavy chain polypeptide of an anti-CHIKV antibody (SEQ ID NO: 1) or a light chain polypeptide of an anti-CHIKV antibody (SEQ ID NO: 3).

In some embodiments, a polynucleotide of the present disclosure comprises a nucleotide sequence comprising an open reading frame (ORF) that is at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to SEQ ID NO: 2 or SEQ ID NO:4.

In some embodiments, a polynucleotide of the present disclosure comprises a nucleotide sequence comprising an open reading frame (ORF) that is at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a nucleotide sequence encoding a heavy chain variable region of an anti-CHIKV antibody, e.g., nucleotides 61-426 of SEQ ID NO:2.

In some embodiments, a polynucleotide of the present disclosure comprises a nucleotide sequence comprising an open reading frame (ORF) that is at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a nucleotide sequence encoding a heavy chain of an anti-CHIKV antibody, e.g., nucleotides 61-1416 of SEQ ID NO:2.

In some embodiments, a polynucleotide of the present disclosure comprises a nucleotide sequence comprising an open reading frame (ORF) that is at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a nucleotide sequence encoding a light chain variable region of an anti-CHIKV antibody, e.g., nucleotides 61-384 of SEQ ID NO:4.

In some embodiments, a polynucleotide of the present disclosure comprises a nucleotide sequence comprising an open reading frame (ORF) that is at least 70%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to a nucleotide sequence encoding a light chain of an anti-CHIKV antibody, e.g., nucleotides 61-705 of SEQ ID NO:4.

In some embodiments, a polynucleotide of the present disclosure, for example a polynucleotide comprising an mRNA nucleotide sequence encoding a polypeptide, comprises (1) a 5' cap provided above, for example, CAP1, (2) a 5' UTR, (3) a nucleotide sequence ORF selected from SEQ ID NO:2 or SEQ ID NO:4, (3) a stop codon, (4) a 3' UTR, and (5) a poly-A tail provided above, for example, a poly-A tail of about 100 residues.

Exemplary anti-CHIKV antibody nucleotide constructs are described below:

SEQ ID NO:5 consists from 5' to 3' end: 5' UTR of SEQ ID NO:13, anti-CHIKV antibody nucleotide ORF of SEQ ID NO:2, and 3' UTR of SEQ ID NO:14.

SEQ ID NO:6 consists from 5' to 3' end: 5' UTR of SEQ ID NO:13, anti-CHIKV antibody nucleotide ORF of SEQ ID NO:4, and 3' UTR of SEQ ID NO:14.

In certain embodiments, in constructs with SEQ ID NOs. 5 and 6, all uracils therein are methylpseudouracils. In certain embodiments, in constructs with SEQ ID NOs.: 5 and 6, all uracils therein are 5-methoxyuracils.

In some embodiments, a polynucleotide of the present disclosure, for example a polynucleotide comprising an mRNA nucleotide sequence encoding an anti-CHIKV antibody polypeptide, comprises (1) a 5' cap provided above, for example, CAP1, (2) a nucleotide sequence selected from SEQ ID NO:5 or SEQ ID NO:6, and (3) a poly-A tail provided above, for example, a poly A tail of ~100 residues. In certain embodiments, in constructs with SEQ ID NOs.: 5 and 6, all uracils therein are N1 methylpseudouracils. In certain embodiments, in constructs with SEQ ID NOs.: 5 and 6, all uracils therein are 5-methoxyuracils.

TABLE 5

Modified mRNA constructs including ORFs encoding a human anti-CHIKV antibody polypeptide (each of constructs #1 to #4 comprises a Cap1 5' terminal cap and a 3' terminal PolyA region)

| Anti-CHIKV antibody mRNA construct | 5' UTR SEQ ID NO | ORF Name (Chemistry) | ORF SEQ ID NO | 3' UTR SEQ ID NO: |
|---|---|---|---|---|
| #1 (SEQ ID NO: 5) | 13 | CHIKV24 heavy chain (G5) | 2 | 14 |

TABLE 5-continued

Modified mRNA constructs including ORFs encoding a human anti-CHIKV antibody polypeptide (each of constructs #1 to #4 comprises a Cap1 5' terminal cap and a 3' terminal PolyA region)

| Anti-CHIKV | 5' UTR | ORF | | 3' UTR |
|---|---|---|---|---|
| antibody mRNA construct | SEQ ID NO | Name (Chemistry) | SEQ ID NO | SEQ ID NO: |
| #2 (SEQ ID NO: 6) | 13 | CHIKV24 light chain (G5) | 4 | 14 |

18. Methods of Making Polynucleotides

The present disclosure also provides methods for making a polynucleotide of the present disclosure (e.g., a polynucleotide comprising a nucleotide sequence encoding an anti-CHIKV antibody polypeptide) or a complement thereof.

In some aspects, a polynucleotide (e.g., a RNA, e.g., an mRNA) disclosed herein, and encoding an anti-CHIKV antibody polypeptide, can be constructed using in vitro transcription. In other aspects, a polynucleotide (e.g., a RNA, e.g., an mRNA) disclosed herein, and encoding an antibody, can be constructed by chemical synthesis using an oligonucleotide synthesizer.

In other aspects, a polynucleotide (e.g., a RNA, e.g., an mRNA) disclosed herein, and encoding an anti-CHIKV antibody polypeptide is made by using a host cell. In certain aspects, a polynucleotide (e.g., a RNA, e.g., an mRNA) disclosed herein, and encoding an anti-CHIKV antibody polypeptide is made by one or more combination of the IVT, chemical synthesis, host cell expression, or any other methods known in the art.

Naturally occurring nucleosides, non-naturally occurring nucleosides, or combinations thereof, can totally or partially naturally replace occurring nucleosides present in the candidate nucleotide sequence and can be incorporated into a sequence-optimized nucleotide sequence (e.g., a RNA, e.g., an mRNA) encoding an anti-CHIKV antibody polypeptide. The resultant polynucleotides, e.g., mRNAs, can then be examined for their ability to produce protein and/or produce a therapeutic outcome.

a. In Vitro Transcription/Enzymatic Synthesis

The polynucleotides of the present disclosure disclosed herein (e.g., a polynucleotide comprising a nucleotide sequence encoding an anti-CHIKV antibody polypeptide) can be transcribed using an in vitro transcription (IVT) system. The system typically comprises a transcription buffer, nucleotide triphosphates (NTPs), an RNase inhibitor and a polymerase. The NTPs can be selected from, but are not limited to, those described herein including natural and unnatural (modified) NTPs. The polymerase can be selected from, but is not limited to, T7 RNA polymerase, T3 RNA polymerase and mutant polymerases such as, but not limited to, polymerases able to incorporate polynucleotides disclosed herein. See U.S. Publ. No. US20130259923, which is herein incorporated by reference in its entirety.

Any number of RNA polymerases or variants can be used in the synthesis of the polynucleotides of the present disclosure. RNA polymerases can be modified by inserting or deleting amino acids of the RNA polymerase sequence. As a non-limiting example, the RNA polymerase can be modified to exhibit an increased ability to incorporate a 2'-modified nucleotide triphosphate compared to an unmodified RNA polymerase (see International Publication WO2008078180 and U.S. Pat. No. 8,101,385; herein incorporated by reference in their entireties).

Variants can be obtained by evolving an RNA polymerase, optimizing the RNA polymerase amino acid and/or nucleic acid sequence and/or by using other methods known in the art. As a non-limiting example, T7 RNA polymerase variants can be evolved using the continuous directed evolution system set out by Esvelt et al. (Nature 472:499-503 (2011); herein incorporated by reference in its entirety) where clones of T7 RNA polymerase can encode at least one mutation such as, but not limited to, lysine at position 93 substituted for threonine (K93T), 14M, A7T, E63V, V64D, A65E, D66Y, T76N, C125R, S128R, A136T, N165S, G175R, H176L, Y178H, F182L, L196F, G198V, D208Y, E222K, S228A, Q239R, T243N, G259D, M2671, G280C, H300R, D351A, A354S, E356D, L360P, A383V, Y385C, D388Y, S397R, M401T, N410S, K450R, P451T, G452V, E484A, H523L, H524N, G542V, E565K, K577E, K577M, N601S, S684Y, L6991, K713E, N748D, Q754R, E775K, A827V, D851N or L864F. As another non-limiting example, T7 RNA polymerase variants can encode at least mutation as described in U.S. Pub. Nos. 20100120024 and 20070117112; herein incorporated by reference in their entireties. Variants of RNA polymerase can also include, but are not limited to, substitutional variants, conservative amino acid substitution, insertional variants, deletional variants and/or covalent derivatives.

In one aspect, the polynucleotide can be designed to be recognized by the wild type or variant RNA polymerases. In doing so, the polynucleotide can be modified to contain sites or regions of sequence changes from the wild type or parent chimeric polynucleotide.

Polynucleotide or nucleic acid synthesis reactions can be carried out by enzymatic methods utilizing polymerases. Polymerases catalyze the creation of phosphodiester bonds between nucleotides in a polynucleotide or nucleic acid chain. Currently known DNA polymerases can be divided into different families based on amino acid sequence comparison and crystal structure analysis. DNA polymerase I (pol I) or A polymerase family, including the Klenow fragments of *E. coli, Bacillus* DNA polymerase I, *Thermus aquaticus* (Taq) DNA polymerases, and the T7 RNA and DNA polymerases, is among the best studied of these families. Another large family is DNA polymerase a (pol u) or B polymerase family, including all eukaryotic replicating DNA polymerases and polymerases from phages T4 and RB69. Although they employ similar catalytic mechanism, these families of polymerases differ in substrate specificity, substrate analog-incorporating efficiency, degree and rate for primer extension, mode of DNA synthesis, exonuclease activity, and sensitivity against inhibitors.

DNA polymerases are also selected based on the optimum reaction conditions they require, such as reaction temperature, pH, and template and primer concentrations. Sometimes a combination of more than one DNA polymerases is employed to achieve the desired DNA fragment size and synthesis efficiency. For example, Cheng et al. increase pH, add glycerol and dimethyl sulfoxide, decrease denaturation times, increase extension times, and utilize a secondary thermostable DNA polymerase that possesses a 3' to 5' exonuclease activity to effectively amplify long targets from cloned inserts and human genomic DNA. (Cheng et al., PNAS 91:5695-5699 (1994), the contents of which are incorporated herein by reference in their entirety). RNA polymerases from bacteriophage T3, T7, and SP6 have been widely used to prepare RNAs for biochemical and biophysical studies. RNA polymerases, capping enzymes, and poly-A polymerases are disclosed in the co-pending International Publication No. WO2014028429, the contents of which are incorporated herein by reference in their entirety.

In one aspect, the RNA polymerase which can be used in the synthesis of the polynucleotides of the present disclosure is a Syn5 RNA polymerase. (see Zhu et al. Nucleic Acids Research 2013, doi:10.1093/nar/gkt1193, which is herein incorporated by reference in its entirety). The Syn5 RNA polymerase was recently characterized from marine cyanophage Syn5 by Zhu et al. where they also identified the promoter sequence (see Zhu et al. Nucleic Acids Research 2013, the contents of which is herein incorporated by reference in its entirety). Zhu et al. found that Syn5 RNA polymerase catalyzed RNA synthesis over a wider range of temperatures and salinity as compared to T7 RNA polymerase. Additionally, the requirement for the initiating nucleotide at the promoter was found to be less stringent for Syn5 RNA polymerase as compared to the T7 RNA polymerase making Syn5 RNA polymerase promising for RNA synthesis.

In one aspect, a Syn5 RNA polymerase can be used in the synthesis of the polynucleotides described herein. As a non-limiting example, a Syn5 RNA polymerase can be used in the synthesis of the polynucleotide requiring a precise 3'-terminus.

In one aspect, a Syn5 promoter can be used in the synthesis of the polynucleotides. As a non-limiting example, the Syn5 promoter can be 5'-ATTGGGCACCCGTAAGGG-3' (SEQ ID NO: 229), as described by Zhu et al. (Nucleic Acids Research 2013.

In one aspect, a Syn5 RNA polymerase can be used in the synthesis of polynucleotides comprising at least one chemical modification described herein and/or known in the art (see e.g., the incorporation of pseudo-UTP and 5Me-CTP described in Zhu et al. Nucleic Acids Research 2013).

In one aspect, the polynucleotides described herein can be synthesized using a Syn5 RNA polymerase which has been purified using modified and improved purification procedure described by Zhu et al. (Nucleic Acids Research 2013).

Various tools in genetic engineering are based on the enzymatic amplification of a target gene which acts as a template. For the study of sequences of individual genes or specific regions of interest and other research needs, it is necessary to generate multiple copies of a target gene from a small sample of polynucleotides or nucleic acids. Such methods can be applied in the manufacture of the polynucleotides of the present disclosure.

For example, polymerase chain reaction (PCR), strand displacement amplification (SDA), nucleic acid sequence-based amplification (NASBA), also called transcription mediated amplification (TMA), and rolling-circle amplification (RCA) can be utilized in the manufacture of one or more regions of the polynucleotides of the present disclosure.

Assembling polynucleotides or nucleic acids by a ligase is also widely used. DNA or RNA ligases promote intermolecular ligation of the 5' and 3' ends of polynucleotide chains through the formation of a phosphodiester bond.

b. Chemical Synthesis

Standard methods can be applied to synthesize an isolated polynucleotide sequence encoding an isolated polypeptide of interest, such as a polynucleotide of the present disclosure (e.g., a polynucleotide comprising a nucleotide sequence encoding an antibody). For example, a single DNA or RNA oligomer containing a codon-optimized nucleotide sequence coding for the particular isolated polypeptide can be synthesized. In other aspects, several small oligonucleotides coding for portions of the desired polypeptide can be synthesized and then ligated. In some aspects, the individual oligonucleotides typically contain 5' or 3' overhangs for complementary assembly.

A polynucleotide disclosed herein (e.g., a RNA, e.g., an mRNA) can be chemically synthesized using chemical synthesis methods and potential nucleobase substitutions known in the art. See, for example, International Publication Nos. WO2014093924, WO2013052523; WO2013039857, WO2012135805, WO2013151671; U.S. Publ. No. US20130115272; or U.S. Pat. Nos. U.S. Pat. No. 8,999,380 or 8,710,200, all of which are herein incorporated by reference in their entireties.

c. Purification of Polynucleotides Encoding an Antibody

Purification of the polynucleotides described herein (e.g., a polynucleotide comprising a nucleotide sequence encoding an anti-CHIKV antibody polypeptide) can include, but is not limited to, polynucleotide clean-up, quality assurance and quality control. Clean-up can be performed by methods known in the arts such as, but not limited to, AGENCOURT® beads (Beckman Coulter Genomics, Danvers, MA), poly-T beads, LNA™ oligo-T capture probes (EXIQON® Inc., Vedbaek, Denmark) or HPLC based purification methods such as, but not limited to, strong anion exchange HPLC, weak anion exchange HPLC, reverse phase HPLC (RP-HPLC), and hydrophobic interaction HPLC (HIC-HPLC).

The term "purified" when used in relation to a polynucleotide such as a "purified polynucleotide" refers to one that is separated from at least one contaminant. As used herein, a "contaminant" is any substance that makes another unfit, impure or inferior. Thus, a purified polynucleotide (e.g., DNA and RNA) is present in a form or setting different from that in which it is found in nature, or a form or setting different from that which existed prior to subjecting it to a treatment or purification method.

In some embodiments, purification of a polynucleotide of the present disclosure (e.g., a polynucleotide comprising a nucleotide sequence encoding an antibody) removes impurities that can reduce or remove an unwanted immune response, e.g., reducing cytokine activity.

In some embodiments, the polynucleotide of the present disclosure (e.g., a polynucleotide comprising a nucleotide sequence encoding an anti-CHIKV antibody polypeptide) is purified prior to administration using column chromatography (e.g., strong anion exchange HPLC, weak anion exchange HPLC, reverse phase HPLC (RP-HPLC), and hydrophobic interaction HPLC (HIC-HPLC), or (LCMS)).

In some embodiments, the polynucleotide of the present disclosure (e.g., a polynucleotide comprising a nucleotide sequence an anti-CHIKV antibody polypeptide) purified using column chromatography (e.g., strong anion exchange HPLC, weak anion exchange HPLC, reverse phase HPLC (RP-HPLC, hydrophobic interaction HPLC (HIC-HPLC), or (LCMS)) presents increased expression of the encoded antibody compared to the expression level obtained with the same polynucleotide of the present disclosure purified by a different purification method.

In some embodiments, a column chromatography (e.g., strong anion exchange HPLC, weak anion exchange HPLC, reverse phase HPLC (RP-HPLC), hydrophobic interaction HPLC (HIC-HPLC), or (LCMS)) purified polynucleotide comprises a nucleotide sequence encoding an anti-CHIKV antibody polypeptide comprising one or more of the point mutations known in the art.

In some embodiments, the use of RP-HPLC purified polynucleotide increases anti-CHIKV antibody polypeptide expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the expression levels of antibody in the cells before the RP-HPLC purified polynucleotide was introduced in the cells, or after a non-RP-HPLC purified polynucleotide was introduced in the cells.

In some embodiments, the use of RP-HPLC purified polynucleotide increases functional anti-CHIKV antibody polypeptide expression levels in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the functional expression levels of antibody in the cells before the RP-HPLC purified polynucleotide was introduced in the cells, or after a non-RP-HPLC purified polynucleotide was introduced in the cells.

In some embodiments, the use of RP-HPLC purified polynucleotide increases detectable anti-CHIKV antibody polypeptide activity in cells when introduced into those cells, e.g., by 10-100%, i.e., at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 90%, at least about 95%, or at least about 100% with respect to the activity levels of functional antibody in the cells before the RP-HPLC purified polynucleotide was introduced in the cells, or after a non-RP-HPLC purified polynucleotide was introduced in the cells.

In some embodiments, the purified polynucleotide is at least about 80% pure, at least about 85% pure, at least about 90% pure, at least about 95% pure, at least about 96% pure, at least about 97% pure, at least about 98% pure, at least about 99% pure, or about 100% pure.

A quality assurance and/or quality control check can be conducted using methods such as, but not limited to, gel electrophoresis, UV absorbance, or analytical HPLC. In another embodiment, the polynucleotide can be sequenced by methods including, but not limited to reverse-transcriptase-PCR.

d. Quantification of Expressed Polynucleotides Encoding Antibody

In some embodiments, the polynucleotides of the present disclosure (e.g., a polynucleotide comprising a nucleotide sequence encoding an anti-CHIKV antibody polypeptide), their expression products, as well as degradation products and metabolites can be quantified according to methods known in the art.

In some embodiments, the polynucleotides of the present disclosure can be quantified in exosomes or when derived from one or more bodily fluid. As used herein "bodily fluids" include peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, cowper's fluid or pre-ejaculatory fluid, sweat, fecal matter, hair, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, and umbilical cord blood. Alternatively, exosomes can be retrieved from an organ selected from the group consisting of lung, heart, pancreas, stomach, intestine, bladder, kidney, ovary, testis, skin, colon, breast, prostate, brain, esophagus, liver, and placenta.

In the exosome quantification method, a sample of not more than 2 mL is obtained from the subject and the exosomes isolated by size exclusion chromatography, density gradient centrifugation, differential centrifugation, nanomembrane ultrafiltration, immunoabsorbent capture, affinity purification, microfluidic separation, or combinations thereof. In the analysis, the level or concentration of a polynucleotide can be an expression level, presence, absence, truncation or alteration of the administered construct. It is advantageous to correlate the level with one or more clinical phenotypes or with an assay for a human disease biomarker.

The assay can be performed using construct specific probes, cytometry, qRT-PCR, real-time PCR, PCR, flow cytometry, electrophoresis, mass spectrometry, or combinations thereof while the exosomes can be isolated using immunohistochemical methods such as enzyme linked immunosorbent assay (ELISA) methods. Exosomes can also be isolated by size exclusion chromatography, density gradient centrifugation, differential centrifugation, nanomembrane ultrafiltration, immunoabsorbent capture, affinity purification, microfluidic separation, or combinations thereof.

These methods afford the investigator the ability to monitor, in real time, the level of polynucleotides remaining or delivered. This is possible because the polynucleotides of the present disclosure differ from the endogenous forms due to the structural or chemical modifications.

In some embodiments, the polynucleotide can be quantified using methods such as, but not limited to, ultraviolet visible spectroscopy (UV/Vis). A non-limiting example of a UV/Vis spectrometer is a NANODROP® spectrometer (ThermoFisher, Waltham, MA). The quantified polynucleotide can be analyzed in order to determine if the polynucleotide can be of proper size, check that no degradation of the polynucleotide has occurred. Degradation of the polynucleotide can be checked by methods such as, but not limited to, agarose gel electrophoresis, HPLC based purification methods such as, but not limited to, strong anion exchange HPLC, weak anion exchange HPLC, reverse phase HPLC (RP-HPLC), and hydrophobic interaction HPLC (HIC-HPLC), liquid chromatography-mass spectrometry (LCMS), capillary electrophoresis (CE) and capillary gel electrophoresis (CGE).

19. Pharmaceutical Compositions and Formulations Provided herein are compositions (e.g., pharmaceutical compositions), methods, kits and reagents for prevention and/or treatment of disease in humans and other mammals. The present invention provides pharmaceutical compositions and formulations that comprise any of the polynucleotides described above. In some embodiments, the composition or formulation further comprises a delivery agent.

In some embodiments, the composition or formulation can contain a polynucleotide comprising a sequence optimized nucleic acid sequence disclosed herein which encodes an anti-CHIKV antibody polypeptide. In some embodiments, the composition or formulation can contain a polynucleotide (e.g., a RNA, e.g., an mRNA) comprising a polynucleotide (e.g., an ORF) having significant sequence identity to a sequence optimized nucleic acid sequence disclosed herein which encodes an anti-CHIKV antibody polypeptide. In some embodiments, the polynucleotide further comprises a miRNA binding site, e.g., a miRNA binding site that binds miR-126, miR-142, miR-144, miR-146, miR-150, miR-155, miR-16, miR-21, miR-223, miR-24, miR-27 and miR-26a.

In some embodiments, the pharmaceutical compositions described herein have a first polynucleotide comprising a first mRNA comprising (i) a first 5' UTR, (ii) a first open reading frame (ORF) encoding a first polypeptide comprising a heavy chain antibody sequence of SEQ ID NO:1, wherein the first ORF comprises a first nucleic acid sequence that is at least 80% identical to SEQ ID NO:2, (iii) a first stop codon, and (iv) a first 3' UTR; a second polynucleotide comprising a second mRNA comprising (i) a second 5' UTR, (ii) a second ORF encoding a second polypeptide comprising the light chain antibody sequence of SEQ ID NO:3, wherein the second ORF comprises a second nucleic acid sequence that is at least 80% identical to SEQ ID NO:4, (iii) a second stop codon, and (iv) a second 3' UTR; and a delivery agent, wherein the first polypeptide when paired with the second polypeptide forms an anti-Chikungunya virus antibody.

In some embodiments, the pharmaceutical compositions described herein have a first polynucleotide comprising a first mRNA comprising (i) a first 5' UTR, (ii) a first open reading frame (ORF) encoding a first polypeptide comprising the heavy chain variable region of the heavy chain antibody sequence of SEQ ID NO:1, wherein the first ORF comprises a first nucleic acid sequence that is at least 80% identical to nucleotides 61-426 of SEQ ID NO:2, (iii) a first stop codon, and (iv) a first 3' UTR; a second polynucleotide comprising a second mRNA comprising (i) a second 5' UTR, (ii) a second ORF encoding a second polypeptide comprising the light chain variable region of the light chain antibody sequence of SEQ ID NO:3, wherein the second ORF comprises a second nucleic acid sequence that is at least 80% identical to nucleotides 61-384 of SEQ ID NO:4, (iii) a second stop codon, and (iv) a second 3' UTR; and a delivery agent, wherein the first polypeptide when paired with the second polypeptide forms an anti-Chikungunya virus antibody or an anti-Chikungunya virus antibody fragment.

In some embodiments, the pharmaceutical compositions described herein have a first polynucleotide comprising a first mRNA comprising (i) a first 5' UTR, (ii) a first open reading frame (ORF) encoding a first polypeptide comprising the heavy chain of the heavy chain antibody sequence of SEQ ID NO:1, wherein the first ORF comprises a first nucleic acid sequence that is at least 80% identical to nucleotides 61-1416 of SEQ ID NO:2, (iii) a first stop codon, and (iv) a first 3' UTR; a second polynucleotide comprising a second mRNA comprising (i) a second 5' UTR, (ii) a second ORF encoding a second polypeptide comprising the light chain of the light chain antibody sequence of SEQ ID NO:3, wherein the second ORF comprises a second nucleic acid sequence that is at least 80% identical to nucleotides 61-705 of SEQ ID NO:4, (iii) a second stop codon, and (iv) a second 3' UTR; and a delivery agent, wherein the first polypeptide when paired with the second polypeptide forms an anti-Chikungunya virus antibody or an anti-Chikungunya virus antibody fragment.

In some embodiments, a pharmaceutical composition described herein has a first mRNA with the nucleic acid sequence of SEQ ID NO:5 and a second mRNA with the nucleic acid sequence of SEQ ID NO:6.

In some embodiments, a first mRNA comprising a first open reading frame (ORF) encoding a first polypeptide comprising a heavy chain variable region of an anti-CHIKV antibody (e.g., an anti-CHIKV heavy chain polypeptide) is co-formulated in a lipid nanoparticle (LNP) with a second mRNA comprising a second open reading frame (ORF) encoding a second polypeptide comprising a light chain variable region of an anti-CHIKV (e.g., an anti-CHIKV light chain polypeptide) at a ratio w/w of 1:1, 2:1, 3:1, 4:1, 5:1, 6:1, 7:1, 8:1, 9:1, 10:1, 1:2, 1:3, 1:4, 1:5, 1:6, 1:7, 1:8, 1:9, 1:10, 3:2, 5:7, or 7:9, respectively. In some embodiments, a first mRNA comprising a first open reading frame (ORF) encoding a first polypeptide comprising a heavy chain variable region of an anti-CHIKV antibody (e.g., an anti-CHIKV heavy chain polypeptide) and a second mRNA comprising a first open reading frame (ORF) encoding a second polypeptide comprising a light chain variable region of an anti-CHIKV (e.g., an anti-CHIKV light chain polypeptide) are co-formulated at a 2:1 ratio w/w (2:1 first mRNA:second mRNA) in an lipid nanoparticle (LNP). In some embodiments, the pharmaceutical composition comprises an LNP with a first mRNA with the nucleic acid sequence of SEQ ID NO:5 and a second mRNA with the nucleic acid sequence of SEQ ID NO:6 at a ratio of 2:1 w/w.

In some embodiments, a pharmaceutical composition has a first mRNA comprising a first open reading frame (ORF) encoding a first polypeptide comprising a heavy chain variable region of an anti-chikungunya virus antibody and a second mRNA comprising a second ORF encoding a second polypeptide comprising a light chain variable region of the anti-chikungunya virus antibody, wherein the first polypeptide and the second polypeptide pair to form the anti-chikungunya virus antibody, and wherein the pharmaceutical composition when administered to a human subject in need thereof as a single dose administration is sufficient to: (i) protect the human subject from chikungunya virus infection, after exposure to a chikungunya virus, for at least 24 hours, 48 hours, 72 hours, 96 hours, 168 hours, 336 hours, or 720 hours after the single dose administration; (ii) protect the human subject from onset of chikungunya fever, after exposure to a chikungunya virus, for at least 24 hours, 48 hours, 72 hours, 96 hours, 168 hours, 336 hours, or 720 hours after the single dose administration; and/or (iii) provide systemic production of the anti-chikungunya virus antibody in the human subject at a level of at least 5 μg/ml, 10 μg/ml, 15 μg/ml, 20 μg/ml, 25 μg/ml, or 30 μg/ml for at least 24 hours, 48 hours, 72 hours, 96 hours, 168 hours, 336 hours, or 720 hours after the single dose administration.

Pharmaceutical compositions or formulation can optionally comprise one or more additional active substances, e.g., therapeutically and/or prophylactically active substances. Pharmaceutical compositions or formulation of the present invention can be sterile and/or pyrogen-free. General considerations in the formulation and/or manufacture of pharmaceutical agents can be found, for example, in Remington: The Science and Practice of Pharmacy 21st ed., Lippincott Williams & Wilkins, 2005 (incorporated herein by reference in its entirety). In some embodiments, compositions are administered to humans, human patients or subjects. For the purposes of the present disclosure, the phrase "active ingredient" generally refers to polynucleotides to be delivered as described herein.

Formulations and pharmaceutical compositions described herein can be prepared by any method known or hereafter developed in the art of pharmacology. In general, such preparatory methods include the step of associating the active ingredient with an excipient and/or one or more other accessory ingredients, and then, if necessary and/or desirable, dividing, shaping and/or packaging the product into a desired single- or multi-dose unit.

A pharmaceutical composition or formulation in accordance with the present disclosure can be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the present disclosure can vary, depending upon the identity, size, and/or condition of the subject being treated and further depending upon the route by which the composition is to be administered.

In some embodiments, the compositions and formulations described herein can contain at least one polynucleotide of the invention. As a non-limiting example, the composition or formulation can contain 1, 2, 3, 4 or 5 polynucleotides of the invention. In some embodiments, the compositions or formulations described herein can comprise more than one type of polynucleotide. In some embodiments, the composition or formulation can comprise a polynucleotide in linear and circular form. In another embodiment, the composition or formulation can comprise a circular polynucleotide and an in vitro transcribed (IVT) polynucleotide. In yet another embodiment, the composition or formulation can comprise an IVT polynucleotide, a chimeric polynucleotide and a circular polynucleotide.

Although the descriptions of pharmaceutical compositions and formulations provided herein are principally directed to pharmaceutical compositions and formulations that are suitable for administration to humans, it will be understood by the skilled artisan that such compositions are generally suitable for administration to any other animal, e.g., to non-human animals, e.g. non-human mammals.

The present invention provides pharmaceutical formulations that comprise a polynucleotide described herein (e.g., a polynucleotide comprising a nucleotide sequence encoding an anti-CHIKV antibody polypeptide). The polynucleotides described herein can be formulated using one or more excipients to: (1) increase stability; (2) increase cell transfection; (3) permit the sustained or delayed release (e.g., from a depot formulation of the polynucleotide); (4) alter the biodistribution (e.g., target the polynucleotide to specific tissues or cell types); (5) increase the translation of encoded protein in vivo; and/or (6) alter the release profile of encoded protein in vivo. In some embodiments, the pharmaceutical formulation further comprises a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 50:10:38.5:1.5. In some embodiments, the delivery agent comprises Compound II, DSPC, Cholesterol, and Compound I or PEG-DMG, e.g., with a mole ratio of about 47.5:10.5:39.0:3.0. In some embodiments, the delivery agent comprises Compound II, DSPC, Cholesterol, and Compound I or PEG-DMG, e.g., with a mole ratio of about 50:10:38:2. In some embodiments, the delivery agent comprises Compound VI, DSPC, Cholesterol, and Compound I or PEG-DMG, e.g., with a mole ratio of about 50:10:38.5:1.5. In some embodiments, the delivery agent comprises Compound VI, DSPC, Cholesterol, and Compound I or PEG-DMG, e.g., with a mole ratio of about 47.5:10.5:39.0:3.0.

A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21st Edition, A. R. Gennaro (Lippincott, Williams & Wilkins, Baltimore, MD, 2006; incorporated herein by reference in its entirety).

Exemplary diluents include, but are not limited to, calcium or sodium carbonate, calcium phosphate, calcium hydrogen phosphate, sodium phosphate, lactose, sucrose, cellulose, microcrystalline cellulose, kaolin, mannitol, sorbitol, etc., and/or combinations thereof.

Exemplary granulating and/or dispersing agents include, but are not limited to, starches, pregelatinized starches, or microcrystalline starch, alginic acid, guar gum, agar, poly (vinyl-pyrrolidone), (providone), cross-linked poly(vinylpyrrolidone) (crospovidone), cellulose, methylcellulose, carboxymethyl cellulose, cross-linked sodium carboxymethyl cellulose (croscarmellose), magnesium aluminum silicate (VEEGUM®), sodium lauryl sulfate, etc., and/or combinations thereof.

Exemplary surface active agents and/or emulsifiers include, but are not limited to, natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), sorbitan fatty acid esters (e.g., polyoxyethylene sorbitan monooleate [TWEEN®80], sorbitan monopalmitate [SPAN®40], glyceryl monooleate, polyoxyethylene esters, polyethylene glycol fatty acid esters (e.g., CREMOPHOR®), polyoxyethylene ethers (e.g., polyoxyethylene lauryl ether [BRIJ®30]), PLUORINC®F 68, POLOXAMER®188, etc. and/or combinations thereof.

Exemplary binding agents include, but are not limited to, starch, gelatin, sugars (e.g., sucrose, glucose, dextrose, dextrin, molasses, lactose, lactitol, mannitol), amino acids (e.g., glycine), natural and synthetic gums (e.g., acacia, sodium alginate), ethylcellulose, hydroxyethylcellulose, hydroxypropyl methylcellulose, etc., and combinations thereof.

Oxidation is a potential degradation pathway for mRNA, especially for liquid mRNA formulations. In order to prevent oxidation, antioxidants can be added to the formulations. Exemplary antioxidants include, but are not limited to, alpha tocopherol, ascorbic acid, ascorbyl palmitate, benzyl alcohol, butylated hydroxyanisole, m-cresol, methionine, butylated hydroxytoluene, monothioglycerol, sodium or potassium metabisulfite, propionic acid, propyl gallate, sodium ascorbate, etc., and combinations thereof.

Exemplary chelating agents include, but are not limited to, ethylenediaminetetraacetic acid (EDTA), citric acid monohydrate, disodium edetate, fumaric acid, malic acid, phosphoric acid, sodium edetate, tartaric acid, trisodium edetate, etc., and combinations thereof.

Exemplary antimicrobial or antifungal agents include, but are not limited to, benzalkonium chloride, benzethonium chloride, methyl paraben, ethyl paraben, propyl paraben, butyl paraben, benzoic acid, hydroxybenzoic acid, potassium or sodium benzoate, potassium or sodium sorbate, sodium propionate, sorbic acid, etc., and combinations thereof.

Exemplary preservatives include, but are not limited to, vitamin A, vitamin C, vitamin E, beta-carotene, citric acid, ascorbic acid, butylated hydroxyanisol, ethylenediamine, sodium lauryl sulfate (SLS), sodium lauryl ether sulfate (SLES), etc., and combinations thereof.

In some embodiments, the pH of polynucleotide solutions are maintained between pH and pH 8 to improve stability. Exemplary buffers to control pH can include, but are not limited to sodium phosphate, sodium citrate, sodium succinate, histidine (or histidine-HCl), sodium malate, sodium carbonate, etc., and/or combinations thereof.

Exemplary lubricating agents include, but are not limited to, magnesium stearate, calcium stearate, stearic acid, silica, talc, malt, hydrogenated vegetable oils, polyethylene glycol, sodium benzoate, sodium or magnesium lauryl sulfate, etc., and combinations thereof.

The pharmaceutical composition or formulation described here can contain a cryoprotectant to stabilize a polynucleotide described herein during freezing. Exemplary cryoprotectants include, but are not limited to mannitol, sucrose, trehalose, lactose, glycerol, dextrose, etc., and combinations thereof.

The pharmaceutical composition or formulation described here can contain a bulking agent in lyophilized polynucleotide formulations to yield a "pharmaceutically elegant" cake, stabilize the lyophilized polynucleotides during long term (e.g., 36 month) storage. Exemplary bulking agents of the present invention can include, but are not limited to sucrose, trehalose, mannitol, glycine, lactose, raffinose, and combinations thereof.

In some embodiments, the pharmaceutical composition or formulation further comprises a delivery agent. The delivery agent of the present disclosure can include, without limitation, liposomes, lipid nanoparticles, lipidoids, polymers, lipoplexes, microvesicles, exosomes, peptides, proteins, cells transfected with polynucleotides, hyaluronidase, nanoparticle mimics, nanotubes, conjugates, and combinations thereof.

The polynucleotides encoding anti-CHIKV antibodies can be used as therapeutic or prophylactic agents. Pharmaceutical compositions can be administered once, twice, three times, four times or more. In some aspects, the compositions can be administered to an infected individual to achieve a therapeutic response. Dosing may need to be adjusted accordingly.

It is envisioned that there may be situations where persons are at risk for infection with more than one strain of type of infectious agent. RNA (mRNA) therapeutic treatments are particularly amenable to combination vaccination approaches due to a number of factors including, but not limited to, speed of manufacture, ability to rapidly tailor treatments to accommodate perceived geographical threat, and the like. To protect against more than one strain of virus, a combination treatment can be administered that includes mRNA encoding at least one polypeptide (or portion thereof) that binds to an antigen of a first strain, and further includes mRNA encoding at least one polypeptide (or portion thereof) that binds to an antigen of a second strain of virus. RNAs (mRNAs) can be co-formulated, for example, in a single lipid nanoparticle (LNP) or can be formulated in separate LNPs destined for co-administration.

A prophylactically effective dose is a therapeutically effective dose that prevents infection with the virus at a clinically acceptable level. In some embodiments, the therapeutically effective dose is a dose listed in a package insert for the treatment. A prophylactic therapy as used herein refers to a therapy that prevents, to some extent, the infection from increasing. The infection may be prevented completely or partially.

The methods of the mention involve, in some aspects, passively immunizing a mammalian subject against a chikungunya virus infection. The method involves administering to the subject a composition comprising at least one RNA polynucleotide having an open reading frame encoding at least one antibody polypeptide (e.g., the heavy and light chains of an antibody) that targets (e.g., binds to) a chikungunya virus protein. In some aspects, methods of the present disclosure provide prophylactic treatments against a chikungunya virus infection.

Therapeutic methods of treatment are also included within the invention. Methods of treating a chikungunya virus infection in a subject are provided in aspects of the disclosure. The method involves administering to the subject having a chikungunya virus infection a composition comprising at least one RNA polynucleotide having an open reading frame encoding at least one anti-CHIKV antibody polypeptide that targets (e.g., binds to) a chikungunya virus protein.

As used herein, the terms "treat", "treated", or "treating" when used with respect to a disorder such as a viral infection, refers to a treatment which increases the resistance of a subject to development of the disease or, in other words, decreases the likelihood that the subject will develop the disease in response to infection with the virus as well as a treatment after the subject has developed the disease in order to fight the infection or prevent the infection from becoming worse.

An "effective amount" of an mRNA therapeutic is provided based, at least in part, on the target tissue, target cell type, means of administration, physical characteristics of the polynucleotide (e.g., size, and extent of modified nucleosides), and other components of the RNA treatment, and other determinants. Increased antibody production may be demonstrated by increased cell transfection (the percentage of cells transfected with the RNA treatment), increased protein translation from the polynucleotide, decreased nucleic acid degradation (as demonstrated, for example, by increased duration of protein translation from a modified polynucleotide), or altered response of the host cell.

In some embodiments, the polynucleotides described herein in accordance with the present disclosure may be used for treatment of the disease.

The polynucleotides (e.g., mRNA) described herein may be administered prophylactically or therapeutically as part of an active immunization scheme to healthy individuals or early in infection during the incubation phase or during active infection after onset of symptoms. In some embodiments, the amount of polynucleotides of the present disclosure provided to a cell, a tissue or a subject may be an amount effective for immune prophylaxis.

In some embodiments, the polynucleotides (e.g., mRNA) described herein can be used in combination with another therapy or treatment for chikungunya infection. By way of example, one or more polynucleotides described herein can be administered to a subject with a chikungunya virus infection in combination with, e.g., supportive care e.g., rest, fluids, et.), antipyretics, and/or analgesics.

The polynucleotides (e.g., mRNA) described herein may be administered with other prophylactic or therapeutic compounds. As a non-limiting example, a prophylactic or therapeutic compound may be a vaccine containing a virus treatment with or without an adjuvant or a booster. As used herein, when referring to a prophylactic composition, such as a treatment or vaccine, the term "booster" refers to an extra administration of the prophylactic composition. A booster (or booster vaccine) may be given after an earlier administration of the prophylactic composition. The time of administration between the initial administration of the prophylactic composition and the booster may be, but is not limited to, 1 minute, 2 minutes, 3 minutes, 4 minutes, 5 minutes, 6 minutes, 7 minutes, 8 minutes, 9 minutes, 10 minutes, 15 minutes, 20 minutes 35 minutes, 40 minutes, 45 minutes, 50 minutes, 55 minutes, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 1 day, 36 hours, 2 days, 3 days, 4 days, 5 days, 6 days, 1 week, 10 days, 2 weeks, 3 weeks, 1 month, 2 months, 3 months, 4 months, 5 months, 6 months, 7 months, 8 months, 9 months, 10 months, 11 months, 1 year, 18 months, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, years, 40 years, 45 years, 50 years, 55 years, 60 years, 65 years, 70 years, 75 years, 80 years, 85 years, 90 years, 95 years, or more than 99 years. In exemplary embodiments, the time of administration between the initial administration of the prophylactic composition and the booster may be, but is not limited to, 1 week, 2 weeks, 3 weeks, 1 month, 2 months, 3 months, 6 months, or 1 year.

In some embodiments, the polynucleotides (e.g., mRNA) described herein may be administered subcutaneously, intraocularly, intravitreally, parenterally, subcutaneously, intravenously, intracerebro-ventricularly, intramuscularly, intrathecally, orally, intraperitoneally, by oral or nasal inhalation, or by direct injection to one or more cells, tissues, or organs.

Provided herein are pharmaceutical compositions including the polynucleotides described herein (e.g., mRNA) and/or complexes optionally in combination with one or more pharmaceutically acceptable excipients.

The polynucleotides described herein (e.g., mRNA) may be formulated or administered in combination with one or more pharmaceutically-acceptable excipients. In some embodiments, compositions comprise at least one additional active substances, such as, for example, a therapeutically-active substance, a prophylactically-active substance, or a combination of both. Treatment compositions may be sterile, pyrogen-free or both sterile and pyrogen-free. General considerations in the formulation and/or manufacture of pharmaceutical agents, such as treatment compositions, may be found, for example, in Remington: The Science and Practice of Pharmacy 21st ed., Lippincott Williams & Wilkins, 2005 (incorporated herein by reference in its entirety).

In some embodiments, RNA treatments (e.g., a composition containing at least one mRNA described herein) are administered to humans, human patients, or subjects. For the purposes of the present disclosure, the phrase "active ingredient" generally refers to the polynucleotide or polynucleotides contained in a therapeutic composition therein, for example, RNA polynucleotides (e.g., mRNA polynucleotides) encoding anti-CHIKV antibody polypeptides.

Relative amounts of the active ingredient, the pharmaceutically acceptable excipient, and/or any additional ingredients in a pharmaceutical composition in accordance with the disclosure will vary, depending upon the identity, size, and/or condition of the subject treated and further depending upon the route by which the composition is to be administered. By way of example, the composition may comprise between 0.1% and 100%, e.g., between 0.5 and 50%, between 1-30%, between 5-80%, at least 80% (w/w) active ingredient.

In some embodiments, the RNA treatment may include one or more stabilizing elements. Stabilizing elements may include, for instance, a histone stem-loop. A stem-loop binding protein (SLBP), a 32 kDa protein has been identified. It is associated with the histone stem-loop at the 3'-end of the histone messages in both the nucleus and the cytoplasm. Its expression level is regulated by the cell cycle; it is peaks during the S-phase, when histone mRNA levels are also elevated. The protein has been shown to be essential for efficient 3'-end processing of histone pre-mRNA by the U7 snRNP. SLBP continues to be associated with the stem-loop after processing, and then stimulates the translation of mature histone mRNAs into histone proteins in the cytoplasm. The RNA binding domain of SLBP is conserved through metazoa and protozoa; its binding to the histone stem-loop depends on the structure of the loop. The minimum binding site includes at least three nucleotides 5' and two nucleotides 3' relative to the stem-loop.

In some embodiments, the RNA treatments include a coding region, at least one histone stem-loop, and optionally, a poly(A) sequence or polyadenylation signal. The poly(A) sequence or polyadenylation signal generally should enhance the expression level of the encoded protein. The encoded protein, in some embodiments, is not a histone protein, a reporter protein (e.g. Luciferase, GFP, EGFP, β-Galactosidase, EGFP), or a marker or selection protein (e.g. alpha-Globin, Galactokinase and Xanthine:guanine phosphoribosyl transferase (GPT)).

In some embodiments, the combination of a poly(A) sequence or polyadenylation signal and at least one histone stem-loop, even though both represent alternative mechanisms in nature, acts synergistically to increase the protein expression beyond the level observed with either of the individual elements. It has been found that the synergistic effect of the combination of poly(A) and at least one histone stem-loop does not depend on the order of the elements or the length of the poly(A) sequence.

20. Delivery Agents

In one set of embodiments, lipid nanoparticles (LNPs) are provided. In one embodiment, a lipid nanoparticle comprises lipids including an ionizable lipid, a structural lipid, a phospholipid, and mRNA. Each of the LNPs described herein may be used as a formulation for the mRNA described herein. In one embodiment, a lipid nanoparticle comprises an ionizable lipid, a structural lipid, a phospholipid, and mRNA. In some embodiments, the LNP comprises an ionizable lipid, a PEG-modified lipid, a phospholipid and a structural lipid. In some embodiments, the LNP has a molar ratio of about 20-60% ionizable lipid: about 5-25% phospholipid: about 25-55% structural lipid; and about 0.5-15% PEG-modified lipid. In some embodiments, the LNP comprises a molar ratio of about 50% ionizable lipid, about 1.5% PEG-modified lipid, about 38.5% structural lipid and about 10% phospholipid. In some embodiments, the LNP comprises a molar ratio of about 55% ionizable lipid, about 2.5% PEG lipid, about 32.5% structural lipid and about 10% phospholipid. In some embodiments, the LNP comprises a molar ratio of about 50% ionizable lipid, about 2% PEG lipid, about 38% structural lipid and about 10% phospholipid. In some embodiments, the ionizable lipid is an ionizable amino or cationic lipid and the phospholipid is a neutral lipid, and the structural lipid is a cholesterol. In some embodiments, the LNP has a molar ratio of 50:38.5:10:1.5 of ionizable lipid: cholesterol:DSPC: PEG2000-DMG. In some embodiments, the LNP has a molar ratio of 50:38:10:2 of ionizable lipid: cholesterol:DSPC: PEG-lipid.

a. Lipid Compound

The present disclosure provides pharmaceutical compositions with advantageous properties. The lipid compositions described herein may be advantageously used in lipid nanoparticle compositions for the delivery of therapeutic and/or prophylactic agents, e.g., mRNAs, to mammalian cells or organs. For example, the lipids described herein have little or no immunogenicity. For example, the lipid compounds disclosed herein have a lower immunogenicity as compared to a reference lipid (e.g., MC3, KC2, or DLinDMA). For example, a formulation comprising a lipid disclosed herein and a therapeutic or prophylactic agent, e.g., mRNA, has an increased therapeutic index as compared to a corresponding formulation which comprises a reference lipid (e.g., MC3, KC2, or DLinDMA) and the same therapeutic or prophylactic agent.

In certain embodiments, the present application provides pharmaceutical compositions comprising:

(a) a polynucleotide comprising a nucleotide sequence encoding an anti-CHIKV antibody polypeptide; and (b) a delivery agent.

Lipid Nanoparticle Formulations

In some embodiments, nucleic acids of the invention (e.g. anti-CHIKV antibody mRNA) are formulated in a lipid nanoparticle (LNP). Lipid nanoparticles typically comprise ionizable cationic lipid, non-cationic lipid, sterol and PEG lipid components along with the nucleic acid cargo of interest. The lipid nanoparticles of the invention can be generated using components, compositions, and methods as are generally known in the art, see for example PCT/US2016/052352; PCT/US2016/068300; PCT/US2017/037551; PCT/US2015/027400; PCT/US2016/047406; PCT/US2016000129; PCT/US2016/014280; PCT/US2016/014280; PCT/US2017/038426; PCT/US2014/027077; PCT/US2014/055394; PCT/US2016/52117; PCT/US2012/069610; PCT/US2017/027492; PCT/US2016/059575 and PCT/US2016/069491 all of which are incorporated by reference herein in their entirety.

Nucleic acids of the present disclosure (e.g. anti-CHIKV antibody mRNA) are typically formulated in lipid nanoparticle. In some embodiments, the lipid nanoparticle comprises at least one ionizable cationic lipid, at least one non-cationic lipid, at least one sterol, and/or at least one polyethylene glycol (PEG)-modified lipid.

In some embodiments, the lipid nanoparticle comprises a molar ratio of 20-60% ionizable cationic lipid. For example, the lipid nanoparticle may comprise a molar ratio of 20-50%, 20-40%, 20-30%, 30-60%, 30-50%, 30-40%, 40-60%, 40-50%, or 50-60% ionizable cationic lipid. In some embodiments, the lipid nanoparticle comprises a molar ratio of 20%, 30%, 40%, 50, or 60% ionizable cationic lipid.

In some embodiments, the lipid nanoparticle comprises a molar ratio of 5-25% non-cationic lipid. For example, the lipid nanoparticle may comprise a molar ratio of 5-20%, 5-15%, 5-10%, 10-25%, 10-20%, 10-25%, 15-25%, 15-20%, or 20-25% non-cationic lipid. In some embodiments, the lipid nanoparticle comprises a molar ratio of 5%, 10%, 15%, 20%, or 25% non-cationic lipid.

In some embodiments, the lipid nanoparticle comprises a molar ratio of 25-55% sterol. For example, the lipid nanoparticle may comprise a molar ratio of 25-50%, 25-45%, 25-40%, 25-35%, 25-30%, 30-55%, 30-50%, 30-45%, 30-40%, 30-35%, 35-55%, 35-50%, 35-45%, 35-40%, 40-55%, 40-50%, 40-45%, 45-55%, 45-50%, or 50-55% sterol. In some embodiments, the lipid nanoparticle comprises a molar ratio of 25%, 30%, 35%, 38%, 40%, 45%, 50%, or 55% sterol.

In some embodiments, the lipid nanoparticle comprises a molar ratio of 0.5-15% PEG-modified lipid. For example, the lipid nanoparticle may comprise a molar ratio of 0.5-10%, 0.5-5%, 1-15%, 1-10%, 1-5%, 2-15%, 2-10%, 2-5%, 5-15%, 5-10%, or 10-15%. In some embodiments, the lipid nanoparticle comprises a molar ratio of 0.5%, 1%, 2%, 3%, 4%, 5%, 6%, 7%, 8%, 9%, 10%, 11%, 12%, 13%, 14%, or 15% PEG-modified lipid.

In some embodiments, the lipid nanoparticle comprises a molar ratio of 20-60% ionizable cationic lipid, 5-25% non-cationic lipid, 25-55% sterol, and 0.5-15% PEG-modified lipid.

Ionizable Lipids

In some aspects, the ionizable lipids of the present disclosure may be one or more of compounds of Formula (I):

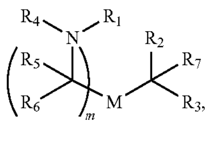

(I)

or their N-oxides, or salts or isomers thereof, wherein:

$R_1$ is selected from the group consisting of $C_{5-30}$ alkyl, $C_{5-20}$ alkenyl, —R*YR", —YR", and —R"M'R';

$R_2$ and $R_3$ are independently selected from the group consisting of H, $C_{1-14}$ alkyl, $C_{2-14}$ alkenyl, —R*YR", —YR", and —R*OR", or $R_2$ and $R_3$, together with the atom to which they are attached, form a heterocycle or carbocycle;

$R_4$ is selected from the group consisting of hydrogen, a $C_{3-6}$ carbocycle, —$(CH_2)_nQ$, —$(CH_2)_nCHQR$, —CHQR, —$CQ(R)_2$, and unsubstituted $C_{1-6}$ alkyl, where Q is selected from a carbocycle, heterocycle, —OR, —$O(CH_2)_nN(R)_2$, —C(O)OR, —OC(O)R, —$CX_3$, —$CX_2H$, —$CXH_2$, —CN, —$N(R)_2$, —C(O)$N(R)_2$, —N(R)C(O)R, —N(R)S(O)$_2$R, —N(R)C(O)$N(R)_2$, —N(R)C(S)$N(R)_2$, —N(R)$R_8$, —N(R)S(O)$_2R_8$, —O($C_H$2)$_n$OR, —N(R)C(=$NR_9$)N(R)$_2$, —N(R)C(=$CHR_9$)N(R)$_2$, —OC(O)N(R)$_2$, —N(R)C(O)OR, —N(OR)C(O)R, —N(OR)S(O)$_2$R, —N(OR)C(O)OR, —N(OR)C(O)N(R)$_2$, —N(OR)C(S)N(R)$_2$, —N(OR)C(=$NR_9$)N(R)$_2$, —N(OR)C(=$CHR_9$)N(R)$_2$, —C(=$NR_9$)N(R)$_2$, —C(=$NR_9$)R, —C(O)N(R)OR, and —C(R)N(R)$_2$C(O)OR, and each n is independently selected from 1, 2, 3, 4, and 5;

each $R_5$ is independently selected from the group consisting of $C_{1-3}$ alkyl, $C_{2-3}$ alkenyl, and H;

each $R_6$ is independently selected from the group consisting of $C_{1-3}$ alkyl, $C_{2-3}$ alkenyl, and H;

M and M' are independently selected from —C(O)O—, —OC(O)—, —OC(O)-M"-C(O)O—, —C(O)N(R')—, —N(R')C(O)—, —C(O)—, —C(S)—, —C(S)S—, —SC(S)—, —CH(OH)—, —P(O)(OR')O—, $—S(O)_2—$, —S—S—, an aryl group, and a heteroaryl group, in which M" is a bond, $C_{1-13}$ alkyl or $C_{2-13}$ alkenyl;

$R_7$ is selected from the group consisting of $C_{1-3}$ alkyl, $C_{2-3}$ alkenyl, and H;

$R_8$ is selected from the group consisting of $C_{3-6}$ carbocycle and heterocycle;

$R_9$ is selected from the group consisting of H, CN, $NO_2$, $C_{1-6}$ alkyl, —OR, $—S(O)_2R$, $—S(O)_2N(R)_2$, $C_{2-6}$ alkenyl, $C_{3-6}$ carbocycle and heterocycle;

each R is independently selected from the group consisting of $C_{1-3}$ alkyl, $C_{2-3}$ alkenyl, and H;

each R' is independently selected from the group consisting of $C_{1-18}$ s alkyl, $C_{2-18}$ alkenyl, —R*YR", —YR", and H;

each R" is independently selected from the group consisting of $C_{3-15}$ alkyl and $C_{3-15}$ alkenyl;

each R* is independently selected from the group consisting of $C_{1-12}$ alkyl and $C_{2-12}$ alkenyl;

each Y is independently a $C_{3-6}$ carbocycle;

each X is independently selected from the group consisting of F, Cl, Br, and I; and m is selected from 5, 6, 7, 8, 9, 10, 11, 12, and 13; and wherein when $R_4$ is $—(CH_2)_nQ$, $—(CH_2)_nCHQR$, —CHQR, or $—CQ(R)_2$, then (i) Q is not $—N(R)_2$ when n is 1, 2, 3, 4 or 5, or (ii) Q is not 5, 6, or 7-membered heterocycloalkyl when n is 1 or 2.

In certain embodiments, a subset of compounds of Formula (I) includes those of Formula (IA):

(IA)

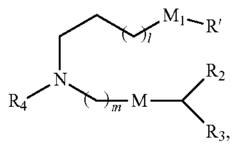

or its N-oxide, or a salt or isomer thereof, wherein l is selected from 1, 2, 3, 4, and 5; m is selected from 5, 6, 7, 8, and 9; $M_1$ is a bond or M'; $R_4$ is hydrogen, unsubstituted $C_{1-3}$ alkyl, or $—(CH_2)_nQ$, in which Q is OH, $—NHC(S)N(R)_2$, $—NHC(O)N(R)_2$, —N(R)C(O)R, $—N(R)S(O)_2R$, $—N(R)R_8$, $—NHC(=NR_9)N(R)_2$, $—NHC(=CHR_9)N(R)_2$, $—OC(O)N(R)_2$, —N(R)C(O)OR, heteroaryl or heterocycloalkyl; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, C1-14 alkyl, and $C_{2-14}$ alkenyl. For example, m is 5, 7, or 9. For example, Q is OH, $—NHC(S)N(R)_2$, or $—NHC(O)N(R)_2$. For example, Q is —N(R)C(O)R, or $—N(R)S(O)_2R$.

In certain embodiments, a subset of compounds of Formula (I) includes those of Formula (IB):

(IB)

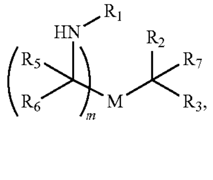

or its N-oxide, or a salt or isomer thereof in which all variables are as defined herein. For example, m is selected from 5, 6, 7, 8, and 9;

$R_4$ is hydrogen, unsubstituted $C_{1-3}$ alkyl, or $—(CH_2)_nQ$, in which Q is OH, $—NHC(S)N(R)_2$, $—NHC(O)N(R)_2$, —N(R)C(O)R, $—N(R)S(O)_2R$, $—N(R)R_8$, $—NHC(=NR_9)N(R)_2$, $—NHC(=CHR_9)N(R)_2$, $—OC(O)N(R)_2$, —N(R)C(O)OR, heteroaryl or heterocycloalkyl; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, $C_{1-14}$ alkyl, and $C_{2-14}$ alkenyl. For example, m is 5, 7, or 9. For example, Q is OH, $—NHC(S)N(R)_2$, or $—NHC(O)N(R)_2$. For example, Q is —N(R)C(O)R, or $—N(R)S(O)_2R$.

In certain embodiments, a subset of compounds of Formula (I) includes those of Formula (II):

(II)

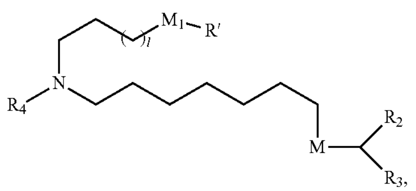

or its N-oxide, or a salt or isomer thereof, wherein l is selected from 1, 2, 3, 4, and 5; $M_1$ is a bond or M'; $R_4$ is hydrogen, unsubstituted $C_{1-3}$ alkyl, or $—(CH_2)_nQ$, in which n is 2, 3, or 4, and Q is OH, $—NHC(S)N(R)_2$, $—NHC(O)N(R)_2$, —N(R)C(O)R, $—N(R)S(O)_2R$, $—N(R)R_8$, $—NHC(=NR_9)N(R)_2$, $—NHC(=CHR_9)N(R)_2$, $—OC(O)N(R)_2$, —N(R)C(O)OR, heteroaryl or heterocycloalkyl; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, C1-14 alkyl, and $C_{2-14}$ alkenyl.

In one embodiment, the compounds of Formula (I) are of Formula (IIa), (IIa)

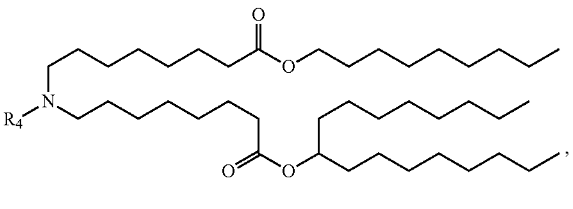

or their N-oxides, or salts or isomers thereof, wherein $R_4$ is as described herein.

In another embodiment, the compounds of Formula (I) are of Formula (IIb), (IIb)

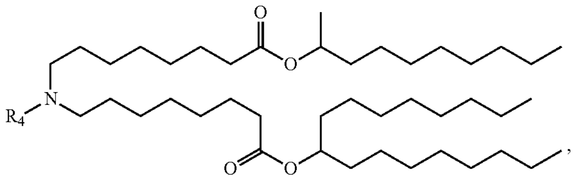

or their N-oxides, or salts or isomers thereof, wherein $R_4$ is as described herein.

In another embodiment, the compounds of Formula (I) are of Formula (IIc) or (IIe):

(IIc)

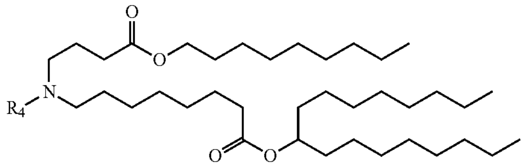

or (IIe)

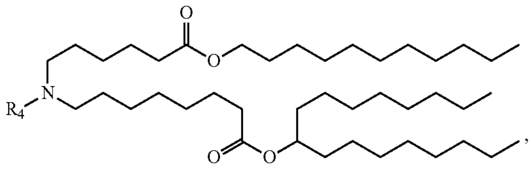

or their N-oxides, or salts or isomers thereof, wherein $R_4$ is as described herein.

In another embodiment, the compounds of Formula (I) are of Formula (IIf):

(IIf)

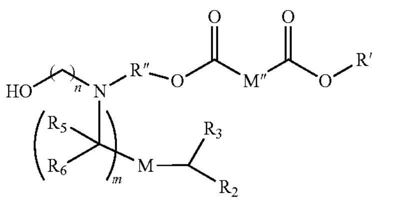

or their N-oxides, or salts or isomers thereof, wherein M is —C(O)O— or —OC(O)—, M" is $C_{1-6}$ alkyl or $C_{2-6}$ alkenyl, $R_2$ and $R_3$ are independently selected from the group consisting of $C_{5-14}$ alkyl and $C_{5-14}$ alkenyl, and n is selected from 2, 3, and 4.

In a further embodiment, the compounds of Formula (I) are of Formula (IId), (IId)

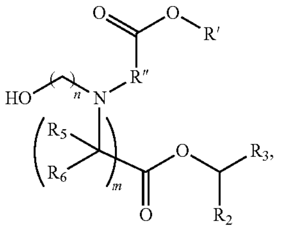

or their N-oxides, or salts or isomers thereof, wherein n is 2, 3, or 4; and m, R', R", and $R_2$ through $R_6$ are as described herein. For example, each of $R_2$ and $R_3$ may be independently selected from the group consisting of $C_{5-14}$ alkyl and $C_{5-14}$ alkenyl.

In a further embodiment, the compounds of Formula (I) are of Formula (IIg), (IIg)

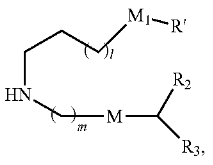

or their N-oxides, or salts or isomers thereof, wherein 1 is selected from 1, 2, 3, 4, and 5; m is selected from 5, 6, 7, 8, and 9; $M_1$ is a bond or M'; M and M' are independently selected from —C(O)O—, —OC(O)—, —OC(O)-M"-C(O)O—, —C(O)N(R')—, —P(O)(OR')O—, —S—S—, an aryl group, and a heteroaryl group; and $R_2$ and $R_3$ are independently selected from the group consisting of H, C1-14 alkyl, and $C_{2-14}$ alkenyl. For example, M" is $C_{1-6}$ alkyl (e.g., C1-4 alkyl) or $C_{2-6}$ alkenyl (e.g. $C_{2-4}$ alkenyl). For example, $R_2$ and $R_3$ are independently selected from the group consisting of $C_{5-14}$ alkyl and $C_{5-14}$ alkenyl.

In some embodiments, the ionizable lipids are one or more of the compounds described in U.S. Application Nos. 62/220,091, 62/252,316, 62/253,433, 62/266,460, 62/333,557, 62/382,740, 62/393,940, 62/471,937, 62/471,949, 62/475,140, and 62/475,166, and PCT Application No. PCT/US2016/052352.

In some embodiments, the ionizable lipids are selected from Compounds 1-280 described in U.S. Application No. 62/475,166.

In some embodiments, the ionizable lipid is (Compound II)

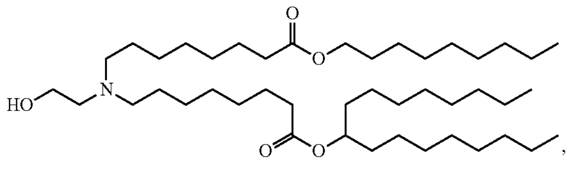

or a salt thereof.

In some embodiments, the ionizable lipid is (Compound III)

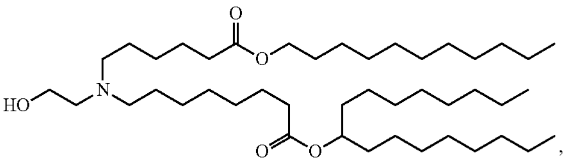

or a salt thereof.

In some embodiments, the ionizable lipid is (Compound IV)

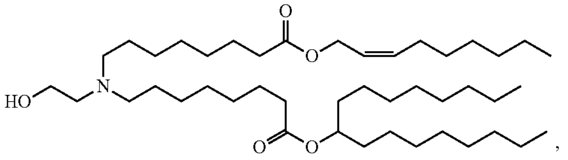

or a salt thereof.

In some embodiments, the ionizable lipid is (Compound V)

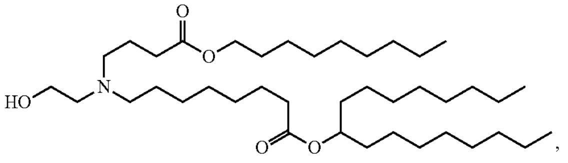

or a salt thereof.

The central amine moiety of a lipid according to Formula (I), (IA), (IB), (II), (IIa), (IIb), (IIc), (IId), (IIe), (IIf), or (IIg) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

In some aspects, the ionizable lipids of the present disclosure may be one or more of compounds of formula (III), (III)

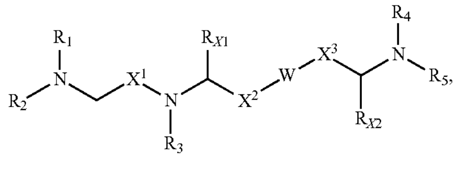

or salts or isomers thereof, wherein

W is

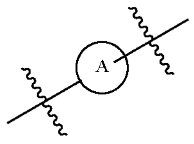

or

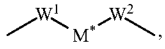

ring A is

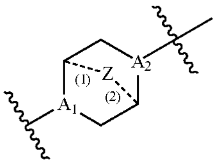

or

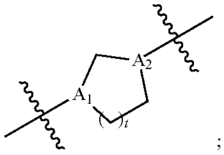

;

t is 1 or 2;

$A_1$ and $A_2$ are each independently selected from CH or N;

Z is $CH_2$ or absent wherein when Z is $CH_2$, the dashed lines (1) and (2) each represent a single bond; and when Z is absent, the dashed lines (1) and (2) are both absent;

$R_1$, $R_2$, $R_3$, $R_4$, and $R_5$ are independently selected from the group consisting of $C_{5-20}$ alkyl, $C_{5-20}$ alkenyl, —R"MR', —R*YR", —YR", and —R*OR";

$R_{X1}$ and $R_{X2}$ are each independently H or $C_{1-3}$ alkyl;

each M is independently selected from the group consisting of —C(O)O—, —OC(O)—, —OC(O)O—, —C(O)N(R')—, —N(R')C(O)—, —C(O)—, —C(S)—, —C(S)S—, —SC(S)—, —$C_H$(OH)—, —P(O)(OR')O—, —$S(O)_2$—, —C(O)S—, —SC(O)—, an aryl group, and a heteroaryl group;

M* is C1-C6 alkyl, $W^1$ and $W^2$ are each independently selected from the group consisting of —O— and —N($R_6$)—;

each $R_6$ is independently selected from the group consisting of H and $C_{15}$ alkyl;

$X^1$, $X^2$, and $X^3$ are independently selected from the group consisting of a bond, —$CH_2$—, —$(CH_2)_2$—, —CHR—, —CHY—, —C(O)—, —C(O)O—, —OC(O)—, —$(CH_2)_n$—C(O)—, —C(O)—$(CH_2)_n$—, —$(CH_2)_n$—C(O)O—, —OC(O)—$(CH_2)_n$—, —$(CH_2)_n$—OC(O)—, —C(O)O—$(CH_2)_n$—, —$C_H$(OH)—, —C(S)—, and —$C_H$(SH)—;

each Y is independently a $C_{3-6}$ carbocycle;

each R* is independently selected from the group consisting of $C_{1-12}$ alkyl and $C_{2-12}$ alkenyl;

each R is independently selected from the group consisting of $C_{1-3}$ alkyl and a $C_{3-6}$ carbocycle;

each R' is independently selected from the group consisting of C1-12 alkyl, $C_{2-12}$ alkenyl, and H;

each R" is independently selected from the group consisting of $C_{3-12}$ alkyl, $C_{3-12}$ alkenyl and —R*MR'; and n is an integer from 1-6;

wherein when ring A is

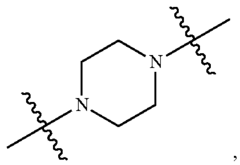 [SMILES: *N1CCN(*)CC1]

, then i) at least one of $X^1$, $X^2$, and $X^3$ is not —$CH_2$—; and/or ii) at least one of $R_1$, $R_2$, $R_3$, $R_4$, and $R_5$ is —R"MR'.

In some embodiments, the compound is of any of formulae (IIIa1)-(IIIa8):

(IIIa1)

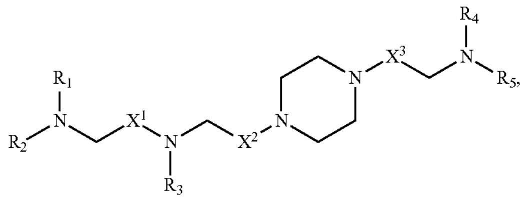

(IIIa2)

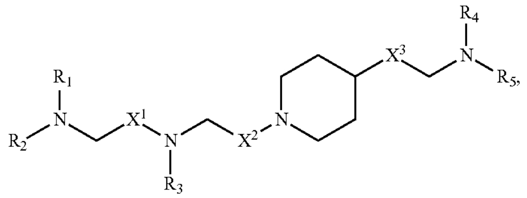

(IIIa3)

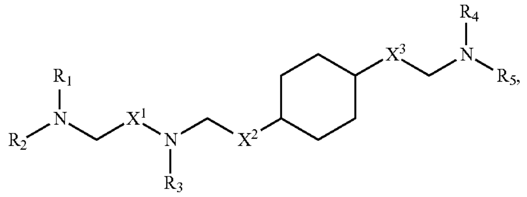

(IIIa4)

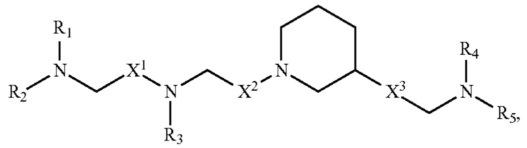

-continued (IIIa5')

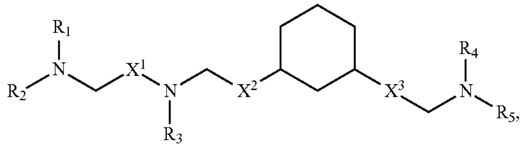

(IIIa6)

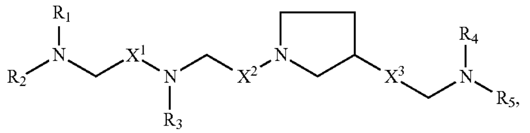

(IIIa7)

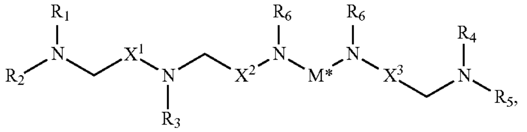

or (IIIa8)

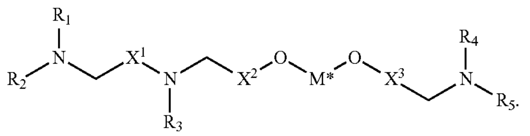

In some embodiments, the ionizable lipids are one or more of the compounds described in U.S. Application Nos. 62/271,146, 62/338,474, 62/413,345, and 62/519,826, and PCT Application No. PCT/US2016/068300.

In some embodiments, the ionizable lipids are selected from Compounds 1-156 described in U.S. Application No. 62/519,826.

In some embodiments, the ionizable lipids are selected from Compounds 1-16, 42-66, 68-76, and 78-156 described in U.S. Application No. 62/519,826.

In some embodiments, the ionizable lipid is (Compound VI)

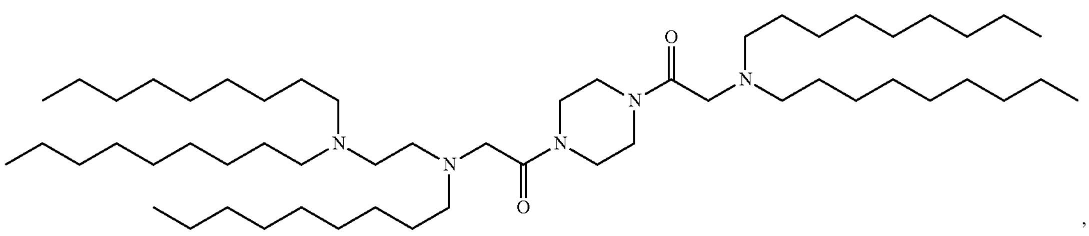

, or a salt thereof.

The central amine moiety of a lipid according to Formula (III), (IIIa1), (IIIa2), (IIIa3), (IIIa4), (IIIa5), (IIIa6), (IIIa7), or (IIIa8) may be protonated at a physiological pH. Thus, a lipid may have a positive or partial positive charge at physiological pH. Such lipids may be referred to as cationic or ionizable (amino)lipids. Lipids may also be zwitterionic, i.e., neutral molecules having both a positive and a negative charge.

Phospholipids

The lipid composition of the lipid nanoparticle composition disclosed herein can comprise one or more phospholipids, for example, one or more saturated or (poly)unsaturated phospholipids or a combination thereof. In general, phospholipids comprise a phospholipid moiety and one or more fatty acid moieties.

A phospholipid moiety can be selected, for example, from the non-limiting group consisting of phosphatidyl choline, phosphatidyl ethanolamine, phosphatidyl glycerol, phosphatidyl serine, phosphatidic acid, 2-lysophosphatidyl choline, and a sphingomyelin.

A fatty acid moiety can be selected, for example, from the non-limiting group consisting of lauric acid, myristic acid, myristoleic acid, palmitic acid, palmitoleic acid, stearic acid, oleic acid, linoleic acid, alpha-linolenic acid, erucic acid, phytanoic acid, arachidic acid, arachidonic acid, eicosapentaenoic acid, behenic acid, docosapentaenoic acid, and docosahexaenoic acid.

Particular phospholipids can facilitate fusion to a membrane. For example, a cationic phospholipid can interact with one or more negatively charged phospholipids of a membrane (e.g., a cellular or intracellular membrane). Fusion of a phospholipid to a membrane can allow one or more elements (e.g., a therapeutic agent) of a lipid-containing composition (e.g., LNPs) to pass through the membrane permitting, e.g., delivery of the one or more elements to a target tissue.

Non-natural phospholipid species including natural species with modifications and substitutions including branching, oxidation, cyclization, and alkynes are also contemplated. For example, a phospholipid can be functionalized with or cross-linked to one or more alkynes (e.g., an alkenyl group in which one or more double bonds is replaced with a triple bond). Under appropriate reaction conditions, an alkyne group can undergo a copper-catalyzed cycloaddition upon exposure to an azide. Such reactions can be useful in functionalizing a lipid bilayer of a nanoparticle composition to facilitate membrane permeation or cellular recognition or in conjugating a nanoparticle composition to a useful component such as a targeting or imaging moiety (e.g., a dye).

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin.

In some embodiments, a phospholipid of the invention comprises 1,2-distearoyl-sn-glycero-3-phosphocholine (DSPC), 1,2-dioleoyl-sn-glycero-3-phosphoethanolamine (DOPE), 1,2-dilinoleoyl-sn-glycero-3-phosphocholine (DLPC), 1,2-dimyristoyl-sn-gly cero-phosphocholine (DMPC), 1,2-dioleoyl-sn-glycero-3-phosphocholine (DOPC), 1,2-dipalmitoyl-sn-glycero-3-phosphocholine (DPPC), 1,2-diundecanoyl-sn-glycero-phosphocholine (DUPC), 1-palmitoyl-2-oleoyl-sn-glycero-3-phosphocholine (POPC), 1,2-di-O-octadecenyl-sn-glycero-3-phosphocholine (18:0 Diether PC), 1-oleoyl-2 cholesterylhemisuccinoyl-sn-glycero-3-phosphocholine (OChemsPC), 1-hexadecyl-sn-glycero-3-phosphocholine (C16 Lyso PC), 1,2-dilinolenoyl-sn-glycero-3-phosphocholine, 1,2-diarachidonoyl-sn-glycero-3-phosphocholine, 1,2-didocosahexaenoyl-sn-glycero-3-phosphocholine, 1,2-diphytanoyl-sn-glycero-3-phosphoethanolamine (ME 16.0 PE), 1,2-distearoyl-sn-glycero-3-phosphoethanolamine, 1,2-dilinoleoyl-sn-glycero-3-phosphoethanolamine, 1,2-dilinolenoyl-sn-glycero-3-phosphoethanolamine, 1,2-diarachidonoyl-sn-glycero-3-phosphoethanolamine, 1,2-didocosahexaenoyl-sn-glycero-3-phosphoethanolamine, 1,2-dioleoyl-sn-glycero-3-phospho-rac-(1-glycerol) sodium salt (DOPG), sphingomyelin, and mixtures thereof.

In certain embodiments, a phospholipid useful or potentially useful in the present invention is an analog or variant of DSPC. In certain embodiments, a phospholipid useful or potentially useful in the present invention is a compound of Formula (IV):

(IV)

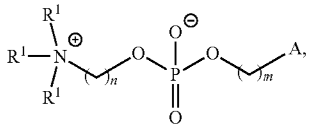

or a salt thereof, wherein:

each $R^1$ is independently optionally substituted alkyl; or optionally two $R^1$ are joined together with the intervening atoms to form optionally substituted monocyclic carbocyclyl or optionally substituted monocyclic heterocyclyl; or optionally three $R^1$ are joined together with the intervening atoms to form optionally substituted bicyclic carbocyclyl or optionally substitute bicyclic heterocyclyl;

n is 1, 2, 3, 4, 5, 6, 7, 8, 9, or 10;

m is 0, 1, 2, 3, 4, 5, 6, 7, 8, 9, or 10;

A is of the formula:

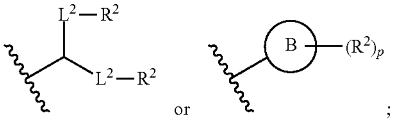

each instance of $L^2$ is independently a bond or optionally substituted $C_{1-6}$ alkylene, wherein one methylene unit of the optionally substituted $C_{1-6}$ alkylene is optionally replaced with 0, $N(R^N)$, S, C(O), $C(O)N(R^N)$, $NR^NC(O)$, C(O)O, OC(O), OC(O)O, $OC(O)N(R^N)$, $NR^NC(O)$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$, C(O)O, OC(O), OC(O)O, $OC(O)N(R^N)$, $NR^NC(O)O$, C(O)S, SC(O), $C(=NR^N)$, $C(=NR^N)N(R^N)$, $—NR^NC(=NR^N)$, $NR^NC(=NR^N)N(R^N)$, C(S), $C(S)N(R^N)$, $NR^NC(S)$, $NR^NC(S)N(R^N)$, S(O)—OS(O), S(O)O, OS(O)O, $OS(O)_2$, $S(O)_2O$, $OS(O)_2O$, $N(R^N)S(O)$, $S(O)N(R^N)$, $—N(R^N)S(O)N(R^N)$, $OS(O)N(R^N)$, $N(R^N)S(O)O$, $S(O)_2$, $N(R^N)S(O)_2$, $S(O)_2N(R^N)$, $—N(R^N)S(O)_2N(R^N)$, $OS(O)_2N(R^N)$, or $N(R^N)S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2;

provided that the compound is not of the formula:

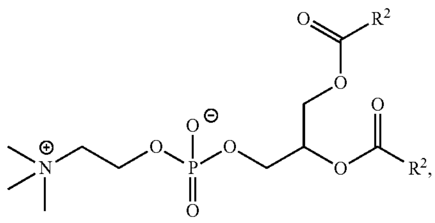

wherein each instance of $R_2$ is independently unsubstituted alkyl, unsubstituted alkenyl, or unsubstituted alkynyl.

In some embodiments, the phospholipids may be one or more of the phospholipids described in U.S. Application No. 62/520,530.

i) Phospholipid Head Modifications

In certain embodiments, a phospholipid useful or potentially useful in the present invention comprises a modified phospholipid head (e.g., a modified choline group). In certain embodiments, a phospholipid with a modified head is DSPC, or analog thereof, with a modified quaternary amine. For example, in embodiments of Formula (IV), at least one of $R^1$ is not methyl. In certain embodiments, at least one of $R^1$ is not hydrogen or methyl. In certain embodiments, the compound of Formula (IV) is of one of the following formulae:

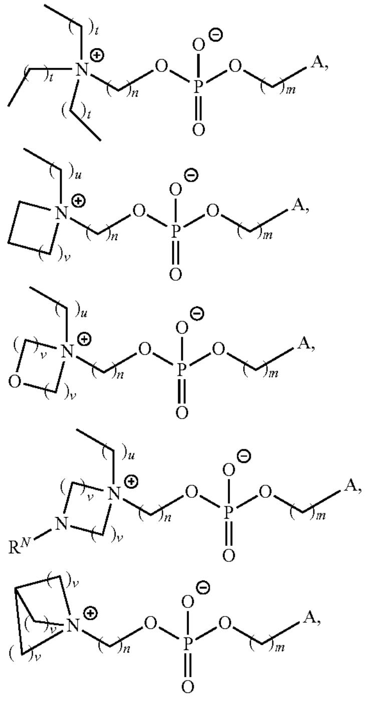

or a salt thereof, wherein:

each t is independently 1, 2, 3, 4, 5, 6, 7, 8, 9, or 10;

each u is independently 0, 1, 2, 3, 4, 5, 6, 7, 8, 9, or 10; and each v is independently 1, 2, or 3.

In certain embodiments, a compound of Formula (IV) is of Formula (IV-a):

(IV-a)

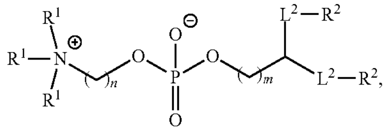

or a salt thereof.

In certain embodiments, a phospholipid useful or potentially useful in the present invention comprises a cyclic moiety in place of the glyceride moiety. In certain embodiments, a phospholipid useful in the present invention is DSPC, or analog thereof, with a cyclic moiety in place of the glyceride moiety. In certain embodiments, the compound of Formula (IV) is of Formula (IV-b):

(IV-b)

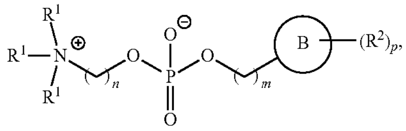

or a salt thereof.

(ii) Phospholipid Tail Modifications

In certain embodiments, a phospholipid useful or potentially useful in the present invention comprises a modified tail. In certain embodiments, a phospholipid useful or potentially useful in the present invention is DSPC, or analog thereof, with a modified tail. As described herein, a "modified tail" may be a tail with shorter or longer aliphatic chains, aliphatic chains with branching introduced, aliphatic chains with substituents introduced, aliphatic chains wherein one or more methylenes are replaced by cyclic or heteroatom groups, or any combination thereof. For example, in certain embodiments, the compound of (IV) is of Formula (IV-a), or a salt thereof, wherein at least one instance of $R^2$ is each instance of $R^2$ is optionally substituted $C_{1-30}$ alkyl, wherein one or more methylene units of $R_2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$, C(O)O, OC(O), OC(O)O, $OC(O)N(R^NNR^NC(O)O$, C(O)S, SC(O), $C(=NR^N)$, $C(=NR^N)N(R^N)$, $NR^NC(=NR^N)$, $NR^NC(=NR^N)N(R^N)$, C(S), $C(S)N(R^N)$, $NR^NC(S)$, $NR^NC(S)N(R^N)$, S(O), OS(O), S(O)O, OS(O)O, $OS(O)_2$, $-S(O)_2O$, $OS(O)_2O$, $N(R^N)S(O)$, $S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_2O$.

In certain embodiments, the compound of Formula (IV) is of Formula (IV-c):

(IV-c)

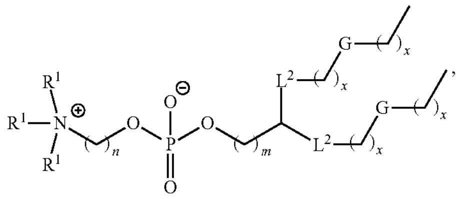

or a salt thereof, wherein:

each x is independently an integer between 0-30, inclusive; and each instance is G is independently selected from the group consisting of optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $—NR^NC(O)N(R^N)$, C(O)O, OC(O), OC(O)O, $OC(O)N(R^N)$, $NR^NC(O)$, C(O)S, SC(O), $—C(═NR^N)$, $C(═NR^N)N(R^N)$, $NR^NC(═NR^N)$, $NR^NC(═NR^N)N(R^N)$, C(S), $C(S)N(R^N)$, $NR^NC(S)$, $NR^NC(S)N(R^N)$, S(O), OS(O), S(O)O, OS(O)O, $OS(O)_2$, $S(O)_2O$, $OS(O)_2O$, $N(R^N)S(O)$, $—S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_2O$. Each possibility represents a separate embodiment of the present invention.

In certain embodiments, a phospholipid useful or potentially useful in the present invention comprises a modified phosphocholine moiety, wherein the alkyl chain linking the quaternary amine to the phosphoryl group is not ethylene (e.g., n is not 2). Therefore, in certain embodiments, a phospholipid useful or potentially useful in the present invention is a compound of Formula (IV), wherein n is 1, 3, 4, 5, 6, 7, 8, 9, or 10. For example, in certain embodiments, a compound of Formula (IV) is of one of the following formulae:

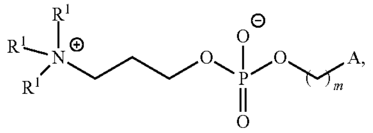

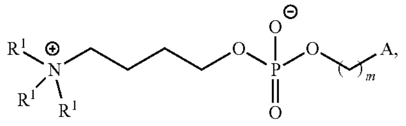

or a salt thereof.

Alternative Lipids

In certain embodiments, an alternative lipid is used in place of a phospholipid of the present disclosure.

In certain embodiments, an alternative lipid of the invention is oleic acid.

In certain embodiments, the alternative lipid is one of the following:

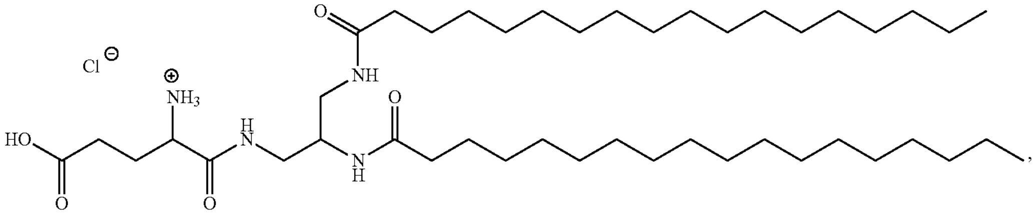

,

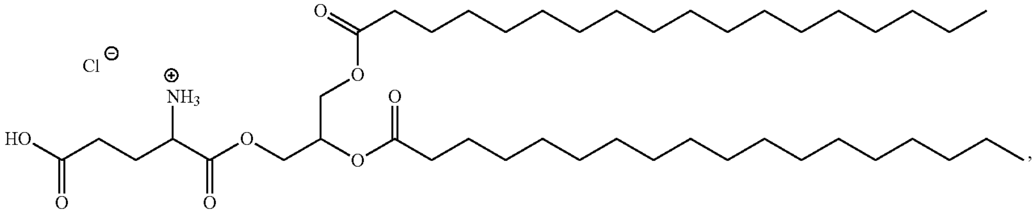

,

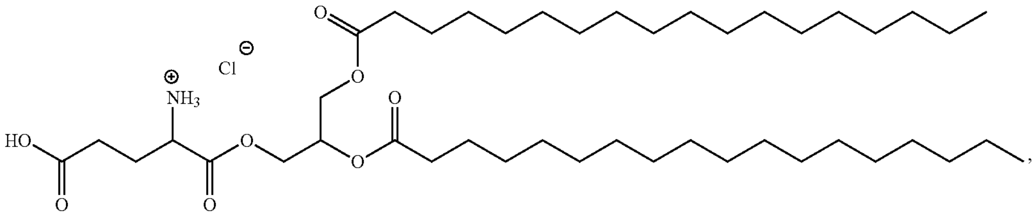

,

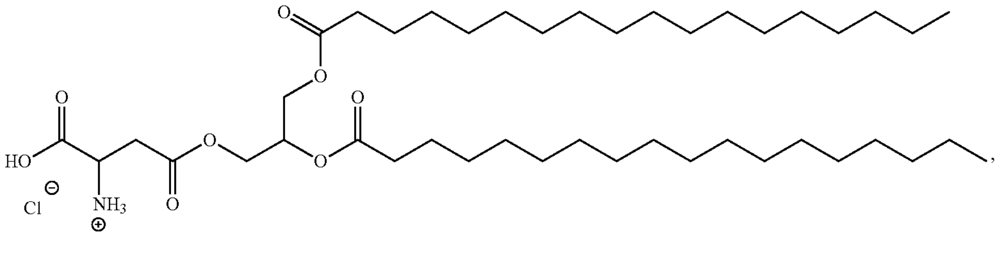

,

-continued

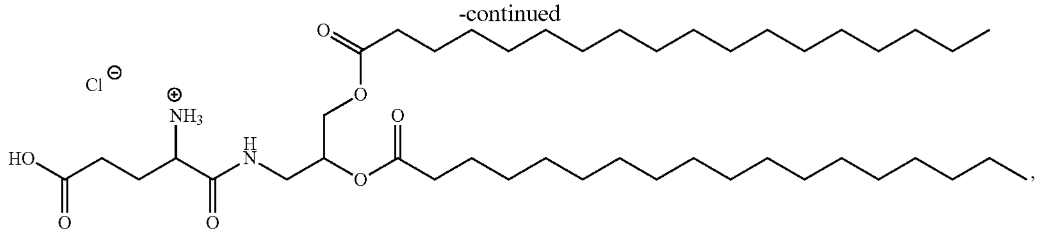

,

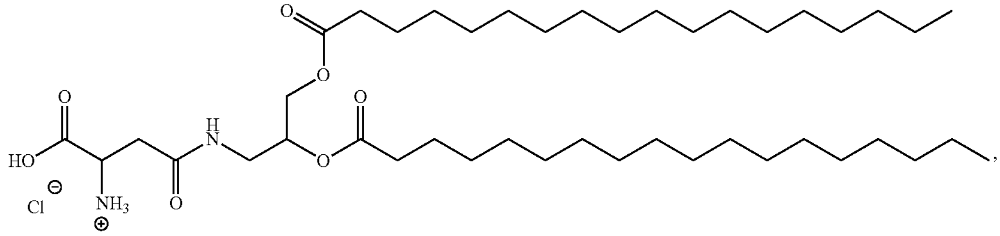

, and

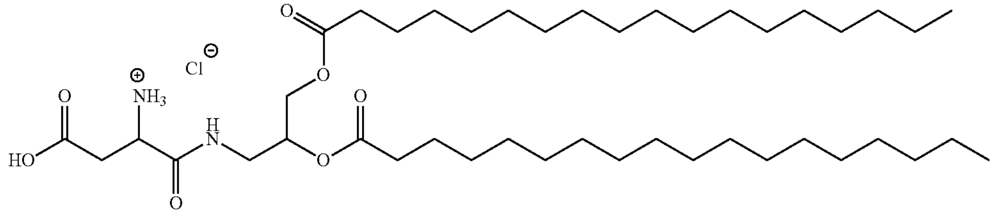

.

Structural Lipids

The lipid composition of a pharmaceutical composition disclosed herein can comprise one or more structural lipids. As used herein, the term "structural lipid" refers to sterols and also to lipids containing sterol moieties.

Incorporation of structural lipids in the lipid nanoparticle may help mitigate aggregation of other lipids in the particle. Structural lipids can be selected from the group including but not limited to, cholesterol, fecosterol, sitosterol, ergosterol, campesterol, stigmasterol, brassicasterol, tomatidine, tomatine, ursolic acid, alpha-tocopherol, hopanoids, phytosterols, steroids, and mixtures thereof. In some embodiments, the structural lipid is a sterol. As defined herein, "sterols" are a subgroup of steroids consisting of steroid alcohols. In certain embodiments, the structural lipid is a steroid. In certain embodiments, the structural lipid is cholesterol. In certain embodiments, the structural lipid is an analog of cholesterol. In certain embodiments, the structural lipid is alpha-tocopherol.

In some embodiments, the structural lipids may be one or more of the structural lipids described in U.S. Application No. 62/520,530.

Polyethylene Glycol (PEG)-Lipids

The lipid composition of a pharmaceutical composition disclosed herein can comprise one or more a polyethylene glycol (PEG) lipid.

As used herein, the term "PEG-lipid" refers to polyethylene glycol (PEG)-modified lipids. Non-limiting examples of PEG-lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG-DMPE, PEG-DPPC, or a PEG-DSPE lipid.

In some embodiments, the PEG-lipid includes, but not limited to 1,2-dimyristoyl-sn-glycerol methoxypolyethylene glycol (PEG-DMG), 1,2-distearoyl-sn-glycero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA).

In one embodiment, the PEG-lipid is selected from the group consisting of a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof.

In some embodiments, the lipid moiety of the PEG-lipids includes those having lengths of from about $C_{14}$ to about $C_{22}$, preferably from about $C_{14}$ to about $C_{16}$. In some embodiments, a PEG moiety, for example a mPEG-$NH_2$, has a size of about 1000, 2000, 5000, 10,000, 15,000 or 20,000 daltons. In one embodiment, the PEG-lipid is PEG2k-DMG.

In one embodiment, the lipid nanoparticles described herein can comprise a PEG lipid which is a non-diffusible PEG. Non-limiting examples of non-diffusible PEGs include PEG-DSG and PEG-DSPE.

PEG-lipids are known in the art, such as those described in U.S. Pat. No. 8,158,601 and International Publ. No. WO 2015/130584 A2, which are incorporated herein by reference in their entirety.

In general, some of the other lipid components (e.g., PEG lipids) of various formulae, described herein may be synthesized as described International Patent Application No. PCT/US2016/000129, filed Dec. 10, 2016, entitled "Compositions and Methods for Delivery of Therapeutic Agents," which is incorporated by reference in its entirety.

The lipid component of a lipid nanoparticle composition may include one or more molecules comprising polyethylene glycol, such as PEG or PEG-modified lipids. Such species may be alternately referred to as PEGylated lipids. A PEG lipid is a lipid modified with polyethylene glycol. A PEG lipid may be selected from the non-limiting group including PEG-modified phosphatidylethanolamines, PEG-modified phosphatidic acids, PEG-modified ceramides, PEG-modified dialkylamines, PEG-modified diacylglycerols, PEG-modified dialkylglycerols, and mixtures thereof. For example, a PEG lipid may be PEG-c-DOMG, PEG-DMG, PEG-DLPE, PEG-DMPE, PEG-DPPC, or a PEG-DSPE lipid.

In some embodiments the PEG-modified lipids are a modified form of PEG DMG. PEG-DMG has the following structure:

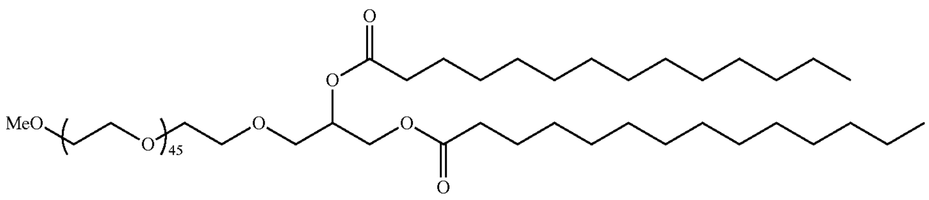

In one embodiment, PEG lipids useful in the present invention can be PEGylated lipids described in International Publication No. WO2012099755, the contents of which is herein incorporated by reference in its entirety. Any of these exemplary PEG lipids described herein may be modified to comprise a hydroxyl group on the PEG chain. In certain embodiments, the PEG lipid is a PEG-OH lipid. As generally defined herein, a "PEG-OH lipid" (also referred to herein as "hydroxy-PEGylated lipid") is a PEGylated lipid having one or more hydroxyl (—OH) groups on the lipid. In certain embodiments, the PEG-OH lipid includes one or more hydroxyl groups on the PEG chain. In certain embodiments, a PEG-OH or hydroxy-PEGylated lipid comprises an —OH group at the terminus of the PEG chain. Each possibility represents a separate embodiment of the present invention.

In certain embodiments, a PEG lipid useful in the present invention is a compound of Formula (V). Provided herein are compounds of Formula (V):

(V)

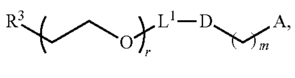

or salts thereof, wherein:

$R_3$ is —$OR^O$;

$R^O$ is hydrogen, optionally substituted alkyl, or an oxygen protecting group;

r is an integer between 1 and 100, inclusive;

$L^1$ is optionally substituted $C_{1-10}$ alkylene, wherein at least one methylene of the optionally substituted $C_{1-10}$ alkylene is independently replaced with optionally substituted carbocyclylene, optionally substituted heterocyclylene, optionally substituted arylene, optionally substituted heteroarylene, O, $N(R^N)$, S, C(O), $C(O)N(R^N)$, $NR^NC(O)$, C(O)O, OC(O), OC(O)O, $OC(O)N(R^N)$, $NR^NC(O)O$, or $NR^NC(O)N(R^N)$;

D is a moiety obtained by click chemistry or a moiety cleavable under physiological conditions;

m is 0, 1, 2, 3, 4, 5, 6, 7, 8, 9, or 10;

A is of the formula:

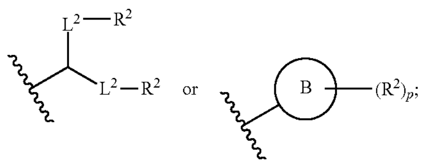

each instance of $L^2$ is independently a bond or optionally substituted $C_{1-6}$ alkylene, wherein one methylene unit of the optionally substituted $C_{1-6}$ alkylene is optionally replaced with O, $N(R^N)$, S, C(O), $C(O)N(R^N)$, $NR^NC(O)$, C(O)O, OC(O), OC(O)O, $OC(O)N(R^N)$, $NR^NC(O)O$, or $NR^NC(O)N(R^N)$;

each instance of $R^2$ is independently optionally substituted $C_{1-30}$ alkyl, optionally substituted $C_{1-30}$ alkenyl, or optionally substituted $C_{1-30}$ alkynyl; optionally wherein one or more methylene units of $R^2$ are independently replaced with optionally substituted carbocyclylene, optionally substituted heterocyclylene, optionally substituted arylene, optionally substituted heteroarylene, $N(R^N)$, O, S, C(O), $C(O)N(R^N)$, $NR^NC(O)$, $NR^NC(O)N(R^N)$, C(O)O, OC(O), OC(O)O, $OC(O)N(R^N)$, $NR^NC(O)O$, C(O)S, SC(O), $C(=NR^N)$, $C(=NR^N)N(R^N)$, —$NR^NC(=NR^N)$, $NR^NC(=NR^N)N(R^N)$, C(S), $C(S)N(R^N)$, $NR^NC(S)$, $NR^NC(S)N(R^N)$, S(O), —OS(O), S(O)O, OS(O)O, $OS(O)_2$, $S(O)_2O$, $OS(O)_2O$, $N(R^N)S(O)$, $S(O)N(R^N)$, —$N(R^N)S(O)N(R^N)$, $OS(O)N(R^N)$, $N(R^N)S(O)O$, $S(O)_2$, $N(R^N)S(O)_2$, $S(O)_2N(R^N)$, —$N(R^N)S(O)_2N(R^N)$, $OS(O)_2N(R^N)$, or $N(R^N)S(O)_2O$;

each instance of $R^N$ is independently hydrogen, optionally substituted alkyl, or a nitrogen protecting group;

Ring B is optionally substituted carbocyclyl, optionally substituted heterocyclyl, optionally substituted aryl, or optionally substituted heteroaryl; and p is 1 or 2.

In certain embodiments, the compound of Formula (V) is a PEG-OH lipid (i.e., $R^3$ is —$OR^O$, and $R^O$ is hydrogen). In certain embodiments, the compound of Formula (V) is of Formula (V-OH):

(V-OH)

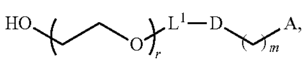

or a salt thereof.

In certain embodiments, a PEG lipid useful in the present invention is a PEGylated fatty acid. In certain embodiments, a PEG lipid useful in the present invention is a compound of Formula (VI). Provided herein are compounds of Formula (VI)

(VI)

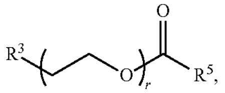

or a salts thereof, wherein:

$R^3$ is —$OR^O$;

$R^O$ is hydrogen, optionally substituted alkyl or an oxygen protecting group;

r is an integer between 1 and 100, inclusive;

$R^5$ is optionally substituted $C_{10-40}$ alkyl, optionally substituted $C_{10-40}$ alkenyl, or optionally substituted $C_{10-40}$ alkynyl; and optionally one or more methylene groups of $R^5$ are replaced with optionally substituted carbocyclylene, optionally substituted heterocyclylene, optionally substituted arylene, optionally substituted heteroarylene, $N(R^N)$, O, S, C(O), $C(O)N(R^N)$, —$NR^NC$(O), $NR^NC(O)N(R^N)$, C(O)O, OC(O), OC(O)O, OC(O)$N(R^N)$, $NR^NC(O)O$ C(O)S, —SC(O), $C(=NR^N)$, $C(=NR^N)N(R^N)$, $NR^NC(=NR^N)$, $NR^NC(=NR^N)N(R^N)$, C(S), $C(S)N(R^N)$, —$NR^NC(S)$, $NR^NC(S)N(R^N)$, S(O), OS(O), S(O)O, OS(O)O, $OS(O)_2$, $S(O)_2O$, $OS(O)_2O$, —$N(R^N)S(O)$, $S(O)N(R^N)$, $N(R^N)S(O)N(R^N)$, $OS(O)N(R^N)$, $N(R^N)S(O)O$, $S(O)_2$, $N(R^N)S(O)_2$, $S(O)_2N(R^N)$, $N(R^N)S(O)_2N(R^N)$, $OS(O)_2N(R^N)$, or $N(R^N)S(O)_2O$; and each instance of $R^N$ is independently hydrogen, optionally substituted alkyl, or a nitrogen protecting group.

In certain embodiments, the compound of Formula (VI) is of Formula (VI-OH):

(VI-OH)

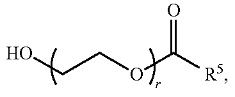

or a salt thereof. In some embodiments, r is 45.

In yet other embodiments the compound of Formula (VI) is:

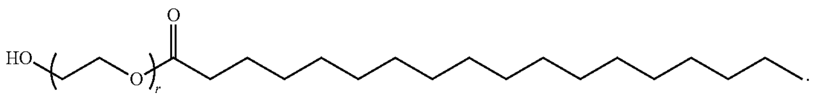

or a salt thereof.

In one embodiment, the compound of Formula (VI) is (Compound I)

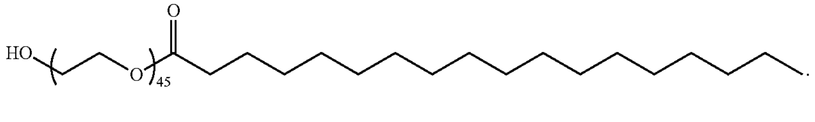

In some aspects, the lipid composition of the pharmaceutical compositions disclosed herein does not comprise a PEG-lipid.

In some embodiments, the PEG-lipids may be one or more of the PEG lipids described in U.S. Application No. 62/520,530.

In some embodiments, a PEG lipid of the invention comprises a PEG-modified phosphatidylethanolamine, a PEG-modified phosphatidic acid, a PEG-modified ceramide, a PEG-modified dialkylamine, a PEG-modified diacylglycerol, a PEG-modified dialkylglycerol, and mixtures thereof. In some embodiments, the PEG-modified lipid is PEG-DMG, PEG-c-DOMG (also referred to as PEG-DOMG), PEG-DSG and/or PEG-DPG.

In some embodiments, a LNP of the invention comprises an ionizable cationic lipid of any of Formula I, II or III, a phospholipid comprising DSPC, a structural lipid, and a PEG lipid comprising PEG-DMG.

In some embodiments, a LNP of the invention comprises an ionizable cationic lipid of any of Formula I, II or III, a phospholipid comprising DSPC, a structural lipid, and a PEG lipid comprising a compound having Formula VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid comprising a compound having Formula IV, a structural lipid, and the PEG lipid comprising a compound having Formula V or VI.

In some embodiments, a LNP of the invention comprises an ionizable cationic lipid of Formula I, II or III, a phospholipid having Formula IV, a structural lipid, and a PEG lipid comprising a compound having Formula VI.

In some embodiments, a LNP of the invention comprises an ionizable cationic lipid of

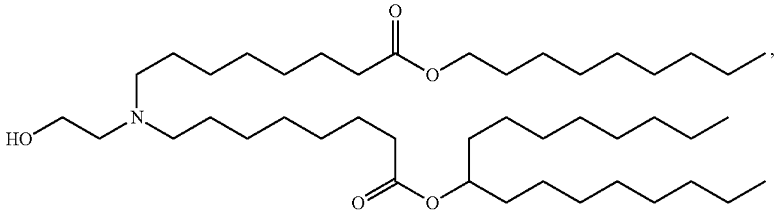 [SMILES: CCCCCCCCCOC(=O)CCCCCCCN(CCO)CCCCCCCC(=O)OC(CCCCCCCC)CCCCCCCC]

and a PEG lipid comprising Formula VI.

In some embodiments, a LNP of the invention comprises an ionizable cationic lipid of

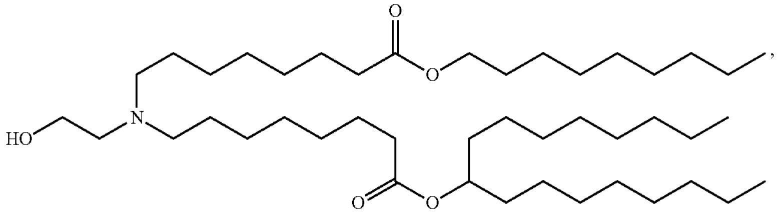 [SMILES: CCCCCCCCCOC(=O)CCCCCCCN(CCO)CCCCCCCC(=O)OC(CCCCCCCC)CCCCCCCC]

and an alternative lipid comprising oleic acid.

In some embodiments, a LNP of the invention comprises an ionizable cationic lipid of

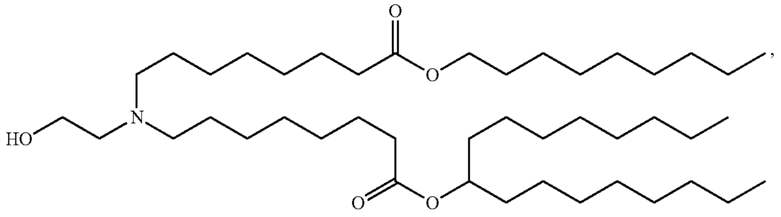 [SMILES: CCCCCCCCCOC(=O)CCCCCCCN(CCO)CCCCCCCC(=O)OC(CCCCCCCC)CCCCCCCC]

an alternative lipid comprising oleic acid, a structural lipid comprising cholesterol, and a PEG lipid comprising a compound having Formula VI.

In some embodiments, a LNP of the invention comprises an ionizable cationic lipid of

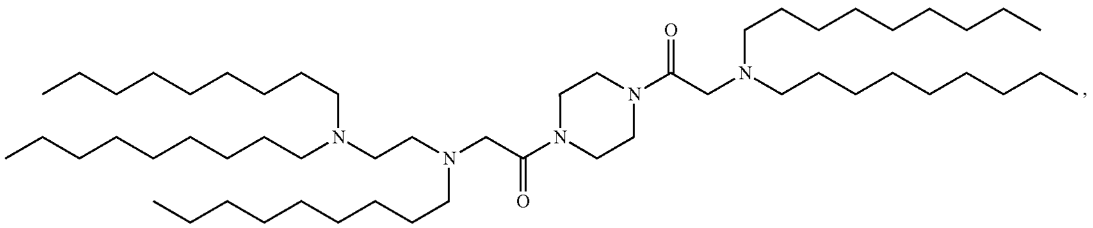 [SMILES: CCCCCCCCCN(CCCCCCCCC)CCN(CCCCCCCCC)CC(=O)N1CCN(C(=O)CN(CCCCCCCCC)CCCCCCCCC)CC1]

a phospholipid comprising DOPE, a structural lipid comprising cholesterol, and a PEG lipid comprising a compound having Formula VI.

In some embodiments, a LNP of the invention comprises an ionizable cationic lipid of a phospholipid comprising DOPE, a structural lipid comprising cholesterol, and a PEG lipid comprising a compound having Formula VII.

In some embodiments, a LNP of the invention comprises an N:P ratio of from about 2:1 to about 30:1.

In some embodiments, a LNP of the invention comprises an N:P ratio of about 6:1.

In some embodiments, a LNP of the invention comprises an N:P ratio of about 3:1.

In some embodiments, a LNP of the invention comprises a wt/wt ratio of the ionizable cationic lipid component to the RNA of from about 10:1 to about 100:1.

In some embodiments, a LNP of the invention comprises a wt/wt ratio of the ionizable cationic lipid component to the RNA of about 20:1.

In some embodiments, a LNP of the invention comprises a wt/wt ratio of the ionizable cationic lipid component to the RNA of about 10:1.

In some embodiments, a LNP of the invention has a mean diameter from about 50 nm to about 150 nm.

In some embodiments, a LNP of the invention has a mean diameter from about 70 nm to about 120 nm.

As used herein, the term "alkyl", "alkyl group", or "alkylene" means a linear or branched, saturated hydrocarbon including one or more carbon atoms (e.g., one, two, three, four, five, six, seven, eight, nine, ten, eleven, twelve, thirteen, fourteen, fifteen, sixteen, seventeen, eighteen, nineteen, twenty, or more carbon atoms), which is optionally substituted. The notation "C1-14 alkyl" means an optionally substituted linear or branched, saturated hydrocarbon including 1-14 carbon atoms. Unless otherwise specified, an alkyl group described herein refers to both unsubstituted and substituted alkyl groups.

As used herein, the term "alkenyl", "alkenyl group", or "alkenylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one double bond, which is optionally substituted. The notation "$C_{2-14}$ alkenyl" means an optionally substituted linear or branched hydrocarbon including 2-14 carbon atoms and at least one carbon-carbon double bond. An alkenyl group may include one, two, three, four, or more carbon-carbon double bonds. For example, C18 alkenyl may include one or more double bonds. A C18 alkenyl group including two double bonds may be a linoleyl group. Unless otherwise specified, an alkenyl group described herein refers to both unsubstituted and substituted alkenyl groups.

As used herein, the term "alkynyl", "alkynyl group", or "alkynylene" means a linear or branched hydrocarbon including two or more carbon atoms (e.g., two, three, four, five, six, seven, eight, nine, ten, eleven, twelve, thirteen, fourteen, fifteen, sixteen, seventeen, eighteen, nineteen, twenty, or more carbon atoms) and at least one carbon-carbon triple bond, which is optionally substituted. The notation "$C_{2-14}$ alkynyl" means an optionally substituted linear or branched hydrocarbon including 2-14 carbon atoms and at least one carbon-carbon triple bond. An alkynyl group may include one, two, three, four, or more carbon-carbon triple bonds. For example, C18 alkynyl may include one or more carbon-carbon triple bonds. Unless otherwise specified, an alkynyl group described herein refers to both unsubstituted and substituted alkynyl groups.

As used herein, the term "carbocycle" or "carbocyclic group" means an optionally substituted mono- or multi-cyclic system including one or more rings of carbon atoms. Rings may be three, four, five, six, seven, eight, nine, ten, eleven, twelve, thirteen, fourteen, fifteen, sixteen, seventeen, eighteen, nineteen, or twenty membered rings. The notation "C3-6 carbocycle" means a carbocycle including a single ring having 3-6 carbon atoms. Carbocycles may include one or more carbon-carbon double or triple bonds and may be non-aromatic or aromatic (e.g., cycloalkyl or aryl groups). Examples of carbocycles include cyclopropyl, cyclopentyl, cyclohexyl, phenyl, naphthyl, and 1,2-dihydronaphthyl groups. The term "cycloalkyl" as used herein means a non-aromatic carbocycle and may or may not include any double or triple bond. Unless otherwise specified, carbocycles described herein refers to both unsubstituted and substituted carbocycle groups, i.e., optionally substituted carbocycles.

As used herein, the term "heterocycle" or "heterocyclic group" means an optionally substituted mono- or multi-cyclic system including one or more rings, where at least one ring includes at least one heteroatom. Heteroatoms may be, for example, nitrogen, oxygen, or sulfur atoms. Rings may be three, four, five, six, seven, eight, nine, ten, eleven, twelve, thirteen, or fourteen membered rings. Heterocycles may include one or more double or triple bonds and may be non-aromatic or aromatic (e.g., heterocycloalkyl or heteroaryl groups). Examples of heterocycles include imidazolyl, imidazolidinyl, oxazolyl, oxazolidinyl, thiazolyl, thiazolidinyl, pyrazolidinyl, pyrazolyl, isoxazolidinyl, isoxazolyl, isothiazolidinyl, isothiazolyl, morpholinyl, pyrrolyl, pyrrolidinyl, furyl, tetrahydrofuryl, thiophenyl, pyridinyl, piperidinyl, quinolyl, and isoquinolyl groups. The term "heterocycloalkyl" as used herein means a non-aromatic heterocycle and may or may not include any double or triple bond. Unless otherwise specified, heterocycles described herein refers to both unsubstituted and substituted heterocycle groups, i.e., optionally substituted heterocycles.

As used herein, the term "heteroalkyl", "heteroalkenyl", or "heteroalkynyl", refers respectively to an alkyl, alkenyl, alkynyl group, as defined herein, which further comprises one or more (e.g., 1, 2, 3, or 4) heteroatoms (e.g., oxygen, sulfur, nitrogen, boron, silicon, phosphorus) wherein the one or more heteroatoms is inserted between adjacent carbon atoms within the parent carbon chain and/or one or more heteroatoms is inserted between a carbon atom and the parent molecule, i.e., between the point of attachment. Unless otherwise specified, heteroalkyls, heteroalkenyls, or heteroalkynyls described herein refers to both unsubstituted and substituted heteroalkyls, heteroalkenyls, or heteroalkynyls, i.e., optionally substituted heteroalkyls, heteroalkenyls, or heteroalkynyls.

As used herein, a "biodegradable group" is a group that may facilitate faster metabolism of a lipid in a mammalian entity. A biodegradable group may be selected from the group consisting of, but is not limited to, —C(O)O—, —OC(O)—, —C(O)N(R')—, —N(R')C(O)—, —C(O)—, —C(S)—, —C(S)S—, —SC(S)—, —CH(OH)—, —P(O)(OR')O—, —$S(O)_2$—, an aryl group, and a heteroaryl group. As used herein, an "aryl group" is an optionally substituted carbocyclic group including one or more aromatic rings. Examples of aryl groups include phenyl and naphthyl groups. As used herein, a "heteroaryl group" is an optionally substituted heterocyclic group including one or more aromatic rings. Examples of heteroaryl groups include pyrrolyl, furyl, thiophenyl, imidazolyl, oxazolyl, and thiazolyl. Both aryl and heteroaryl groups may be optionally substituted. For example, M and M' can be selected from the non-limiting group consisting of optionally substituted phenyl, oxazole, and thiazole. In the formulas herein, M and M' can be independently selected from the list of biodegradable groups above. Unless otherwise specified, aryl or heteroaryl groups described herein refers to both unsubstituted and substituted groups, i.e., optionally substituted aryl or heteroaryl groups.

Alkyl, alkenyl, and cyclyl (e.g., carbocyclyl and heterocyclyl) groups may be optionally substituted unless otherwise specified. Optional substituents may be selected from the group consisting of, but are not limited to, a halogen atom (e.g., a chloride, bromide, fluoride, or iodide group), a carboxylic acid (e.g., —C(O)OH), an alcohol (e.g., a hydroxyl, —OH), an ester (e.g., —C(O)OR—OC(O)R), an aldehyde (e.g., —C(O)H), a carbonyl (e.g., —C(O)R, alternatively represented by C═O), an acyl halide (e.g., —C(O)X, in which X is a halide selected from bromide, fluoride, chloride, and iodide), a carbonate (e.g., —OC(O)OR), an alkoxy (e.g., —OR), an acetal (e.g., $—C(OR)_2R''''$, in which each OR are alkoxy groups that can be the same or different and R'''' is an alkyl or alkenyl group), a phosphate (e.g., P(O)43-), a thiol (e.g., —SH), a sulfoxide (e.g., —S(O)R), a sulfinic acid (e.g., —S(O)OH), a sulfonic acid (e.g., —S(O)2OH), a thial (e.g., —C(S)H), a sulfate (e.g., S(O)42-), a sulfonyl (e.g., —S(O)2-), an amide (e.g., —C(O)NR2, or —N(R)C(O)R), an azido (e.g., —N3), a nitro (e.g., —NO2), a cyano (e.g., —CN), an isocyano (e.g., —NC), an acyloxy (e.g., —OC(O)R), an amino (e.g., —NR2, —NRH, or —NH2), a carbamoyl (e.g., —OC(O)NR2, —OC(O)NRH, or —OC(O)NH2), a sulfonamide (e.g., —S(O)2NR2, —S(O)2NRH, —S(O)2NH2, —N(R)S(O)2R, —N(H)S(O)2R, —N(R)S(O)2H, or —N(H)S(O)2H), an alkyl group, an alkenyl group, and a cyclyl (e.g., carbocyclyl or heterocyclyl) group. In any of the preceding, R is an alkyl or alkenyl group, as defined herein. In some embodiments, the substituent groups themselves may be further substituted with, for example, one, two, three, four, five, or six substituents as defined herein. For example, a $C_{1-6}$ alkyl group may be further substituted with one, two, three, four, five, or six substituents as described herein.

Compounds of the disclosure that contain nitrogens can be converted to N-oxides by treatment with an oxidizing agent (e.g., 3-chloroperoxybenzoic acid (mCPBA) and/or hydrogen peroxides) to afford other compounds of the disclosure. Thus, all shown and claimed nitrogen-containing compounds are considered, when allowed by valency and structure, to include both the compound as shown and its N-oxide derivative (which can be designated as N□O or N+—O—). Furthermore, in other instances, the nitrogens in the compounds of the disclosure can be converted to N-hydroxy or N-alkoxy compounds. For example, N-hydroxy compounds can be prepared by oxidation of the parent amine by an oxidizing agent such as m-CPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted C1-C6 alkyl, C1-C6 alkenyl, C1-C6 alkynyl, 3-14-membered carbocycle or 3-14-membered heterocycle) derivatives.

About, approximately: As used herein, the terms "approximately" and "about," as applied to one or more values of interest, refer to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value). For example, when used in the context of an amount of a given compound in a lipid component of a nanoparticle composition, "about" may mean +/−10% of the recited value. For instance, a nanoparticle composition including a lipid component having about 40% of a given compound may include 30-50% of the compound.

As used herein, the term "compound," is meant to include all isomers and isotopes of the structure depicted. "Isotopes" refers to atoms having the same atomic number but different mass numbers resulting from a different number of neutrons in the nuclei. For example, isotopes of hydrogen include tritium and deuterium. Further, a compound, salt, or complex of the present disclosure can be prepared in combination with solvent or water molecules to form solvates and hydrates by routine methods.

(vi) Other Lipid Composition Components

The lipid composition of a pharmaceutical composition disclosed herein can include one or more components in addition to those described above. For example, the lipid composition can include one or more permeability enhancer molecules, carbohydrates, polymers, surface altering agents (e.g., surfactants), or other components. For example, a permeability enhancer molecule can be a molecule described by U.S. Patent Application Publication No. 2005/0222064. Carbohydrates can include simple sugars (e.g., glucose) and polysaccharides (e.g., glycogen and derivatives and analogs thereof).

A polymer can be included in and/or used to encapsulate or partially encapsulate a pharmaceutical composition disclosed herein (e.g., a pharmaceutical composition in lipid nanoparticle form). A polymer can be biodegradable and/or biocompatible. A polymer can be selected from, but is not limited to, polyamines, polyethers, polyamides, polyesters, polycarbamates, polyureas, polycarbonates, polystyrenes, polyimides, polysulfones, polyurethanes, polyacetylenes, polyethylenes, polyethyleneimines, polyisocyanates, polyacrylates, polymethacrylates, polyacrylonitriles, and polyarylates.

The ratio between the lipid composition and the polynucleotide range can be from about 10:1 to about 60:1 (wt/wt).

In some embodiments, the ratio between the lipid composition and the polynucleotide can be about 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1 or 60:1 (wt/wt). In some embodiments, the wt/wt ratio of the lipid composition to the polynucleotide encoding a therapeutic agent is about 20:1 or about 15:1.

In some embodiments, the pharmaceutical composition disclosed herein can contain more than one polypeptides. For example, a pharmaceutical composition disclosed herein can contain two or more polynucleotides (e.g., RNA, e.g., mRNA).

In one embodiment, the lipid nanoparticles described herein can comprise polynucleotides (e.g., mRNA) in a lipid:polynucleotide weight ratio of 5:1, 10:1, 15:1, 20:1, 25:1, 30:1, 35:1, 40:1, 45:1, 50:1, 55:1, 60:1 or 70:1, or a range or any of these ratios such as, but not limited to, 5:1 to about 10:1, from about 5:1 to about 15:1, from about 5:1 to about 20:1, from about 5:1 to about 25:1, from about 5:1 to about 30:1, from about 5:1 to about 35:1, from about 5:1 to about 40:1, from about 5:1 to about 45:1, from about 5:1 to about 50:1, from about 5:1 to about 55:1, from about 5:1 to about 60:1, from about 5:1 to about 70:1, from about 10:1 to about 15:1, from about 10:1 to about 20:1, from about 10:1 to about 25:1, from about 10:1 to about 30:1, from about 10:1 to about 35:1, from about 10:1 to about 40:1, from about 10:1 to about 45:1, from about 10:1 to about 50:1, from about 10:1 to about 55:1, from about 10:1 to about 60:1, from about 10:1 to about 70:1, from about 15:1 to about 20:1, from about 15:1 to about 25:1, from about 15:1 to about 30:1, from about 15:1 to about 35:1, from about 15:1 to about 40:1, from about 15:1 to about 45:1, from about 15:1 to about 50:1, from about 15:1 to about 55:1, from about 15:1 to about 60:1 or from about 15:1 to about 70:1.

In one embodiment, the lipid nanoparticles described herein can comprise the polynucleotide in a concentration from approximately 0.1 mg/ml to 2 mg/ml such as, but not limited to, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml or greater than 2.0 mg/ml.

(vii) Nanoparticle Compositions

In some embodiments, the pharmaceutical compositions disclosed herein are formulated as lipid nanoparticles (LNP). Accordingly, the present disclosure also provides nanoparticle compositions comprising (i) a lipid composition comprising a delivery agent such as compound as described herein, and (ii) a polynucleotide encoding an anti-CHIKV antibody polypeptide. In such nanoparticle composition, the lipid composition disclosed herein can encapsulate the polynucleotide encoding an anti-CHIKV antibody polypeptide.

Nanoparticle compositions are typically sized on the order of micrometers or smaller and can include a lipid bilayer. Nanoparticle compositions encompass lipid nanoparticles (LNPs), liposomes (e.g., lipid vesicles), and lipoplexes. For example, a nanoparticle composition can be a liposome having a lipid bilayer with a diameter of 500 nm or less.

Nanoparticle compositions include, for example, lipid nanoparticles (LNPs), liposomes, and lipoplexes. In some embodiments, nanoparticle compositions are vesicles including one or more lipid bilayers. In certain embodiments, a nanoparticle composition includes two or more concentric bilayers separated by aqueous compartments. Lipid bilayers can be functionalized and/or crosslinked to one another. Lipid bilayers can include one or more ligands, proteins, or channels.

In one embodiment, a lipid nanoparticle comprises an ionizable lipid, a structural lipid, a phospholipid, and mRNA. In some embodiments, the LNP comprises an ionizable lipid, a PEG-modified lipid, a sterol and a structural lipid. In some embodiments, the LNP has a molar ratio of about 20-60% ionizable lipid: about 5-25% structural lipid: about 25-55% sterol; and about 0.5-15% PEG-modified lipid.

In some embodiments, the LNP has a polydispersity value of less than 0.4. In some embodiments, the LNP has a net neutral charge at a neutral pH. In some embodiments, the LNP has a mean diameter of 50-150 nm. In some embodiments, the LNP has a mean diameter of 80-100 nm.

As generally defined herein, the term "lipid" refers to a small molecule that has hydrophobic or amphiphilic properties. Lipids may be naturally occurring or synthetic. Examples of classes of lipids include, but are not limited to, fats, waxes, sterol-containing metabolites, vitamins, fatty acids, glycerolipids, glycerophospholipids, sphingolipids, saccharolipids, and polyketides, and prenol lipids. In some instances, the amphiphilic properties of some lipids leads them to form liposomes, vesicles, or membranes in aqueous media.

In some embodiments, a lipid nanoparticle (LNP) may comprise an ionizable lipid. As used herein, the term "ionizable lipid" has its ordinary meaning in the art and may refer to a lipid comprising one or more charged moieties. In some embodiments, an ionizable lipid may be positively charged or negatively charged. An ionizable lipid may be positively charged, in which case it can be referred to as "cationic lipid". In certain embodiments, an ionizable lipid molecule may comprise an amine group, and can be referred to as an ionizable amino lipid. As used herein, a "charged moiety" is a chemical moiety that carries a formal electronic charge, e.g., monovalent (+1, or −1), divalent (+2, or −2), trivalent (+3, or −3), etc. The charged moiety may be anionic (i.e., negatively charged) or cationic (i.e., positively charged). Examples of positively-charged moieties include amine groups (e.g., primary, secondary, and/or tertiary amines), ammonium groups, pyridinium group, guanidine groups, and imidizolium groups. In a particular embodiment, the charged moieties comprise amine groups. Examples of negatively-charged groups or precursors thereof, include carboxylate groups, sulfonate groups, sulfate groups, phosphonate groups, phosphate groups, hydroxyl groups, and the like. The charge of the charged moiety may vary, in some cases, with the environmental conditions, for example, changes in pH may alter the charge of the moiety, and/or cause the moiety to become charged or uncharged. In general, the charge density of the molecule may be selected as desired.

It should be understood that the terms "charged" or "charged moiety" does not refer to a "partial negative charge" or "partial positive charge" on a molecule. The terms "partial negative charge" and "partial positive charge" are given its ordinary meaning in the art. A "partial negative charge" may result when a functional group comprises a bond that becomes polarized such that electron density is pulled toward one atom of the bond, creating a partial negative charge on the atom. Those of ordinary skill in the art will, in general, recognize bonds that can become polarized in this way.

In some embodiments, the ionizable lipid is an ionizable amino lipid, sometimes referred to in the art as an "ionizable cationic lipid". In one embodiment, the ionizable amino lipid may have a positively charged hydrophilic head and a hydrophobic tail that are connected via a linker structure.

In addition to these, an ionizable lipid may also be a lipid including a cyclic amine group.

In one embodiment, the ionizable lipid may be selected from, but not limited to, a ionizable lipid described in International Publication Nos. WO2013086354 and WO2013116126; the contents of each of which are herein incorporated by reference in their entirety.

In yet another embodiment, the ionizable lipid may be selected from, but not limited to, formula CLI-CLXXXXII of U.S. Pat. No. 7,404,969; each of which is herein incorporated by reference in their entirety.

In one embodiment, the lipid may be a cleavable lipid such as those described in International Publication No. WO2012170889, herein incorporated by reference in its entirety. In one embodiment, the lipid may be synthesized by methods known in the art and/or as described in International Publication Nos. WO2013086354; the contents of each of which are herein incorporated by reference in their entirety.

Nanoparticle compositions can be characterized by a variety of methods. For example, microscopy (e.g., transmission electron microscopy or scanning electron microscopy) can be used to examine the morphology and size distribution of a nanoparticle composition. Dynamic light scattering or potentiometry (e.g., potentiometric titrations) can be used to measure zeta potentials. Dynamic light scattering can also be utilized to determine particle sizes. Instruments such as the Zetasizer Nano ZS (Malvern Instruments Ltd, Malvern, Worcestershire, UK) can also be used to measure multiple characteristics of a nanoparticle composition, such as particle size, polydispersity index, and zeta potential. The size of the nanoparticles can help counter biological reactions such as, but not limited to, inflammation, or can increase the biological effect of the polynucleotide. As used herein, "size" or "mean size" in the context of nanoparticle compositions refers to the mean diameter of a nanoparticle composition.

In one embodiment, the polynucleotide encoding an anti-CHIKV antibody polypeptide are formulated in lipid nanoparticles having a diameter from about 10 to about 100 nm such as, but not limited to, about 10 to about 20 nm, about 10 to about 30 nm, about to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm, about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In one embodiment, the nanoparticles have a diameter from about 10 to 500 nm. In one embodiment, the nanoparticle has a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the largest dimension of a nanoparticle composition is 1 μm or shorter (e.g., 1 μm, 900 nm, 800 nm, 700 nm, 600 nm, 500 nm, 400 nm, 300 nm, 200 nm, 175 nm, 150 nm, 125 nm, 100 nm, 75 nm, 50 nm, or shorter).

A nanoparticle composition can be relatively homogenous. A polydispersity index can be used to indicate the homogeneity of a nanoparticle composition, e.g., the particle size distribution of the nanoparticle composition. A small (e.g., less than 0.3) polydispersity index generally indicates a narrow particle size distribution. A nanoparticle composition can have a polydispersity index from about 0 to about 0.25, such as 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, or 0.25. In some embodiments, the polydispersity index of a nanoparticle composition disclosed herein can be from about 0.10 to about 0.20.

The zeta potential of a nanoparticle composition can be used to indicate the electrokinetic potential of the composition. For example, the zeta potential can describe the surface charge of a nanoparticle composition. Nanoparticle compositions with relatively low charges, positive or negative, are generally desirable, as more highly charged species can interact undesirably with cells, tissues, and other elements in the body. In some embodiments, the zeta potential of a nanoparticle composition disclosed herein can be from about −10 mV to about +20 mV, from about −10 mV to about +15 mV, from about 10 mV to about +10 mV, from about −10 mV to about +5 mV, from about −10 mV to about 0 mV, from about −10 mV to about −5 mV, from about −5 mV to about +20 mV, from about −5 mV to about +15 mV, from about −5 mV to about +10 mV, from about −5 mV to about +5 mV, from about −5 mV to about 0 mV, from about 0 mV to about +20 mV, from about 0 mV to about +15 mV, from about 0 mV to about +10 mV, from about 0 mV to about +5 mV, from about +5 mV to about +20 mV, from about +5 mV to about +15 mV, or from about +5 mV to about +10 mV.

In some embodiments, the zeta potential of the lipid nanoparticles can be from about 0 mV to about 100 mV, from about 0 mV to about 90 mV, from about 0 mV to about 80 mV, from about 0 mV to about 70 mV, from about 0 mV to about 60 mV, from about 0 mV to about 50 mV, from about 0 mV to about 40 mV, from about 0 mV to about 30 mV, from about 0 mV to about 20 mV, from about 0 mV to about 10 mV, from about 10 mV to about 100 mV, from about 10 mV to about 90 mV, from about 10 mV to about 80 mV, from about mV to about 70 mV, from about 10 mV to about 60 mV, from about 10 mV to about 50 mV, from about 10 mV to about 40 mV, from about 10 mV to about 30 mV, from about 10 mV to about 20 mV, from about 20 mV to about 100 mV, from about 20 mV to about 90 mV, from about 20 mV to about 80 mV, from about 20 mV to about 70 mV, from about 20 mV to about 60 mV, from about 20 mV to about 50 mV, from about 20 mV to about 40 mV, from about 20 mV to about 30 mV, from about 30 mV to about 100 mV, from about 30 mV to about 90 mV, from about 30 mV to about 80 mV, from about 30 mV to about 70 mV, from about 30 mV to about 60 mV, from about 30 mV to about 50 mV, from about 30 mV to about mV, from about 40 mV to about 100 mV, from about 40 mV to about 90 mV, from about mV to about 80 mV, from about 40 mV to about 70 mV, from about 40 mV to about 60 mV, and from about 40 mV to about 50 mV. In some embodiments, the zeta potential of the lipid nanoparticles can be from about 10 mV to about 50 mV, from about 15 mV to about 45 mV, from about 20 mV to about 40 mV, and from about 25 mV to about 35 mV. In some embodiments, the zeta potential of the lipid nanoparticles can be about 10 mV, about 20 mV, about 30 mV, about 40 mV, about 50 mV, about 60 mV, about 70 mV, about 80 mV, about 90 mV, and about 100 mV.

The term "encapsulation efficiency" of a polynucleotide describes the amount of the polynucleotide that is encapsulated by or otherwise associated with a nanoparticle composition after preparation, relative to the initial amount provided. As used herein, "encapsulation" can refer to complete, substantial, or partial enclosure, confinement, surrounding, or encasement.

Encapsulation efficiency is desirably high (e.g., close to 100%). The encapsulation efficiency can be measured, for example, by comparing the amount of the polynucleotide in a solution containing the nanoparticle composition before and after breaking up the nanoparticle composition with one or more organic solvents or detergents.

Fluorescence can be used to measure the amount of free polynucleotide in a solution. For the nanoparticle compositions described herein, the encapsulation efficiency of a polynucleotide can be at least 50%, for example 50%, 55%, 60%, 65%, 70%, 75%, 80%, 85%, 90%, 91%, 92%, 93%, 94%, 95%, 96%, 97%, 98%, 99%, or 100%. In some embodiments, the encapsulation efficiency can be at least 80%. In certain embodiments, the encapsulation efficiency can be at least 90%.

The amount of a polynucleotide present in a pharmaceutical composition disclosed herein can depend on multiple factors such as the size of the polynucleotide, desired target and/or application, or other properties of the nanoparticle composition as well as on the properties of the polynucleotide.

For example, the amount of an mRNA useful in a nanoparticle composition can depend on the size (expressed as length, or molecular mass), sequence, and other characteristics of the mRNA. The relative amounts of a polynucleotide in a nanoparticle composition can also vary.

The relative amounts of the lipid composition and the polynucleotide present in a lipid nanoparticle composition of the present disclosure can be optimized according to considerations of efficacy and tolerability. For compositions including an mRNA as a polynucleotide, the N:P ratio can serve as a useful metric.

As the N:P ratio of a nanoparticle composition controls both expression and tolerability, nanoparticle compositions with low N:P ratios and strong expression are desirable. N:P ratios vary according to the ratio of lipids to RNA in a nanoparticle composition.

In general, a lower N:P ratio is preferred. The one or more RNA, lipids, and amounts thereof can be selected to provide an N:P ratio from about 2:1 to about 30:1, such as 2:1, 3:1, 4:1, 5:1, 6:1, 7:1, 8:1, 9:1, 10:1, 12:1, 14:1, 16:1, 18:1, 20:1, 22:1, 24:1, 26:1, 28:1, or 30:1. In certain embodiments, the N:P ratio can be from about 2:1 to about 8:1. In other embodiments, the N:P ratio is from about 5:1 to about 8:1. In certain embodiments, the N:P ratio is between 5:1 and 6:1. In one specific aspect, the N:P ratio is about is about 5.67:1.

In addition to providing nanoparticle compositions, the present disclosure also provides methods of producing lipid nanoparticles comprising encapsulating a polynucleotide. Such method comprises using any of the pharmaceutical compositions disclosed herein and producing lipid nanoparticles in accordance with methods of production of lipid nanoparticles known in the art. See, e.g., Wang et al. (2015) "Delivery of oligonucleotides with lipid nanoparticles" Adv. Drug Deliv. Rev. 87:68-80; Silva et al. (2015) "Delivery Systems for Biopharmaceuticals. Part I: Nanoparticles and Microparticles" Curr. Pharm. Technol. 16: 940-954; Naseri et al. (2015) "Solid Lipid Nanoparticles and Nanostructured Lipid Carriers: Structure, Preparation and Application" Adv. Pharm. Bull. 5:305-13; Silva et al. (2015) "Lipid nanoparticles for the delivery of biopharmaceuticals" Curr. Pharm. Biotechnol. 16:291-302, and references cited therein.

21. Other Delivery Agents a. Liposomes, Lipoplexes, and Lipid Nanoparticles

In some embodiments, the compositions or formulations of the present disclosure comprise a delivery agent, e.g., a liposome, a lioplexes, a lipid nanoparticle, or any combination thereof. The polynucleotides described herein (e.g., a polynucleotide comprising a nucleotide sequence encoding an anti-CHIKV antibody polypeptide) can be formulated using one or more liposomes, lipoplexes, or lipid nanoparticles. Liposomes, lipoplexes, or lipid nanoparticles can be used to improve the efficacy of the polynucleotides directed protein production as these formulations can increase cell transfection by the polynucleotide; and/or increase the translation of encoded protein. The liposomes, lipoplexes, or lipid nanoparticles can also be used to increase the stability of the polynucleotides.

Liposomes are artificially-prepared vesicles that can primarily be composed of a lipid bilayer and can be used as a delivery vehicle for the administration of pharmaceutical formulations. Liposomes can be of different sizes. A multilamellar vesicle (MLV) can be hundreds of nanometers in diameter, and can contain a series of concentric bilayers separated by narrow aqueous compartments. A small unicellular vesicle (SUV) can be smaller than 50 nm in diameter, and a large unilamellar vesicle (LUV) can be between 50 and 500 nm in diameter. Liposome design can include, but is not limited to, opsonins or ligands to improve the attachment of liposomes to unhealthy tissue or to activate events such as, but not limited to, endocytosis. Liposomes can contain a low or a high pH value in order to improve the delivery of the pharmaceutical formulations.

The formation of liposomes can depend on the pharmaceutical formulation entrapped and the liposomal ingredients, the nature of the medium in which the lipid vesicles are dispersed, the effective concentration of the entrapped substance and its potential toxicity, any additional processes involved during the application and/or delivery of the vesicles, the optimal size, polydispersity and the shelf-life of the vesicles for the intended application, and the batch-to-batch reproducibility and scale up production of safe and efficient liposomal products, etc.

As a non-limiting example, liposomes such as synthetic membrane vesicles can be prepared by the methods, apparatus and devices described in U.S. Pub. Nos. US20130177638, US20130177637, US20130177636, US20130177635, US20130177634, US20130177633, US20130183375, US20130183373, and US20130183372. In some embodiments, the polynucleotides described herein can be encapsulated by the liposome and/or it can be contained in an aqueous core that can then be encapsulated by the liposome as described in, e.g., Intl. Pub. Nos. W2012031046, W2012031043, W2012030901, WO2012006378, and WO2013086526; and U.S. Pub. Nos. US20130189351, US20130195969 and US20130202684. Each of the references in herein incorporated by reference in its entirety.

In some embodiments, the polynucleotides described herein can be formulated in a cationic oil-in-water emulsion where the emulsion particle comprises an oil core and a cationic lipid that can interact with the polynucleotide anchoring the molecule to the emulsion particle. In some embodiments, the polynucleotides described herein can be formulated in a water-in-oil emulsion comprising a continuous hydrophobic phase in which the hydrophilic phase is dispersed. Exemplary emulsions can be made by the methods described in Intl. Pub. Nos. WO2012006380 and WO201087791, each of which is herein incorporated by reference in its entirety.

In some embodiments, the polynucleotides described herein can be formulated in a lipid-polycation complex. The formation of the lipid-polycation complex can be accomplished by methods as described in, e.g., U.S. Pub. No. US20120178702. As a non-limiting example, the polycation can include a cationic peptide or a polypeptide such as, but not limited to, polylysine, polyornithine and/or polyarginine and the cationic peptides described in Intl. Pub. No.

WO2012013326 or U.S. Pub. No. US20130142818. Each of the references is herein incorporated by reference in its entirety.

In some embodiments, the polynucleotides described herein can be formulated in a lipid nanoparticle (LNP) such as those described in Intl. Pub. Nos. W2013123523, WO2012170930, WO2011127255 and WO2008103276; and U.S. Pub. No. US20130171646, each of which is herein incorporated by reference in its entirety.

Lipid nanoparticle formulations typically comprise one or more lipids. In some embodiments, the lipid is an ionizable lipid (e.g., an ionizable amino lipid), sometimes referred to in the art as an "ionizable cationic lipid". In some embodiments, lipid nanoparticle formulations further comprise other components, including a phospholipid, a structural lipid, and a molecule capable of reducing particle aggregation, for example a PEG or PEG-modified lipid.

Exemplary ionizable lipids include, but not limited to, any one of Compounds 1-342 disclosed herein, DLin-MC3-DMA (MC3), DLin-DMA, DLenDMA, DLin-D-DMA, DLin-K-DMA, DLin-M-C2-DMA, DLin-K-DMA, DLin-KC2-DMA, DLin-KC3-DMA, DLin-KC4-DMA, DLin-C2K-DMA, DLin-MP-DMA, DODMA, 98N12-5, C12-200, DLin-C-DAP, DLin-DAC, DLinDAP, DLinAP, DLin-EG-DMA, DLin-2-DMAP, KL10, KL22, KL25, Octyl-CLinDMA, Octyl-CLinDMA (2R), Octyl-CLinDMA (2S), and any combination thereof. Other exemplary ionizable lipids include, (13Z,16Z)—N,N-dimethyl-3-nonyldocosa-13,16-dien-1-amine (L608), (20Z,23Z)—N,N-dimethyl-nonacosa-20,23-dien-10-amine, (17Z,20Z)—N,N-dimemyl-hexacosa-17,20-dien-9-amine, (16Z,19Z)—N5N-dimethylpentacosa-16,19-dien-8-amine, (13Z,16Z)—N,N-dimethyldocosa-13,16-dien-5-amine, (12Z,15Z)—N,N-dimethylhenicosa-12,15-dien-4-amine, (14Z,17Z)—N,N-dimethyltricosa-14,17-dien-6-amine, (15Z,18Z)—N,N-dimethyltetracosa-15,18-dien-7-amine, (18Z,21Z)—N,N-dimethylheptacosa-18,21-dien-10-amine, (15Z,18Z)—N,N-dimethyltetracosa-15,18-dien-5-amine, (14Z,17Z)—N,N-dimethyltricosa-14,17-dien-4-amine, (19Z,22Z)—N,N-dimeihyloctacosa-19,22-dien-9-amine, (18Z,21Z)—N,N-dimethylheptacosa-18,21-dien-8-amine, (17Z,20Z)—N,N-dimethylhexacosa-17,20-dien-7-amine, (16Z,19Z)—N,N-dimethylpentacosa-16,19-dien-6-amine, (22Z,25Z)—N,N-dimethylhentriaconta-22,25-dien-10-amine, (21Z,24Z)—N,N-dimethyltriaconta-21,24-dien-9-amine, (18Z)—N,N-dimetylheptacos-18-en-10-amine, (17Z)—N,N-dimethylhexacos-17-en-9-amine, (19Z,22Z)—N,N-dimethyloctacosa-19,22-dien-7-amine, N,N-dimethylheptacosan-10-amine, (20Z,23Z)—N-ethyl-N-methylnonacosa-20,23-dien-10-amine, 1-[(11Z,14Z)-1-nonylicosa-11,14-dien-1-yl]pyrrolidine, (20Z)—N,N-dimethylheptacos-20-en-10-amine, (15Z)—N,N-dimethyl eptacos-15-en-10-amine, (14Z)—N,N-dimethylnonacos-14-en-10-amine, (17Z)—N,N-dimethylnonacos-17-en-10-amine, (24Z)—N,N-dimethyltritriacont-24-en-10-amine, (20Z)—N,N-dimethylnonacos-20-en-10-amine, (22Z)—N,N-dimethylhentriacont-22-en-10-amine, (16Z)—N,N-dimethylpentacos-16-en-8-amine, (12Z,15Z)—N,N-dimethyl-2-nonylhenicosa-12,15-dien-1-amine, N,N-dimethyl-1-[(S,2R)-2-octylcyclopropyl] eptadecan-8-amine, 1-[(1S,2R)-2-hexylcyclopropyl]-N,N-dimethylnonadecan-10-amine, N,N-dimethyl-1-[(1S,2R)-2-octylcyclopropyl]nonadecan-10-amine, N,N-dimethyl-21-[(1S,2R)-2-octylcyclopropyl]henicosan-10-amine, N,N-dimethyl-1-[(1S,2S)-2-{[(1R,2R)-2-pentylcyclopropyl]methyl}cyclopropyl]nonadecan-10-amine, N,N-dimethyl-1-[(1S,2R)-2-octylcyclopropyl]hexadecan-8-amine, N,N-dimethyl-[(1R,2S)-2-undecylcyclopropyl]tetradecan-5-amine, N,N-dimethyl-3-{7-[(1S,2R)-2-octylcyclopropyl]heptyl}dodecan-1-amine, 1-[(1R,2S)-2-heptylcyclopropyl]-N,N-dimethyloctadecan-9-amine, 1-[(1S,2R)-2-decylcyclopropyl]-N,N-dimethylpentadecan-6-amine, N,N-dimethyl-1-[(S,2R)-2-octylcyclopropyl]pentadecan-8-amine, R—N,N-dimethyl-1-[(9Z,12Z)-octadeca-9,12-dien-1-yloxy]-3-(octyloxy)propan-2-amine, S—N,N-dimethyl-1-[(9Z,12Z)-octadeca-9,12-dien-1-yloxy]-3-(octyloxy)propan-2-amine, 1-{2-[(9Z,12Z)-octadeca-9,12-dien-1-yloxy]-1-[(octyloxy)methyl]ethyl}pyrrolidine, (2S)—N,N-dimethyl-1-[(9Z,12Z)-octadeca-9,12-dien-1-yloxy]-3-[(5Z)-oct-5-en-1-yloxy]propan-2-amine, 1-{2-[(9Z,12Z)-octadeca-9,12-dien-1-yloxy]-1-[(octyloxy)methyl]ethyl}azetidine, (2S)-1-(hexyloxy)-N,N-dimethyl-3-[(9Z,12Z)-octadeca-9,12-dien-1-yloxy]propan-2-amine, (2S)-1-(heptyloxy)-N,N-dimethyl-3-[(9Z,12Z)-octadeca-9,12-dien-1-yloxy]propan-2-amine, N,N-dimethyl-1-(nonyloxy)-3-[(9Z,12Z)-octadeca-9,12-dien-1-yloxy]propan-2-amine, N,N-dimethyl-1-[(9Z)-octadec-9-en-1-yloxy]-3-(octyloxy)propan-2-amine; (2S)—N,N-dimethyl-1-[(6Z,9Z,12Z)-octadeca-6,9,12-trien-1-yloxy]-3-(octyloxy)propan-2-amine, (2S)-1-[(11Z,14Z)-icosa-11,14-dien-1-yloxy]-N,N-dimethyl-3-(pentyloxy)propan-2-amine, (2S)-1-(hexyloxy)-3-[(11Z,14Z)-icosa-11,14-dien-1-yloxy]-N,N-dimethylpropan-2-amine, 1-[(11Z,14Z)-icosa-11,14-dien-1-yloxy]-N,N-dimethyl-3-(octyloxy)propan-2-amine, 1-[(13Z,16Z)-docosa-13,16-dien-1-yloxy]-N,N-dimethyl-3-(octyloxy)propan-2-amine, (2S)-1-[(13Z,16Z)-docosa-13,16-dien-1-yloxy]-3-(hexyloxy)-N,N-dimethylpropan-2-amine, (2S)-1-[(13Z)-docos-13-en-1-yloxy]-3-(hexyloxy)-N,N-dimethylpropan-2-amine, 1-[(13Z)-docos-13-en-1-yloxy]-N,N-dimethyl-3-(octyloxy)propan-2-amine, 1-[(9Z)-hexadec-9-en-1-yloxy]-N,N-dimethyl-3-(octyloxy)propan-2-amine, (2R)—N,N-dimethyl-H(1-metoyloctyl)oxy]-3-[(9Z,12Z)-octadeca-9,12-dien-1-yloxy]propan-2-amine, (2R)-1-[(3,7-dimethyloctyl)oxy]-N,N-dimethyl-3-[(9Z,12Z)-octadeca-9,12-dien-1-yloxy]propan-2-amine, N,N-dimethyl-1-(octyloxy)-3-({8-[(1S,2S)-2-{[(1R,2R)-2-pentylcyclopropyl]methyl}cyclopropyl]octyl}oxy)propan-2-amine, N,N-dimethyl-1-{[8-(2-oclylcyclopropyl)octyl]oxy}-3-(octyloxy)propan-2-amine, and (11E,20Z,23Z)—N,N-dimethylnonacosa-11,20,2-trien-10-amine, and any combination thereof.

Phospholipids include, but are not limited to, glycerophospholipids such as phosphatidylcholines, phosphatidylethanolamines, phosphatidylserines, phosphatidylinositols, phosphatidy glycerols, and phosphatidic acids. Phospholipids also include phosphosphingolipid, such as sphingomyelin. In some embodiments, the phospholipids are DLPC, DMPC, DOPC, DPPC, DSPC, DUPC, 18:0 Diether PC, DLnPC, DAPC, DHAPC, DOPE, 4ME 16:0 PE, DSPE, DLPE, DLnPE, DAPE, DHAPE, DOPG, and any combination thereof. In some embodiments, the phospholipids are MPPC, MSPC, PMPC, PSPC, SMPC, SPPC, DHAPE, DOPG, and any combination thereof. In some embodiments, the amount of phospholipids (e.g., DSPC) in the lipid composition ranges from about 1 mol % to about 20 mol %.

The structural lipids include sterols and lipids containing sterol moieties. In some embodiments, the structural lipids include cholesterol, fecosterol, sitosterol, ergosterol, campesterol, stigmasterol, brassicasterol, tomatidine, tomatine, ursolic acid, alpha-tocopherol, and mixtures thereof. In some embodiments, the structural lipid is cholesterol. In some embodiments, the amount of the structural lipids (e.g., cholesterol) in the lipid composition ranges from about 20 mol % to about 60 mol %.

The PEG-modified lipids include PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Such lipids are also referred to as PEGylated lipids. For example, a PEG lipid can be PEG-c-DOMG, PEG-DMG, PEG-DLPE, PEG DMPE, PEG-DPPC, or a PEG-DSPE lipid. In some embodiments, the PEG-lipid are 1,2-dimyristoyl-sn-glycerol methoxypolyethylene glycol (PEG-DMG), 1,2-distearoyl-sn-gly cero-3-phosphoethanolamine-N-[amino(polyethylene glycol)] (PEG-DSPE), PEG-disteryl glycerol (PEG-DSG), PEG-dipalmetoleyl, PEG-dioleyl, PEG-distearyl, PEG-diacylglycamide (PEG-DAG), PEG-dipalmitoyl phosphatidylethanolamine (PEG-DPPE), or PEG-1,2-dimyristyloxlpropyl-3-amine (PEG-c-DMA). In some embodiments, the PEG moiety has a size of about 1000, 2000, 5000, 10,000, 15,000 or 20,000 daltons. In some embodiments, the amount of PEG-lipid in the lipid composition ranges from about 0 mol % to about 5 mol %.

In some embodiments, the LNP formulations described herein can additionally comprise a permeability enhancer molecule. Non-limiting permeability enhancer molecules are described in U.S. Pub. No. US20050222064, herein incorporated by reference in its entirety.

The LNP formulations can further contain a phosphate conjugate. The phosphate conjugate can increase in vivo circulation times and/or increase the targeted delivery of the nanoparticle. Phosphate conjugates can be made by the methods described in, e.g., Intl. Pub. No. WO2013033438 or U.S. Pub. No. US20130196948. The LNP formulation can also contain a polymer conjugate (e.g., a water soluble conjugate) as described in, e.g., U.S. Pub. Nos. US20130059360, US20130196948, and US20130072709. Each of the references is herein incorporated by reference in its entirety.

The LNP formulations can comprise a conjugate to enhance the delivery of nanoparticles of the present invention in a subject. Further, the conjugate can inhibit phagocytic clearance of the nanoparticles in a subject. In some embodiments, the conjugate can be a "self" peptide designed from the human membrane protein CD47 (e.g., the "self" particles described by Rodriguez et al, Science 2013 339, 971-975, herein incorporated by reference in its entirety). As shown by Rodriguez et al. the self peptides delayed macrophage-mediated clearance of nanoparticles which enhanced delivery of the nanoparticles.

The LNP formulations can comprise a carbohydrate carrier. As a non-limiting example, the carbohydrate carrier can include, but is not limited to, an anhydride-modified phytoglycogen or glycogen-type material, phytoglycogen octenyl succinate, phytoglycogen beta-dextrin, anhydride-modified phytoglycogen beta-dextrin (e.g., Intl. Pub. No. WO2012109121, herein incorporated by reference in its entirety).

The LNP formulations can be coated with a surfactant or polymer to improve the delivery of the particle. In some embodiments, the LNP can be coated with a hydrophilic coating such as, but not limited to, PEG coatings and/or coatings that have a neutral surface charge as described in U.S. Pub. No. US20130183244, herein incorporated by reference in its entirety.

The LNP formulations can be engineered to alter the surface properties of particles so that the lipid nanoparticles can penetrate the mucosal barrier as described in U.S. Pat. No. 8,241,670 or Intl. Pub. No. WO2013110028, each of which is herein incorporated by reference in its entirety.

The LNP engineered to penetrate mucus can comprise a polymeric material (i.e., a polymeric core) and/or a polymer-vitamin conjugate and/or a tri-block co-polymer. The polymeric material can include, but is not limited to, polyamines, polyethers, polyamides, polyesters, polycarbamates, polyureas, polycarbonates, poly(styrenes), polyimides, polysulfones, polyurethanes, polyacetylenes, polyethylenes, polyethyeneimines, polyisocyanates, polyacrylates, polymethacrylates, polyacrylonitriles, and polyarylates.

LNP engineered to penetrate mucus can also include surface altering agents such as, but not limited to, polynucleotides, anionic proteins (e.g., bovine serum albumin), surfactants (e.g., cationic surfactants such as for example dimethyldioctadecyl-ammonium bromide), sugars or sugar derivatives (e.g., cyclodextrin), nucleic acids, polymers (e.g., heparin, polyethylene glycol and poloxamer), mucolytic agents (e.g., N-acetylcysteine, mugwort, bromelain, papain, clerodendrum, acetylcysteine, bromhexine, carbocisteine, eprazinone, mesna, ambroxol, sobrerol, domiodol, letosteine, stepronin, tiopronin, gelsolin, thymosin 04 domase alfa, neltenexine, erdosteine) and various DNases including rhDNase.

In some embodiments, the mucus penetrating LNP can be a hypotonic formulation comprising a mucosal penetration enhancing coating. The formulation can be hypotonic for the epithelium to which it is being delivered. Non-limiting examples of hypotonic formulations can be found in, e.g., Intl. Pub. No. W2013110028, herein incorporated by reference in its entirety.

In some embodiments, the polynucleotide described herein is formulated as a lipoplex, such as, without limitation, the ATUPLEX™ system, the DACC system, the DBTC system and other siRNA-lipoplex technology from Silence Therapeutics (London, United Kingdom), STEMFECT™ from STEMGENT® (Cambridge, MA), and polyethylenimine (PEI) or protamine-based targeted and non-targeted delivery of nucleic acids (Aleku et al. Cancer Res. 2008 68:9788-9798; Strumberg et al. Int J Clin Pharmacol Ther 2012 50:76-78; Santel et al., Gene Ther 2006 13:1222-1234; Santel et al., Gene Ther 2006 13:1360-1370; Gutbier et al., Pulm Pharmacol. Ther. 2010 23:334-344; Kaufmann et al. Microvasc Res 2010 80:286-293 Weide et al. J Immunother. 2009 32:498-507; Weide et al. J Immunother. 2008 31:180-188; Pascolo Expert Opin. Biol. Ther. 4:1285-1294; Fotin-Mleczek et al., 2011 J. Immunother. 34:1-15; Song et al., Nature Biotechnol. 2005, 23:709-717; Peer et al., Proc Natl Acad Sci USA. 2007 6; 104:4095-4100; deFougerolles Hum Gene Ther. 2008 19:125-132; all of which are incorporated herein by reference in its entirety).

In some embodiments, the polynucleotides described herein are formulated as a solid lipid nanoparticle (SLN), which can be spherical with an average diameter between 10 to 1000 nm. SLN possess a solid lipid core matrix that can solubilize lipophilic molecules and can be stabilized with surfactants and/or emulsifiers. Exemplary SLN can be those as described in Intl. Pub. No. WO2013105101, herein incorporated by reference in its entirety.

In some embodiments, the polynucleotides described herein can be formulated for controlled release and/or targeted delivery. As used herein, "controlled release" refers to a pharmaceutical composition or compound release profile that conforms to a particular pattern of release to effect a therapeutic outcome. In one embodiment, the polynucleotides can be encapsulated into a delivery agent described herein and/or known in the art for controlled release and/or targeted delivery. As used herein, the term "encapsulate" means to enclose, surround or encase. As it relates to the formulation of the compounds of the invention, encapsulation can be substantial, complete or partial. The term "substantially encapsulated" means that at least greater than 50, 60, 70, 80, 85, 90, 95, 96, 97, 98, 99, or greater than 99% of the pharmaceutical composition or compound of the invention can be enclosed, surrounded or encased within the delivery agent. "Partially encapsulation" means that less than 10, 10, 20, 30, 40 50 or less of the pharmaceutical composition or compound of the invention can be enclosed, surrounded or encased within the delivery agent.

Advantageously, encapsulation can be determined by measuring the escape or the activity of the pharmaceutical composition or compound of the invention using fluorescence and/or electron micrograph. For example, at least 1, 5, 10, 20, 30, 40, 50, 60, 70, 80, 85, 90, 95, 96, 97, 98, 99, 99.9, or greater than 99% of the pharmaceutical composition or compound of the invention are encapsulated in the delivery agent.

In some embodiments, the polynucleotides described herein can be encapsulated in a therapeutic nanoparticle, referred to herein as "therapeutic nanoparticle polynucleotides." Therapeutic nanoparticles can be formulated by methods described in, e.g., Intl. Pub. Nos. WO2010005740, WO2010030763, WO2010005721, WO2010005723, and WO2012054923; and U.S. Pub. Nos. US20110262491, US20100104645, US20100087337, US20100068285, US20110274759, US20100068286, US20120288541, US20120140790, US20130123351 and US20130230567; and U.S. Pat. Nos. 8,206,747, 8,293,276, 8,318,208 and 8,318,211, each of which is herein incorporated by reference in its entirety.

In some embodiments, the therapeutic nanoparticle polynucleotide can be formulated for sustained release. As used herein, "sustained release" refers to a pharmaceutical composition or compound that conforms to a release rate over a specific period of time. The period of time can include, but is not limited to, hours, days, weeks, months and years. As a non-limiting example, the sustained release nanoparticle of the polynucleotides described herein can be formulated as disclosed in Intl. Pub. No. W2010075072 and U.S. Pub. Nos. US20100216804, US20110217377, US20120201859 and US20130150295, each of which is herein incorporated by reference in their entirety.

In some embodiments, the therapeutic nanoparticle polynucleotide can be formulated to be target specific, such as those described in Intl. Pub. Nos. W2008121949, WO2010005726, WO2010005725, WO2011084521 and WO2011084518; and U.S. Pub. Nos. US20100069426, US20120004293 and US20100104655, each of which is herein incorporated by reference in its entirety.

The LNPs can be prepared using microfluidic mixers or micromixers. Exemplary microfluidic mixers can include, but are not limited to, a slit interdigital micromixer including, but not limited to those manufactured by Microinnova (Allerheiligen bei Wildon, Austria) and/or a staggered herringbone micromixer (SHM) (see Zhigaltsev et al., "Bottom-up design and synthesis of limit size lipid nanoparticle systems with aqueous and triglyceride cores using millisecond microfluidic mixing," Langmuir 28:3633-40 (2012); Belliveau et al., "Microfluidic synthesis of highly potent limit-size lipid nanoparticles for in vivo delivery of siRNA," Molecular Therapy-Nucleic Acids. 1:e37 (2012); Chen et al., "Rapid discovery of potent siRNA-containing lipid nanoparticles enabled by controlled microfluidic formulation," J. Am. Chem. Soc. 134(16):6948-51 (2012); each of which is herein incorporated by reference in its entirety). Exemplary micromixers include Slit Interdigital Microstructured Mixer (SIMM-V2) or a Standard Slit Interdigital Micro Mixer (SSIMM) or Caterpillar (CPMM) or Impinging-jet (IJMM,) from the Institut für Mikrotechnik Mainz GmbH, Mainz Germany. In some embodiments, methods of making LNP using SHM further comprise mixing at least two input streams wherein mixing occurs by microstructure-induced chaotic advection (MICA). According to this method, fluid streams flow through channels present in a herringbone pattern causing rotational flow and folding the fluids around each other. This method can also comprise a surface for fluid mixing wherein the surface changes orientations during fluid cycling. Methods of generating LNPs using SHM include those disclosed in U.S. Pub. Nos. US20040262223 and US20120276209, each of which is incorporated herein by reference in their entirety.

In some embodiments, the polynucleotides described herein can be formulated in lipid nanoparticles using microfluidic technology (see Whitesides, George M., "The Origins and the Future of Microfluidics," Nature 442: 368-373 (2006); and Abraham et al., "Chaotic Mixer for Microchannels," Science 295: 647-651 (2002); each of which is herein incorporated by reference in its entirety). In some embodiments, the polynucleotides can be formulated in lipid nanoparticles using a micromixer chip such as, but not limited to, those from Harvard Apparatus (Holliston, MA) or Dolomite Microfluidics (Royston, UK). A micromixer chip can be used for rapid mixing of two or more fluid streams with a split and recombine mechanism.

In some embodiments, the polynucleotides described herein can be formulated in lipid nanoparticles having a diameter from about 1 nm to about 100 nm such as, but not limited to, about 1 nm to about 20 nm, from about 1 nm to about 30 nm, from about 1 nm to about 40 nm, from about 1 nm to about 50 nm, from about 1 nm to about 60 nm, from about 1 nm to about 70 nm, from about 1 nm to about 80 nm, from about 1 nm to about 90 nm, from about 5 nm to about from 100 nm, from about 5 nm to about 10 nm, about 5 nm to about 20 nm, from about 5 nm to about 30 nm, from about 5 nm to about 40 nm, from about 5 nm to about 50 nm, from about 5 nm to about 60 nm, from about 5 nm to about 70 nm, from about 5 nm to about 80 nm, from about 5 nm to about 90 nm, about 10 to about 20 nm, about 10 to about nm, about 10 to about 40 nm, about 10 to about 50 nm, about 10 to about 60 nm, about 10 to about 70 nm, about 10 to about 80 nm, about 10 to about 90 nm, about 20 to about 30 nm, about 20 to about 40 nm, about 20 to about 50 nm, about 20 to about 60 nm, about 20 to about 70 nm, about 20 to about 80 nm, about 20 to about 90 nm, about 20 to about 100 nm, about 30 to about 40 nm, about 30 to about 50 nm, about 30 to about 60 nm, about 30 to about 70 nm, about 30 to about 80 nm, about 30 to about 90 nm, about 30 to about 100 nm, about 40 to about 50 nm, about 40 to about 60 nm, about 40 to about 70 nm, about 40 to about 80 nm, about 40 to about 90 nm, about 40 to about 100 nm, about 50 to about 60 nm, about 50 to about 70 nm about 50 to about 80 nm, about 50 to about 90 nm, about 50 to about 100 nm, about 60 to about 70 nm, about 60 to about 80 nm, about 60 to about 90 nm, about 60 to about 100 nm, about 70 to about 80 nm, about 70 to about 90 nm, about 70 to about 100 nm, about 80 to about 90 nm, about 80 to about 100 nm and/or about 90 to about 100 nm.

In some embodiments, the lipid nanoparticles can have a diameter from about 10 to 500 nm. In one embodiment, the lipid nanoparticle can have a diameter greater than 100 nm, greater than 150 nm, greater than 200 nm, greater than 250 nm, greater than 300 nm, greater than 350 nm, greater than 400 nm, greater than 450 nm, greater than 500 nm, greater than 550 nm, greater than 600 nm, greater than 650 nm, greater than 700 nm, greater than 750 nm, greater than 800 nm, greater than 850 nm, greater than 900 nm, greater than 950 nm or greater than 1000 nm.

In some embodiments, the polynucleotides can be delivered using smaller LNPs. Such particles can comprise a diameter from below 0.1 μm up to 100 nm such as, but not limited to, less than 0.1 μm, less than 1.0 μm, less than 5 μm, less than 10 μm, less than 15 um, less than 20 um, less than 25 um, less than 30 um, less than 35 um, less than 40 um, less than 50 um, less than 55 um, less than 60 um, less than 65 um, less than 70 um, less than 75 um, less than 80 um, less than 85 um, less than 90 um, less than 95 um, less than 100 um, less than 125 um, less than 150 um, less than 175 um, less than 200 um, less than 225 um, less than 250 um, less than 275 um, less than 300 um, less than 325 um, less than 350 um, less than 375 um, less than 400 um, less than 425 um, less than 450 um, less than 475 um, less than 500 um, less than 525 um, less than 550 um, less than 575 um, less than 600 um, less than 625 um, less than 650 um, less than 675 um, less than 700 um, less than 725 um, less than 750 um, less than 775 um, less than 800 um, less than 825 um, less than 850 um, less than 875 um, less than 900 um, less than 925 um, less than 950 um, or less than 975 um.

The nanoparticles and microparticles described herein can be geometrically engineered to modulate macrophage and/or the immune response. The geometrically engineered particles can have varied shapes, sizes and/or surface charges to incorporate the polynucleotides described herein for targeted delivery such as, but not limited to, pulmonary delivery (see, e.g., Intl. Pub. No. WO2013082111, herein incorporated by reference in its entirety). Other physical features the geometrically engineering particles can include, but are not limited to, fenestrations, angled arms, asymmetry and surface roughness, charge that can alter the interactions with cells and tissues.

In some embodiment, the nanoparticles described herein are stealth nanoparticles or target-specific stealth nanoparticles such as, but not limited to, those described in U.S. Pub. No. US20130172406, herein incorporated by reference in its entirety. The stealth or target-specific stealth nanoparticles can comprise a polymeric matrix, which can comprise two or more polymers such as, but not limited to, polyethylenes, polycarbonates, polyanhydrides, polyhydroxyacids, polypropylfumerates, polycaprolactones, polyamides, polyacetals, polyethers, polyesters, poly(orthoesters), poly cyanoacrylates, polyvinyl alcohols, polyurethanes, polyphosphazenes, polyacrylates, polymethacrylates, polycyanoacrylates, polyureas, polystyrenes, polyamines, polyesters, polyanhydrides, polyethers, polyurethanes, polymethacrylates, polyacrylates, polycyanoacrylates, or combinations thereof.

b. Lipidoids

In some embodiments, the compositions or formulations of the present disclosure comprise a delivery agent, e.g., a lipidoid. The polynucleotides described herein (e.g., a polynucleotide comprising a nucleotide sequence encoding an anti-CHIKV antibody polypeptide) can be formulated with lipidoids. Complexes, micelles, liposomes or particles can be prepared containing these lipidoids and therefore to achieve an effective delivery of the polynucleotide, as judged by the production of an encoded protein, following the injection of a lipidoid formulation via localized and/or systemic routes of administration. Lipidoid complexes of polynucleotides can be administered by various means including, but not limited to, intravenous, intramuscular, or subcutaneous routes.

The synthesis of lipidoids is described in literature (see Mahon et al., Bioconjug. Chem. 2010 21:1448-1454; Schroeder et al., J Intern Med. 2010 267:9-21; Akinc et al., Nat Biotechnol. 2008 26:561-569; Love et al., Proc Natl Acad Sci USA. 2010 107:1864-1869; Siegwart et al., Proc Natl Acad Sci USA. 2011 108:12996-3001; all of which are incorporated herein in their entireties).

Formulations with the different lipidoids, including, but not limited to penta[3-(1-laurylaminopropionyl)]-triethylenetetramine hydrochloride (TETA-5LAP; also known as 98N12-5, see Murugaiah et al., Analytical Biochemistry, 401:61 (2010)), C12-200 (including derivatives and variants), and MD1, can be tested for in vivo activity. The lipidoid "98N12-5" is disclosed by Akinc et al., Mol Ther. 2009 17:872-879. The lipidoid "C12-200" is disclosed by Love et al., Proc Natl Acad Sci USA. 2010 107:1864-1869 and Liu and Huang, Molecular Therapy. 2010 669-670. Each of the references is herein incorporated by reference in its entirety.

In one embodiment, the polynucleotides described herein can be formulated in an aminoalcohol lipidoid. Aminoalcohol lipidoids can be prepared by the methods described in U.S. Pat. No. 8,450,298 (herein incorporated by reference in its entirety).

The lipidoid formulations can include particles comprising either 3 or 4 or more components in addition to polynucleotides. Lipidoids and polynucleotide formulations comprising lipidoids are described in Intl. Pub. No. WO 2015051214 (herein incorporated by reference in its entirety.

c. Hyaluronidase

In some embodiments, the polynucleotides described herein (e.g., a polynucleotide comprising a nucleotide sequence encoding an anti-CHIKV antibody polypeptide) and hyaluronidase for injection (e.g., intramuscular or subcutaneous injection). Hyaluronidase catalyzes the hydrolysis of hyaluronan, which is a constituent of the interstitial barrier. Hyaluronidase lowers the viscosity of hyaluronan, thereby increases tissue permeability (Frost, Expert Opin. Drug Deliv. (2007) 4:427-440). Alternatively, the hyaluronidase can be used to increase the number of cells exposed to the polynucleotides administered intramuscularly, or subcutaneously.

d. Nanoparticle Mimics

In some embodiments, the polynucleotides described herein (e.g., a polynucleotide comprising a nucleotide sequence encoding an anti-CHIKV antibody polypeptide) is encapsulated within and/or absorbed to a nanoparticle mimic. A nanoparticle mimic can mimic the delivery function organisms or particles such as, but not limited to, pathogens, viruses, bacteria, fungus, parasites, prions and cells. As a non-limiting example, the polynucleotides described herein can be encapsulated in a non-viron particle that can mimic the delivery function of a virus (see e.g., Intl. Pub. No. WO2012006376 and U.S. Pub. Nos. US20130171241 and US20130195968, each of which is herein incorporated by reference in its entirety).

e. Self-Assembled Nanoparticles, or Self-Assembled Macromolecules

In some embodiments, the compositions or formulations of the present disclosure comprise the polynucleotides described herein (e.g., a polynucleotide comprising a nucleotide sequence encoding an anti-CHIKV antibody polypeptide) in self-assembled nanoparticles, or amphiphilic macromolecules (AMs) for delivery. AMs comprise biocompatible amphiphilic polymers that have an alkylated sugar backbone covalently linked to poly(ethylene glycol). In aqueous solution, the AMs self-assemble to form micelles.

Nucleic acid self-assembled nanoparticles are described in Intl. Appl. No. PCT/US2014/027077, and AMs and methods of forming AMs are described in U.S. Pub. No. US20130217753, each of which is herein incorporated by reference in its entirety.

f. Cations and Anions

In some embodiments, the compositions or formulations of the present disclosure comprise the polynucleotides described herein (e.g., a polynucleotide comprising a nucleotide sequence encoding an anti-CHIKV antibody polypeptide) and a cation or anion, such as Zn2+, Ca2+, Cu2+, Mg2+ and combinations thereof. Exemplary formulations can include polymers and a polynucleotide complexed with a metal cation as described in, e.g., U.S. Pat. Nos. 6,265,389 and 6,555,525, each of which is herein incorporated by reference in its entirety. In some embodiments, cationic nanoparticles can contain a combination of divalent and monovalent cations. The delivery of polynucleotides in cationic nanoparticles or in one or more depot comprising cationic nanoparticles can improve polynucleotide bioavailability by acting as a long-acting depot and/or reducing the rate of degradation by nucleases.

g. Amino Acid Lipids

In some embodiments, the compositions or formulations of the present disclosure comprise the polynucleotides described herein (e.g., a polynucleotide comprising a nucleotide sequence encoding an anti-CHIKV antibody polypeptide) that is formulation with an amino acid lipid. Amino acid lipids are lipophilic compounds comprising an amino acid residue and one or more lipophilic tails. Non-limiting examples of amino acid lipids and methods of making amino acid lipids are described in U.S. Pat. No. 8,501,824. The amino acid lipid formulations can deliver a polynucleotide in releasable form that comprises an amino acid lipid that binds and releases the polynucleotides. As a non-limiting example, the release of the polynucleotides described herein can be provided by an acid-labile linker as described in, e.g., U.S. Pat. Nos. 7,098,032, 6,897,196, 6,426,086, 7,138,382, 5,563,250, and 5,505,931, each of which is herein incorporated by reference in its entirety.

h. Interpolyelectrolyte Complexes

In some embodiments, the compositions or formulations of the present disclosure comprise the polynucleotides described herein (e.g., a polynucleotide comprising a nucleotide sequence encoding an anti-CHIKV antibody polypeptide) in an interpolyelectrolyte complex. Interpolyelectrolyte complexes are formed when charge-dynamic polymers are complexed with one or more anionic molecules. Non-limiting examples of charge-dynamic polymers and interpolyelectrolyte complexes and methods of making interpolyelectrolyte complexes are described in U.S. Pat. No. 8,524,368, herein incorporated by reference in its entirety.

i. Crystalline Polymeric Systems

In some embodiments, the compositions or formulations of the present disclosure comprise the polynucleotides described herein (e.g., a polynucleotide comprising a nucleotide sequence encoding an anti-CHIKV antibody polypeptide) in crystalline polymeric systems. Crystalline polymeric systems are polymers with crystalline moieties and/or terminal units comprising crystalline moieties. Exemplary polymers are described in U.S. Pat. No. 8,524,259 (herein incorporated by reference in its entirety).

j. Polymers, Biodegradable Nanoparticles, and Core-Shell Nanoparticles

In some embodiments, the compositions or formulations of the present disclosure comprise the polynucleotides described herein (e.g., a polynucleotide comprising a nucleotide sequence encoding an anti-CHIKV antibody polypeptide) and a natural and/or synthetic polymer. The polymers include, but not limited to, polyethenes, polyethylene glycol (PEG), poly(l-lysine)(PLL), PEG grafted to PLL, cationic lipopolymer, biodegradable cationic lipopolymer, polyethyleneimine (PEI), cross-linked branched poly (alkylene imines), a polyamine derivative, a modified poloxamer, elastic biodegradable polymer, biodegradable copolymer, biodegradable polyester copolymer, biodegradable polyester copolymer, multiblock copolymers, poly[α-(4-aminobutyl)-L-glycolic acid) (PAGA), biodegradable cross-linked cationic multi-block copolymers, polycarbonates, polyanhydrides, polyhydroxyacids, polypropylfumerates, polycaprolactones, polyamides, polyacetals, polyethers, polyesters, poly(orthoesters), polycyanoacrylates, polyvinyl alcohols, polyurethanes, polyphosphazenes, polyureas, polystyrenes, polyamines, polylysine, poly(ethylene imine), poly(serine ester), poly(L-lactide-co-L-lysine), poly(4-hydroxy-L-proline ester), amine-containing polymers, dextran polymers, dextran polymer derivatives or combinations thereof.

Exemplary polymers include, DYNAMIC POLYCONJUGATE® (Arrowhead Research Corp., Pasadena, CA) formulations from MIRUS® Bio (Madison, WI) and Roche Madison (Madison, WI), PHASERX™ polymer formulations such as, without limitation, SMARTT POLYMER TECHNOLOGY™ (PHASERX®, Seattle, WA), DMRI/DOPE, poloxamer, VAXFECTIN® adjuvant from Vical (San Diego, CA), chitosan, cyclodextrin from Calando Pharmaceuticals (Pasadena, CA), dendrimers and poly(lactic-co-glycolic acid) (PLGA) polymers. RONDEL™ (RNAi/Oligonucleotide Nanoparticle Delivery) polymers (Arrowhead Research Corporation, Pasadena, CA) and pH responsive co-block polymers such as PHASERX® (Seattle, WA).

The polymer formulations allow a sustained or delayed release of the polynucleotide (e.g., following intramuscular or subcutaneous injection). The altered release profile for the polynucleotide can result in, for example, translation of an encoded protein over an extended period of time. The polymer formulation can also be used to increase the stability of the polynucleotide. Sustained release formulations can include, but are not limited to, PLGA microspheres, ethylene vinyl acetate (EVAc), poloxamer, GELSITE® (Nanotherapeutics, Inc. Alachua, FL), HYLENEX® (Halozyme Therapeutics, San Diego CA), surgical sealants such as fibrinogen polymers (Ethicon Inc. Cornelia, GA), TISSELL® (Baxter International, Inc. Deerfield, IL), PEG-based sealants, and COSEAL® (Baxter International, Inc. Deerfield, IL).

As a non-limiting example modified mRNA can be formulated in PLGA microspheres by preparing the PLGA microspheres with tunable release rates (e.g., days and weeks) and encapsulating the modified mRNA in the PLGA microspheres while maintaining the integrity of the modified mRNA during the encapsulation process. EVAc are non-biodegradable, biocompatible polymers that are used extensively in pre-clinical sustained release implant applications (e.g., extended release products Ocusert a pilocarpine ophthalmic insert for glaucoma or progestasert a sustained release progesterone intrauterine device; transdermal delivery systems Testoderm, Duragesic and Selegiline; catheters). Poloxamer F-407 NF is a hydrophilic, non-ionic surfactant triblock copolymer of polyoxyethylene-polyoxypropylene-polyoxyethylene having a low viscosity at temperatures less than 5° C. and forms a solid gel at temperatures greater than 15° C.

As a non-limiting example, the polynucleotides described herein can be formulated with the polymeric compound of PEG grafted with PLL as described in U.S. Pat. No. 6,177,274. As another non-limiting example, the polynucleotides described herein can be formulated with a block copolymer such as a PLGA-PEG block copolymer (see e.g., U.S. Pub. No. US20120004293 and U.S. Pat. Nos. 8,236,330 and 8,246,968), or a PLGA-PEG-PLGA block copolymer (see e.g., U.S. Pat. No. 6,004,573). Each of the references is herein incorporated by reference in its entirety.

In some embodiments, the polynucleotides described herein can be formulated with at least one amine-containing polymer such as, but not limited to polylysine, polyethylene imine, poly(amidoamine) dendrimers, poly(amine-co-esters) or combinations thereof. Exemplary polyamine polymers and their use as delivery agents are described in, e.g., U.S. Pat. Nos. 8,460,696, 8,236,280, each of which is herein incorporated by reference in its entirety.

In some embodiments, the polynucleotides described herein can be formulated in a biodegradable cationic lipopolymer, a biodegradable polymer, or a biodegradable copolymer, a biodegradable polyester copolymer, a biodegradable polyester polymer, a linear biodegradable copolymer, PAGA, a biodegradable cross-linked cationic multi-block copolymer or combinations thereof as described in, e.g., U.S. Pat. Nos. 6,696,038, 6,517,869, 6,267,987, 6,217,912, 6,652,886, 8,057,821, and 8,444,992; U.S. Pub. Nos. US20030073619, US20040142474, US20100004315, US2012009145 and US20130195920; and Intl Pub. Nos. WO2006063249 and W2013086322, each of which is herein incorporated by reference in its entirety.

In some embodiments, the polynucleotides described herein can be formulated in or with at least one cyclodextrin polymer as described in U.S. Pub. No. US20130184453. In some embodiments, the polynucleotides described herein can be formulated in or with at least one crosslinked cation-binding polymers as described in Intl. Pub. Nos. WO2013106072, WO2013106073 and WO2013106086. In some embodiments, the polynucleotides described herein can be formulated in or with at least PEGylated albumin polymer as described in U.S. Pub. No. US20130231287. Each of the references is herein incorporated by reference in its entirety.

In some embodiments, the polynucleotides disclosed herein can be formulated as a nanoparticle using a combination of polymers, lipids, and/or other biodegradable agents, such as, but not limited to, calcium phosphate. Components can be combined in a core-shell, hybrid, and/or layer-by-layer architecture, to allow for fine-tuning of the nanoparticle for delivery (Wang et al., Nat Mater. 2006 5:791-796; Fuller et al., Biomaterials. 2008 29:1526-1532; DeKoker et al., Adv Drug Deliv Rev. 2011 63:748-761; Endres et al., Biomaterials. 2011 32:7721-7731; Su et al., Mol Pharm. 2011 Jun. 6; 8(3):774-87; herein incorporated by reference in their entireties). As a non-limiting example, the nanoparticle can comprise a plurality of polymers such as, but not limited to hydrophilic-hydrophobic polymers (e.g., PEG-PLGA), hydrophobic polymers (e.g., PEG) and/or hydrophilic polymers (Intl. Pub. No. WO20120225129, herein incorporated by reference in its entirety).

The use of core-shell nanoparticles has additionally focused on a high-throughput approach to synthesize cationic cross-linked nanogel cores and various shells (Siegwart et al., Proc Natl Acad Sci USA. 2011 108:12996-13001; herein incorporated by reference in its entirety). The complexation, delivery, and internalization of the polymeric nanoparticles can be precisely controlled by altering the chemical composition in both the core and shell components of the nanoparticle. For example, the core-shell nanoparticles can efficiently deliver siRNA to mouse hepatocytes after they covalently attach cholesterol to the nanoparticle.

In some embodiments, a hollow lipid core comprising a middle PLGA layer and an outer neutral lipid layer containing PEG can be used to delivery of the polynucleotides as described herein. In some embodiments, the lipid nanoparticles can comprise a core of the polynucleotides disclosed herein and a polymer shell, which is used to protect the polynucleotides in the core. The polymer shell can be any of the polymers described herein and are known in the art. The polymer shell can be used to protect the polynucleotides in the core.

Core-shell nanoparticles for use with the polynucleotides described herein are described in U.S. Pat. No. 8,313,777 or Intl. Pub. No. WO2013124867, each of which is herein incorporated by reference in their entirety.

k. Peptides and Proteins

In some embodiments, the compositions or formulations of the present disclosure comprise the polynucleotides described herein (e.g., a polynucleotide comprising a nucleotide sequence encoding an anti-CHIKV antibody polypeptide) that is formulated with peptides and/or proteins to increase transfection of cells by the polynucleotide, and/or to alter the biodistribution of the polynucleotide (e.g., by targeting specific tissues or cell types), and/or increase the translation of encoded protein (e.g., Intl. Pub. Nos. WO2012110636 and WO2013123298. In some embodiments, the peptides can be those described in U.S. Pub. Nos. US20130129726, US20130137644 and US20130164219. Each of the references is herein incorporated by reference in its entirety.

l. Conjugates

In some embodiments, the compositions or formulations of the present disclosure comprise the polynucleotides described herein (e.g., a polynucleotide comprising a nucleotide sequence encoding an anti-CHIKV antibody polypeptide) that is covalently linked to a carrier or targeting group, or including two encoding regions that together produce a fusion protein (e.g., bearing a targeting group and therapeutic protein or peptide) as a conjugate. The conjugate can be a peptide that selectively directs the nanoparticle to neurons in a tissue or organism, or assists in crossing the blood-brain barrier.

The conjugates include a naturally occurring substance, such as a protein (e.g., human serum albumin (HSA), low-density lipoprotein (LDL), high-density lipoprotein (HDL), or globulin); an carbohydrate (e.g., a dextran, pullulan, chitin, chitosan, inulin, cyclodextrin or hyaluronic acid); or a lipid. The ligand can also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrene-maleic acid anhydride copolymer, poly (L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

In some embodiments, the conjugate can function as a carrier for the polynucleotide disclosed herein. The conjugate can comprise a cationic polymer such as, but not limited to, polyamine, polylysine, polyalkylenimine, and polyethylenimine that can be grafted to with poly(ethylene glycol). Exemplary conjugates and their preparations are described in U.S. Pat. No. 6,586,524 and U.S. Pub. No. US20130211249, each of which herein is incorporated by reference in its entirety.

The conjugates can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Targeting groups can be proteins, e.g., glycoproteins, or peptides, e.g., molecules having a specific affinity for a co-ligand, or antibodies e.g., an antibody, that binds to a specified cell type such as an endothelial cell or bone cell. Targeting groups can also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent frucose, or aptamers. The ligand can be, for example, a lipopolysaccharide, or an activator of p38 MAP kinase.

The targeting group can be any ligand that is capable of targeting a specific receptor. Examples include, without limitation, folate, GaNAc, galactose, mannose, mannose-6P, apatamers, integrin receptor ligands, chemokine receptor ligands, transferrin, biotin, serotonin receptor ligands, PSMA, endothelin, GCPII, somatostatin, LDL, and HDL ligands. In particular embodiments, the targeting group is an aptamer. The aptamer can be unmodified or have any combination of modifications disclosed herein. As a non-limiting example, the targeting group can be a glutathione receptor (GR)-binding conjugate for targeted delivery across the blood-central nervous system barrier as described in, e.g., U.S. Pub. No. US2013021661012 (herein incorporated by reference in its entirety).

In some embodiments, the conjugate can be a synergistic biomolecule-polymer conjugate, which comprises a long-acting continuous-release system to provide a greater therapeutic efficacy. The synergistic biomolecule-polymer conjugate can be those described in U.S. Pub. No. US20130195799. In some embodiments, the conjugate can be an aptamer conjugate as described in Intl. Pat. Pub. No. WO2012040524. In some embodiments, the conjugate can be an amine containing polymer conjugate as described in U.S. Pat. No. 8,507,653. Each of the references is herein incorporated by reference in its entirety. In some embodiments, the polynucleotides can be conjugated to SMARTT POLYMER TECHNOLOGY® (PHASERX®, Inc. Seattle, WA).

In some embodiments, the polynucleotides described herein are covalently conjugated to a cell penetrating polypeptide, which can also include a signal sequence or a targeting sequence. The conjugates can be designed to have increased stability, and/or increased cell transfection; and/or altered the biodistribution (e.g., targeted to specific tissues or cell types).

In some embodiments, the polynucleotides described herein can be conjugated to an agent to enhance delivery. In some embodiments, the agent can be a monomer or polymer such as a targeting monomer or a polymer having targeting blocks as described in Intl. Pub. No. WO2011062965. In some embodiments, the agent can be a transport agent covalently coupled to a polynucleotide as described in, e.g., U.S. Pat. Nos. 6,835,393 and 7,374,778. In some embodiments, the agent can be a membrane barrier transport enhancing agent such as those described in U.S. Pat. Nos. 7,737,108 and 8,003,129. Each of the references is herein incorporated by reference in its entirety.

22. Accelerated Blood Clearance

The invention provides compounds, compositions and methods of use thereof for reducing the effect of ABC on a repeatedly administered active agent such as a biologically active agent. As will be readily apparent, reducing or eliminating altogether the effect of ABC on an administered active agent effectively increases its half-life and thus its efficacy.

In some embodiments the term reducing ABC refers to any reduction in ABC in comparison to a positive reference control ABC inducing LNP such as an MC3 LNP. ABC inducing LNPs cause a reduction in circulating levels of an active agent upon a second or subsequent administration within a given time frame. Thus a reduction in ABC refers to less clearance of circulating agent upon a second or subsequent dose of agent, relative to a standard LNP. The reduction may be, for instance, at least 10%, 15%, 20%, 25%, 30%, 35%, 40%, 45%, 50%, 55%, 60%, 65%, 70%, 75%, 80%, 85%, 90%, 95%, 98%, or 100%. In some embodiments the reduction is 10-100%, 10-50%, 20-100%, 20-50%, 30-100%, 30-50%, 40%-100%, 40-80%, 50-90%, or 50-100%. Alternatively, the reduction in ABC may be characterized as at least a detectable level of circulating agent following a second or subsequent administration or at least a 2 fold, 3 fold, 4 fold, 5 fold increase in circulating agent relative to circulating agent following administration of a standard LNP. In some embodiments the reduction is a 2-100 fold, 2-50 fold, 3-100 fold, 3-50 fold, 3-20 fold, 4-100 fold, 4-50 fold, 4-40 fold, 4-30 fold, 4-25 fold, 4-20 fold, 4-15 fold, 4-10 fold, 4-5 fold, 5-100 fold, 5-50 fold, 5-40 fold, 5-30 fold, 5-25 fold, 5-20 fold, 5-15 fold, 5-10 fold, 6-100 fold, 6-50 fold, 6-40 fold, 6-30 fold, 6-25 fold, 6-20 fold, 6-15 fold, 6-10 fold, 8-100 fold, 8-50 fold, 8-40 fold, 8-30 fold, 8-25 fold, 8-20 fold, 8-15 fold, 8-10 fold, 10-100 fold, 10-50 fold, 10-40 fold, 10-30 fold, 10-25 fold, 10-20 fold, 10-15 fold, 20-100 fold, 20-50 fold, 20-fold, 20-30 fold, or 20-25 fold.

The disclosure provides lipid-comprising compounds and compositions that are less susceptible to clearance and thus have a longer half-life in vivo. This is particularly the case where the compositions are intended for repeated including chronic administration, and even more particularly where such repeated administration occurs within days or weeks.

Significantly, these compositions are less susceptible or altogether circumvent the observed phenomenon of accelerated blood clearance (ABC). ABC is a phenomenon in which certain exogenously administered agents are rapidly cleared from the blood upon second and subsequent administrations. This phenomenon has been observed, in part, for a variety of lipid-containing compositions including but not limited to lipidated agents, liposomes or other lipid-based delivery vehicles, and lipid-encapsulated agents. Heretofore, the basis of ABC has been poorly understood and in some cases attributed to a humoral immune response and accordingly strategies for limiting its impact in vivo particularly in a clinical setting have remained elusive.

This disclosure provides compounds and compositions that are less susceptible, if at all susceptible, to ABC. In some important aspects, such compounds and compositions are lipid-comprising compounds or compositions. The lipid-containing compounds or compositions of this disclosure, surprisingly, do not experience ABC upon second and subsequent administration in vivo. This resistance to ABC renders these compounds and compositions particularly suitable for repeated use in vivo, including for repeated use within short periods of time, including days or 1-2 weeks. This enhanced stability and/or half-life is due, in part, to the inability of these compositions to activate B1a and/or B1b cells and/or conventional B cells, pDCs and/or platelets.

This disclosure therefore provides an elucidation of the mechanism underlying accelerated blood clearance (ABC). It has been found, in accordance with this disclosure and the inventions provided herein, that the ABC phenomenon at least as it relates to lipids and lipid nanoparticles is mediated, at least in part an innate immune response involving B1a and/or B1b cells, pDC and/or platelets. B1a cells are normally responsible for secreting natural antibody, in the form of circulating IgM. This IgM is poly-reactive, meaning that it is able to bind to a variety of antigens, albeit with a relatively low affinity for each.

It has been found in accordance with the invention that some lipidated agents or lipid-comprising formulations such as lipid nanoparticles administered in vivo trigger and are subject to ABC. It has now been found in accordance with the invention that upon administration of a first dose of the LNP, one or more cells involved in generating an innate immune response (referred to herein as sensors) bind such agent, are activated, and then initiate a cascade of immune factors (referred to herein as effectors) that promote ABC and toxicity. For instance, B1a and B1b cells may bind to LNP, become activated (alone or in the presence of other sensors such as pDC and/or effectors such as IL6) and secrete natural IgM that binds to the LNP. Pre-existing natural IgM in the subject may also recognize and bind to the LNP, thereby triggering complement fixation. After administration of the first dose, the production of natural IgM begins within 1-2 hours of administration of the LNP. Typically, by about 2-3 weeks the natural IgM is cleared from the system due to the natural half-life of IgM. Natural IgG is produced beginning around 96 hours after administration of the LNP. The agent, when administered in a naïve setting, can exert its biological effects relatively unencumbered by the natural IgM produced post-activation of the B1a cells or B1b cells or natural IgG. The natural IgM and natural IgG are non-specific and thus are distinct from anti-PEG IgM and anti-PEG IgG.

Although Applicant is not bound by mechanism, it is proposed that LNPs trigger ABC and/or toxicity through the following mechanisms. It is believed that when an LNP is administered to a subject the LNP is rapidly transported through the blood to the spleen. The LNPs may encounter immune cells in the blood and/or the spleen. A rapid innate immune response is triggered in response to the presence of the LNP within the blood and/or spleen. Applicant has shown herein that within hours of administration of an LNP several immune sensors have reacted to the presence of the LNP. These sensors include but are not limited to immune cells involved in generating an immune response, such as B cells, pDC, and platelets. The sensors may be present in the spleen, such as in the marginal zone of the spleen and/or in the blood. The LNP may physically interact with one or more sensors, which may interact with other sensors. In such a case the LNP is directly or indirectly interacting with the sensors. The sensors may interact directly with one another in response to recognition of the LNP. For instance, many sensors are located in the spleen and can easily interact with one another. Alternatively, one or more of the sensors may interact with LNP in the blood and become activated. The activated sensor may then interact directly with other sensors or indirectly (e.g., through the stimulation or production of a messenger such as a cytokine e.g., IL6).

In some embodiments the LNP may interact directly with and activate each of the following sensors: pDC, B1a cells, B1b cells, and platelets. These cells may then interact directly or indirectly with one another to initiate the production of effectors which ultimately lead to the ABC and/or toxicity associated with repeated doses of LNP. For instance, Applicant has shown that LNP administration leads to pDC activation, platelet aggregation and activation and B cell activation. In response to LNP platelets also aggregate and are activated and aggregate with B cells. pDC cells are activated. LNP has been found to interact with the surface of platelets and B cells relatively quickly. Blocking the activation of any one or combination of these sensors in response to LNP is useful for dampening the immune response that would ordinarily occur. This dampening of the immune response results in the avoidance of ABC and/or toxicity.

The sensors once activated produce effectors. An effector, as used herein, is an immune molecule produced by an immune cell, such as a B cell. Effectors include but are not limited to immunoglobulin such as natural IgM and natural IgG and cytokines such as IL6. B1a and B1b cells stimulate the production of natural IgMs within 2-6 hours following administration of an LNP. Natural IgG can be detected within 96 hours. IL6 levels are increased within several hours. The natural IgM and IgG circulate in the body for several days to several weeks. During this time the circulating effectors can interact with newly administered LNPs, triggering those LNPs for clearance by the body. For instance, an effector may recognize and bind to an LNP. The Fc region of the effector may be recognized by and trigger uptake of the decorated LNP by macrophage. The macrophage are then transported to the spleen. The production of effectors by immune sensors is a transient response that correlates with the timing observed for ABC.

If the administered dose is the second or subsequent administered dose, and if such second or subsequent dose is administered before the previously induced natural IgM and/or IgG is cleared from the system (e.g., before the 2-3 window time period), then such second or subsequent dose is targeted by the circulating natural IgM and/or natural IgG or Fc which trigger alternative complement pathway activation and is itself rapidly cleared. When LNP are administered after the effectors have cleared from the body or are reduced in number, ABC is not observed.

Thus, it is useful according to aspects of the invention to inhibit the interaction between LNP and one or more sensors, to inhibit the activation of one or more sensors by LNP (direct or indirect), to inhibit the production of one or more effectors, and/or to inhibit the activity of one or more effectors. In some embodiments the LNP is designed to limit or block interaction of the LNP with a sensor. For instance, the LNP may have an altered PC and/or PEG to prevent interactions with sensors. Alternatively, or additionally, an agent that inhibits immune responses induced by LNPs may be used to achieve any one or more of these effects.

It has also been determined that conventional B cells are also implicated in ABC. Specifically, upon first administration of an agent, conventional B cells, referred to herein as CD19(+), bind to and react against the agent. Unlike B1a and Bb cells though, conventional B cells are able to mount first an IgM response (beginning around 96 hours after administration of the LNPs) followed by an IgG response (beginning around 14 days after administration of the LNPs) concomitant with a memory response. Thus conventional B cells react against the administered agent and contribute to IgM (and eventually IgG) that mediates ABC. The IgM and IgG are typically anti-PEG IgM and anti-PEG IgG.

It is contemplated that in some instances, the majority of the ABC response is mediated through B1a cells and B1a-mediated immune responses. It is further contemplated that in some instances, the ABC response is mediated by both IgM and IgG, with both conventional B cells and B1a cells mediating such effects. In yet still other instances, the ABC response is mediated by natural IgM molecules, some of which are capable of binding to natural IgM, which may be produced by activated B1a cells. The natural IgMs may bind to one or more components of the LNPs, e.g., binding to a phospholipid component of the LNPs (such as binding to the PC moiety of the phospholipid) and/or binding to a PEG-lipid component of the LNPs (such as binding to PEG-DMG, in particular, binding to the PEG moiety of PEG-DMG). Since B1a expresses CD36, to which phosphatidylcholine is a ligand, it is contemplated that the CD36 receptor may mediate the activation of B1a cells and thus production of natural IgM. In yet still other instances, the ABC response is mediated primarily by conventional B cells.

It has been found in accordance with the invention that the ABC phenomenon can be reduced or abrogated, at least in part, through the use of compounds and compositions (such as agents, delivery vehicles, and formulations) that do not activate B1a cells. Compounds and compositions that do not activate B1a cells may be referred to herein as B1a inert compounds and compositions. It has been further found in accordance with the invention that the ABC phenomenon can be reduced or abrogated, at least in part, through the use of compounds and compositions that do not activate conventional B cells. Compounds and compositions that do not activate conventional B cells may in some embodiments be referred to herein as CD19-inert compounds and compositions. Thus, in some embodiments provided herein, the compounds and compositions do not activate B1a cells and they do not activate conventional B cells. Compounds and compositions that do not activate B1a cells and conventional B cells may in some embodiments be referred to herein as B1a/CD19-inert compounds and compositions.

These underlying mechanisms were not heretofore understood, and the role of B1a and B1b cells and their interplay with conventional B cells in this phenomenon was also not appreciated.

Accordingly, this disclosure provides compounds and compositions that do not promote ABC. These may be further characterized as not capable of activating B1a and/or Bib cells, platelets and/or pDC, and optionally conventional B cells also. These compounds (e.g., agents, including biologically active agents such as prophylactic agents, therapeutic agents and diagnostic agents, delivery vehicles, including liposomes, lipid nanoparticles, and other lipid-based encapsulating structures, etc.) and compositions (e.g., formulations, etc.) are particularly desirable for applications requiring repeated administration, and in particular repeated administrations that occur within with short periods of time (e.g., within 1-2 weeks). This is the case, for example, if the agent is a nucleic acid based therapeutic that is provided to a subject at regular, closely-spaced intervals. The findings provided herein may be applied to these and other agents that are similarly administered and/or that are subject to ABC.

Of particular interest are lipid-comprising compounds, lipid-comprising particles, and lipid-comprising compositions as these are known to be susceptible to ABC. Such lipid-comprising compounds particles, and compositions have been used extensively as biologically active agents or as delivery vehicles for such agents. Thus, the ability to improve their efficacy of such agents, whether by reducing the effect of ABC on the agent itself or on its delivery vehicle, is beneficial for a wide variety of active agents.

Also provided herein are compositions that do not stimulate or boost an acute phase response (ARP) associated with repeat dose administration of one or more biologically active agents.

The composition, in some instances, may not bind to IgM, including but not limited to natural IgM.

The composition, in some instances, may not bind to an acute phase protein such as but not limited to C-reactive protein.

The composition, in some instances, may not trigger a CD5(+) mediated immune response. As used herein, a CD5(+) mediated immune response is an immune response that is mediated by B1a and/or B1b cells. Such a response may include an ABC response, an acute phase response, induction of natural IgM and/or IgG, and the like.

The composition, in some instances, may not trigger a CD19(+) mediated immune response. As used herein, a CD19(+) mediated immune response is an immune response that is mediated by conventional CD19(+), CD5(−) B cells. Such a response may include induction of IgM, induction of IgG, induction of memory B cells, an ABC response, an anti-drug antibody (ADA) response including an anti-protein response where the protein may be encapsulated within an LNP, and the like.

B1a cells area subset of B cells involved in innate immunity. These cells are the source of circulating IgM, referred to as natural antibody or natural serum antibody. Natural IgM antibodies are characterized as having weak affinity for a number of antigens, and therefore they are referred to as “poly-specific” or “poly-reactive”, indicating their ability to bind to more than one antigen. B1a cells are not able to produce IgG. Additionally, they do not develop into memory cells and thus do not contribute to an adaptive immune response. However, they are able to secrete IgM upon activation. The secreted IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In humans, B1a cells are CD19(+), CD20(+), CD27(+), CD43(+), CD70(−) and CD5(+). In mice, B1a cells are CD19(+), CD5(+), and CD45 B cell isoform B220(+). It is the expression of CD5 which typically distinguishes B1a cells from other convention B cells. B1a cells may express high levels of CD5, and on this basis may be distinguished from other B-1 cells such as B-1b cells which express low or undetectable levels of CD5. CD5 is a pan-T cell surface glycoprotein. B1a cells also express CD36, also known as fatty acid translocase. CD36 is a member of the class B scavenger receptor family. CD36 can bind many ligands, including oxidized low density lipoproteins, native lipoproteins, oxidized phospholipids, and long-chain fatty acids.

B1b cells are another subset of B cells involved in innate immunity. These cells are another source of circulating natural IgM. Several antigens, including PS, are capable of inducing T cell independent immunity through B1b activation. CD27 is typically upregulated on B1b cells in response to antigen activation. Similar to B1a cells, the Bb cells are typically located in specific body locations such as the spleen and peritoneal cavity and are in very low abundance in the blood. The B1b secreted natural IgM is typically cleared within about 2-3 weeks, at which point the immune system is rendered relatively naïve to the previously administered antigen. If the same antigen is presented after this time period (e.g., at about 3 weeks after the initial exposure), the antigen is not rapidly cleared. However, significantly, if the antigen is presented within that time period (e.g., within 2 weeks, including within 1 week, or within days), then the antigen is rapidly cleared. This delay between consecutive doses has rendered certain lipid-containing therapeutic or diagnostic agents unsuitable for use.

In some embodiments it is desirable to block B1a and/or B1b cell activation. One strategy for blocking B1a and/or B1b cell activation involves determining which components of a lipid nanoparticle promote B cell activation and neutralizing those components. It has been discovered herein that at least PEG and phosphatidylcholine (PC) contribute to B1a and B1b cell interaction with other cells and/or activation. PEG may play a role in promoting aggregation between B1 cells and platelets, which may lead to activation. PC (a helper lipid in LNPs) is also involved in activating the B1 cells, likely through interaction with the CD36 receptor on the B cell surface. Numerous particles have PEG-lipid alternatives, PEG-less, and/or PC replacement lipids (e.g. oleic acid or analogs thereof) have been designed and tested. Applicant has established that replacement of one or more of these components within an LNP that otherwise would promote ABC upon repeat administration, is useful in preventing ABC by reducing the production of natural IgM and/or B cell activation. Thus, the invention encompasses LNPs that have reduced ABC as a result of a design which eliminates the inclusion of B cell triggers.

Another strategy for blocking B1a and/or B1b cell activation involves using an agent that inhibits immune responses induced by LNPs. These types of agents are discussed in more detail below. In some embodiments these agents block the interaction between B1a/B1b cells and the LNP or platelets or pDC. For instance, the agent may be an antibody or other binding agent that physically blocks the interaction. An example of this is an antibody that binds to CD36 or CD6. The agent may also be a compound that prevents or disables the B1a/B1b cell from signaling once activated or prior to activation. For instance, it is possible to block one or more components in the B1a/B1b signaling cascade the results from B cell interaction with LNP or other immune cells. In other embodiments the agent may act one or more effectors produced by the B1a/B1b cells following activation. These effectors include for instance, natural IgM and cytokines.

It has been demonstrated according to aspects of the invention that when activation of pDC cells is blocked, B cell activation in response to LNP is decreased. Thus, in order to avoid ABC and/or toxicity, it may be desirable to prevent pDC activation. Similar to the strategies discussed above, pDC cell activation may be blocked by agents that interfere with the interaction between pDC and LNP and/or B cells/platelets. Alternatively, agents that act on the pDC to block its ability to get activated or on its effectors can be used together with the LNP to avoid ABC.

Platelets may also play an important role in ABC and toxicity. Very quickly after a first dose of LNP is administered to a subject platelets associate with the LNP, aggregate and are activated. In some embodiments it is desirable to block platelet aggregation and/or activation. One strategy for blocking platelet aggregation and/or activation involves determining which components of a lipid nanoparticle promote platelet aggregation and/or activation and neutralizing those components. It has been discovered herein that at least PEG contribute to platelet aggregation, activation and/or interaction with other cells. Numerous particles have PEG-lipid alternatives and PEG-less have been designed and tested. Applicant has established that replacement of one or more of these components within an LNP that otherwise would promote ABC upon repeat administration, is useful in preventing ABC by reducing the production of natural IgM and/or platelet aggregation. Thus, the invention encompasses LNPs that have reduced ABC as a result of a design which eliminates the inclusion of platelet triggers. Alternatively agents that act on the platelets to block its activity once it is activated or on its effectors can be used together with the LNP to avoid ABC.

(i) Measuring ABC Activity and Related Activities Various compounds and compositions provided herein, including LNPs, do not promote ABC activity upon administration in vivo. These LNPs may be characterized and/or identified through any of a number of assays, such as but not limited to those described below, as well as any of the assays disclosed in the Examples section, include the methods subsection of the Examples.

In some embodiments the methods involve administering an LNP without producing an immune response that promotes ABC. An immune response that promotes ABC involves activation of one or more sensors, such as B1 cells, pDC, or platelets, and one or more effectors, such as natural IgM, natural IgG or cytokines such as IL6. Thus administration of an LNP without producing an immune response that promotes ABC, at a minimum involves administration of an LNP without significant activation of one or more sensors and significant production of one or more effectors. Significant used in this context refers to an amount that would lead to the physiological consequence of accelerated blood clearance of all or part of a second dose with respect to the level of blood clearance expected for a second dose of an ABC triggering LNP. For instance, the immune response should be dampened such that the ABC observed after the second dose is lower than would have been expected for an ABC triggering LNP.

(ii) B1a or B1b Activation Assay

Certain compositions provided in this disclosure do not activate B cells, such as B1a or B1b cells (CD19+ CD5+) and/or conventional B cells (CD19+ CD5−). Activation of B1a cells, B1b cells, or conventional B cells may be determined in a number of ways, some of which are provided below. B cell population may be provided as fractionated B cell populations or unfractionated populations of splenocytes or peripheral blood mononuclear cells (PBMC). If the latter, the cell population may be incubated with the LNP of choice for a period of time, and then harvested for further analysis. Alternatively, the supernatant may be harvested and analyzed.

(iii) Upregulation of Activation Marker Cell Surface Expression

Activation of B1a cells, B1b cells, or conventional B cells may be demonstrated as increased expression of B cell activation markers including late activation markers such as CD86. In an exemplary non-limiting assay, unfractionated B cells are provided as a splenocyte population or as a PBMC population, incubated with an LNP of choice for a particular period of time, and then stained for a standard B cell marker such as CD19 and for an activation marker such as CD86, and analyzed using for example flow cytometry. A suitable negative control involves incubating the same population with medium, and then performing the same staining and visualization steps. An increase in CD86 expression in the test population compared to the negative control indicates B cell activation.

(iv) Pro-Inflammatory Cytokine Release

B cell activation may also be assessed by cytokine release assay. For example, activation may be assessed through the production and/or secretion of cytokines such as IL-6 and/or TNF-alpha upon exposure with LNPs of interest.

Such assays may be performed using routine cytokine secretion assays well known in the art. An increase in cytokine secretion is indicative of B cell activation.

(v) LNP Binding/Association to and/or Uptake by B Cells

LNP association or binding to B cells may also be used to assess an LNP of interest and to further characterize such LNP. Association/binding and/or uptake/internalization may be assessed using a detectably labeled, such as fluorescently labeled, LNP and tracking the location of such LNP in or on B cells following various periods of incubation.

The invention further contemplates that the compositions provided herein may be capable of evading recognition or detection and optionally binding by downstream mediators of ABC such as circulating IgM and/or acute phase response mediators such as acute phase proteins (e.g., C-reactive protein (CRP).

(vi) Methods of Use for Reducing ABC

Also provided herein are methods for delivering LNPs, which may encapsulate an agent such as a therapeutic agent, to a subject without promoting ABC.

In some embodiments, the method comprises administering any of the LNPs described herein, which do not promote ABC, for example, do not induce production of natural IgM binding to the LNPs, do not activate B1a and/or B1b cells. As used herein, an LNP that "does not promote ABC" refers to an LNP that induces no immune responses that would lead to substantial ABC or a substantially low level of immune responses that is not sufficient to lead to substantial ABC. An LNP that does not induce the production of natural IgMs binding to the LNP refers to LNPs that induce either no natural IgM binding to the LNPs or a substantially low level of the natural IgM molecules, which is insufficient to lead to substantial ABC. An LNP that does not activate B1a and/or B1b cells refer to LNPs that induce no response of B1a and/or B1b cells to produce natural IgM binding to the LNPs or a substantially low level of B1a and/or B1b responses, which is insufficient to lead to substantial ABC.

In some embodiments the terms do not activate and do not induce production are a relative reduction to a reference value or condition. In some embodiments the reference value or condition is the amount of activation or induction of production of a molecule such as IgM by a standard LNP such as an MC3 LNP. In some embodiments the relative reduction is a reduction of at least 30%, for example at least 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100%. In other embodiments the terms do not activate cells such as B cells and do not induce production of a protein such as IgM may refer to an undetectable amount of the active cells or the specific protein.

(vii) Platelet Effects and Toxicity

The invention is further premised in part on the elucidation of the mechanism underlying dose-limiting toxicity associated with LNP administration. Such toxicity may involve coagulopathy, disseminated intravascular coagulation (DIC, also referred to as consumptive coagulopathy), whether acute or chronic, and/or vascular thrombosis. In some instances, the dose-limiting toxicity associated with LNPs is acute phase response (APR) or complement activation-related psudoallergy (CARPA).

As used herein, coagulopathy refers to increased coagulation (blood clotting) in vivo. The findings reported in this disclosure are consistent with such increased coagulation and significantly provide insight on the underlying mechanism. Coagulation is a process that involves a number of different factors and cell types, and heretofore the relationship between and interaction of LNPs and platelets has not been understood in this regard. This disclosure provides evidence of such interaction and also provides compounds and compositions that are modified to have reduced platelet effect, including reduced platelet association, reduced platelet aggregation, and/or reduced platelet aggregation. The ability to modulate, including preferably down-modulate, such platelet effects can reduce the incidence and/or severity of coagulopathy post-LNP administration. This in turn will reduce toxicity relating to such LNP, thereby allowing higher doses of LNPs and importantly their cargo to be administered to patients in need thereof.

CARPA is a class of acute immune toxicity manifested in hypersensitivity reactions (HSRs), which may be triggered by nanomedicines and biologicals. Unlike allergic reactions, CARPA typically does not involve IgE but arises as a consequence of activation of the complement system, which is part of the innate immune system that enhances the body's abilities to clear pathogens. One or more of the following pathways, the classical complement pathway (CP), the alternative pathway (AP), and the lectin pathway (LP), may be involved in CARPA. Szebeni, Molecular Immunology, 61:163-173 (2014).

The classical pathway is triggered by activation of the C1-complex, which contains. C1q, C1r, C1s, or C1qr2s2. Activation of the C1-complex occurs when C1q binds to IgM or IgG complexed with antigens, or when C1 q binds directly to the surface of the pathogen. Such binding leads to conformational changes in the C1 q molecule, which leads to the activation of C1r, which in turn, cleave C1s. The C1r2s2 component now splits C4 and then C2, producing C4a, C4b, C2a, and C2b. C4b and C2b bind to form the classical pathway C3-convertase (C4b2b complex), which promotes cleavage of C3 into C3a and C3b. C3b then binds the C3 convertase to from the C5 convertase (C4b2b3b complex). The alternative pathway is continuously activated as a result of spontaneous C3 hydrolysis. Factor P (properdin) is a positive regulator of the alternative pathway. Oligomerization of properdin stabilizes the C3 convertase, which can then cleave much more C3. The C3 molecules can bind to surfaces and recruit more B, D, and P activity, leading to amplification of the complement activation.

Acute phase response (APR) is a complex systemic innate immune response for preventing infection and clearing potential pathogens. Numerous proteins are involved in APR and C-reactive protein is a well-characterized one.

It has been found, in accordance with the invention, that certain LNP are able to associate physically with platelets almost immediately after administration in vivo, while other LNP do not associate with platelets at all or only at background levels. Significantly, those LNPs that associate with platelets also apparently stabilize the platelet aggregates that are formed thereafter. Physical contact of the platelets with certain LNPs correlates with the ability of such platelets to remain aggregated or to form aggregates continuously for an extended period of time after administration. Such aggregates comprise activated platelets and also innate immune cells such as macrophages and B cells.

23. Methods of Use

The polynucleotides, pharmaceutical compositions and formulations described herein are used in the preparation, manufacture and therapeutic use of to treat and/or prevent diseases, disorders or conditions related to chikungunya virus (CHIKV) infection. In some embodiments, the polynucleotides, compositions and formulations of the present disclosure are used to treat and/or prevent infectious disease such as chikungunya fever.

In some embodiments, the polynucleotides, pharmaceutical compositions and formulations of the invention (e.g., at least one mRNA encoding anti-CHIKV antibody polypeptide, such as mRNAs expressing the heavy and light chains of anti-CHIKV antibody) are used in methods for reducing the levels of virus in a subject in need thereof, e.g., a subject infected with chikungunya virus. In some embodiments, administration of a polynucleotide, pharmaceutical composition, or formulation described herein, to a subject reduces the viral load of CHIKV in the subject, e.g., reduces the viral load of CHIKV in the tissues and/or blood of a subject. In some embodiments, administration of a polynucleotide, pharmaceutical composition, or formulation described herein, to a subject reduces the amount of virus in the subject by at least 10%, e.g., by 10%, 15%, 20%, 30%, 40%, 45%, 50%, 55%, 60%, 65%, 70%, 75%, 80%, 85%, 90%, 95%, or 100%. In some embodiments, administration of a polynucleotide, pharmaceutical composition, or formulation described herein, to a subject reduces the amount of virus in a particular tissue of the subject by at least 10%, e.g., by 10%, 15%, 20%, 30%, 40%, 45%, 50%, 55%, 60%, 65%, 70%, 75%, 80%, 85%, 90%, 95%, or 100%. In some embodiments, administration of a polynucleotide, pharmaceutical composition, or formulation described herein, to a subject reduces viremia in a subject, e.g., by reducing the amount of virus in the blood of a subject by at least 10%, e.g., by 10%, 15%, 20%, 30%, 40%, 45%, 50%, 55%, 60%, 65%, 70%, 75%, 80%, 85%, 90%, 95%, or 100%.

One aspect of the invention provides a method of neutralizing CHIKV infection in a subject comprising the administration of a polynucleotide, pharmaceutical composition, or formulation described herein to a subject (e.g., at least one mRNA encoding anti-CHIKV antibody polypeptide, such as mRNAs expressing the heavy and light chains of anti-CHIKV antibody). In some embodiments, administration of a polynucleotide, pharmaceutical composition, or formulation described herein to a subject causes the expression of at least one anti-CHIKV antibody polynucleotide in the subject, wherein the at least one anti-CHIKV antibody polynucleotide binds specifically to CHIKV and neutralizes CHIKV in the subject, thereby preventing or reducing the levels of further virus infection. In some embodiments, mRNAs encoding the heavy and light chains of anti-CHIKV antibody are administered to a subject infected with CHIKV, so that the heavy and light chains are expressed in the subject and associate to form anti-CHIKV antibody that neutralizes CHIKV in the subject. The anti-CHIKV antibody polypeptides described herein can neutralize CHIKV by several potential mechanisms, including, by way of example of example only, interfering with virion binding to receptors, blocking uptake of virions into cells, preventing uncoating of virus genomes in endosomes, or causing aggregation of virus particles. In some embodiments, administration of a polynucleotide, pharmaceutical composition, or formulation described herein neutralizes at least 10% of the CHIKV virions in a subject infected with CHIKV, e.g., neutralizes 10%, 15%, 20%, 30%, 40%, 45%, 50%, 55%, 60%, 65%, 70%, 75%, 80%, 85%, 90%, 95%, or 100% of the CHIKV virions in a subject.

One aspect of the invention provides a method of alleviating the symptoms of CHIKV infection in a subject that is known to be infected with CHIKV, or suspected of being infected with CHIKV, comprising the administration of a polynucleotide, composition or formulation described herein to a subject (e.g., at least one mRNA encoding anti-CHIKV antibody polypeptide, such as mRNAs expressing the heavy and light chains of anti-CHIKV antibody). Chikungunya fever is an acute febrile illness that is caused by chikungunya virus infection. Chikungunya fever symptoms develop abruptly with high fever that can last for several days, and severe and often debilitating polyarthralgias. Arthritis with joint swelling can also occur. In some cases, individuals infected with CHIKV can develop a maculopapular rash, and/or non-specific symptoms, such as headache, fatigue, nausea, vomiting, conjunctivitis, and myalgias. In some embodiments, administration of a polynucleotide, pharmaceutical composition, or formulation described herein to a subject with chikungunya fever reduces the severity of at least one symptom of the disease in the subject, e.g., reduces the severity fever and/or polyarthralgia in a subject. In some embodiments, administration of a polynucleotide, pharmaceutical composition, or formulation described herein to a subject with chikungunya fever reduces the duration of at least one symptom of the disease in the subject, e.g., reduces the duration of fever, polyarthralgia, and/or arthritis in a subject. In some embodiments, administration of a polynucleotide, pharmaceutical composition, or formulation described herein to a subject with chikungunya fever reduces the duration of at least one symptom of the disease in the subject, e.g., reduces the duration of fever, polyarthralgia, and/or arthritis in a subject. In some embodiments, administration of a polynucleotide, pharmaceutical composition, or formulation described herein to a subject with chikungunya fever reduces the duration of at least one symptom of the disease in the subject by 1 day, 2 days, 3 days, 4 days, 5 days, 6 days, 7 days, 8 days, 9 days, 10 days, 11 days, 12 days, 13 days, 14 days, 15 days, 20 days, 25 days, or 30 or more days. In some embodiments, administration of a polynucleotide, pharmaceutical composition, or formulation described herein to a subject with chikungunya fever reduces the duration of at least one symptom of the disease in the subject by at least 6 hours, at least 12 hours, at least 24 hours, at least 36 hours, at least 48 hours, at least 72 hours, at least 96 hours, at least 168 hours, at least 336 hours, or at least 720 hours or more.

One aspect of the invention provides a method of protecting a human subject from chikungunya virus infection after the subject has been exposed to chikungunya virus. In some embodiments, the administration of the polynucleotide, pharmaceutical composition or formulation of the invention protects the human subject from chikungunya virus for at least 24 hours, 48 hours, 72 hours, 96 hours, 168 hours, 336 hours, or 720 hours or more. In some embodiments, the administration of a single dose of a polynucleotide, pharmaceutical composition or formulation described herein protects the human subject from chikungunya virus for at least 24 hours, 48 hours, 72 hours, 96 hours, 168 hours, 336 hours, or 720 hours or more.

One aspect of the invention provides a method of protecting a human subject from the onset of chikungunya fever after the subject has been exposed to chikungunya virus. In some embodiments, the administration of the polynucleotide, pharmaceutical composition or formulation of the invention protects the human subject from the onset of chikungunya fever for at least 24 hours, 48 hours, 72 hours, 96 hours, 168 hours, 336 hours, or 720 hours or more. In some embodiments, the administration of a single dose of a polynucleotide, pharmaceutical composition or formulation described herein protects the human subject from the onset of chikungunya fever for at least 24 hours, 48 hours, 72 hours, 96 hours, 168 hours, 336 hours, or 720 hours or more.

One aspect of the invention provides a method of systematically producing an anti-chikungunya virus antibody (anti-CHIKV antibody) in a human subject at a level of at least 5 μg/ml, 10 μg/ml, 15 μg/ml, 20 μg/ml, 25 μg/ml, or 30 μg/ml for at least 24 hours, 48 hours, 72 hours, 96 hours, 168 hours, 336 hours, 720 hours or more after a single dose administration of a polynucleotide, pharmaceutical composition or formulation described herein.

In some embodiments, the administration of the polynucleotide, pharmaceutical composition or formulation of the invention results in expression of an anti-CHIKV antibody, or functional portion thereof, in cells of the subject. For example, in some embodiments, the polynucleotides of the present invention are used in methods of administering a composition or formulation comprising an mRNA encoding at least one anti-CHIKV antibody polypeptide to a subject, wherein the method results expression of at least one anti-CHIKV antibody polypeptide in at least some cells of a subject.

In some embodiments, the administration of the polynucleotide, pharmaceutical composition or formulation of the invention results in expression of an anti-CHIKV antibody, or functional portion thereof, in at least some of the cells of a subject that persists for a period of time sufficient to allow some neutralization of CHIKV to occur, e.g., neutralization of 10%, 15%, 20%, 25%, 30%, 35%, 40%, 45%, 50%, 55%, 60%, 65%, 70%, 75%, 80%, 85%, 90%, 95%, or 100% of CHIKV in the cells.

In some embodiments, the method or use comprises administering at least one polynucleotide, e.g., mRNA, comprising a nucleotide sequence having sequence similarity to a polynucleotide selected from SEQ ID NO:2 and SEQ ID NO:4, or at least one polynucleotide selected from SEQ ID NO:5 and SEQ ID NO:6, wherein the polynucleotide encodes an anti-CHIKV antibody polypeptide. In some embodiments, the method of use comprises administering two polynucleotides, e.g., mRNAs, wherein the two polynucleotides have nucleotide sequences having sequence similarity to SEQ ID NOs: 2 and 4, respectively, or the two polynucleotides are SEQ ID NOs: 5 and 6.

Other aspects of the present disclosure relate to transplantation of cells containing polynucleotides to a mammalian subject. Administration of cells to mammalian subjects is known to those of ordinary skill in the art, and includes, but is not limited to, local implantation (e.g., topical or subcutaneous administration), organ delivery or systemic injection (e.g., intravenous injection or inhalation), and the formulation of cells in pharmaceutically acceptable carriers.

In some embodiments, the polynucleotides (e.g., mRNA), pharmaceutical compositions and formulations used in the methods of the invention comprise a uracil-modified sequence encoding an anti-CHIKV antibody polypeptide disclosed herein and a miRNA binding site disclosed herein, e.g., a miRNA binding site that binds to miR-142 and/or a miRNA binding site that binds to miR-126. In some embodiments, the uracil-modified sequence encoding an anti-CHIKV antibody polypeptide comprises at least one chemically modified nucleobase, e.g., N1 methylpseudouracil or 5-methoxyuracil. In some embodiments, at least 95% of a type of nucleobase (e.g., uracil) in a uracil-modified sequence encoding an anti-CHIKV antibody polypeptide of the invention are modified nucleobases. In some embodiments, at least 95% of uracil in a uracil-modified sequence encoding an anti-CHIKV antibody polypeptide is 1-N-methylpseudouridine or 5-methoxyuridine. In some embodiments, the polynucleotide (e.g., a RNA, e.g., a mRNA) disclosed herein is formulated with a delivery agent comprising, e.g., a compound having the Formula (I), e.g., any of Compounds 1-232, e.g., Compound II; a compound having the Formula (III), (IV), (V), or (VI), e.g., any of Compounds 233-342, e.g., Compound VI; or a compound having the Formula (VIII), e.g., any of Compounds 419-428, e.g., Compound I, or any combination thereof. In some embodiments, the delivery agent comprises Compound II, DSPC, Cholesterol, and Compound I or PEG-DMG, e.g., with a mole ratio of about 47.5:10.5:39.0:3.0 or about 50:10:38.5:1.5 or about 50:10:38:2. In some embodiments, the delivery agent comprises Compound VI, DSPC, Cholesterol, and Compound I or PEG-DMG, e.g., with a mole ratio in the range of about 30 to about 60 mol % Compound II or VI (or related suitable amino lipid) (e.g., 30-40, 40-45, 45-50, 50-55 or 55-60 mol % Compound II or VI (or related suitable amino lipid)), about 5 to about 20 mol % phospholipid (or related suitable phospholipid or "helper lipid") (e.g., 5-10, 10-15, or 15-20 mol % phospholipid (or related suitable phospholipid or "helper lipid")), about 20 to about 50 mol % cholesterol (or related sterol or "non-cationic" lipid) (e.g., about 20-30, 30-35, 35-40, 40-45, or 45-50 mol % cholesterol (or related sterol or "non-cationic" lipid)) and about 0.05 to about 10 mol % PEG lipid (or other suitable PEG lipid) (e.g., 0.05-1, 1-2, 2-3, 3-4, 4-5, 5-7, or 7-10 mol % PEG lipid (or other suitable PEG lipid)). An exemplary delivery agent can comprise mole ratios of, for example, 47.5:10.5:39.0:3.0 or 50:10:38.5:1.5. In certain instances, an exemplary delivery agent can comprise mole ratios of, for example, 47.5:10.5:39.0:3; 47.5:10:39.5:3; 47.5:11:39.5:2; 47.5:10.5:39.5:2.5; 47.5:11:39:2.5; 48.5:10:38.5:3; 48.5:10.5:39:2; 48.5:10.5:38.5:2.5; 48.5:10.5:39.5:1.5; 48.5:10.5:38.0:3; 47:10.5:39.5:3; 47:10:40.5:2.5; 47:11:40:2; 47:10.5:39.5:3; 48:10.5:38.5:3; 48:10:39.5:2.5; 48:11:39:2; or 48:10.5:38.5:3. In some embodiments, the delivery agent comprises Compound II or VI, DSPC, Cholesterol, and Compound I or PEG-DMG, e.g., with a mole ratio of about 47.5:10.5:39.0:3.0. In some embodiments, the delivery agent comprises Compound II or VI, DSPC, Cholesterol, and Compound I or PEG-DMG, e.g., with a mole ratio of about 47.5:10.5:39.0:3.0 or about 50:10:38.5:1.5. In some embodiments, the delivery agent comprises Compound II, DSPC, Cholesterol, and Compound I with a mole ratio of about 50:10:38:2. In some embodiments, the delivery agent comprises Compound II, DSPC, Cholesterol, and Compound I or PEG-DMG, e.g., with a mole ratio in the range of about 30 to about 60 mol % Compound II (or related suitable amino lipid) (e.g., 30-40, 40-45, 45-50, 50-55 or 55-60 mol % Compound II (or related suitable amino lipid)), about 5 to about 20 mol % phospholipid (or related suitable phospholipid or "helper lipid") (e.g., 5-10, 10-15, or 15-20 mol % phospholipid (or related suitable phospholipid or "helper lipid")), about 20 to about 50 mol % cholesterol (or related sterol or "non-cationic" lipid) (e.g., about 20-30, 30-35, 35-40, 40-45, or 45-50 mol % cholesterol (or related sterol or "non-cationic" lipid)) and about 0.05 to about 10 mol % PEG lipid (or other suitable PEG lipid) (e.g., 0.05-1, 1-2, 2-3, 3-4, 4-5, 5-7, or 7-10 mol % PEG lipid (or other suitable PEG lipid)).

The skilled artisan will appreciate that the therapeutic effectiveness of a drug or a treatment of the instant invention can be characterized or determined by measuring the level of expression of an encoded protein (e.g., antibody polypeptide) in a sample or in samples taken from a subject (e.g., from a preclinical test subject (rodent, primate, etc.) or from a clinical subject (human). Likewise, the therapeutic effectiveness of a drug or a treatment of the instant invention can be characterized or determined by measuring the level of activity of an encoded protein (e.g., antibody polypeptide) in a sample or in samples taken from a subject (e.g., from a preclinical test subject (rodent, primate, etc.) or from a clinical subject (human). Furthermore, the therapeutic effectiveness of a drug or a treatment of the instant invention can be characterized or determined by measuring the level of virus in sample(s) taken from a subject. Levels of protein and/or virus can be determined post-administration with a single dose of an mRNA therapeutic of the invention or can be determined and/or monitored at several time points following administration with a single dose or can be determined and/or monitored throughout a course of treatment, e.g., a multi-dose treatment.

The polynucleotides, pharmaceutical compositions, and formulations described herein may be administered by any route which results in a therapeutically effective outcome. These include, but are not limited, to intradermal, intramuscular, and/or subcutaneous administration. The present disclosure provides methods comprising administering RNA treatments to a subject in need thereof. The exact amount required will vary from subject to subject, depending on the species, age, and general condition of the subject, the severity of the disease, the particular composition, its mode of administration, its mode of activity, and the like. mRNA compositions are typically formulated in dosage unit form for ease of administration and uniformity of dosage. It will be understood, however, that the total daily usage of mRNA compositions may be decided by the attending physician within the scope of sound medical judgment. The specific therapeutically effective, prophylactically effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

In some embodiments, mRNA compositions may be administered at dosage levels sufficient to deliver 0.0001 mg/kg to 100 mg/kg, 0.001 mg/kg to 0.05 mg/kg, 0.005 mg/kg to 0.05 mg/kg, 0.001 mg/kg to 0.005 mg/kg, 0.05 mg/kg to 0.5 mg/kg, 0.01 mg/kg to 50 mg/kg, 0.1 mg/kg to 40 mg/kg, 0.5 mg/kg to 30 mg/kg, 0.01 mg/kg to 10 mg/kg, 0.1 mg/kg to 10 mg/kg, or 1 mg/kg to 25 mg/kg, of subject body weight per day, one or more times a day, per week, per month, etc. to obtain the desired therapeutic, diagnostic, prophylactic, or imaging effect (see e.g., the range of unit doses described in International Publication No WO2013078199, herein incorporated by reference in its entirety). The desired dosage may be delivered three times a day, two times a day, once a day, every other day, every third day, every week, every two weeks, every three weeks, every four weeks, every 2 months, every three months, every 6 months, etc. In certain embodiments, the desired dosage may be delivered using multiple administrations (e.g., two, three, four, five, six, seven, eight, nine, ten, eleven, twelve, thirteen, fourteen, or more administrations). When multiple administrations are employed, split dosing regimens such as those described herein may be used. In exemplary embodiments, mRNA compositions may be administered at dosage levels sufficient to deliver 0.0005 mg/kg to 0.01 mg/kg, e.g., about 0.0005 mg/kg to about 0.0075 mg/kg, e.g., about 0.0005 mg/kg, about 0.001 mg/kg, about 0.002 mg/kg, about 0.003 mg/kg, about 0.004 mg/kg or about 0.005 mg/kg.

In some embodiments, mRNA compositions may be administered once or twice (or more) at dosage levels sufficient to deliver 0.025 mg/kg to 0.250 mg/kg, 0.025 mg/kg to 0.500 mg/kg, 0.025 mg/kg to 0.750 mg/kg, or 0.025 mg/kg to 1.0 mg/kg.

In some embodiments, mRNA compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.0100 mg, 0.025 mg, 0.050 mg, 0.075 mg, 0.100 mg, 0.125 mg, 0.150 mg, 0.175 mg, 0.200 mg, 0.225 mg, 0.250 mg, 0.275 mg, 0.300 mg, 0.325 mg, 0.350 mg, 0.375 mg, 0.400 mg, 0.425 mg, 0.450 mg, 0.475 mg, 0.500 mg, 0.525 mg, 0.550 mg, 0.575 mg, 0.600 mg, 0.625 mg, 0.650 mg, 0.675 mg, 0.700 mg, 0.725 mg, 0.750 mg, 0.775 mg, 0.800 mg, 0.825 mg, 0.850 mg, 0.875 mg, 0.900 mg, 0.925 mg, 0.950 mg, 0.975 mg, or 1.0 mg. Higher and lower dosages and frequency of administration are encompassed by the present disclosure. For example, an RNA treatment composition may be administered three or four times.

In some embodiments, mRNA compositions may be administered twice (e.g., Day 0 and Day 7, Day 0 and Day 14, Day 0 and Day 21, Day 0 and Day 28, Day 0 and Day 60, Day 0 and Day 90, Day 0 and Day 120, Day 0 and Day 150, Day 0 and Day 180, Day 0 and 3 months later, Day 0 and 6 months later, Day 0 and 9 months later, Day 0 and 12 months later, Day 0 and 18 months later, Day 0 and 2 years later, Day 0 and 5 years later, or Day 0 and 10 years later) at a total dose of or at dosage levels sufficient to deliver a total dose of 0.010 mg, 0.025 mg, 0.100 mg or 0.400 mg.

In some embodiments, the RNA for use in a method of treating a subject is administered to the subject in a single dosage of between 10 μg/kg and 400 μg/kg of the nucleic acid treatment in an effective amount to treat the subject. In some embodiments, the RNA for use in a method of treating a subject is administered to the subject in a single dosage of between 10 μg and 400 μg of the nucleic acid treatment in an effective amount to treat the subject.

An RNA pharmaceutical composition described herein can be formulated into a dosage form described herein, such as an intranasal, intratracheal, or injectable (e.g., intravenous, intraocular, intravitreal, intramuscular, intradermal, intracardiac, intraperitoneal, and subcutaneous).

This disclosure is not limited in its application to the details of construction and the arrangement of components set forth in the following description or illustrated in the drawings. The disclosure is capable of other embodiments and of being practiced or of being carried out in various ways. Also, the phraseology and terminology used herein is for the purpose of description and should not be regarded as limiting.

Construct Sequences

| | mRNA Name | ORF Sequence (Amino Acid) | ORF Sequence (Nucleotide) | 5' UTR Sequence | 3' UTR Sequence | Construct Sequence |
|---|---|---|---|---|---|---|
| SEQ ID NO: | | 1 | 2 | 13 | 14 | 5 |
| | ChikV24 heavy chain | METDTLLLWVLLLWVPGSTGQVQLVESGGGVVQPGKSLRLSCAASGFTFRNYGMHWVRQAPGKGLDWVALISYDGTHKYYKDSLKGRFTISRDNFQNTVDLQINSLRPDDTAVYYCAKELATSGVVEPLDSWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVLHEALHSHYTQKSLSLSPGK | AUGGAAACCGACACACUGCUGCUGUGGGUGCUGCUUCUUUGGGUGCCCGGAUCUACAGGACAGGUGCAGCUGGUUGAAUCUGGCGGCGGAGUUGUGCAGCCUGGCAAGUCUCUGAGACUGAGCUGUGCCGCCAGCGGCUUCACCUUCAGAAACUACGGCAUGCACUGGGUCCGACAGGCUCCAGGCAAAGGCCUUGAUUGGGUCGCCCUGAUCAGCUACGACGGCACCCACAAGUACUACAAGGACAGCCUGAAGGGCAGAUUCACCAUCAGCCGGGACAACUUCCAGAACACCGUGGACCUGCAGAUCAACAGCCUGAGGCCUGACGACACCGCCGUGUACUACUGCGCCAAAGAGCUGGCUACAAGCGGCGUGGUGGAACCUCUGGAUUCUUGGGGACAGGGCACCCUGGUCACAGUGUCUAGCGCCUCUACAAAGGGACCCAGCGUGUUCCCUCUGGCUCCUAGCAGCAAGAGCACAAGCGGAGGAACAGCCGCUCUGGGCUGUCUGGUCAAGGACUACUUUCCCGAGCCUGUGACCGUGUCCUGGAAUUCUGGCGCUCUGACAUCCGGCGUGCACACCUUUCCAGCUGUGCUGCAAAGCAGCGGCCUGUACUCUCUGAGCAGCGUCGUGACAGUGCCAAGCAGCUCUCUGGGCACCCAGACCUACAUCUGCAACGUGAACCACAAGCCUAGCAACACCAAGGUGGACAAGAAGGUGGAACCCAAGAGCUGCGACAAGACCCACACCUGUCCACCCUGUCCUGCUCCAGAACUGCUCGGCGGACCUUCCGUGUUCCUGUUUCCUCCAAAGCCUAAGGACACCCUGAUGAUCAGCAGAACACCCGAAGUGACCUGCGUGGUGGUGGACGUGUCUCACGAGGACCCUGAAGUGAAGUUCAAUUGGUACGUGGACGGCGUGGAA | GGGAAAUAAGAGAGAAAAGAAGAGUAAGAAGAAAUAUAAGACCCCGGCGCCGCCACC | UGAUAAUAGGCUGGAGCCUCGGUGGCCUAGCUUCUUGCCCCUUGGGCCUCCCCCCAGCCCCUCCUCCCCUUCCUGCACCCGUACCCCCGUGGUCUUUGAAUAAAGUCUGAGUGGGCGGC | SEQ ID NO: 5 consists from 5' to 3' end: 5' UTR of SEQ ID NO: 13, ORF sequence of SEQ ID NO: 2, and 3' UTR of SEQ ID NO: 14 |

-continued

| | | | | | | |
|---|---|---|---|---|---|---|
| | | | GUGCACAACGCCAA<br>GACCAAGCCUAGAG<br>AGGAACAGUACAAC<br>AGCACCUACAGAGU<br>GGUGUCCGUGCUGA<br>CCGUGCUGCACCAG<br>GAUUGGCUGAACGG<br>CAAAGAGUACAAGU<br>GCAAGGUGUCCAAC<br>AAGGCCCUGCCUGC<br>UCCUAUCGAGAAGA<br>CCAUCAGCAAGGCC<br>AAGGGCCAGCCUAG<br>GGAACCUCAGGUGU<br>ACACACUGCCUCCA<br>AGCAGGGACGAGCU<br>GACCAAGAAUCAGG<br>UGUCCCUGACCUGC<br>CUCGUGAAGGGCUU<br>CUACCCUUCCGAUA<br>UCGCCGUGGAGUGG<br>GAGAGCAACGGCCA<br>GCCUGAGAACAACU<br>ACAAGACCACUCCU<br>CCUGUGCUGGACAG<br>CGACGGCUCAUUCU<br>UCCUGUACAGCAAG<br>CUGACAGUGGACAA<br>GUCCAGGUGGCAGC<br>AGGGCAACGUGUUC<br>AGCUGCAGCGUGCU<br>GCACGAAGCCCUGC<br>ACAGCCACUACACC<br>CAGAAGUCCCUGUC<br>UCUGAGCCCUGGCA<br>AA | | | |

| ChikV24 heavy chain portions | | |
|---|---|---|
| Signal sequence | Amino acids 1-20 of SEQ ID NO: 1 | Nucleotides 1-60 of SEQ ID NO: 2 |
| Variable region (VH) | Amino acids 21-142 of SEQ ID NO: 1 | Nucleotides 61-426 of SEQ ID NO: 2 |
| HCDR1 | Amino acids 46-53 of SEQ ID NO: 1 (underlined) | Nucleotides 136-159 of SEQ ID NO: 2 (underlined) |
| HCDR2 | Amino acids 71-78 of SEQ ID NO: 1 (underlined) | Nucleotides 211-234 of SEQ ID NO: 2 (underlined) |
| HCDR3 | Amino acids 117-131 of SEQ ID NO: 1 (underlined) | Nucleotides 349-393 of SEQ ID NO: 2 (underlined) |
| Constant region | Amino acids 143-472 of SEQ ID NO: 1 | Nucleotides 427-1416 of SEQ ID NO: 2 |

Chemistry: G5 - all uracils (U) in the mRNA are N1-methylpseudouracils

Cap: C1

PolyA tail: 100 nt

| | mRNA Name | ORF Sequence (Amino Acid) | ORF Sequence (Nucleotide) | 5' UTR Sequence | 3' UTR Sequence | Construct Sequence |
|---|---|---|---|---|---|---|
| SEQ ID NO: | | 3 | 4 | 13 | 14 | 6 |
| | ChikV24 light chain | METPAQLLFLLLLWL<br>PDTTGEIVLTQSPGTL<br>SLSPGERATLSCRAS<br>QSLVSSYFGWYQQK<br>RGQSPRLLIYAASTR<br>ATGIPDRFSGSGSGTD<br>FTLTISRLEPEDFAVY<br>YCQQYGNTPFTFGGG<br>TKVEIKRTVAAPSVFI | AUGGAAACACCCGC<br>UCAGCUGCUGUUCC<br>UGCUGCUGCUGUGG<br>CUGCCUGAUACCAC<br>AGGCGAGAUCGUGC<br>UGACACAGAGCCCU<br>GGCACACUGUCACU<br>GUCUCCAGGCGAAA<br>GAGCCACACUGAGC | GGGAAA<br>UAAGAG<br>AGAAAA<br>GAAGAG<br>UAAGAA<br>GAAAUA<br>UAAGAC<br>CCCGGC<br>GCCGCC | UGAUAA<br>UAGGCU<br>GGAGCC<br>UCGGUG<br>GCCUAG<br>CUUCUU<br>GCCCCU<br>UGGGCC<br>UCCCCC | SEQ ID NO: 6 consists from 5' to 3' end: 5' UTR of SEQ ID NO: 13, ORF |

-continued

| | | | | | |
|---|---|---|---|---|---|
| | FPPSDEQLKSGTASV<br>VCLLNNFYPREAKVQ<br>WKVDNALQSGNSQE<br>SVTEQDSKDSTYSLS<br>STLTLSKADYEKHKV<br>YACEVTHQGLSSPVT<br>KSFNRGEC | UGUAGAGCCAGCCA<br>GAGCCUGGUGUCCA<br>GCUACUUCGGCUGG<br>UAUCAGCAGAAGAG<br>AGGCCAGUCUCCUC<br>GGCUGCUGAUCUAC<br>GCCGCUUCUACAAG<br>AGCCACCGGCAUUC<br>CCGAUAGAUUCAGC<br>GGCUCUGGCAGCGG<br>CACCGAUUUCACCC<br>UGACAAUCAGCAGA<br>CUGGAACCCGAGGA<br>CUUCGCCGUGUACU<br>ACUGUCAGCAGUAC<br>GGCAACACACCCUU<br>CACCUUUGGCGGAG<br>GCACCAAGGUGGAA<br>AUCAAGAGAACAGU<br>GGCUGCUCCCAGCG<br>UGUUCAUCUUCCCA<br>CCUUCCGACGAGCA<br>GCUGAAGUCUGGCA<br>CAGCCUCUGUCGUG<br>UGCCUGCUGAACAA<br>CUUCUACCCUCGGG<br>AAGCCAAGGUGCAG<br>UGGAAGGUGGACAA<br>CGCCCUGCAGAGCG<br>GCAACAGCCAAGAG<br>AGCGUGACAGAGCA<br>GGACAGCAAGGACU<br>CCACCUACAGCCUG<br>AGCAGCACACUGAC<br>CCUGAGCAAGGCCG<br>ACUACGAGAAGCAC<br>AAGGUGUACGCCUG<br>CGAAGUGACACACC<br>AGGGCCUGUCUAGC<br>CCUGUGACCAAGAG<br>CUUCAACAGAGGCG<br>AGUGC | ACC | CAGCCC<br>CUCCUC<br>CCCUUC<br>CUGCAC<br>CCGUAC<br>CCCCGU<br>GGUCUU<br>UGAAUA<br>AAGUCU<br>GAGUGG<br>GCGGC | sequence<br>of SEQ ID<br>NO: 4, and<br>3' UTR of<br>SEQ ID<br>NO: 14 |

| ChikV24 light chain portions | | |
|---|---|---|
| Signal sequence | Amino acids 1-20 of SEQ ID NO: 3 | Nucleotides 1-60 of SEQ ID NO: 4 |
| Variable region (VL) | Amino acids 21-128 of SEQ ID NO: 3 | Nucleotides 61-384 of SEQ ID NO: 4 |
| LCDR1 | Amino acids 47-53 of SEQ ID NO: 3 (underlined) | Nucleotides 139-159 of SEQ ID NO: 4 (underlined) |
| LCDR2 | Amino acids 71-73 of SEQ ID NO: 3 (underlined) | Nucleotides 211-219 of SEQ ID NO: 4 (underlined) |
| LCDR3 | Amino acids 110-118 of SEQ ID NO: 3 (underlined) | Nucleotides 328-354 of SEQ ID NO: 4 (underlined) |
| Constant region | Amino acids 129-235 of SEQ ID NO: 3 | Nucleotides 385-705 of SEQ ID NO: 4 |

Chemistry: G5 - all uracils (U) in the mRNA are N1-methylpseudouracils

Cap: C1

PolyA tail: 100 nt

EXAMPLES

Example 1: Chimeric Polynucleotide Synthesis

A. Triphosphate Route

Two regions or parts of a chimeric polynucleotide can be joined or ligated using triphosphate chemistry. According to this method, a first region or part of 100 nucleotides or less can be chemically synthesized with a 5' monophosphate and terminal 3'desOH or blocked OH. If the region is longer than 80 nucleotides, it can be synthesized as two strands for ligation.

If the first region or part is synthesized as a non-positionally modified region or part using in vitro transcription (IVT), conversion the 5'monophosphate with subsequent capping of the 3' terminus can follow. Monophosphate protecting groups can be selected from any of those known in the art.

The second region or part of the chimeric polynucleotide can be synthesized using either chemical synthesis or IVT methods. IVT methods can include an RNA polymerase that can utilize a primer with a modified cap. Alternatively, a cap of up to 80 nucleotides can be chemically synthesized and coupled to the IVT region or part.

It is noted that for ligation methods, ligation with DNA T4 ligase, followed by treatment with DNAse should readily avoid concatenation.

The entire chimeric polynucleotide need not be manufactured with a phosphate-sugar backbone. If one of the regions or parts encodes a polypeptide, then such region or part can comprise a phosphate-sugar backbone.

Ligation can then be performed using any known click chemistry, orthoclick chemistry, solulink, or other bioconjugate chemistries known to those in the art.

B. Synthetic Route

The chimeric polynucleotide can be made using a series of starting segments. Such segments include:

(a) Capped and protected 5' segment comprising a normal 3'OH (SEG. 1)

(b) 5' triphosphate segment which can include the coding region of a polypeptide and comprising a normal 3'OH (SEG. 2)

(c) 5' monophosphate segment for the 3' end of the chimeric polynucleotide (e.g., the tail) comprising cordycepin or no 3'OH (SEG. 3)

After synthesis (chemical or IVT), segment 3 (SEG. 3) can be treated with cordycepin and then with pyrophosphatase to create the 5'monophosphate.

Segment 2 (SEG. 2) can then be ligated to SEG. 3 using RNA ligase. The ligated polynucleotide can then be purified and treated with pyrophosphatase to cleave the diphosphate. The treated SEG. 2-SEG. 3 construct is then purified and SEG. 1 is ligated to the 5' terminus. A further purification step of the chimeric polynucleotide can be performed.

Where the chimeric polynucleotide encodes a polypeptide, the ligated or joined segments can be represented as: 5' UTR (SEG. 1), open reading frame or ORF (SEG. 2) and 3' UTR+PolyA (SEG. 3).

The yields of each step can be as much as 90-95%.

Example 2: PCR for cDNA Production

PCR procedures for the preparation of cDNA can be performed using 2×KAPA HIFI™ HotStart ReadyMix by Kapa Biosystems (Woburn, MA). This system includes 2×KAPA ReadyMix12.5 μl; Forward Primer (10 μM) 0.75 μl; Reverse Primer (10 μM) 0.75 μl; Template cDNA—100 ng; and $dH_2O$ diluted to 25.0 μl. The PCR reaction conditions can be: at 95° C. for 5 min. and 25 cycles of 98° C. for 20 sec, then 58° C. for 15 sec, then 72° C. for 45 sec, then 72° C. for 5 min. then 4° C. to termination.

The reverse primer of the instant invention can incorporate a poly-T120 for a poly-A120 in the mRNA. Other reverse primers with longer or shorter poly(T) tracts can be used to adjust the length of the poly(A) tail in the polynucleotide mRNA.

The reaction can be cleaned up using Invitrogen's PURELINK™ PCR Micro Kit (Carlsbad, CA) per manufacturer's instructions (up to 5 μg). Larger reactions will require a cleanup using a product with a larger capacity. Following the cleanup, the cDNA can be quantified using the NANODROP™ and analyzed by agarose gel electrophoresis to confirm the cDNA is the expected size. The cDNA can then be submitted for sequencing analysis before proceeding to the in vitro transcription reaction.

Example 3: In Vitro Transcription (IVT)

The in vitro transcription reactions can generate polynucleotides containing uniformly modified polynucleotides. Such uniformly modified polynucleotides can comprise a region or part of the polynucleotides of the invention. The input nucleotide triphosphate (NTP) mix can be made using natural and un-natural NTPs.

A typical in vitro transcription reaction can include the following:

1 Template cDNA—1.0 μg 2 10× transcription buffer (400 mM Tris-HCl pH 8.0, 190 mM $MgCl_2$, 50 mM DTT, 10 mM Spermidine)—2.0 μl 3 Custom NTPs (25 mM each)—7.2 μl 4 RNase Inhibitor—20 U 5 T7 RNA polymerase—3000 U 6 $dH_2O$—Up to 20.0 μl. and 7 Incubation at 37° C. for 3 hr-5 hrs.

The crude IVT mix can be stored at 4° C. overnight for cleanup the next day. 1 U of RNase-free DNase can then be used to digest the original template. After 15 minutes of incubation at 37° C., the mRNA can be purified using Ambion's MEGACLEAR™ Kit (Austin, TX) following the manufacturer's instructions. This kit can purify up to 500 μg of RNA. Following the cleanup, the RNA can be quantified using the NanoDrop and analyzed by agarose gel electrophoresis to confirm the RNA is the proper size and that no degradation of the RNA has occurred.

Example 4: Enzymatic Capping

Capping of a polynucleotide can be performed with a mixture includes: IVT RNA 60 μg-180 μg and $dH_2O$ up to 72 μl. The mixture can be incubated at 65° C. for 5 minutes to denature RNA, and then can be transferred immediately to ice.

The protocol can then involve the mixing of 10× Capping Buffer (0.5 M Tris-HCl (pH 8.0), 60 mM KCl, 12.5 mM $MgCl_2$) (10.0 μl); 20 mM GTP (5.0 μl); 20 mM S-Adenosyl Methionine (2.5 μl); RNase Inhibitor (100 U); 2'-O-Methyltransferase (400U); Vaccinia capping enzyme (Guanylyl transferase) (40 U); $dH_2O$ (Up to 28 μl); and incubation at 37° C. for 30 minutes for 60 μg RNA or up to 2 hours for 180 μg of RNA.

The polynucleotide can then be purified using Ambion's MEGACLEAR™ Kit (Austin, TX) following the manufacturer's instructions. Following the cleanup, the RNA can be quantified using the NANODROP™ (ThermoFisher, Waltham, MA) and analyzed by agarose gel electrophoresis to confirm the RNA is the proper size and that no degradation of the RNA has occurred. The RNA product can also be sequenced by running a reverse-transcription-PCR to generate the cDNA for sequencing.

Example 5: PolyA Tailing Reaction

Without a poly-T in the cDNA, a poly-A tailing reaction must be performed before cleaning the final product. This can be done by mixing Capped IVT RNA (100 μl); RNase Inhibitor (20 U); 10× Tailing Buffer (0.5 M Tris-HCl (pH 8.0), 2.5 M NaCl, 100 mM $MgCl_2$)(12.0 μl); 20 mM ATP (6.0 μl); Poly-A Polymerase (20 U); $dH_2O$ up to 123.5 μl and incubating at 37° C. for 30 min. If the poly-A tail is already in the transcript, then the tailing reaction can be skipped and proceed directly to cleanup with Ambion's MEGACLEAR™ kit (Austin, TX) (up to 500 μg). Poly-A Polymerase is, in some cases, a recombinant enzyme expressed in yeast.

It should be understood that the processivity or integrity of the polyA tailing reaction does not always result in an exact size polyA tail. Hence polyA tails of approximately between 40-200 nucleotides, e.g., about 40, 50, 60, 70, 80, 90, 91, 92, 93, 94, 95, 96, 97, 98, 99, 100, 101, 102, 103, 104, 105, 106, 107, 108, 109, 110, 150-165, 155, 156, 157, 158, 159, 160, 161, 162, 163, 164 or 165 are within the scope of the invention.

Example 6: Natural 5' Caps and 5' Cap Analogues

5'-capping of polynucleotides can be completed concomitantly during the in vitro-transcription reaction using the following chemical RNA cap analogs to generate the 5'-guanosine cap structure according to manufacturer protocols: 3'-O-Me-m7G(5')ppp(5') G [the ARCA cap]; G(5')ppp(5')A; G(5')ppp(5')G; m7G(5')ppp(5')A; m7G(5')ppp(5')G (New England BioLabs, Ipswich, MA). 5'-capping of modified RNA can be completed post-transcriptionally using a Vaccinia Virus Capping Enzyme to generate the "Cap 0" structure: m7G(5')ppp(5')G (New England BioLabs, Ipswich, MA). Cap 1 structure can be generated using both Vaccinia Virus Capping Enzyme and a 2'-O methyl-transferase to generate: m7G(5')ppp(5')G-2'-O-methyl. Cap 2 structure can be generated from the Cap 1 structure followed by the 2'-O-methylation of the 5'-antepenultimate nucleotide using a 2'-O methyl-transferase. Cap 3 structure can be generated from the Cap 2 structure followed by the 2'-O-methylation of the 5'-preantepenultimate nucleotide using a 2'-O methyl-transferase. Enzymes can be derived from a recombinant source.

When transfected into mammalian cells, the modified mRNAs can have a stability of between 12-18 hours or more than 18 hours, e.g., 24, 36, 48, 60, 72 or greater than 72 hours.

Example 7: Capping Assays

A. Protein Expression Assay

Polynucleotides encoding a polypeptide, containing any of the caps taught herein, can be transfected into cells at equal concentrations. After 6, 12, 24 and 36 hours post-transfection, the amount of protein secreted into the culture medium can be assayed by ELISA. Synthetic polynucleotides that secrete higher levels of protein into the medium would correspond to a synthetic polynucleotide with a higher translationally-competent Cap structure.

B. Purity Analysis Synthesis

Polynucleotides encoding a polypeptide, containing any of the caps taught herein, can be compared for purity using denaturing Agarose-Urea gel electrophoresis or HPLC analysis. Polynucleotides with a single, consolidated band by electrophoresis correspond to the higher purity product compared to polynucleotides with multiple bands or streaking bands. Synthetic polynucleotides with a single HPLC peak would also correspond to a higher purity product. The capping reaction with a higher efficiency would provide a more pure polynucleotide population.

C. Cytokine Analysis

Polynucleotides encoding a polypeptide, containing any of the caps taught herein, can be transfected into cells at multiple concentrations. After 6, 12, 24 and 36 hours post-transfection the amount of pro-inflammatory cytokines such as TNF-alpha and IFN-beta secreted into the culture medium can be assayed by ELISA. Polynucleotides resulting in the secretion of higher levels of pro-inflammatory cytokines into the medium would correspond to polynucleotides containing an immune-activating cap structure.

D. Capping Reaction Efficiency

Polynucleotides encoding a polypeptide, containing any of the caps taught herein, can be analyzed for capping reaction efficiency by LC-MS after nuclease treatment. Nuclease treatment of capped polynucleotides would yield a mixture of free nucleotides and the capped 5'-5-triphosphate cap structure detectable by LC-MS. The amount of capped product on the LC-MS spectra can be expressed as a percent of total polynucleotide from the reaction and would correspond to capping reaction efficiency. The cap structure with higher capping reaction efficiency would have a higher amount of capped product by LC-MS.

Example 8: Agarose Gel Electrophoresis of Modified RNA or RT PCR Products

Individual polynucleotides (200-400 ng in a 20 μl volume) or reverse transcribed PCR products (200-400 ng) can be loaded into a well on a non-denaturing 1.2% Agarose E-Gel (Invitrogen, Carlsbad, CA) and run for 12-15 minutes according to the manufacturer protocol.

Example 9: Nanodrop Modified RNA Quantification and UV Spectral Data

Modified polynucleotides in TE buffer (1 μl) can be used for Nanodrop UV absorbance readings to quantitate the yield of each polynucleotide from a chemical synthesis or in vitro transcription reaction.

Example 10: Formulation of Modified mRNA Using Lipidoids

Polynucleotides can be formulated for in vitro experiments by mixing the polynucleotides with the lipidoid at a set ratio prior to addition to cells. In vivo formulation can require the addition of extra ingredients to facilitate circulation throughout the body. To test the ability of these lipidoids to form particles suitable for in vivo work, a standard formulation process used for siRNA-lipidoid formulations can be used as a starting point. After formation of the particle, polynucleotide can be added and allowed to integrate with the complex. The encapsulation efficiency can be determined using a standard dye exclusion assays.

Example 11: Protection Studies in Mice

Mice studies were conducted in accordance with the approval of the Institutional Animal Care and Use Committee of Utah State University (Protocol #2339). The work was performed in the AAALAC-accredited Laboratory Animal Research Center of Utah State University (PHS Assurance no. A3801-01) in accordance with the National Institutes of Health Guide for the Care and Use of Laboratory Animals (Revision; 2010).

Male and female AG129 mice, bred in an in-house colony at Utah State University, were used for protection studies. Animals were assigned randomly to experimental groups and individually marked with ear tags. The CHIKV-LR-2006 stock was prepared by passaging the virus twice in C6/36 *Aedes albopictus* cells. The CHIKV stock had a titer of 109-5 $TCID_{50}$/mL. The CHIKV-specific monoclonal antibody, CHIKV24 was collected from hybridoma supernatants and purified by protein G chromatography, and the antibody suspension was supplied in a ready-to-treat liquid form. Virus titers in sera were assayed using an infectious cell culture assay where a specific volume of serum was added to the first tube of a series of dilution tubes. Serial dilutions were made and added to Vero cell culture monolayers. Three days later cytopathic effect (CPE) was used to identify the end-point of infection. Four replicates were used to calculate the $TCID_{50}$ per mL of serum.

Cages of mice were assigned randomly to groups of 5 animals. Groups of mice were treated with the ChikV24 antibody via a single IV injection 24 h prior to virus challenge (Example 12). Alternatively, similar groups of animals were given mRNA encoding human antibodies by the IV route (Example 15). Mice then were anesthetized with isoflurane prior to subcutaneous injection in the footpad and hock of the right leg with 1015 $TCID_{50}$ of CHIKV in a total volume of 0.1 mL (0.05 mL each site). Survival was monitored twice daily through the critical period of disease to 7 days post-infection. Serum was collected by cheek vein bleed on day 2 post-infection to measure viremia.

Example 12: Multiple-Dose Study of Anti-Chikungunya Virus Antibody in Mice

A multiple-dose study was conducted to determine to what extent an antibody against chikungunya virus can protect mice from the disease. AG129 mice lack receptors for interferon-α/β and -γ and are highly vulnerable to infection with CHIKV and thus this is a highly stringent model for testing antiviral compounds or the protective efficacy of CHIKV24 antibody (Couderc et al., PLoS Pathog 4, e29 (2008); Kaur and Chu, Drug Discov Today, (2013); Partidos et al., Vaccine 29, 3067-3073 (2011); and Wang et al., Journal of virology 85, 9249-9252(2011)). AG129 mice were intravenously injected with a single 10 mg/kg, 2 mg/kg, or 0.4 mg/kg dose of the CHIKV24 antibody, an anti-CHIKV antibody, or the CR9114 anti-influenza antibody as a negative control, via tail vein IV bolus. Five mice were tested at each dose. Mice were challenged 24 hours later with a lethal dose of CHIKV (chikungunya virus strain LR06 (LR2006-OPY1, 2C6) strain at a dose of $10^{2.5}$ $TCID_{50}$) by inoculation of the footpad and hock of the right leg (total volume of 0.1 mL of the diluted virus (0.05 mL each site)). Animals were monitored daily for morbidity (e.g., by measuring weight loss) and mortality for up to 21 days after challenge. Naïve mice that were not injected with antibody or challenged with virus were also used as a control. Mice injected with antibody were bled at 24-hours post-injection to measure total human IgG (huIgG) concentration. Protein was detected using a total human IgG ELISAkit (Abcam, ab100547).

FIG. 1A shows that there was a dose-dependent concentration of human IgG in mouse serum. Mice that had received 10 mg/kg (200 μg), 2 mg/kg (40 μg) or 0.4 mg/kg (8 μg) of recombinant CHIKV24 IgG protein had mean systemic CHIKV24 IgG concentrations of 78 μg/mL, 10 μg/mL or 3 μg/mL, respectively. The serum concentration of the influenza control antibody was similar to that of CHIKV24. (n=5 at each dose).

Figure 1B:
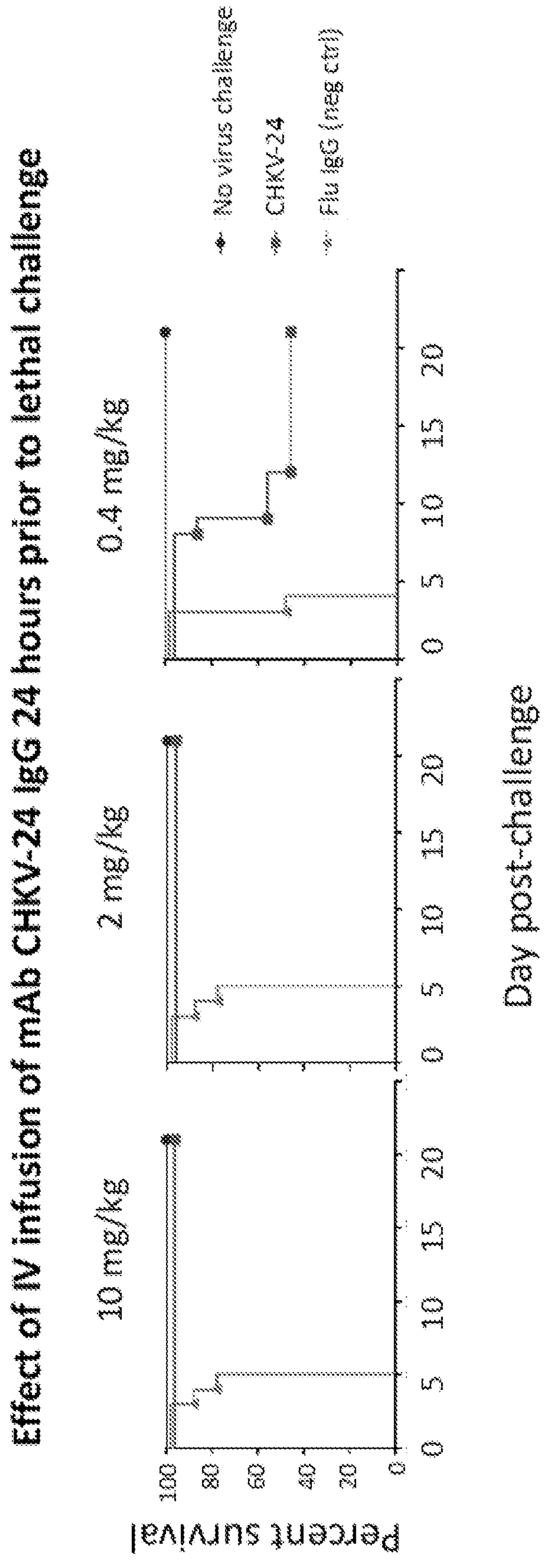
FIG. 1B is a Kaplan-Meier survival plot showing the percent survival of AG129 mice intravenously administered 10 mg/kg, 2 mg/kg, or 0.4 mg/kg of purified ChikV24 antibody or a control influenza antibody over the course of 21 days following challenge with virus. Survival data were analyzed using the Wilcoxon log-rank survival analysis. The number of animals in each group was 10.

FIG. 1B shows that 100% of the mice that had received a prior infusion of either a 10 mg/kg dose or a 2 mg/kg dose of the CHIKV24 antibody survived for 21 days following challenge with virus. Intermediate survival was observed after treatment with 0.4 mg/kg of the antibody, as 50% of the mice injected with the CHIKV24 antibody survived for 21 days following challenge with virus. By contrast, all of the control mice injected with an anti-influenza antibody died by 5 days following challenge with chikungunya virus. All unchallenged control animals survived. A comparison of the survival results with the achieved concentration levels of serum human IgG (FIG. 1A) indicated that the CHIKV24 IgG could protect AG129 mice in a lethal challenge model at systemic levels of 10 μg/mL of antibody at the time of challenge.

Viruses

Virus suspensions of CHIKV attenuated vaccine strain 181/25 were grown on Vero cell monolayer cultures, and supernatant was harvested 36 hours post-inoculation and clarified by centrifugation at 2,000×rpm for 10 min at 4° C. The CHIKV East/Central/South African [ECSA] genotype strain used for neutralization screening in this study was SL15649 (accession number GU189061). For in vivo studies, the Reunion Island CHIKV isolate LR2006-OPYI was obtained. Stocks for these viruses were prepared in C6/36 *Aedes albopictus* cells.

Example 13: Synthesis of mRNA Encoding Human Anti-Chikungunya Antibody

Sequence optimized polynucleotides encoding human anti-chikungunya antibody heavy chain polypeptides, i.e., SEQ ID NO:1, and light chain polypeptides, i.e., SEQ ID NO:3, are synthesized and characterized as described in Examples 1 to 11, and prepared for the Examples described below.

An mRNA encoding human anti-chikungunya antibody heavy chain polypeptide can be constructed, e.g., by using an ORF sequence provided in SEQ ID NO:2. An mRNA encoding human anti-chikungunya antibody light chain polypeptide can be constructed, e.g., by using an ORF sequence provided in SEQ ID NO:4. The mRNA sequence includes both 5' and 3' UTR regions flanking the ORF sequence (nucleotide). In an exemplary construct, the 5' UTR and 3' UTR sequences are SEQ ID NO:13 and SEQ ID NO:14, respectively (see Sequence Listing).

```
5'UTR:
                                          (SEQ ID NO: 13)
GGGAAAUAAGAGAGAAAAGAAGAGUAAGAAGAAAUAUAAGACCCCGGCGC

CGCCACC

3'UTR:
                                          (SEQ ID NO: 14)
UGAUAAUAGGCUGGAGCCUCGGUGGCCUAGCUUCUUGCCCCUUGGGCCUC

CCCCCAGCCCCUCCUCCCCUUCCUGCACCCGUACCCCCGUGGUCUUUGAA

UAAAGUCUGAGUGGGCGGC
```

The antibody heavy and light chain mRNA sequences are prepared as modified mRNA. Specifically, during in vitro translation, modified mRNA can be generated using N1-methylpseudouridine-5'-Triphosphate or 5-methoxy-UTP to ensure that the mRNAs contain 100% N1-methylpseudouridine-5'-Triphosphate or 5-methoxy-uridine instead of uridine. Further, mRNA can be synthesized with a primer that introduces a polyA-tail, and a Cap 1 structure is generated on both mRNAs using Vaccinia Virus Capping Enzyme and a 2'-O methyl-transferase to generate: m7G(5') ppp(5')G-2'-O-methyl.

Example 14: Production and Characterization of Nanoparticle Compositions

A. Production of Nanoparticle Compositions

Nanoparticles can be made with mixing processes such as microfluidics and T-junction mixing of two fluid streams, one of which contains the polynucleotide and the other has the lipid components.

Lipid compositions are prepared by combining an ionizable amino lipid disclosed herein, e.g., a lipid according to Formula (I) such as Compound II or a lipid according to Formula (III) such as Compound VI, a phospholipid (such as DOPE or DSPC, obtainable from Avanti Polar Lipids, Alabaster, AL), a PEG lipid (such as 1,2-dimyristoyl-sn-glycerol methoxypolyethylene glycol, also known as PEG-DMG, obtainable from Avanti Polar Lipids, Alabaster, AL), and a structural lipid (such as cholesterol, obtainable from Sigma-Aldrich, Taufkirchen, Germany, or a corticosteroid (such as prednisolone, dexamethasone, prednisone, and hydrocortisone), or a combination thereof) at concentrations of about 50 mM in ethanol. Solutions should be refrigerated for storage at, for example, −20° C. Lipids are combined to yield desired molar ratios and diluted with water and ethanol to a final lipid concentration of between about 5.5 mM and about 25 mM.

Nanoparticle compositions including a polynucleotide and a lipid composition are prepared by combining the lipid solution with a solution including the a polynucleotide at lipid composition to polynucleotide wt:wt ratios between about 5:1 and about 50:1. The lipid solution is rapidly injected using a NanoAssemblr microfluidic based system at flow rates between about 10 ml/min and about 18 ml/min into the polynucleotide solution to produce a suspension with a water to ethanol ratio between about 1:1 and about 4:1.

For nanoparticle compositions including an RNA, solutions of the RNA at concentrations of 0.1 mg/ml in deionized water are diluted in 50 mM sodium citrate buffer at a pH between 3 and 4 to form a stock solution.

Nanoparticle compositions can be processed by dialysis to remove ethanol and achieve buffer exchange. Formulations are dialyzed twice against phosphate buffered saline (PBS), pH 7.4, at volumes 200 times that of the primary product using Slide-A-Lyzer cassettes (Thermo Fisher Scientific Inc., Rockford, IL) with a molecular weight cutoff of 10 kD. The first dialysis is carried out at room temperature for 3 hours. The formulations are then dialyzed overnight at 4° C. The resulting nanoparticle suspension is filtered through 0.2 μm sterile filters (Sarstedt, Nümbrecht, Germany) into glass vials and sealed with crimp closures. Nanoparticle composition solutions of 0.01 mg/ml to 0.10 mg/ml are generally obtained.

The method described above induces nano-precipitation and particle formation. Alternative processes including, but not limited to, T-junction and direct injection, can be used to achieve the same nano-precipitation.

B. Characterization of Nanoparticle Compositions

A Zetasizer Nano ZS (Malvern Instruments Ltd, Malvern, Worcestershire, UK) can be used to determine the particle size, the polydispersity index (PDI) and the zeta potential of the nanoparticle compositions in 1×PBS in determining particle size and 15 mM PBS in determining zeta potential.

Ultraviolet-visible spectroscopy can be used to determine the concentration of a polynucleotide (e.g., RNA) in nanoparticle compositions. 100 μL of the diluted formulation in 1×PBS is added to 900 μL of a 4:1 (v/v) mixture of methanol and chloroform. After mixing, the absorbance spectrum of the solution is recorded, for example, between 230 nm and 330 nm on a DU 800 spectrophotometer (Beckman Coulter, Beckman Coulter, Inc., Brea, CA). The concentration of polynucleotide in the nanoparticle composition can be calculated based on the extinction coefficient of the polynucleotide used in the composition and on the difference between the absorbance at a wavelength of, for example, 260 nm and the baseline value at a wavelength of, for example, 330 nm.

For nanoparticle compositions including an RNA, a QUANT-IT™ RIBOGREEN® RNA assay (Invitrogen Corporation Carlsbad, CA) can be used to evaluate the encapsulation of an RNA by the nanoparticle composition. The samples are diluted to a concentration of approximately 5 μg/mL in a TE buffer solution (10 mM Tris-HCl, 1 mM EDTA, pH 7.5). 50 μL of the diluted samples are transferred to a polystyrene 96 well plate and either 50 μL of TE buffer or 50 μL of a 2% Triton X-100 solution is added to the wells. The plate is incubated at a temperature of 37° C. for 15 minutes. The RIBOGREEN® reagent is diluted 1:100 in TE buffer, and 100 μL of this solution is added to each well. The fluorescence intensity can be measured using a fluorescence plate reader (Wallac Victor 1420 Multilablel Counter; Perkin Elmer, Waltham, MA) at an excitation wavelength of, for example, about 480 nm and an emission wavelength of, for example, about 520 nm. The fluorescence values of the reagent blank are subtracted from that of each of the samples and the percentage of free RNA is determined by dividing the fluorescence intensity of the intact sample (without addition of Triton X-100) by the fluorescence value of the disrupted sample (caused by the addition of Triton X-100).

Exemplary formulations of the nanoparticle compositions are presented in Table 6 below. The term "Compound" refers to an ionizable lipid such as MC3, Compound II, or Compound VI. "Phospholipid" can be DSPC or DOPE. "PEG-lipid" can be PEG-DMG or Compound I.

TABLE 6

Exemplary Formulations of Nanoparticles

| Composition (mol %) | Components |
|---|---|
| 40:20:38.5:1.5 | Compound:Phospholipid:Chol:PEG-lipid |
| 45:15:38.5:1.5 | Compound:Phospholipid:Chol:PEG-lipid |
| 50:10:38.5:1.5 | Compound:Phospholipid:Chol:PEG-lipid |
| 55:5:38.5:1.5 | Compound:Phospholipid:Chol:PEG-lipid |
| 60:5:33.5:1.5 | Compound:Phospholipid:Chol:PEG-lipid |
| 45:20:33.5:1.5 | Compound:Phospholipid:Chol:PEG-lipid |
| 50:20:28.5:1.5 | Compound:Phospholipid:Chol:PEG-lipid |
| 55:20:23.5:1.5 | Compound:Phospholipid:Chol:PEG-lipid |
| 60:20:18.5:1.5 | Compound:Phospholipid:Chol:PEG-lipid |
| 40:15:43.5:1.5 | Compound:Phospholipid:Chol:PEG-lipid |
| 50:15:33.5:1.5 | Compound:Phospholipid:Chol:PEG-lipid |
| 55:15:28.5:1.5 | Compound:Phospholipid:Chol:PEG-lipid |
| 60:15:23.5:1.5 | Compound:Phospholipid:Chol:PEG-lipid |
| 40:10:48.5:1.5 | Compound:Phospholipid:Chol:PEG-lipid |

TABLE 6-continued

| Exemplary Formulations of Nanoparticles | |
|---|---|
| Composition (mol %) | Components |
| 45:10:43.5:1.5 | Compound:Phospholipid:Chol:PEG-lipid |
| 55:10:33.5:1.5 | Compound:Phospholipid:Chol:PEG-lipid |
| 60:10:28.5:1.5 | Compound:Phospholipid:Chol:PEG-lipid |
| 40:5:53.5:1.5 | Compound:Phospholipid:Chol:PEG-lipid |
| 45:5:48.5:1.5 | Compound:Phospholipid:Chol:PEG-lipid |
| 50:5:43.5:1.5 | Compound:Phospholipid:Chol:PEG-lipid |
| 40:20:40:0 | Compound:Phospholipid:Chol:PEG-lipid |
| 45:20:35:0 | Compound:Phospholipid:Chol:PEG-lipid |
| 50:20:30:0 | Compound:Phospholipid:Chol:PEG-lipid |
| 55:20:25:0 | Compound:Phospholipid:Chol:PEG-lipid |
| 60:20:20:0 | Compound:Phospholipid:Chol:PEG-lipid |
| 40:15:45:0 | Compound:Phospholipid:Chol:PEG-lipid |
| 45:15:40:0 | Compound:Phospholipid:Chol:PEG-lipid |
| 50:15:35:0 | Compound:Phospholipid:Chol:PEG-lipid |
| 55:15:30:0 | Compound:Phospholipid:Chol:PEG-lipid |
| 60:15:25:0 | Compound:Phospholipid:Chol:PEG-lipid |
| 40:10:50:0 | Compound:Phospholipid:Chol:PEG-lipid |
| 45:10:45:0 | Compound:Phospholipid:Chol:PEG-lipid |
| 50:10:40:0 | Compound:Phospholipid:Chol:PEG-lipid |
| 55:10:35:0 | Compound:Phospholipid:Chol:PEG-lipid |
| 60:10:30:0 | Compound:Phospholipid:Chol:PEG-lipid |
| 50:10:38:2 | Compound:Phospholipid:Chol:PEG-lipid |

Example 15: Multiple-Dose Study of In Vivo Expression of mRNA Encoding Anti-Chikungunya Antibody in Mice, and Protection Against Lethal Virus Challenge To assess the ability of mRNAs encoding the human heavy and light chains of the ChikV24 antibody to facilitate protein expression in vivo, mRNAs encoding the heavy and light chains were co-formulated at a 2:1 heavy chain:light chain (HC:LC) w/w ratio, and intravenously administered into AG129 mice via tail vein IV bolus at 0.5 mg/kg, 0.1 mg/kg, or 0.02 mg/kg of each mRNA. Five mice were tested at each dose. The mRNA was formulated in Compound II- and PEG-DMG-containing lipid nanoparticles (LNPs) for delivery into the mice and stored at 4° C. until use. Mice were challenged 24 hours later with Chikungunya virus strain LR06 (LR2006-OPY1, 2C6) at a dose of $10^{2.5}$ TCID50 by footpad inoculation. Animals were monitored daily for morbidity (e.g., by measuring weight loss) and mortality for up to 21 days after challenge. Control mice were injected with mRNA encoding an antibody that does not bind to chikungunya virus (the CR9114 anti-influenza antibody, as a control antibody). An additional group of animals was infused with the test mRNA doses at the same time and were bled at 24-hours, 48-hours, and 72-hours post-injection to measure total human IgG (huIgG) concentration (in the absence of virus challenge after infusion). Protein was detected using a total human IgG ELISA kit (Abcam, ab100547).

The virus titers in the tissues and serum of test and control mice were assayed using an infectious cell culture assay where a specific volume of either tissue homogenate or plasma was added to the first tube of a series of dilution tubes. Serial dilutions were made and added to Vero cell monolayer cultures two days after virus challenge to determine virus titer ($\log_{10}$ $TCID_{50}$/mL). Three days later cytopathic effect (CPE) was used to identify the end-point of infection. Four replicates were used to calculate the 50% tissue culture infectious doses ($TCID_{50}$) per mL of plasma or gram of tissues.

Figure 2A:
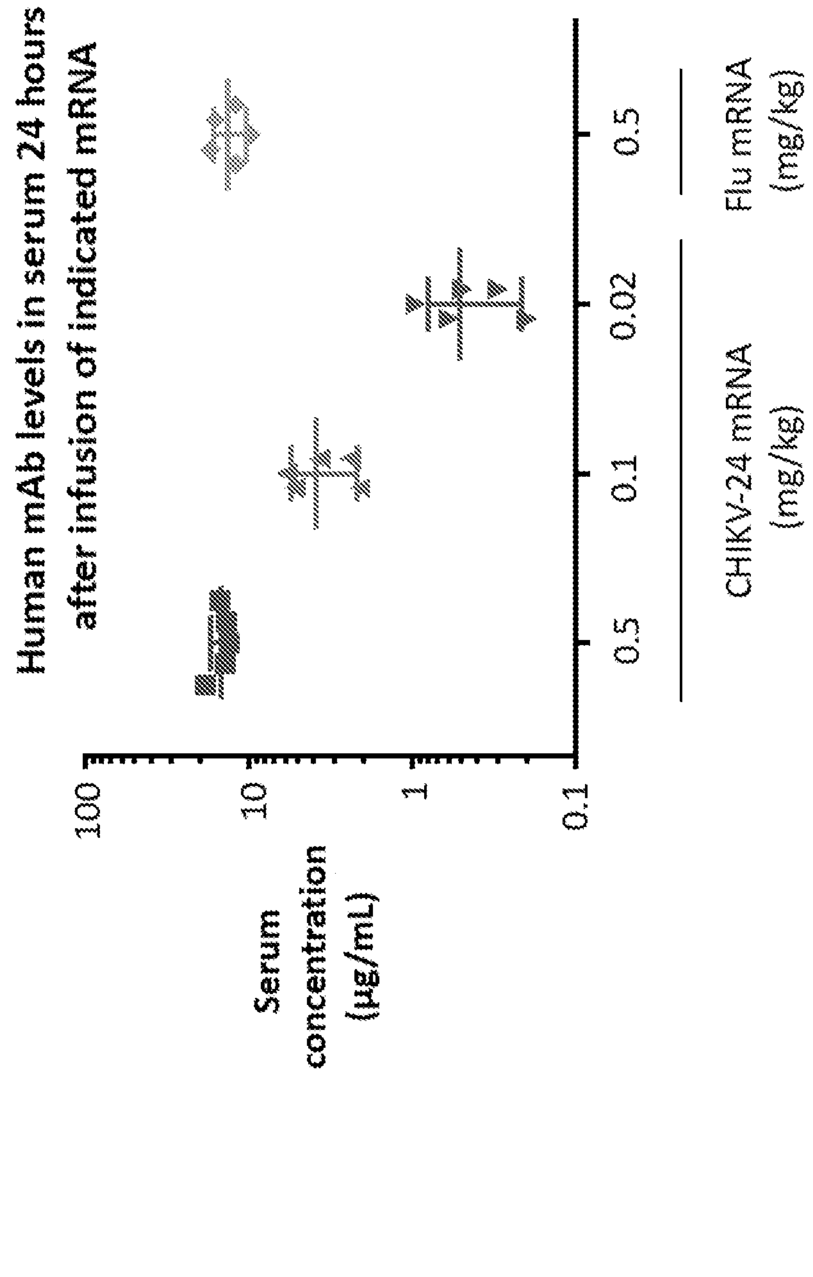
FIG. 2A is a graph showing the serum concentration levels of human ChikV24 antibody in AG129 mice 24 hours after intravenous administration of 0.5 mg/kg, 0.1 mg/kg, or 0.02 mg/kg of mRNAs encoding the heavy and light chains of the ChikV24 antibody. The graph also shows the serum concentration levels of a control influenza antibody 24 hours after intravenous injection of 0.5 mg/kg of mRNAs encoding the control antibody.

FIG. 2A shows that infusion of mice with the mRNAs resulted in the expression of human ChikV24 antibody in vivo. There was a dose-dependent effect, as the highest serum concentrations of human IgG at 24 hours post-injection were observed in mice that were injected with 0.5 mg/kg of the mRNAs. The mean peak serum concentration of the 0.5 mg/kg treated group was 14.9 μg/mL. Each group had 5 animals.

Figure 2B:
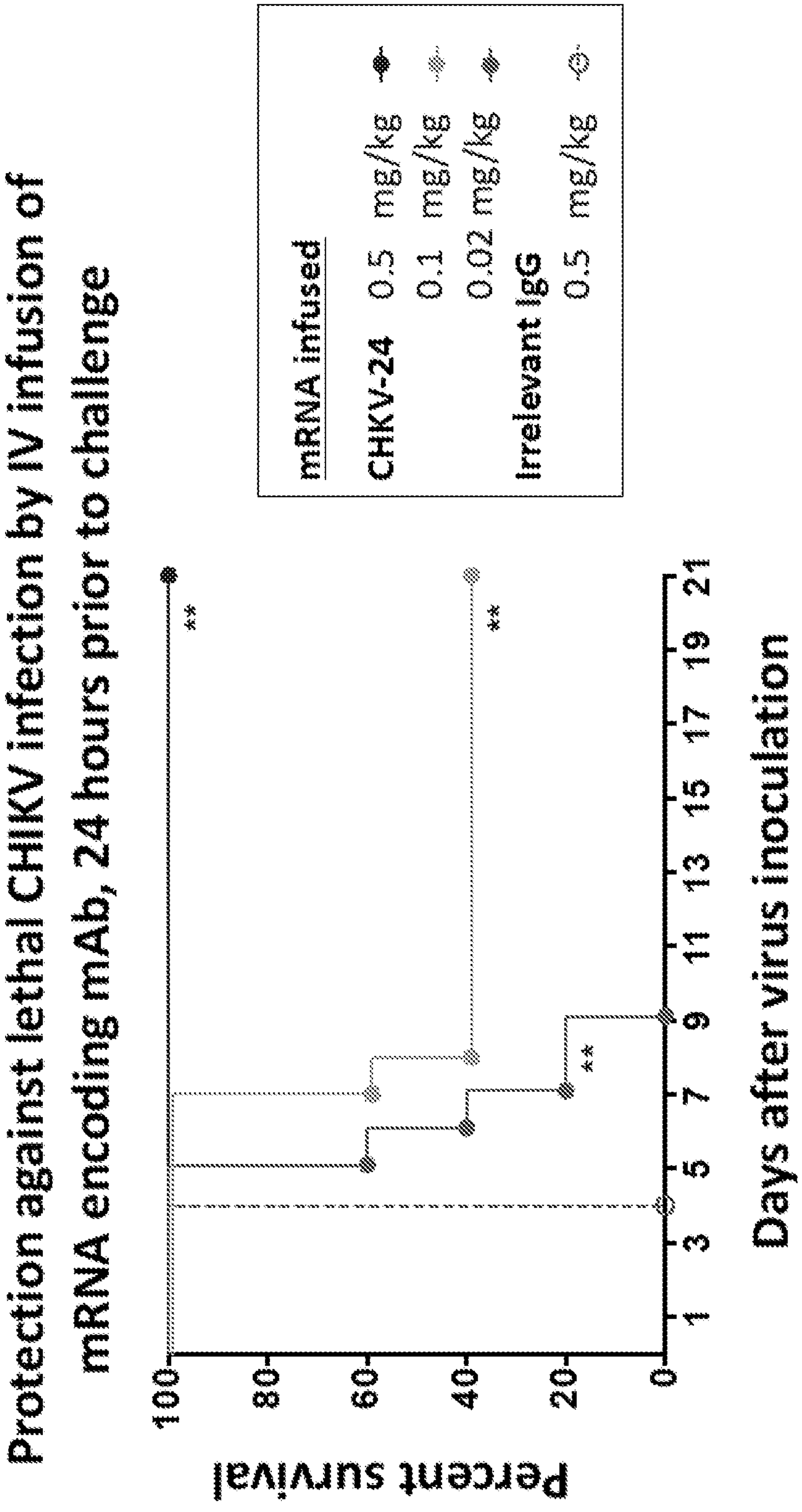
FIG. 2B is a graph showing the percent survival of AG129 mice intravenously administered 0.5 mg/kg (top line), 0.1 mg/kg (middle line), or 0.02 mg/kg (bottom line) of mRNAs encoding the heavy and light chains of the ChikV24 antibody, or 0.5 mg/kg of mRNAs expressing a control antibody (dashed line), over the course of 21 days following challenge with virus. **($P<0.01$) Indicates the survival differed significantly from that of the group treated with 0.5 mg/kg of the irrelevant control IgG (Wilcoxon log-rank survival test).

FIG. 2B shows that a dose-responsive improvement in survival of AG129 mice infected with chikungunya virus was observed after treatment with ChikV24 mRNA administered intravenously 24 hours prior to virus challenge as a prophylaxis (**P<0.01, as compared with placebo). 100% of the mice that were administered 0.5 mg/kg of the mRNAs encoding the heavy and light chains of the ChikV24 antibody (top line, amounting to a serum concentration of approximately 10 μg/mL), and 40% of the mice that were administered 0.1 mg/kg of the mRNAs encoding the ChikV24 antibody (middle line, amounting to a serum concentration of 3 μg/mL) survived for 21 days following challenge with virus. Mice that were administered 0.02 mg/kg of mRNAs encoding the heavy and light chains of ChikV24 (bottom line, amounting to 0.5 μg/mL) did not survive. Despite the lower level of protection at the two lower doses of mRNAs (0.1 mg/kg and 0.02 mg/kg), the survival curves for mice that received these doses were improved (P<0.01), showing delayed mortality, compared to mice that received placebo treatment (mRNA encoding an irrelevant IgG that does not bind chikungunya virus), demonstrating a benefit of the CHIKV24 mRNA treatment even at the lower doses tested. Thus, the mRNA-encoded ChikV24 antibody has potency at equivalent levels as the corresponding purified recombinant antibody. The number of animals in each group was 10.

A comparison of the serum levels of human IgG achieved by mRNA infusion measured in a parallel group of non-challenged animals receiving 0.5 mg/kg or 0.1 mg/kg of IgG (see FIG. 2A) with the results of the survival experiments (FIG. 2B) indicated that the CHIKV24 mRNA treatment could completely protect AG129 mice in the lethal challenge model when a 10 μg/mL concentration of systemic ChikV24 antibody was achieved, while at least half of the virus challenged animals were protected at ChikV24 antibody serum levels of about 3 μg/mL.

Figure 2C:
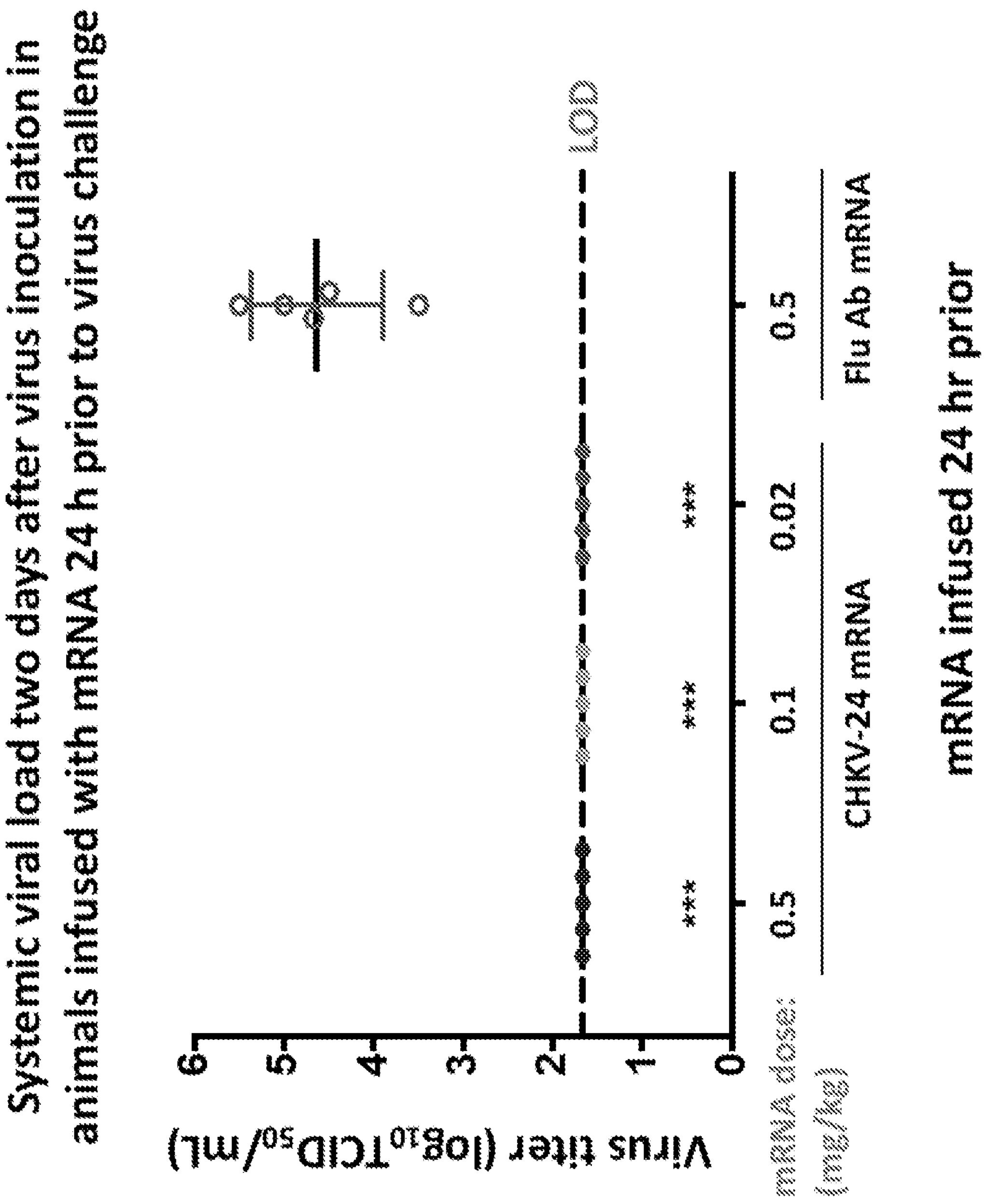
FIG. 2C is a graph showing the chikungunya virus titer in blood samples collected from AG129 mice injected intravenously with 0.5 mg/kg, 0.1 mg/kg, or 0.02 mg/kg of mRNAs expressing the heavy and light chains of the ChikV24 antibody, or 0.5 mg/kg of mRNAs expressing a control antibody, two days after being challenged with virus. The mean values are indicated, and error bars show the standard deviation. Comparisons were made by the Kruskal Wallis test with Dunn's post-test. *** indicates $P<0.0003$, as compared to mice injected with the control IgG.

FIG. 2C shows that mRNA-expressed ChikV24 antibody significantly reduced chikungunya virus titers below the level of detection in the serum of AG129 mice at 2 days following virus challenge at all mRNA doses (0.5 mg/kg, 0.1 mg/kg, and 0.02 mg/kg) relative to control mice that were intravenously administered 0.5 mg/kg of mRNA encoding an antibody that does not bind to chikungunya virus (***P<0.0003 (Kruskal Wallis test with Dunn's post test), as compared to the control IgG). The limit of detection (LOD) was 1.7. Control mice exhibited an average of 4.6 $\log_{10}$ 50% tissue culture infectious doses ($TCID_{50}$). Although virus was not observed in the serum in the low-dose treatment group (0.02 mg/kg), virus likely replicated in other tissues, since mortality occurred. The reduction of viremia to the limit of detection corroborated a therapeutic effect against viral replication. The number of animals in each group was 5.

Example 16: Pharmacokinetics Arm to Multiple-Dose Study of In Vivo Expression of mRNA Encoding Anti-Chikungunya Antibody in Mice To study the pharmacokinetics of the human ChikV24 antibody expressed from modified mRNAs encoding the light and heavy chains of the antibody, AG129 mice were intravenously injected via tail vein IV bolus with 0.5 mg/kg, 0.1 mg/kg, or 0.02 mg/kg of each mRNA. Five mice were injected at each dose, and control mice were administered PBS. mRNAs were formulated in Compound II- and PEG-DMG containing lipid nanoparticles prior to administration. None of the mice were challenged with chikungunya virus after mRNA injection. Mice were bled prior to injection, and at 24-hours, 48-hours, and 72-hours post-injection to measure total human IgG (huIgG) concentration. Protein was detected using a total human IgG ELISA kit (Abcam, ab100547).

The results of the pharmacokinetics analysis are provided in Table 7.

TABLE 7

In vivo duration of IgG Expression over 72 hours

| Group | µg/mL Human IgG | | | |
|---|---|---|---|---|
| dose | 0 hr | 24 hr | 48 hr | 72 hr |
| 0.5 mpk | 0.01 | 18.5 | 10.7 | 11.6 |
| | 0.01 | 3.4 | 3 | 2.3 |
| | 0.01 | 13.9 | 9.5 | 7.1 |
| | 0.01 | 14.1 | 10.1 | 7.4 |
| | 0.01 | 0.01 | 0.01 | 0.01 |
| 0.1 mpk | 0.01 | 3.7 | 3.4 | 2 |
| | 0.01 | 5.9 | 5 | 2.9 |
| | 0.01 | 2.3 | 2.1 | 2 |
| | 0.01 | 1.4 | 1.3 | 1.2 |
| | 0.01 | 5.3 | 6 | 2.5 |
| 0.02 mpk | 0.01 | 0.01 | 0.01 | 0.01 |
| | 0.01 | 0.3 | 0.3 | 0.2 |
| | 0.01 | 0.9 | 1.1 | 0.6 |
| | 0.01 | 0.6 | 0.8 | 0.4 |
| | 0.01 | 0.5 | 0.8 | 0.5 |
| control | 0.01 | 0.01 | 0.01 | 0.01 |
| | 0.01 | 0.01 | 0.01 | 0.01 |
| | 0.01 | 0.01 | 0.01 | 0.01 |
| | 0.01 | 0.01 | 0.01 | 0.01 |

LOQ: 0.01 µg/mL

Figure 3:
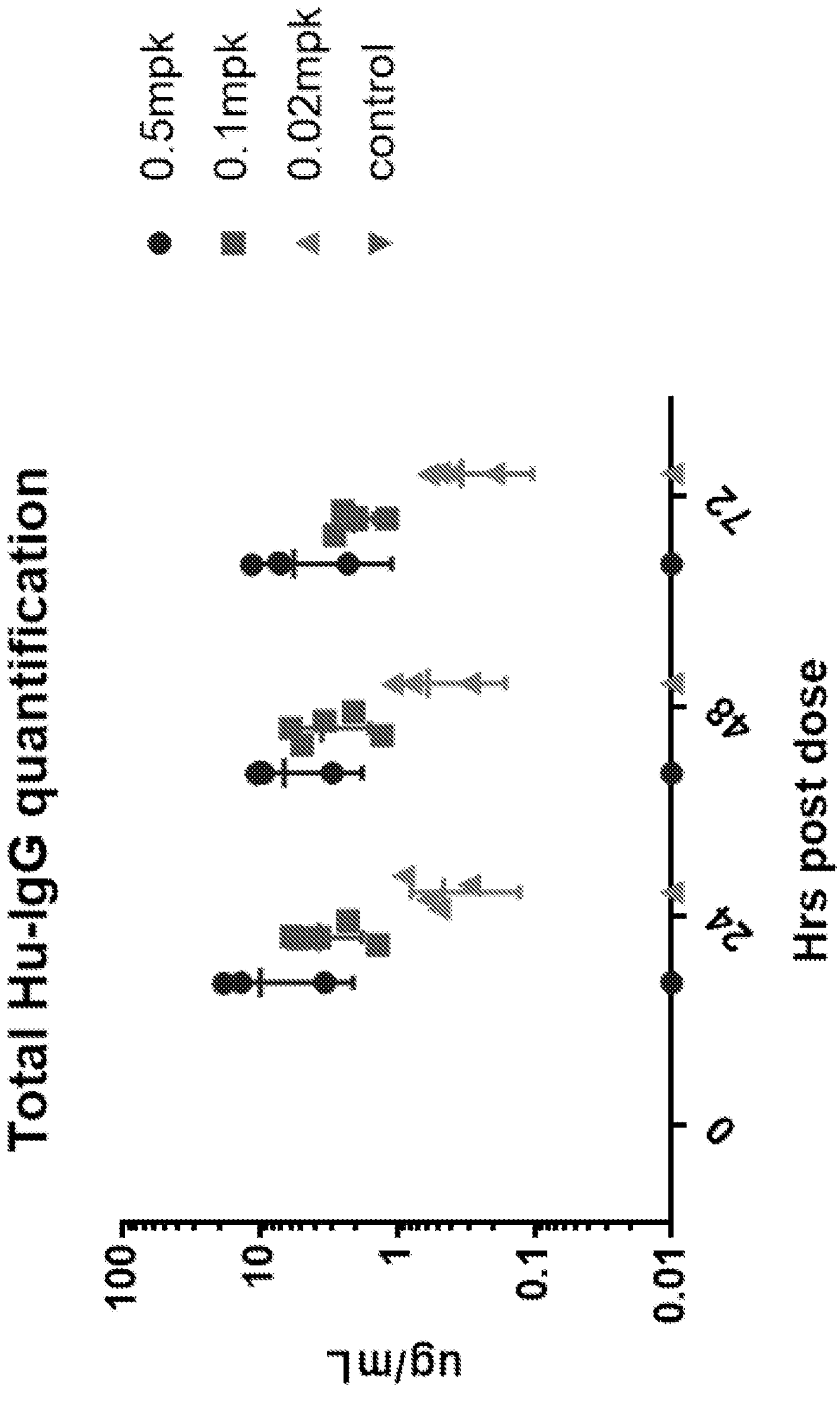
FIG. 3 is a graph showing the serum concentrations of the ChikV24 antibody from AG129 mice injected intravenously with 0.5 mg/kg, 0.1 mg/kg, or 0.02 mg/kg of mRNAs expressing the heavy and light chains of ChikV24 antibody at 24-hours, 48-hours, or 72-hours post-injection.

As shown in FIG. 3 and in Table 7, administration of increasing amounts of mRNA encoding the ChikV24 antibody resulted in greater amounts of antibody in the serum of animals at 24, 48, and 72-hours post-injection. One animal in the 0.5 mg/kg dose group and one animal in the 0.02 mg/kg dose group failed to respond to mRNA injection, i.e., failed to express antibody from injected mRNAs.

Example 17: Single-Dose Study of mRNA Encoding Anti-Chikungunya Antibody in Mice and Protection Against Arthritis and Musculoskeletal Disease While immunocompromised mice provide a stringent protection model for mRNA encoding human anti-ChikV antibody, chikungunya virus infection is rarely fatal in humans but instead causes severe, acute and chronic polyarthralgia and polyarthritis. Accordingly, mRNA encoding ChikV24 antibody was tested to see if it could reduce prevent or reduce symptoms in an immunocompetent mouse model of CHIKV-induced arthritis and musculoskeletal disease by administering the mRNA after virus exposure. In this mouse model, subcutaneous virus infection results in a biphasic swelling of the infected foot peaking at 3 and 7 days post-inoculation (dpi). Four-week-old wild-type C57BL/6J mice (000664; Jackson Laboratories) were inoculated subcutaneously in the left footpad with $10^3$ FFU of CHIKV-LR in Hank's Balanced Salt Solution (HBSS) supplemented 1% heat-inactivated (HI)-FBS. mRNAs encoding the human heavy and light chains of the ChikV24 antibody (co-formulated at a 2:1 heavy chain:light chain (HC:LC) w/w ratio) were intravenously injected via tail vein IV bolus at 10 mg/kg of mRNA into C57BL/6 mice at 4 hours after the mice were challenged with Chikungunya virus strain LR06 (LR2006-OPY1, 2C6) at a lethal dose of $10^{2.5}$ TCID50 by footpad inoculation. The mRNA was formulated in Compound II- and PEG-DMG-containing lipid nanoparticles (LNPs) prior to delivery into the mice. Control mice were injected with mRNA encoding an antibody that does not bind to chikungunya virus (the CR9114 anti-influenza antibody). Ipsilateral foot swelling in the mice was monitored via measurements (width×height) using digital calipers (n=15/group, two experiments, two-way ANOVA with Sidak's post-test). Serum was collected at 2 dpi, and mice were sacrificed and perfused extensively with 20 mL of PBS at 7 dpi and ipsilateral (i.) and contralateral (c.) ankles were harvested. Serum and tissues were titered for chikungunya virus RNA by qRT-PCR using RNA isolated from viral stocks as a standard curve to determine FFU equivalents, as previously described (Fox et al., Broadly Neutralizing Alphavirus Antibodies Bind an Epitope on E2 and Inhibit Entry and Egress. Cell 163, 1095-1107 (2015), herein incorporated by reference in its entirety). Viral RNA was quantified by qRT-PCR in the serum (n=15/group, two experiments, for serum n=10/group, two experiments, Mann Whitney test for each tissue, for ankles). For histology, the ipsilateral feet collected at 7 dpi were fixed in 4% paraformaldehyde (PFA) for 24 hours, rinsed with PBS and water, and decalcified for 14 days in 14% EDTA free acid (Sigma) at pH 7.2. The decalcified tissue was then rinsed, dehydrated, embedded in paraffin, sectioned, and stained with hematoxylin and eosin (H & E). Images were acquired on a Nikon Eclipse E400 microscope.

Figure 4A:
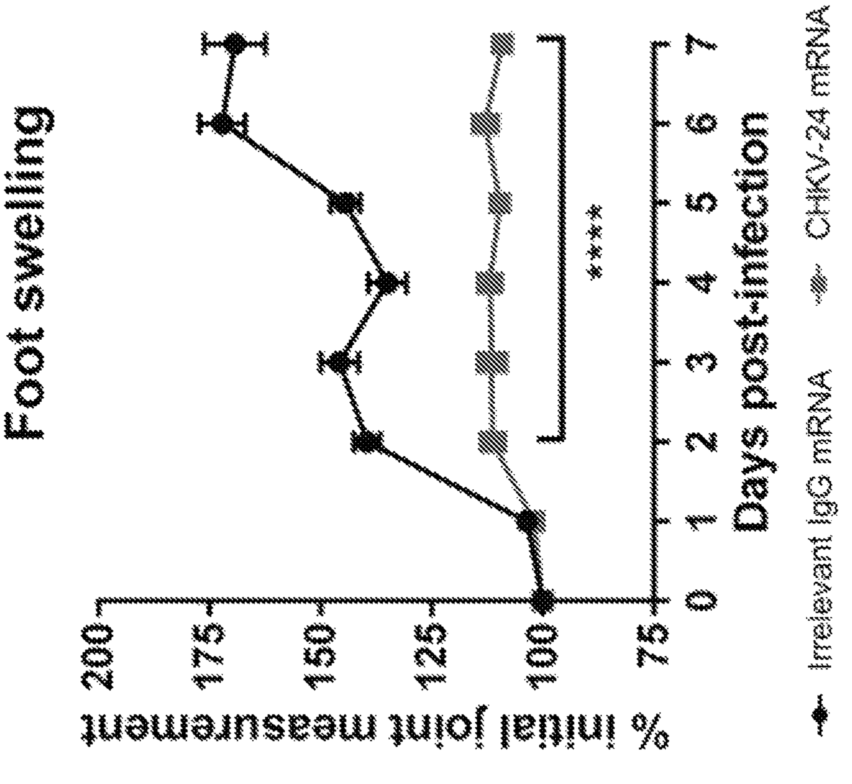
FIG. 4A is a graph showing foot swelling as monitored by digital calipers in either C57BL/6 mice that were injected with 10 mg/kg of mRNAs encoding human ChikV24 antibody, or control C57BL/6 mice that were injected with mRNAs encoding an antibody that does not bind to chikungunya virus, at 4 hours following inoculation with chikungunya virus. The line indicates significance between the groups at each time point. Error bars indicate standard error of the mean.

FIG. 4A shows that wild-type (WT) C57BL/6 mice injected with mRNAs encoding human ChikV24 antibody at 4 hours after virus challenge did not develop foot swelling compared to the control mice that received an mRNA LNP encoding an irrelevant IgG control antibody.

Figure 4B:
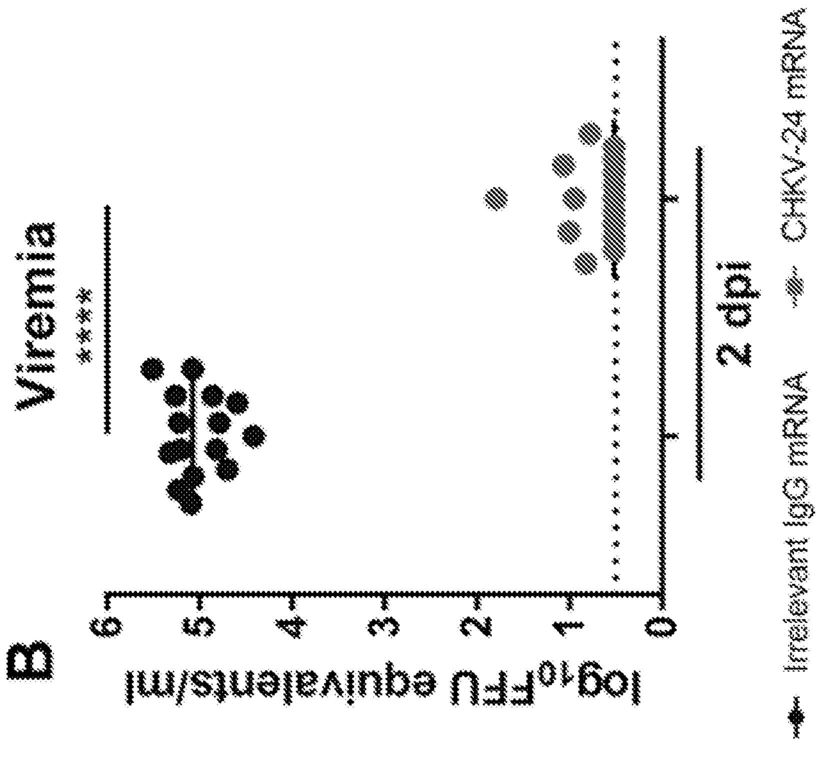
FIG. 4B is a graph showing chikungunya virus RNA levels quantified by qRT-PCR in serum collected at 2 dpi from C57BL/6 mice that were injected with 10 mg/kg of mRNAs encoding human ChikV24 antibody (right area of graph), or control C57BL/6 mice that were injected with mRNAs encoding an antibody that does not bind to chikungunya virus (left area of graph), at 4 hours following inoculation with chikungunya virus. Bars indicate median values. Dotted lines indicate the limit of detection.
Figure 4C:
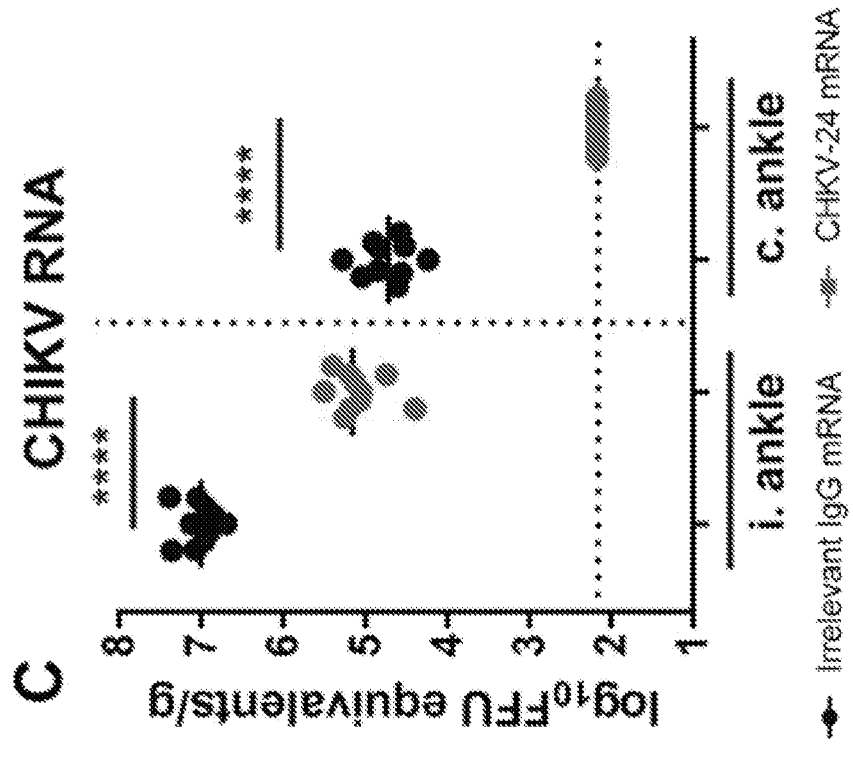
FIG. 4C is a graph showing chikungunya virus RNA levels quantified by qRT-PCR in ipsilateral (i.) and contralateral (c.) ankles that were collected at 7 dpi from C57BL/6 mice that were injected with 10 mg/kg of mRNAs encoding human ChikV24 antibody (right area of graph), or control C57BL/6 mice that were injected with mRNAs encoding an antibody that does not bind to chikungunya virus (left area of graph), at 4 hours following inoculation with chikungunya virus. Bars indicate median values. Dotted lines indicate the limit of detection.

FIG. 4B shows that chikungunya virus titers were very low (at the limit of detection) in the serum collected from most of the mice injected with mRNAs encoding ChikV24 antibody at 2 dpi. By contrast, high levels of viremia were observed in the control mice injected with mRNA encoding an antibody that does not bind to chikungunya virus. FIG. 4C shows that ipsilateral ankles collected from mice injected with mRNAs encoding ChikV24 antibody at 7 dpi had an 80-fold reduction in viral RNA, with no spread to the contralateral ankle, compared to the ipsilateral ankles collected from the control mice.

Figure 4D:
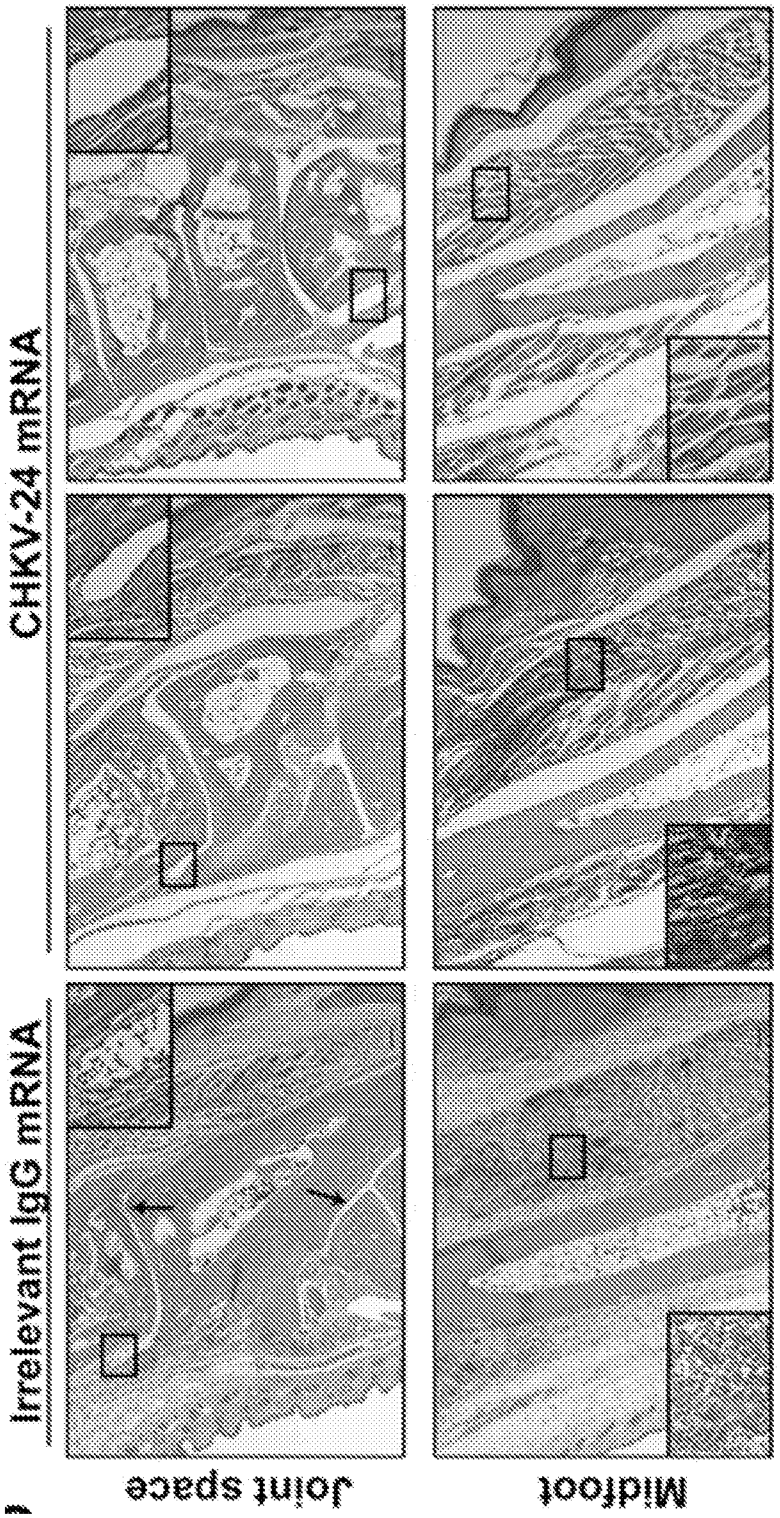
FIG. 4D contains histology section images taken from ipsilateral feet collected at 7 dpi C57BL/6 mice that were injected with 10 mg/kg of mRNAs encoding human ChikV24, or control C57BL/6 mice that were injected with mRNAs encoding an antibody that does not bind to chikungunya virus, at 4 hours following inoculation with chikungunya virus. Images show low-magnification (scale bar 100 μm) with a high magnification inset (scale bar 10 μm). Top and bottom panels are representative images of the joint space and midfoot, respectively (n=5/group, two experiments). Arrows indicate cellular infiltrate in joint space.

FIG. 4D shows the results of the histological analysis of the ipsilateral feet collected from mice injected with mRNAs encoding ChikV24 antibody at 7 dpi compared to the ipsilateral feet collected from control mice that received an mRNA LNP encoding an irrelevant IgG control antibody. The top panels of FIG. 4D show large cellular infiltration of chikungunya virus into the joint space of the control mRNA treated mice (top left panel), whereas cellular infiltration was absent in the mice injected with ChikV24-encoding mRNA (top middle and right panels). The histological results also showed compared the cellular infiltration of chikungunya virus in the midfoot of test mice versus control mice (bottom panels of FIG. 4D). Slides from two of five mice administered mRNAs encoding ChikV24 antibody exhibited minimal cellular infiltration of virus in the midfoot (bottom right panel), although three of the test mice exhibited detectable cellular infiltration in the soft tissue (bottom middle panel). However, the extent of immune cells and edema in the midfoot of mice injected with ChikV24-encoding mRNAs was reduced markedly compared to the midfoot of control mice (bottom left panel). These results show that mRNAs encoding human ChikV24 antibody confer protection in an immunocompetent mouse model of arthritis caused by chikungunya virus infection.

Example 18: Housing of Nonhuman Primates for Studies

Nonhuman primate studies were conducted at Charles River Laboratories (Sherbrooke, Quebec, Canada). Animal experiments and husbandry followed NIH guidelines (NIH Publications No. 8023, eighth edition) and the USA National Research Council and the Canadian Council on Animal Care (CCAC) guidelines. No treatment randomization or blinding methods were used for any of the animal studies. Sample sizes were determined by the resource equation method. The repeat-dose NHP study was conducted under GLP conditions.

Macaques used for study were 2 to 3 years old males and weighed between 2.3 and 2.8 kg at the initiation of dosing. Tuberculin tests were carried out on arrival at the test facility and were negative. Animals were housed socially (up to 3 animals of same sex and same dosing group together) in stainless steel cages equipped with a stainless-steel mesh floor and an automatic watering valve, with the exception of times when they were separated for designated study procedures/activities. Animals were housed in a temperature- and humidity-controlled environment (21-26° C. and 30-70%, respectively), with an automatic 12-hour dark/light cycle. Primary enclosures were as specified in the USDA Animal Welfare Act (9 CFR, Parts 1, 2 and 3) and as described in the *Guide for the Care and Use of Laboratory Animals* (39). PMI Nutrition International Certified Primate Chow No. 5048 (25% protein) was provided twice daily, except during designated procedures. The chow was provided in amounts appropriate for the size and age of the animals. Municipal tap water after treatment by reverse osmosis and ultraviolet irradiation was made freely available to each animal via an automatic watering system (except during designated procedures).

Example 19: Single Dose Study of mRNA-Expressed Chikungunya Virus Antibody in Cynomolgus Monkeys To test the expression levels of human anti-ChikV antibody from modified mRNAs in a nonhuman primate, mRNAs encoding the heavy and light chains of ChikV24 were delivered intravenously into cynomolgus macaques. One goal of the experiment was to determine whether the CHIKV24 mRNAs could induce expression of human IgG in the serum of monkeys at levels that correspond to the protective serum concentrations observed in mice. 0.5 mg/kg of the mRNAs encoding the heavy and light antibody chains were co-formulated in Compound II- and Compound I-containing lipid nanoparticles prior to administration. The mRNAs encoding the ChikV24 antibody were infused over 60 minutes in a volume of 5 mL/kg and a dose concentration of 0.02 mg/mL. A total of 6 monkeys were injected with a single dose of mRNAs encoding the ChikV24 antibody (Study 1). This study was repeated with 6 macaques per group (Study 2). The following parameters and end points were also evaluated in this study: clinical signs, body weights, food evaluation, and human IgG expression in serum.

Figure 5A:
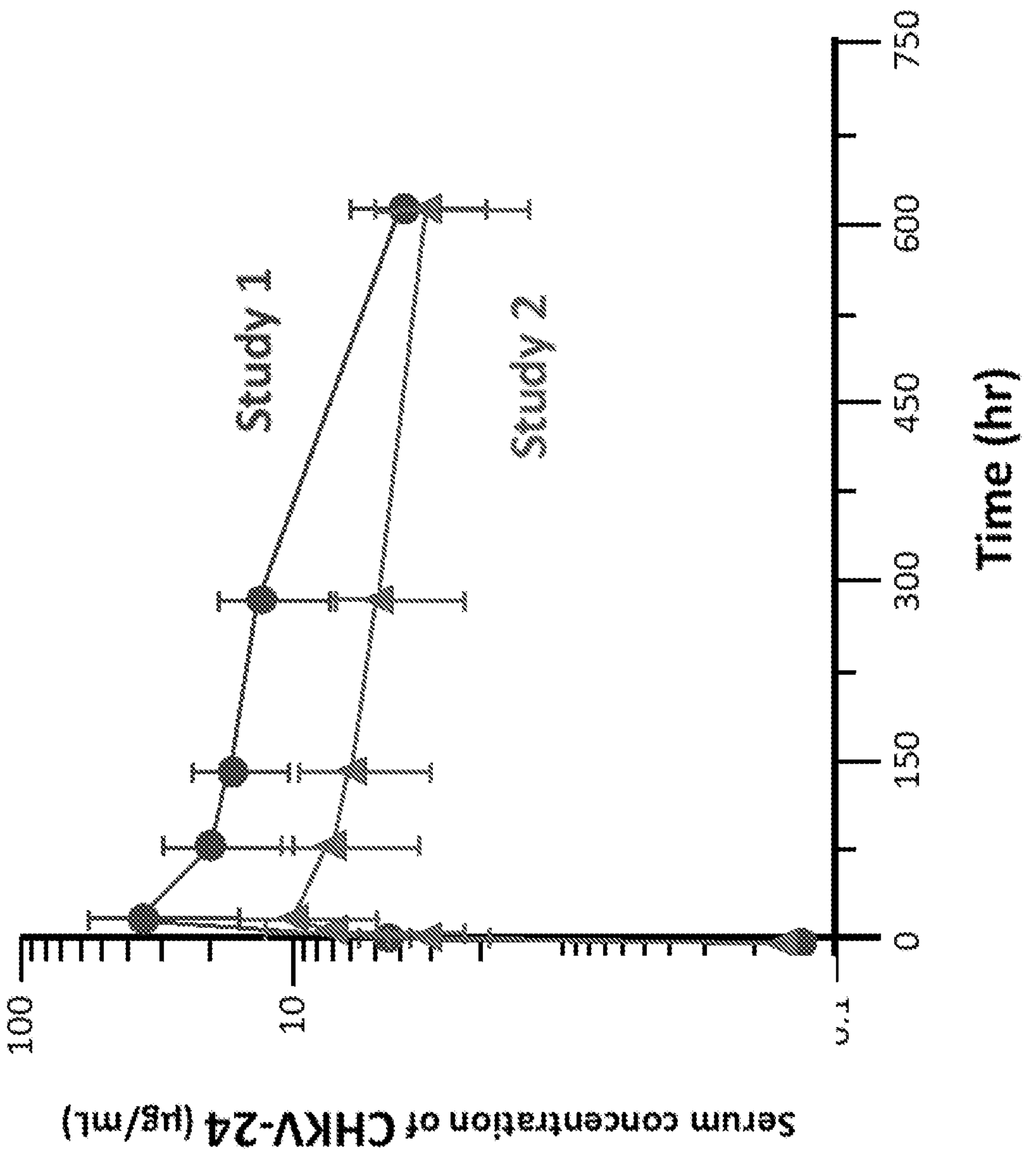
FIG. 5A is a graph showing the serum concentration levels of the human ChikV24 antibody in cynomolgus monkeys injected intravenously with a single 0.5 mg/kg dose of mRNAs expressing the heavy and light chains of the ChikV24 antibody over the course of 720-hours post-injection.

The concentration and duration of human antibody was assayed in serum collected from injected monkeys at all time points. Blood samples (0.3 mL) were collected in serum separator tubes on day 1 (at pre-dose and 6, 24, 96, 168, 336, or 720 hours after the start of infusion) and on day 82. The blood samples were maintained at ambient temperature for a target of 30 min following collection, then processed to serum within 90 min of collection. The samples were centrifuged for 10 min in a refrigerated centrifuge (set to maintain 4° C.) at 1,200×g. The resulting serum was separated, aliquoted, and frozen immediately over dry ice before storage at −80° C. Human IgG in serum was analyzed using an ELISA a Human Therapeutic IgG1 ELISA Kit (Cayman Chemical, #500910). The kit instructions were followed exactly with serum dilutions ranging from 1:100 to 1:1,000. A standard curve of absorbance at 450 nm versus log (concentration) was fit with a 4-parameter logistic equation for IgG1 quantification. Human IgG pharmacokinetic parameters were estimated using Phoenix software (Certara, USA) using a non-compartmental approach (NCA), consistent with the intravenous route of administration. Parameters were estimated using nominal sampling times relative to the start of each dose administration. Concentration values reported as Below Quantifiable Limit were assigned a value of zero. The area under the concentration vs. time curve (AUC) was calculated using the linear trapezoidal method with linear interpolation. AUC values were reported to 3 significant digits, and $t_{1/2}$ values were reported to one decimal place. The terminal elimination phase for each subject was estimated using at least three observed concentration values. The slope of the elimination phase was determined using log linear regression on the unweighted concentration data. As shown in FIG. 5A, the ChikV24 antibody was expressed from modified mRNAs injected in monkeys over the course of 720-hours post-injection. There were no test article-related clinical signs, changes in body weight, or changes in food consumption during the course of this study. IgG1 expression peaked at 24 hours after the start of infusion for animals that received a 0.5 mg/kg dose of mRNAs encoding the ChikV24 antibody. Table 8 shows that the mean human IgG levels at 24 hours post-injection was 10.1 to 35.9 μg/mL (a maximum concentration of 35.9 μg/mL in Study 1 and 10.1 μg/mL in Study 2). The differences in peak expression level across the two studies can be attributed to assay and study variability. The half-life of the mRNA-expressed ChikV24 antibody was 23 days in cynomolgus macaques. Thus, the mRNA infusions achieved protective concentrations of the ChikV24 antibody in macaques.

TABLE 8

Human IgG pharmacokinetic parameters of ChikV24 antibody in macaques following delivery of modified mRNAs encoding the antibody

| $T_{max}$ (hr) | | | $C_{max}$ (μg/mL) | | | $AUC_{0-720\ hr}$ (hr * μg/mL) | | | $t_{1/2}$ (hr) | | |
|---|---|---|---|---|---|---|---|---|---|---|---|
| Mean | SD | CV % | Mean | SD | CV % | Mean | SD | CV % | Mean | SD | CV% |
| 24 | 0 | 0 | 10.1 | 5.36 | 53 | 3,720 | 1,950 | 52.4 | 561 | 65.8 | 11.7 |

Figure 5B:
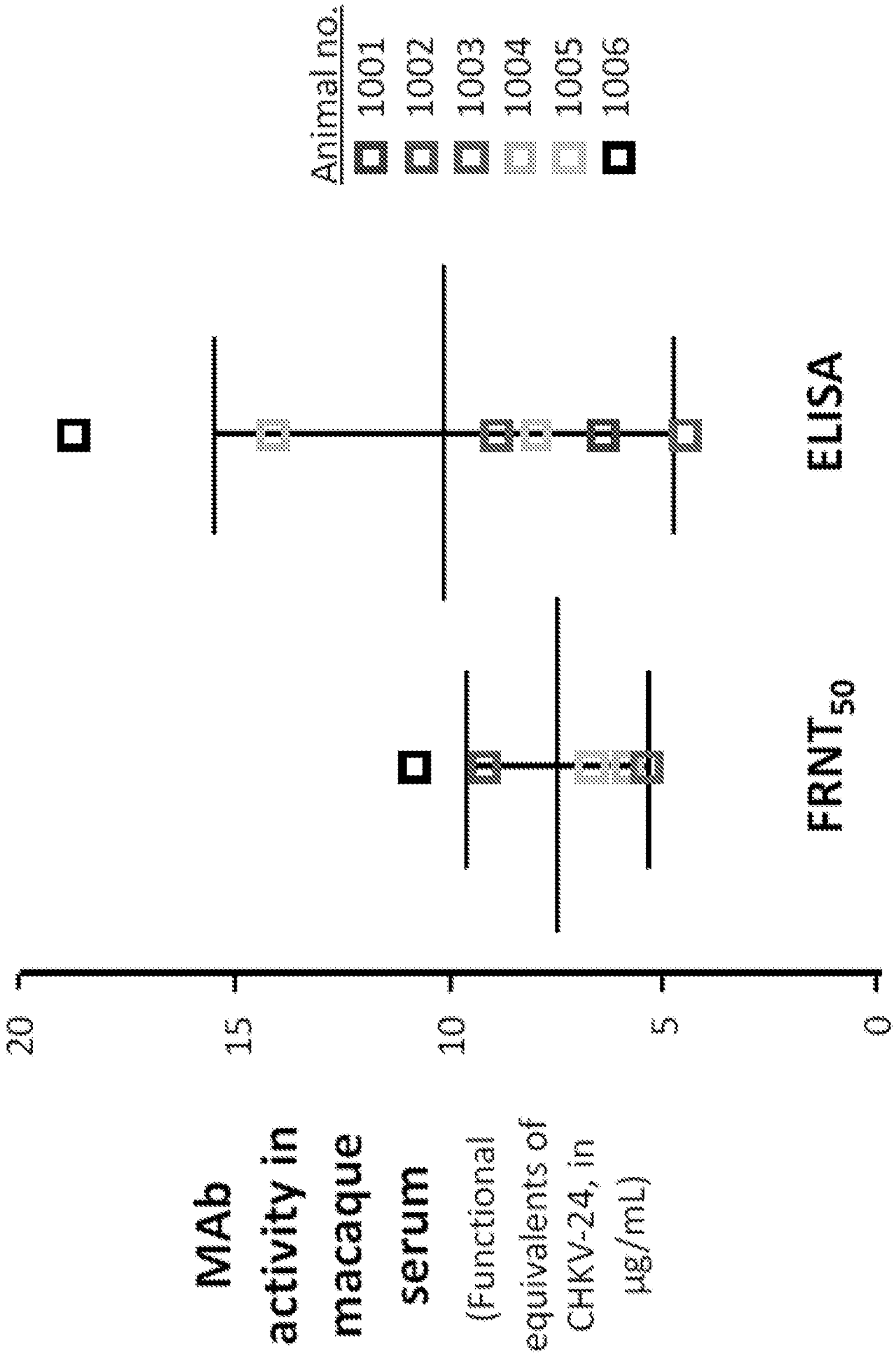
FIG. 5B is a graph showing ChikV24 antibody activity levels (μg/mL) in serum samples collected from cynomolgus monkeys 24 hours after infusion with 0.5 mg/kg of mRNAs encoding the ChikV24 antibody, as measured using a focus reduction neutralization assay ($FRNT_{50}$) and by ELISA.

Next, the function of the ChikV24 antibodies expressed in serum from the injected modified mRNAs was compared to the function of the recombinant ChikV24 monoclonal antibody. The serum samples (from Study 2) at the 24-hour timepoint from the pharmacodynamics studies (FIG. 5A) were tested for the presence of CHIKV-specific binding or neutralizing antibodies. Antibody function was assessed by a 50% focus reduction neutralization test ($FRNT_{50}$) and ELISA. A group of 6 animals was tested (Study 2), and in vitro experiments were conducted twice. A standard curve for concentration versus activity in each assay was generated using dilution curves of purified recombinant ChikV24 antibody at defined concentrations. FIG. 5B shows that the functional equivalents of ChikV24 antibody activity measured using the $FRNT_{50}$ and ELISA methods, by comparison to the activity of the sera with the ChikV24 antibody standard curves, were within the variability of the assays, suggesting that the mRNA-expressed antibody was fully functional.

Example 20: Multiple Dose Study of mRNA-Expressed Chikungunya Virus Antibody in Cynomolgus Monkeys To test the expression of human anti-ChikV antibody over time in non-human primates from multiple doses of modified mRNAs, two doses of mRNAs encoding the heavy and light chains of the ChikV24 antibody were delivered intravenously into cynomolgus monkeys one week apart (on days 0 and 7). Animals were administered mRNA doses of 0.3 mg/kg, 1 mg/kg, or 3.0 mg/kg, or a PBS control. The mRNAs were co-formulated in Compound II- and Compound I-containing lipid nanoparticles prior to administration. Necropsy was then performed on study animals on day 8 (following the second injection of mRNAs), or on day 98 after a 12-week treatment-free recovery period. Multiple serum samples were collected throughout the duration of the study to measure the concentrations of the ChikV24 antibody in serum after multiple mRNA doses. Serum was collected at 6, 24, 48, 72 and 120 hours after the start of infusion of dose 1 and at 6, 12, 24, 48, 72, 120, 168, 216, 288, 360, 432, 528, 720, 1,080 and 2,160 hours after the start of infusion of dose 2. Antibody concentrations after day 8 were calculated only for the highest mRNA dose level (3 mg/kg).

Figure 6:
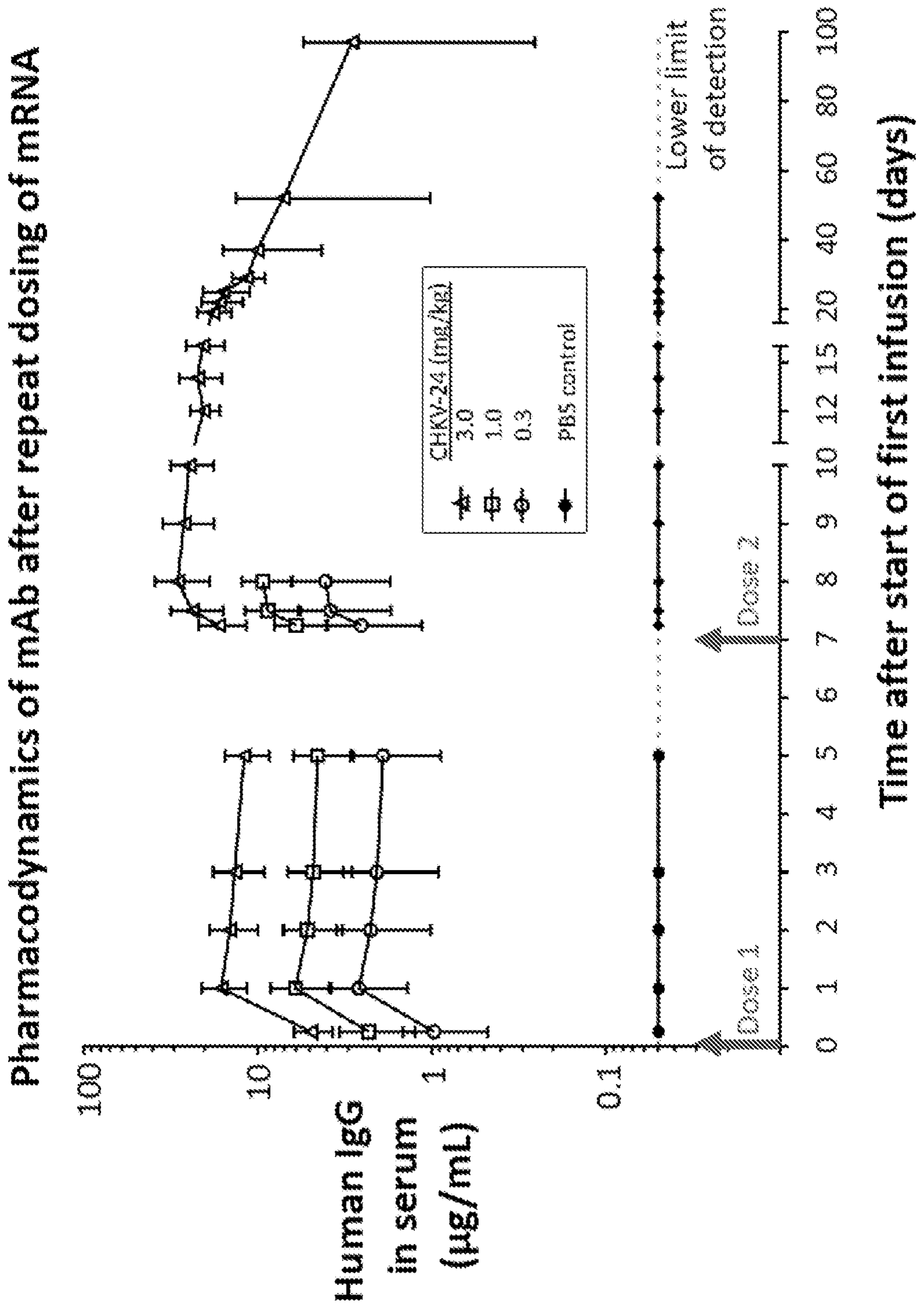
FIG. 6 is a graph showing the serum concentration levels of the human ChikV24 antibody in cynomolgus monkeys injected intravenously with two 0.3 mg/kg, 1 mg/kg, or 3 mg/kg doses of mRNAs expressing the heavy and light chains of the ChikV24 antibody over the course of 2400-hours (100 days) post-injection.

FIG. 6 shows that the ChikV24 antibody was detected in the serum samples of cynomolgus monkeys injected with multiple doses of mRNAs encoding the antibody. A dose-dependent response was observed, as ChikV24 IgG serum concentrations were higher with increasing doses of mRNAs. Maximum ChikV24 IgG serum concentrations of 16.2 μg/mL and 28.8 μg/mL were observed in animals administered the high dose of 3.0 mg/kg mRNA at 24 hours (day 1) following the first dose and 24 hours (day 8) following the second dose, respectively. Sex-based differences were not detected in ChikV24 IgG serum levels. ChikV24 IgG serum levels were detected through 100 days after the second dose (at 3.0 mg/kg, administered on day 7) in animals that had a recovery period, with an average serum concentration of 2.9 μg/mL. Human IgG antibodies were detectable through day 83 when dosed once at 0.5 mg/kg.

Example 21: Administration of mRNAs Encoding Chikungunya Virus Antibody in Humans mRNA constructs encoding the heavy and light chains (SEQ ID NO:5 and SEQ ID NO:6, respectively) of the human ChikV24 antibody are formulated in lipid nanoparticles (LNPs) containing Compound II, DSPC, Cholesterol, and Compound I (at a molar ratio of 50:10:38:2) and are administered intravenously to humans who have been infected with, or are at risk of being infected with, chikungunya virus. Administering the mRNAs encoding the ChikV24 antibody is expected to reduce symptoms associated with chikungunya virus infection in individuals who have been exposed to the virus. Prophylactically administering the mRNAs encoding the ChikV24 antibody to individuals at greater risk of being exposed to chikungunya virus is expected to prevent infection and/or reduce disease symptoms should infection occur.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A polynucleotide comprising an mRNA comprising:

(i) a 5' UTR;

(ii) an open reading frame (ORF) encoding a polypeptide comprising the heavy chain variable region of the heavy chain antibody sequence of SEQ ID NO:1, wherein the ORF comprises a nucleic acid sequence that is at least 80% identical to nucleotides 61-426 of SEQ ID NO:2;

(iii) a stop codon; and (iv) a 3' UTR.

2. A polynucleotide comprising an mRNA comprising:

(i) a 5' UTR;

(ii) an open reading frame (ORF) encoding a polypeptide comprising the light chain variable region of the light chain antibody sequence of SEQ ID NO:3, wherein the ORF comprises a nucleic acid sequence that is at least 80% identical to nucleotides 61-384 of SEQ ID NO:4;

(iii) a stop codon; and (iv) a 3' UTR.

3. A pharmaceutical composition comprising the polynucleotide of claim 1, and a delivery agent.

4. A pharmaceutical composition comprising:

a first polynucleotide comprising a first mRNA comprising (i) a first 5' UTR, (ii) a first open reading frame (ORF) encoding a first polypeptide comprising the heavy chain variable region of the heavy chain antibody sequence of SEQ ID NO:1, wherein the first ORF comprises a first nucleic acid sequence that is at least 80% identical to nucleotides 61-426 of SEQ ID NO:2, (iii) a first stop codon, and (iv) a first 3' UTR;

a second polynucleotide comprising a second mRNA comprising (i) a second 5' UTR, (ii) a second ORF encoding a second polypeptide comprising the light chain variable region of the light chain antibody sequence of SEQ ID NO:3, wherein the second ORF comprises a second nucleic acid sequence that is at least 80% identical to nucleotides 61-384 of SEQ ID NO:4, (iii) a second stop codon, and (iv) a second 3' UTR; and a delivery agent, wherein the first polypeptide when paired with the second polypeptide forms an anti-Chikungunya virus antibody or an anti-Chikungunya virus antibody fragment.

5. The pharmaceutical composition of claim 4, wherein the first nucleic acid sequence is at least 90% identical to SEQ ID NO:2, and wherein the second nucleic acid sequence is at least 90% identical to SEQ ID NO:4.

6. The pharmaceutical composition of claim 4, wherein the first mRNA and the second mRNA each comprise a 5' terminal cap.

7. The pharmaceutical composition of claim 6, wherein each 5' terminal cap comprises a Cap0, Cap0, ARCA, inosine, N1-methyl-guanosine, 2'-fluoro-guanosine, 7-deaza-guanosine, 8-oxo-guanosine, 2-amino-guanosine, LNA-guanosine, 2-azidoguanosine, Cap2, Cap4, 5' methylG cap, or an analog thereof.

8. The pharmaceutical composition of claim 4, wherein the first mRNA and the second mRNA each comprise a poly-A region.

9. The pharmaceutical composition of claim 4, wherein the first mRNA and the second mRNA each comprise at least one chemically modified nucleobase, sugar, backbone, or any combination thereof.

10. The pharmaceutical composition of claim 9 wherein the at least one chemically modified nucleobase is selected from the group consisting of pseudouracil (ψ), N1-methylpseudouracil (m1ψ), 1-ethylpseudouracil, 2-thiouracil (s2U), 4'-thiouracil, 5-methylcytosine, 5-methyluracil, 5-methoxyuracil, and any combination thereof.

11. The pharmaceutical composition of claim 9, wherein all of the uracils of the first mRNA and the second mRNA are N1-methylpseudouracils.

12. A method of expressing an anti-chikungunya virus antibody in a human subject in need thereof, comprising administering to the human subject an effective amount of the pharmaceutical composition of claim 4.

13. A method of reducing chikungunya virus levels in a human subject in need thereof, comprising administering to the human subject an effective amount of the pharmaceutical composition of claim 4.

14. The method of claim 12, wherein the pharmaceutical composition is administered to the human subject multiple times at a frequency of about once a week, about once every two weeks, or about once a month.

15. The method of claim 12, wherein the pharmaceutical composition is administered intravenously.

16. The method of claim 12, wherein the pharmaceutical composition is administered subcutaneously.

17. The pharmaceutical composition of claim 4, wherein the first nucleic acid sequence is at least 80% identical to nucleotides 61-1416 of SEQ ID NO:2, and wherein the second nucleic acid sequence is at least 80% identical to nucleotides 61-705 of SEQ ID NO:4.

18. The pharmaceutical composition of claim 4, wherein the first nucleic acid sequence is at least 80% identical to SEQ ID NO:2, and wherein the second nucleic acid sequence is at least 80% identical to SEQ ID NO:4.

19. The pharmaceutical composition of claim 4, wherein the first nucleic acid sequence is at least 90% identical to nucleotides 61-426 of SEQ ID NO:2, and wherein the second nucleic acid sequence is at least 90% identical to nucleotides 61-384 of SEQ ID NO:4.

20. The pharmaceutical composition of claim 4, wherein the first nucleic acid sequence is at least 90% identical to nucleotides 61-1416 of SEQ ID NO:2, and wherein the second nucleic acid sequence is at least 90% identical to nucleotides 61-705 of SEQ ID NO:4.

21. The pharmaceutical composition of claim 4, wherein the first nucleic acid sequence is 100% identical to nucleotides 61-426 of SEQ ID NO:2, and wherein the second nucleic acid sequence is 100% identical to nucleotides 61-384 of SEQ ID NO:4.

22. The pharmaceutical composition of claim 4, wherein the first nucleic acid sequence is 100% identical to nucleotides 61-1416 of SEQ ID NO:2, and wherein the second nucleic acid sequence is 100% identical to nucleotides 61-705 of SEQ ID NO:4.

23. The pharmaceutical composition of claim 4, wherein the first nucleic acid sequence is 100% identical to SEQ ID NO:2, and wherein the second nucleic acid sequence is 100% identical to SEQ ID NO:4.

* * * * *

UNITED STATES PATENT AND TRADEMARK OFFICE

CERTIFICATE OF CORRECTION

PATENT NO. : 11,802,146 B2
APPLICATION NO. : 16/959828
DATED : October 31, 2023
INVENTOR(S) : Sunny Himansu et al.

It is certified that error appears in the above-identified patent and that said Letters Patent is hereby corrected as shown below:

In the Claims

Column 284, Line 54, Claim 7, delete "Cap0," and insert -- Cap1, --. (second occurrence)

Signed and Sealed this
Thirtieth Day of January, 2024

Katherine Kelly Vidal

Katherine Kelly Vidal
*Director of the United States Patent and Trademark Office*